US012569505B2

(12) United States Patent
Whitehouse et al.

(10) Patent No.: US 12,569,505 B2
(45) Date of Patent: *Mar. 10, 2026

(54) ORAL SOLID DOSAGE FORMS COMPRISING CANNABINOIDS

(71) Applicant: Jazz Pharmaceuticals Research UK Limited, Sittingbourne (GB)

(72) Inventors: Jonathon Oliver Whitehouse, Herne Bay (GB); Md Mushfiq Hossain Akanda, Gillingham (GB); Edward Thomas, Faversham (GB); John Croall, Minster-on-sea (GB); Tammy Iyobosa Morrison, Rochester (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/210,719

(22) Filed: May 16, 2025

(65) Prior Publication Data

US 2025/0275990 A1 Sep. 4, 2025

Related U.S. Application Data

(63) Continuation of application No. 18/597,717, filed on Mar. 6, 2024, which is a continuation of application No. PCT/EP2023/072292, filed on Aug. 11, 2023.

(Continued)

(51) Int. Cl.

*A61K 31/00* (2006.01)
*A61K 9/00* (2006.01)

(Continued)

(52) U.S. Cl.

CPC .......... *A61K 31/658* (2023.05); *A61K 9/1611* (2013.01); *A61K 9/1617* (2013.01); *A61K 9/4866* (2013.01); *A61K 47/22* (2013.01)

(58) Field of Classification Search

None

See application file for complete search history.

(56) References Cited

U.S. PATENT DOCUMENTS 5,958,873 A 9/1999 Sakr et al.
6,294,192 B1 9/2001 Patel et al.

(Continued)

FOREIGN PATENT DOCUMENTS

AU 2016203127 A1 6/2016
CA 2737447 A1 10/2012

(Continued)

OTHER PUBLICATIONS

Alger, "Not too excited? Thank your endocannabinoids," Neuron, 51(4):393-595 (2006).

(Continued)

*Primary Examiner* — Kyung S Chang
(74) *Attorney, Agent, or Firm* — COOLEY LLP

(57) ABSTRACT

The present disclosure relates to drug-containing particles comprising one or more cannabinoids and a porous solid carrier. In embodiments, the one or more cannabinoids are adsorbed onto and/or in a porous solid carrier. In embodiments, the drug-containing particles exhibit improved solubility and bioavailability, among other beneficial properties. Methods of preparation and pharmaceutical compositions are also described.

27 Claims, 43 Drawing Sheets

Related U.S. Application Data

(60) Provisional application No. 63/371,292, filed on Aug. 12, 2022.

(51) Int. Cl.

| | |
|---|---|
| ***A61K 9/14*** | (2006.01) |
| ***A61K 9/16*** | (2006.01) |
| ***A61K 9/48*** | (2006.01) |
| ***A61K 47/02*** | (2006.01) |
| ***A61K 47/22*** | (2006.01) |
| ***A61K 47/26*** | (2006.01) |
| ***A61K 47/36*** | (2006.01) |
| ***A61K 47/38*** | (2006.01) |

(56) References Cited

U.S. PATENT DOCUMENTS

| | | | |
|---|---|---|---|
| 6,403,126 | B1 | 6/2002 | Webster et al. |
| 6,949,582 | B1 | 9/2005 | Wallace |
| 8,293,786 | B2 | 10/2012 | Stinchcomb et al. |
| 8,632,825 | B2 | 1/2014 | Velasco Diez et al. |
| 8,673,368 | B2 | 3/2014 | Guy et al. |
| 8,790,719 | B2 | 7/2014 | Parolaro et al. |
| 8,808,734 | B2 | 8/2014 | Winnicki |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,095,554 | B2 | 8/2015 | Lewis et al. |
| 9,125,859 | B2 | 9/2015 | Whalley et al. |
| 9,168,278 | B2 | 10/2015 | Guy et al. |
| 9,259,449 | B2 | 2/2016 | Raderman |
| 9,345,771 | B2 | 5/2016 | Goskonda et al. |
| 9,474,726 | B2 | 10/2016 | Guy et al. |
| 9,522,123 | B2 | 12/2016 | Whalley et al. |
| 9,675,654 | B2 | 6/2017 | Parolaro et al. |
| 9,730,911 | B2 | 8/2017 | Verzura et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado et al. |
| 10,226,433 | B2 | 3/2019 | Di Marzo et al. |
| 10,441,617 | B2 | 10/2019 | Lewis et al. |
| 10,583,096 | B2 | 3/2020 | Guy et al. |
| 10,603,288 | B2 | 3/2020 | Guy et al. |
| 10,653,641 | B2 | 5/2020 | Robson et al. |
| 10,709,671 | B2 | 7/2020 | Guy et al. |
| 10,709,673 | B2 | 7/2020 | Guy |
| 10,709,674 | B2 | 7/2020 | Guy et al. |
| 10,729,665 | B2 | 8/2020 | Whalley et al. |
| 10,758,514 | B2 | 9/2020 | Liu et al. |
| 10,765,643 | B2 | 9/2020 | Guy et al. |
| 10,799,467 | B2 | 10/2020 | Whalley et al. |
| 10,807,777 | B2 | 10/2020 | Whittle |
| 10,849,860 | B2 | 12/2020 | Guy et al. |
| 10,918,608 | B2 | 2/2021 | Guy et al. |
| 10,966,939 | B2 | 4/2021 | Guy et al. |
| 11,000,486 | B2 | 5/2021 | Wright et al. |
| 11,065,209 | B2 | 7/2021 | Guy et al. |
| 11,065,227 | B2 | 7/2021 | Stott et al. |
| 11,096,905 | B2 | 8/2021 | Guy et al. |
| 11,147,776 | B2 | 10/2021 | Stott et al. |
| 11,147,783 | B2 | 10/2021 | Stott et al. |
| 11,154,516 | B2 | 10/2021 | Guy et al. |
| 11,154,517 | B2 | 10/2021 | Guy et al. |
| 11,160,757 | B1 | 11/2021 | Wilkhu et al. |
| 11,160,795 | B2 | 11/2021 | Guy et al. |
| 11,207,292 | B2 | 12/2021 | Guy et al. |
| 11,229,612 | B2 | 1/2022 | Wright et al. |
| 11,291,631 | B2 | 4/2022 | Shah |
| 11,311,498 | B2 | 4/2022 | Guy et al. |
| 11,318,109 | B2 | 5/2022 | Whalley et al. |
| 11,357,741 | B2 | 6/2022 | Guy et al. |
| 11,400,055 | B2 | 8/2022 | Guy et al. |
| 11,406,623 | B2 | 8/2022 | Guy et al. |
| 11,413,266 | B2 | 8/2022 | Biróet al. |
| 11,419,829 | B2 | 8/2022 | Whalley et al. |
| 11,426,362 | B2 | 8/2022 | Wright et al. |
| 11,439,595 | B2 | 9/2022 | Nowak et al. |
| 11,446,258 | B2 | 9/2022 | Guy et al. |
| 11,590,087 | B2 | 2/2023 | Guy et al. |
| 11,622,957 | B2 | 4/2023 | Odumosu et al. |
| 11,633,369 | B2 | 4/2023 | Guy et al. |
| 11,679,087 | B2 | 6/2023 | Guy et al. |
| 11,684,598 | B2 | 6/2023 | Stott et al. |
| 11,701,330 | B2 | 7/2023 | Guy et al. |
| 11,723,892 | B2 | 8/2023 | Karolchyk |
| 11,766,411 | B2 | 9/2023 | Guy et al. |
| 11,793,770 | B2 | 10/2023 | Stott et al. |
| 11,806,319 | B2 | 11/2023 | Wilkhu et al. |
| 11,865,102 | B2 | 1/2024 | Guy et al. |
| 11,918,690 | B2 | 3/2024 | Nowak et al. |
| 11,963,937 | B2 | 4/2024 | Guy |
| 12,064,398 | B2 | 8/2024 | Wright et al. |
| 12,064,399 | B2 | 8/2024 | Guy et al. |
| 12,102,619 | B2 | 10/2024 | Guy et al. |
| 12,121,499 | B2 | 10/2024 | Whalley et al. |
| 12,161,607 | B2 | 12/2024 | Wright et al. |
| 12,213,985 | B2 | 2/2025 | Shah |
| 12,263,139 | B2 | 4/2025 | Whalley et al. |
| 12,318,356 | B2 | 6/2025 | Guy |
| 12,350,253 | B2 | 7/2025 | Whalley et al. |
| 12,350,371 | B2 | 7/2025 | Nowak et al. |
| 12,357,586 | B2 | 7/2025 | Whalley et al. |
| 12,364,670 | B2 | 7/2025 | Guy et al. |
| 12,383,512 | B2 | 8/2025 | Guy et al. |
| 12,383,567 | B2 | 8/2025 | Guy et al. |
| 12,396,963 | B2 | 8/2025 | Guy et al. |
| 12,403,136 | B2 | 9/2025 | Silcock et al. |
| 12,427,160 | B2 | 9/2025 | Guy et al. |
| 2004/0049059 | A1 | 3/2004 | Mueller |
| 2004/0110828 | A1 | 6/2004 | Chowdhury et al. |
| 2004/0228921 | A1 | 11/2004 | Chowdhury et al. |
| 2005/0042172 | A1 | 2/2005 | Whittle |
| 2005/0266108 | A1 | 12/2005 | Flockhart et al. |
| 2006/0039959 | A1 | 2/2006 | Wessling |
| 2006/0257463 | A1 | 11/2006 | Elsohly et al. |
| 2007/0060638 | A1 | 3/2007 | Olmstead et al. |
| 2007/0060639 | A1 | 3/2007 | Wermeling |
| 2007/0116768 | A1 | 5/2007 | Chorny et al. |
| 2008/0119544 | A1 | 5/2008 | Guy et al. |
| 2008/0188461 | A1 | 8/2008 | Guan et al. |
| 2008/0279940 | A1 | 11/2008 | Rigassi et al. |
| 2009/0035368 | A1 | 2/2009 | Moschwitzer |
| 2009/0264063 | A1 | 10/2009 | Tinsley et al. |
| 2009/0306221 | A1 | 12/2009 | Guy et al. |
| 2010/0239693 | A1 | 9/2010 | Guy et al. |
| 2010/0317729 | A1 | 12/2010 | Guy et al. |
| 2011/0028431 | A1 | 2/2011 | Zerbe et al. |
| 2011/0038958 | A1 | 2/2011 | Kikuchi et al. |
| 2011/0082195 | A1 | 4/2011 | Guy et al. |
| 2011/0142945 | A1 | 6/2011 | Chen et al. |
| 2012/0004251 | A1 | 1/2012 | Whalley et al. |
| 2012/0165402 | A1 | 6/2012 | Whalley et al. |
| 2012/0183606 | A1 | 7/2012 | Bender et al. |
| 2012/0202891 | A1 | 8/2012 | Stinchcomb et al. |
| 2012/0231083 | A1 | 9/2012 | Carley et al. |
| 2012/0270845 | A1 | 10/2012 | Bannister et al. |
| 2013/0089600 | A1 | 4/2013 | Winnicki |
| 2013/0209483 | A1 | 8/2013 | Mcallister |
| 2013/0245110 | A1 | 9/2013 | Guy et al. |
| 2013/0296398 | A1 | 11/2013 | Whalley et al. |
| 2014/0100269 | A1 | 4/2014 | Goskonda et al. |
| 2014/0110828 | A1 | 4/2014 | Otremba et al. |
| 2014/0155456 | A9 | 6/2014 | Whalley et al. |
| 2014/0179745 | A1 | 6/2014 | Bottger et al. |

(56) References Cited

U.S. PATENT DOCUMENTS

| | | | |
|---|---|---|---|
| 2014/0243405 | A1 | 8/2014 | Whalley et al. |
| 2014/0335208 | A1 | 11/2014 | Cawthorne et al. |
| 2014/0343044 | A1 | 11/2014 | Ceulemens et al. |
| 2015/0080443 | A1 | 3/2015 | Bergeron et al. |
| 2015/0111939 | A1 | 4/2015 | Gruening et al. |
| 2015/0181924 | A1 | 7/2015 | Llamas |
| 2015/0250733 | A1 | 9/2015 | Odidi |
| 2015/0320698 | A1 | 11/2015 | Whalley et al. |
| 2015/0335590 | A1 | 11/2015 | Whalley et al. |
| 2015/0342902 | A1 | 12/2015 | Vangara et al. |
| 2015/0343071 | A1 | 12/2015 | Vangara et al. |
| 2015/0359755 | A1 | 12/2015 | Guy et al. |
| 2015/0359756 | A1 | 12/2015 | Guy et al. |
| 2016/0166498 | A1 | 6/2016 | Anastassov et al. |
| 2016/0166514 | A1 | 6/2016 | Guy et al. |
| 2016/0166515 | A1 | 6/2016 | Guy et al. |
| 2016/0184258 | A1 | 6/2016 | Murty et al. |
| 2016/0213624 | A1 | 7/2016 | Lindeman |
| 2016/0220529 | A1 | 8/2016 | Guy et al. |
| 2016/0256411 | A1 | 9/2016 | Aung-Din |
| 2016/0271252 | A1 | 9/2016 | Vangara et al. |
| 2016/0346235 | A1 | 12/2016 | Singh et al. |
| 2016/0367496 | A1 | 12/2016 | Vangara et al. |
| 2017/0007551 | A1 | 1/2017 | Guy et al. |
| 2017/0119660 | A1 | 5/2017 | Temtsin-Krayz et al. |
| 2017/0172939 | A1 | 6/2017 | Guy et al. |
| 2017/0172940 | A1 | 6/2017 | Guy et al. |
| 2017/0172941 | A1 | 6/2017 | Guy et al. |
| 2017/0173043 | A1 | 6/2017 | Guy et al. |
| 2017/0173044 | A1 | 6/2017 | Guy et al. |
| 2017/0181982 | A1 | 6/2017 | Guy et al. |
| 2017/0224634 | A1 | 8/2017 | Vangara et al. |
| 2017/0231923 | A1 | 8/2017 | Guy et al. |
| 2017/0239193 | A1 | 8/2017 | Guy et al. |
| 2017/0246121 | A1 | 8/2017 | Guy et al. |
| 2017/0246622 | A1 | 8/2017 | Nobiki |
| 2017/0266126 | A1 | 9/2017 | Guy et al. |
| 2017/0273913 | A1 | 9/2017 | Whalley et al. |
| 2018/0028489 | A1 | 2/2018 | Vangara et al. |
| 2018/0071210 | A1 | 3/2018 | Wilkhu et al. |
| 2018/0214412 | A1 | 8/2018 | Renwick et al. |
| 2018/0228751 | A1 | 8/2018 | Stott et al. |
| 2018/0289665 | A1 | 10/2018 | Turner et al. |
| 2018/0325861 | A1* | 11/2018 | Domb .................. A61K 9/0053 |
| 2018/0338931 | A1 | 11/2018 | Guy et al. |
| 2019/0083418 | A1 | 3/2019 | Guy et al. |
| 2019/0167583 | A1 | 6/2019 | Shah |
| 2019/0175547 | A1 | 6/2019 | Stott et al. |
| 2019/0240160 | A1 | 8/2019 | He et al. |
| 2019/0314296 | A1 | 10/2019 | Wright et al. |
| 2019/0321307 | A1 | 10/2019 | Guy et al. |
| 2019/0365667 | A1 | 12/2019 | Wright et al. |
| 2020/0046642 | A1* | 2/2020 | Nowak ................ A61K 9/1676 |
| 2020/0046643 | A1 | 2/2020 | Nowak et al. |
| 2020/0046787 | A1 | 2/2020 | Nowak et al. |
| 2020/0061022 | A1 | 2/2020 | Nowak et al. |
| 2020/0138738 | A1 | 5/2020 | Guy et al. |
| 2020/0179303 | A1 | 6/2020 | Guy et al. |
| 2020/0206153 | A1 | 7/2020 | Whalley et al. |
| 2020/0237683 | A1 | 7/2020 | Whalley et al. |
| 2020/0297656 | A1 | 9/2020 | Guy et al. |
| 2020/0352878 | A1 | 11/2020 | Guy et al. |
| 2020/0360286 | A1 | 11/2020 | Vangara et al. |
| 2021/0015789 | A1 | 1/2021 | Guy et al. |
| 2021/0038520 | A1 | 2/2021 | Nowak et al. |
| 2021/0052500 | A1 | 2/2021 | Nowak et al. |
| 2021/0052512 | A1 | 2/2021 | Guy et al. |
| 2021/0059949 | A1 | 3/2021 | Wilkhu et al. |
| 2021/0059960 | A1 | 3/2021 | Wilkhu et al. |
| 2021/0059976 | A1 | 3/2021 | Wilkhu et al. |
| 2021/0069333 | A1 | 3/2021 | Velasco Diez et al. |
| 2021/0100755 | A1 | 4/2021 | Whalley et al. |
| 2021/0169824 | A1 | 6/2021 | Guy et al. |
| 2021/0177773 | A1 | 6/2021 | Guy et al. |
| 2021/0212946 | A1* | 7/2021 | Friedman ............... A61K 31/05 |
| 2021/0220278 | A1 | 7/2021 | Nowak et al. |
| 2021/0290552 | A1 | 9/2021 | Macleman et al. |
| 2021/0290565 | A1 | 9/2021 | Guy et al. |
| 2021/0308072 | A1 | 10/2021 | Wright et al. |
| 2021/0330636 | A1 | 10/2021 | Guy et al. |
| 2021/0330797 | A1 | 10/2021 | Vangara et al. |
| 2021/0401771 | A1 | 12/2021 | Guy et al. |
| 2022/0000800 | A1 | 1/2022 | Guy et al. |
| 2022/0008355 | A1 | 1/2022 | Guy et al. |
| 2022/0016048 | A1 | 1/2022 | Guy et al. |
| 2022/0023232 | A1 | 1/2022 | Guy et al. |
| 2022/0040155 | A1 | 2/2022 | Guy et al. |
| 2022/0062197 | A1 | 3/2022 | Stott et al. |
| 2022/0062211 | A1 | 3/2022 | Stott et al. |
| 2022/0087951 | A1 | 3/2022 | Knappertz |
| 2022/0096397 | A1 | 3/2022 | Wright et al. |
| 2022/0168266 | A1 | 6/2022 | Guy et al. |
| 2022/0183997 | A1 | 6/2022 | Guy et al. |
| 2022/0184000 | A1 | 6/2022 | Guy et al. |
| 2022/0202738 | A1 | 6/2022 | Guy et al. |
| 2022/0211629 | A1 | 7/2022 | Wilkhu et al. |
| 2022/0226257 | A1 | 7/2022 | Guy et al. |
| 2022/0233495 | A1 | 7/2022 | Silcock et al. |
| 2022/0249396 | A1 | 8/2022 | Guy et al. |
| 2022/0257529 | A1 | 8/2022 | Guy et al. |
| 2022/0265573 | A1 | 8/2022 | Guy et al. |
| 2022/0288055 | A1 | 9/2022 | Silcock et al. |
| 2022/0362149 | A1 | 11/2022 | Shah |
| 2022/0378703 | A1 | 12/2022 | Nowak et al. |
| 2022/0378715 | A1 | 12/2022 | Guy et al. |
| 2022/0378738 | A1 | 12/2022 | Guy et al. |
| 2022/0387347 | A1 | 12/2022 | Whalley et al. |
| 2022/0395470 | A1 | 12/2022 | Whalley et al. |
| 2022/0395471 | A1 | 12/2022 | Guy et al. |
| 2023/0000789 | A1 | 1/2023 | Guy et al. |
| 2023/0022487 | A1 | 1/2023 | Guy et al. |
| 2023/0024312 | A1 | 1/2023 | Whalley et al. |
| 2023/0026079 | A1 | 1/2023 | Guy et al. |
| 2023/0032502 | A1 | 2/2023 | Guy et al. |
| 2023/0038423 | A1 | 2/2023 | Silcock et al. |
| 2023/0068885 | A1 | 3/2023 | Guy et al. |
| 2023/0076320 | A1 | 3/2023 | Martin et al. |
| 2023/0143812 | A1 | 5/2023 | Knappertz et al. |
| 2023/0235825 | A1 | 7/2023 | Thompson et al. |
| 2023/0248664 | A1 | 8/2023 | Guy et al. |
| 2023/0263744 | A1 | 8/2023 | Guy |
| 2023/0277560 | A1 | 9/2023 | Checketts et al. |
| 2023/0277561 | A1 | 9/2023 | Checketts et al. |
| 2023/0277562 | A1 | 9/2023 | Checketts et al. |
| 2023/0277563 | A1 | 9/2023 | Checketts et al. |
| 2023/0285419 | A1 | 9/2023 | Checketts et al. |
| 2023/0285420 | A1 | 9/2023 | Checketts et al. |
| 2023/0285421 | A1 | 9/2023 | Checketts et al. |
| 2023/0285422 | A1 | 9/2023 | Checketts et al. |
| 2023/0285423 | A1 | 9/2023 | Checketts et al. |
| 2023/0285424 | A1 | 9/2023 | Checketts et al. |
| 2023/0285425 | A1 | 9/2023 | Checketts et al. |
| 2023/0285426 | A1 | 9/2023 | Checketts et al. |
| 2023/0285427 | A1 | 9/2023 | Checketts et al. |
| 2023/0285428 | A1 | 9/2023 | Checketts et al. |
| 2023/0301934 | A1 | 9/2023 | Whalley et al. |
| 2023/0301936 | A1 | 9/2023 | Guy et al. |
| 2023/0310464 | A1 | 10/2023 | Checketts et al. |
| 2023/0346809 | A1 | 11/2023 | Craig |
| 2023/0372367 | A1 | 11/2023 | Checketts et al. |
| 2023/0372368 | A1 | 11/2023 | Checketts et al. |
| 2024/0016819 | A1 | 1/2024 | Craig |
| 2024/0025858 | A1 | 1/2024 | Silcock et al. |
| 2024/0033229 | A1 | 2/2024 | Guy et al. |
| 2024/0033272 | A1 | 2/2024 | Checketts et al. |
| 2024/0043388 | A1 | 2/2024 | Silcock et al. |
| 2024/0050452 | A1 | 2/2024 | Craig et al. |
| 2024/0091241 | A1 | 3/2024 | Guy et al. |
| 2024/0130981 | A1 | 4/2024 | Wilkhu |
| 2024/0131041 | A1 | 4/2024 | Tse |
| 2024/0165048 | A1 | 5/2024 | Guy |
| 2024/0226032 | A9 | 7/2024 | Wilkhu et al. |
| 2024/0238218 | A1 | 7/2024 | Silcock et al. |
| 2024/0254066 | A1 | 8/2024 | Silcock et al. |

(56) References Cited

U.S. PATENT DOCUMENTS

| | | | |
|---|---|---|---|
| 2024/0254072 | A1 | 8/2024 | Silcock et al. |
| 2024/0261234 | A1 | 8/2024 | Guy |
| 2024/0293762 | A1 | 9/2024 | Loft et al. |
| 2024/0325416 | A1 | 10/2024 | Whitehouse |
| 2024/0350428 | A1 | 10/2024 | Guy et al. |
| 2024/0360060 | A1 | 10/2024 | Silcock et al. |
| 2025/0152521 | A1 | 5/2025 | Guy |
| 2025/0177321 | A1 | 6/2025 | Guy |
| 2025/0248950 | A1 | 8/2025 | Guy et al. |
| 2025/0262228 | A1 | 8/2025 | Chen et al. |
| 2025/0289774 | A1 | 9/2025 | Straker |
| 2025/0319107 | A1 | 10/2025 | Knappertz et al. |
| 2025/0345349 | A1 | 11/2025 | Guy |
| 2025/0381152 | A1 | 12/2025 | Guy et al. |
| 2025/0387418 | A1 | 12/2025 | Guy |

FOREIGN PATENT DOCUMENTS

| | | | |
|---|---|---|---|
| CA | 2859934 | A1 | 3/2016 |
| CN | 101040855 | A | 9/2007 |
| CN | 103110582 | A | 5/2013 |
| CN | 104840967 | A | 8/2015 |
| DE | 102012105063 | A1 | 12/2013 |
| EP | 1071417 | B1 | 2/2005 |
| EP | 2448637 | B1 | 3/2014 |
| EP | 2741750 | A1 | 6/2014 |
| GB | 2384707 | A | 8/2003 |
| GB | 2434097 | A | 7/2007 |
| GB | 2434312 | A | 7/2007 |
| GB | 2438682 | A | 12/2007 |
| GB | 2450753 | A | 1/2009 |
| GB | 2456183 | A | 7/2009 |
| GB | 2471523 | A | 1/2011 |
| GB | 2471565 | A | 1/2011 |
| GB | 2478595 | A | 9/2011 |
| GB | 2479153 | A | 10/2011 |
| GB | 2487712 | A | 8/2012 |
| GB | 2478072 | B | 12/2012 |
| GB | 2478074 | B | 12/2012 |
| GB | 2492487 | A | 1/2013 |
| GB | 2531282 | A | 4/2016 |
| GB | 2539472 | A | 12/2016 |
| GB | 2551987 | A | 1/2018 |
| GB | 2556960 | A | 6/2018 |
| JP | 2010270110 | A | 12/2010 |
| WO | WO-9952524 | A1 | 10/1999 |
| WO | WO-0128590 | A2 | 4/2001 |
| WO | WO-02064109 | A2 | 8/2002 |
| WO | WO-03099302 | A1 | 12/2003 |
| WO | WO-2004016246 | A1 | 2/2004 |
| WO | WO-2004016277 | A2 | 2/2004 |
| WO | WO-2006054057 | A2 | 5/2006 |
| WO | WO-2006133941 | A2 | 12/2006 |
| WO | WO-2007032962 | A2 | 3/2007 |
| WO | WO-2007083098 | A1 | 7/2007 |
| WO | WO-2007138322 | A1 | 12/2007 |
| WO | WO-2008019146 | A2 | 2/2008 |
| WO | WO-2008021394 | A2 | 2/2008 |
| WO | WO-2008024490 | A2 | 2/2008 |
| WO | WO-2008046905 | A1 | 4/2008 |
| WO | WO-2008129258 | A1 | 10/2008 |
| WO | WO-2008144475 | A1 | 11/2008 |
| WO | WO-2008094181 | A3 | 12/2008 |
| WO | WO-2008146006 | A1 | 12/2008 |
| WO | WO-2009007697 | A1 | 1/2009 |
| WO | WO-2009007698 | A1 | 1/2009 |
| WO | WO-2009020666 | A1 | 2/2009 |
| WO | WO-2010012506 | A1 | 2/2010 |
| WO | WO-2011001169 | A1 | 1/2011 |
| WO | WO-2011002285 | A1 | 1/2011 |
| WO | WO-2011121351 | A1 | 10/2011 |
| WO | WO-2012033478 | A1 | 3/2012 |
| WO | WO-2012093255 | A1 | 7/2012 |
| WO | WO-2013024373 | A1 | 2/2013 |
| WO | WO-2013032351 | A1 | 3/2013 |
| WO | WO-2014108574 | A1 | 7/2014 |
| WO | WO-2014146699 | A1 | 9/2014 |
| WO | WO-2015142501 | A1 | 9/2015 |
| WO | WO-2015184127 | A2 | 12/2015 |
| WO | WO-2015193667 | A1 | 12/2015 |
| WO | WO-2015193668 | A1 | 12/2015 |
| WO | WO-2016022936 | A1 | 2/2016 |
| WO | WO-2016059405 | A1 | 4/2016 |
| WO | WO-2016084075 | A1 | 6/2016 |
| WO | WO-2016118391 | A1 | 7/2016 |
| WO | WO-2016140616 | A1 | 9/2016 |
| WO | WO-2016141056 | A1 | 9/2016 |
| WO | WO-2016147186 | A1 | 9/2016 |
| WO | WO-2016199148 | A1 | 12/2016 |
| WO | WO-2017059859 | A1 | 4/2017 |
| WO | WO-2017072762 | A1 | 5/2017 |
| WO | WO-2017072774 | A1 | 5/2017 |
| WO | WO-2017168138 | A1 | 10/2017 |
| WO | WO-2018002636 | A1 | 1/2018 |
| WO | WO-2018002637 | A1 | 1/2018 |
| WO | WO-2018002665 | A1 | 1/2018 |
| WO | WO-2018035030 | A1 | 2/2018 |
| WO | WO-2018037203 | A1 | 3/2018 |
| WO | WO-2019082171 | A1 | 5/2019 |
| WO | WO-2019135075 | A1 | 7/2019 |
| WO | WO-2019135076 | A1 | 7/2019 |
| WO | WO-2019135077 | A1 | 7/2019 |
| WO | WO-2019159174 | A1 | 8/2019 |
| WO | WO-2020016653 | A1 | 1/2020 |
| WO | WO-2020016656 | A3 | 3/2020 |
| WO | WO-2020016658 | A3 | 3/2020 |
| WO | WO-2020016659 | A3 | 3/2020 |
| WO | WO-2020240184 | A1 | 12/2020 |
| WO | WO-2022149103 | A1 | 7/2022 |
| WO | WO-2023240348 | A1 | 12/2023 |
| WO | WO-2024033521 | A1 | 2/2024 |

OTHER PUBLICATIONS

American Epilepsy Society, "Three Studies Shed New Light on the Effectiveness of Cannabis in Epilepsy," Oct. 14, 2014, 2 pages.

Ames et al., "Anticonvulsant effect of cannabidiol," S Afr Med J. Jan. 4, 1986; 69(1):14, 1 page.

Anonymous. High Times [online]; 2017; downloaded from https://hightimes.com/edibles/2017-socal-cannabis-cup-top-10-edibles/ on Dec. 15, 2022; 3 pages. (Year: 2017).

Anonymous. Potvalet [online]; 2017; downloaded from [https://www.pitvalet.com/products/cbd-thc-gel-caps-1-1/] on Dec. 15, 2022; 2 pages. (Year: 2017).

Appendino, J. P. et al., "Position Statement on the Use of Medical Cannabis for the Treatment of Epilepsy in Canada," Can J. Neurol. Sci., 33:783-786 (2006).

Arain, "Pregabalin in the management of partial epilepsy," Neuropsychiatr Dis Treat., 5:407-413 (2009); Epub Aug. 20, 2009.

Arslan, A. & Tirnaksiz, F., "Self-emulsifying Drug Delivery Systems," F ABAD J Pharm Sci, 38(1):55-64 (2013).

Arzimanoglou et al., "All children who experience epileptic falls do not necessarily have Lennox-Gastaut syndrome . . . but many do," Epileptic Discord, 13:S3-S13 (2011).

Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019], 278 pages.

Avoli et al. "Cellular and molecular mechanisms of epilepsy in the human brain," Prog Neurobiol., 77(3):166-200 (2005).

Bakhsh, "Pregabalin in the management of partial epilepsy," Miftaah-al-Khazaain, 1930:607-608, with English translation, 4 pages.

Banerjee et al., "Case Report: Aicardi syndrome: A report of five Indian cases," Neurology India, 54(1):91-93 (2006).

Barker-Haliski et al. "How Clinical Development Can, and Should Inform Translational Science," Neuron, 84:582-593 (2014).

BASF Pharma Ingredients Lutrol® F68 NF [online]. Retrieved on Feb. 22, 2022 from: http://www2.basf.us/Pharma/pdf/Lutrol_F_68.pdf, 2001, 1 page.

(56) References Cited

OTHER PUBLICATIONS

Benowitz & Jones, "Cardiovascular and metabolic considerations in prolonged cannabinoid administration in man," J Clin Pharm, 21:214S-223S (1981).
Benowitz et al. "Metabolic and Psychophysiologic studies of cannabidiol hexobarbital interaction," Clin Pharmacol Ther., 28(1):115-120 (1980).
Bertram, "The Relevance of Kindling for Human Epilepsy," Epilepsia, 48(Suppl. 2):65-74 (2007).
Bhatt et al. "Indigenous plants in traditional healthcare system in Kedarnath valley of western Himalaya," Indian J Tradit Knowl., 7(2):300-310 (2000).
Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry.2009.17.
Bipolar Health Group (Charlotte's Web Hemp Remedy, available online at http:/bipolarhealthgroup.org/index.php/charlottes-web-hemp-remedy/, accessed Sep. 6, 2017, 6 pages.
Booth, "Legalization's opening of medical pot research is dream and nightmare," Denver Post, Dec. 14, 2013, http://www.denverpost.com/ci_24726291/legalizations-opening-medical-pot-research-is-dream-and, 6 pages.
Bostanci et al. "The effects of octanol on penicillin induced epileptiform activity in rats: an in vivo study," Epilepsy Research, 71:188-194 (2006).
Braida, D. et al., "Post-ischemic treatment with cannabidiol prevents electroencephalographic flattening, hyperlocomotion and neuronal injury in gerbils," Neuroscience Letters., 346:61-64 (2003).
Brust et al., "Marijuana use and the risk of new onset seizures," Trans Am Clin Climatol Assoc., 103:176-181 (1992).
Carlini et al., "Hypnotic and antiepileptic effects of cannabidiol," J Clin Pharmacol., 21:417S-427S (1981).
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
cdc.gov [online], "2 to 20 years: Girls Stature-for-age and Weight-for-age percentiles," National Center for Health Statistics and National Center for Chronic Disease Prevention and Health Promotion, last modified Nov. 2000, https://www.cdc.gov/growthcharts/data/set1clinical/cj411022.pdf, 1 page.
Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
Charlotte's Web [online], "When to expect Results from CW Hemp Oil," Mar. 13, 2017, retrieved on May 21, 2018, URL https://www.cwhemp.com/blog/expecting-results-from-hemp, 6 pages.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/ lgs-Lennox-gastaut-syndrome, 10 pages.
Chiron, C. & Dulac, O., "The Pharmacologic Treatment of Dravet Syndrome," Epilepsia, 52 (Suppl. 2):72-75 (2011).
Chiu, P. et al., "The Influence of Cannabidiol and Δ-Tetrahydrocannabinol on Cobalt Epilepsy in Rats," Epilepsia, 20:365-375 (1979).
Chiu, P. et al., "The influence of delta9-tetrahydrocannabinol, cannabinol and cannabidiol on tissue oxygen consumption," Res Commun 12, No. 2, pp. 267-286, 1977.
Chou, "Theoretical basis, experimental design, and computerized simulation of synergism and antagonism in drug combination studies," Pharmacol Rev, 58(3):621-681 (2006).
Conry et al., "Clobazam in the treatment of Lennox-Gastaut syndrome," Epilepsia, 50:1158-1166 (2009).
Consroe et al. "Anticonvulsant drug antagonism of delta9tetrahydrocannabinol-induced seizures in rabbits," Res Commun Chem Pathol Pharmacol., 16(1):1-13 (1977).
Consroe et al. "Anticonvulsant interaction of cannabidiol and ethosuximide in rats," J Pharm Pharmacol., 29(8):500-501 (1977). doi:10.1111/j.2042-7158.1977.tb11378.x.
Consroe et al. "Anticonvulsant nature of marihuana smoking," JAMA, 234(3):306-307 (1975).
Consroe, et al. "Cannabidiol—antiepileptic drug comparisons and interactions in experimentally induced seizures in rats." J Pharmacol Exp Ther. Apr. 1977;201(1):26-32.
Consroe et al. Chapter 12, "Potential Role of Cannabinoids for Therapy of Neurological Disorders," in Marijuana Cannabinoids: Neurobiology and Neurophysiology, Ed. L. Murphy (1992), 72 pages.
Consroe et al,. "Chapter 2: Therapeutic Potential of Cannabinoids in Neurological Disorders," Cannabonioids as Therapeutic Agents, R. Mechoulam, Ed., 1986, pp. 21-49.
Consroe et al., "Controlled clinical trial of cannabidiol in Huntington's Disease," Pharmacology Biochemistry & Behavior, 40:701-708 (1991).
Consroe et al., "Effects of cannabidiol on behavioral seizures caused by convulsant drugs or current in mice," Eur J Pharmacol., 83(3-4):293-298 (1982).
Cortesi et al. "Potential therapeutical effects of cannabidiol in children with pharmacoresistant epilepsy," Med Hypotheses, 68(4):920-921 2007). Epub Nov. 16, 2006.
Cortez & Snead, "Chapter 10: Pharmacologic Models of Generalized Absence Seizures in Rodents," Models of Seizures and Epilepsy, 111-126 (2006).
Crespel et al., "Lennox-Gastaut Syndrome," Chapter 14, in Epileptic Syndromes in Infancy, Childhood, and Adolescence, 5th Edition, ed. M. Bureau, et al., pp. 189-216 (2012).
Crodesta F10 [online] retrieved on Feb. 4, 2023 from:https://www.ulprospector.com/en/na/PersonalCare/Detail/134/30883/Crodesta-F10; 2 pages. (Year: 2023).
Cunha et al., "Chronic Administration of Cannabidiol to Healthy Volunteers and Epileptic Patients," Pharmacology, 21:175-185 (1980).
Curia et al., "The pilocarpine model of temporal lobe epilepsy," J Neuroscience Methods, 172(2-4):143-157 (2008).
Czapinski, et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci. Sep. 1997;150:S162.
Dasa et al. "Key Attributes of TKDL: Ganja," Brhat Nighantu Ratnakara (Saligramanighantubhusanam), RS/4336, vol. IV. 1997:170, with English translation, 5 pages.
Davis et al. "A predominant role for inhibition of the adenylate cyclase/protein kinase A pathway in ERK activation by cannabinoid receptor 1 in NIE-115 neuroblastoma cells." J Biol Chem. 278(49):48973-80 (2003). Epub Sep. 29, 2003.
Davis et al. "Antiepileptic action of marijuana-active substances," Federation Proceedings, 8:284-285 (1949).
De Meijer, E., "The Chemical Phenotypes (Chemotypes) of Cannabis," Chapter 5, Handbook of Cannabis, Roger G. Pertwee (Ed.), pp. 89-110 (2014).
De Oliveira, et al. "Anticonvulsant activity of β-caryophyllene against pentylenetetrazol-induced seizures." Epilepsy Behav. Mar. 2016;56:26-31. doi: 10.1016/j.yebeh.2015.12.040.
Deshpande et al., "Cannabinoid CB1 receptor antagonists cause status epilepticus-like activity in the hippocampal neuronal culture model of acquired epilepsy," Neurosci Lett. Jan. 2007; 411(1):11-6. Epub Nov. 15, 2006.
Devinsky, et al., "Cannabidiol: Pharmacology and potential therapeutic role in epilepsy and other neuropsychiatric disorders," Epilepsia, Jun. 2014, 55(6), 791-802.
Devinsky, O. et al., "Trial of Cannabidiol for Drug-Resistant Seizures in the Dravet Syndrome," N Engl J Med, 376(21):2011-2020 (2017).
Devinsky, Orrin, M.D. of the Department of Neurology for NYU Langone School of Medicine presents his talk on "Cannabidiols: A Brief History," at NYU School of Medicine's Cannabidiol Confer-

(56) References Cited

OTHER PUBLICATIONS ence (Oct. 4, 2013). Video published online. http://faces.med.nyu.edu/research-education/cannabidiol-conference, 16 pages.
Dravet, "The core Dravet syndrome phenotype," Epilepsia, 52 Suppl 2:3-9 (2011); doi: 10.1111/j.1528- 1167.2011.02994.x.
Dreifus, et al., "Proposal for Revised Clinical and Electroencephalographic Classification of Epileptic Seizures," Epilepsie, 22:489-501 (1981).
Dulac, "Use of Lamotrigine in Lennox-Gastaut and Related Epilepsy Syndromes," J. Child Neurolog., 12(Supplement 1): S23-S29 (1997).
Dulac, "Vigabatrin in Childhood Epilepsy," J. Child Neurolog., 6(Supplement 2): S30-S37 (1991).
Eadie, M. J., "Shortcomings in the current treatment of epilepsy," Expert Rev Neurother., 12(12):1419-1427 (2012).
Eggers, "'Temporal lobe epilepsy is a disease of faulty neuronal resonators rather than oscillators, and all seizures are provoked, usually by stress," Med Hypotheses., 69(6):1284-9 (2007).
Elsohly and Gul, "Constituents of Cannabis Sariva," Chapter 1, Handbook of Cannabis, ed. Roger G. Pertwee, pp. 3-22 (2014).
Engel, "Chapter 1, What Should be Modeled," In Models Seizure Epilepsy, 2006, 14 pages.
Engel, "Report of the ILAE classification core group," Epilepsia, 47(9):1558-1568 (2006).
Epidiolex® (cannabidiol) oral solution, CV, Prescribing Information, 2018, 30 pages; https://www.accessdata.fda.gov/drugsatfda_docs/label/2018/210365lbl.pdf.
Fariello, "Parenteral Penicillin in Rats: An Experimental Model of Multifocal Epilepsy," Epilepsia, 17:217- 222 (1976).
FDA [online]. "Warning Letters and Test Results for Cannabidiol-Related Products," 2015 Warning Letters, retrieved on Nov. 14, 2017, URL https://www.fda.gov/newsevents/publichealthfocus/ucm484109.htm, 4 pages.
FDA [online]. "Warning Letters and Test Results for Cannabidiol-Related Products," 2016 Warning Letters, retrieved on Nov. 14, 2017, URL https://www.fda.gov/newsevents/publichealthfocus/ucm484109.htm, 4 pages.
Ferdinand, et al., "Cannabis—psychosis pathway independent of other types of psychopathology," Schizophr Res., 79(2-3):289-295 (2005).
Fisher, et al., "The impact of epilepsy from the patient's perspective I. Descriptions and subjective perceptions," Epilepsy Res.,41(1):39-51 (2000).
Gabor et al. "Lorazepam versus phenobarbital : Candidates for drug of choice for treatment of status epilepticus," J Epilepsy. Jan. 1990;3(1):3-6.
Gallily, R. et al., Overcoming the Bell-Shaped Dose-Response of Cannabidiol by Using Cannabis Extract Enriched in Cannabidiol, Pharmacology & Pharmacy, 2015, 6, 75-85, Published Online Feb. 2015 in SciRes. http://www.scirp.org/journal/pp, http://dx.doi.org/10.4236/pp.2015.62010.
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda- approves-ind-studies-of-cbd, 4 pages.
Gastaut, "Clinical and electroencephalographical classification of epileptic seizures," Epilepsia, 10:Suppl:2-13 (1969).
Gedde M., et al., "Whole Cannabis Extract of High Concentration Cannabidiol May Calm Seizures in Highly Refractory Pediatric Epilepsies," American Epilepsy Society, Dec. 2013, pp. 449-450.
Gedde, M. G., "Clinical Experience with Cannabis in Treatment-Resistant Pediatric Epilepsy," Marijuana for Medical Professionals Health Conference, Sep. 9-11, 2014; https://pediatriccannabissupport.com/images/gedde_presentation.pdf, 45 pages.
Geffrey et al. "Cannabidiol (CBD) Treatment for Refractory Epilepsy," American Epilepsy Society, Annual Meeting Abstract 2.427, 2014, retrieved on Feb. 10, 2017, URL https://www.aesnet.org/meetings_events/annual_meeting_abstracts/view/1868979, 2 pages.
Green, "CBD: An Unconventional Therapy," available online at http://nugs.com/article/cbd-annunconventional- therapy.html, published Mar. 24, 2014, 5 pages.
Gresham et al."Treating Lennox-Gastaut syndrome in epileptic pediatric patients with third generation rufinamide," Neuropsychiatr Dis Treat., 6:639-645, Oct. 5, 2010.
Gross et al. "Marijuana use and epilepsy: prevalence in patients of a tertiary care epilepsy center," Neurology, Jun. 8, 2004;62(11 ):2095-7.
Grotenhermen, "Epilepsiebehandlung des Angelman-Syndromes mit CBD (Cannabidiol) (Epilepsy treatment of Angelman syndrome with CBD (cannabidiol)," Angelman e. V., Jan. 2015, retrieved on Jun. 7, 2019, URL http://s8a5e4d6fcfb04b6.jimcontent.com/download/version/1472724876/module/9873059694/name/Epilepsiebehandlung%20durch%20CBD.pdf (with Machine English translation), 8 pages.
Guerrini, et al., "Lamotrigine and Seizure Aggravation in Severe Myoclonic Epilepsy," Epilepsia, 39(5):508-512 (1998).
Guidance for Industry, Botanical Drug Development, U.S. Department of Health and Human Services, Food and Drug Administration, Center for Drug Evaluation and Research (CDER); Dec. 2016, Pharmaceutical Quality/CMC, 34 pages; https://www.fda.gov/media/93113/download.
Guidance for Industry on Botanical Drug Products; Availability, U.S. Department of Health and Human Services, Food and Drug Administration, 69 FR 32359, Aug. 2000;https://www.federalregister.gov/documents/2004/06/09/04-13031/guidance-for-industry-on-botanical-drug- products-availability, 2004, vol. 69(111), 2 pages.
Guimares, et al., "Antianxiety effect of cannabidiol in the elevated plus-maze," Psychopharmacology (Berl)., 100(4):558-9 (1990); doi: 10.1007/BF02244012.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL https://www.gwpharm.com/about-us/news/gw-pharmaceuticals-announces-preliminary-results-phase-2a-study-its-pipeline-compound, 5 pages.
GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL https://www.gwpharm.com/about-us/news/gw-pharmaceuticals-receives-orphan-drug-designation-fda-epidiolex%C2%AE-treatment-lennox, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL https://www.gwpharm.com/about-us/news/gw-pharmaceuticals-provides-update-orphan-program-childhood-epilepsy-epidiolex%C2%AE, 5 pages.
Heinemann, et al., "An Overview of in Vitro Seizure Models in Acute and Organotypic Slices," Chapter 4, 35-44 (2006).
Hempel, B. J. et al., "An assessment of sex differences in Δ9-tetrahydrocannabinol (THC) taste and place conditioning," Pharmacology, Biochemistry and Behavior, 153:69-75 (2017).
Hill, "Cannabidivarin-rich cannabis extracts are anticonvulsant in mouse and rat via a CB 1 receptor-independent mechanism," British Journal of Pharmacology, 170(3):679-692 (2013).
Hill et al., "Cannabidivarin is anticonvulsant in mouse and rat," Br. J Pharmacol, 167(8):1629-1642 (2012).
Hill, et al., "$\Delta^9$-Tetrahydrocannabivarin suppresses in vitro epileptiform and in vivo seizure activity in adult rats". Epilepsia (Aug. 2010); 51(8): 1522-1532. Epub Feb. 26, 2010.
Holmes et al., "Choosing the correct AED: From Animal Studies to the Clinic," Pediatr Neurol. Mar. 2008; 38(3): 151-162.
Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-1141 (2014); doi: 10.1021/cn5000524.
ICE Epilepsy Alliance, the Dravet Syndrome Spectrum, Nov. 2, 2008, 2 pages.

(56) References Cited

OTHER PUBLICATIONS

IUPHAR/BPS Guide to Pharmacology [online], "Entry for Δ 9-tetrahydrocannabidiol," available on or before Mar. 29, 2016, retrieved on Jun. 20, 2018, URL http://www.guidetopharmacology.org/GRAC/LigandDisplayForward?tab=biology&ligandID=242, 2 pages.
Iuvone et al., "Neuroprotective effect of cannabidiol, a non-psychoactive component from Cannabis sativa, on beta-amyloid-induced toxicity in PC12 cells," J Neurochem., 89(1 ):134-141 (2004).
Izzo, et al., "Non-psychotropic plant cannabinoids: new therapeutic opportunities from an ancient herb," Trends in Pharmacological Sciences, 30(10):515-527 (2009).
Jablan, J. & Jug, M., "Development of Eudragit S100 based pH-responsive microspheres of zaleplon by spray-drying: Tailoring the drug release properties," Powder Technology, 283 (2015) 334-343.
Jacobson, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page. Poster.
Jeavons et al., "Sodium valproate in treatment of epilepsy," Br Med J., 15;2(5919):584-586 (1974).
Jones et al. [online], Info & Metrics / Article Information,"Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.
Jones, N. A. et al., Cannabidiol Displays Antiepileptiform and Antiseizure Properties In Vitro and In Vivo, J Pharmacol Exp Ther, 332(2):569-77 (2010). doi: 10.1124/jpet.109.159145. Epub Nov. 11, 2009.
Joy et al., Marijuana and Medicine. Assessing the Science Bse. National Academy Press., Washington, D.C. 1999, 170 pages.
Kahan et al., "Risk of selection bias in randomized trials," Trials, 16:405 (2015); doi: 10.1186/s13063-015-0920-x.
Kaplan, "F.D.A. Panel Recommends Approval of Cannabis-Based Drug for Epilepsy," NY Times, Apr. 19, 2018, retrieved on Jun. 20, 2018, URL https://www.nytimes.com/2018/04/19/health/epidiolex-fda-cannabis-marajuana.html, 3 pages.
Karler et al., "The anticonvulsant activity of cannabidiol and cannabinol," Life Science, 13:1527-1531 (1973).
Karler, et al., "The cannabinoids as potential antiepileptics," J Clin Pharmacol, 21(8-9 Suppl):437S-447S (1981).
Kelley, et al., "Doose syndrome (myoclonic-astatic epilepsy): 40 years of progress," Developmental Medicine & Child Neurology, 52:988-993 (2010).
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Klitgaard et al. "Electrophysiological, neurochemical and regional effects of levetiracetam in the rat pilocarpine model of temporal lobe epilepsy," Seizure., 12(2):92-100, Mar. 2003.
Klitgaard, et al., "Evidence for a unique profile of levetiracetam in rodent models of seizures and epilepsy," European Journal of Pharmacology, 353(2):191-206 (1998).
Kramer et al., "Febrile infection-related epilepsy syndrome (FIRES): pathogenesis, treatment, and outcome: a multicenter study on 77 children," Epilepsia, 52(11):1956-1965 (2011); doi:10.1111/j.1528-1167.2011.03250.x. Epub Aug. 29, 2011.
Kruk-Slomka et al., "A comparison of mecamylamine and bupropion effects on memory-related responses induced by nicotine and scopolamine in the novel object recognition test in mice," Pharmacological Reports, 66(4):638-646 (2014).
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kurz & Blass, "Use of dronabinol (delta-9-THC) in autism: A prospective single-case-study with an early infantile autistic child," Cannabinoids, 5(4):4-6 (2010).
Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.
Laprarie et al., "Cannabidiol is a negative allosteric modulator of the cannabinoid CB1 receptor," British J Pharmacology, 172(20):4790-4805 (2015).
Lazzari, P. et al., "Antinociceptive activity of Δ9-tetrahydrocannabinol non-ionic microemulsions," International Journal of Pharmaceutics, 393:238-243 (2010).
Leo et al., "Cannabidiol and epilepsy: Rationale and therapeutic potential," Pharmacological Research, 107:85-92 (2016).
Lewis, "Mystery Mechanisms," The Scientist.com, Jul. 29, 2016, retrieved on Nov. 8, 2017, URL https://www.the-scientist.com/?articles.view/articleNo/46688/title/Mystery-Mechanisms/, 2 pages.
Li, C. L., et al., "The use of hypromellose in oral drug delivery", Journal of Pharmacy and Pharmacology (2005); 57(5): 533-546.
Lieu, et al., "Assessment of self-selection bias in a pediatric unilateral hearing loss study," Otolaryngol Head Neck Surg., 142(3):427-433 (2010).
Lindamood et al., "Effects of delta 9-tetrahydrocannabinol and cannabidiol on sodium-dependent high affinity choline uptake in the rat hippocampus," J Pharmacology Experimental Therapeutics, 213(2):216-221 (1980).
Long, et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-678 (2011); doi: 10.1111/j.1528-1167.2011.03024.x.
Lowenstein, "Chapter 363: Seizures and Epilepsy," Diseases of the Central Nervous System, 2498-2512 (2008).
Luttjohann et al. "A revised Racine's scale for PTZ-induced seizures in rats." Physiol Behav. Dec. 7, 2009;98(5):579-86. doi: 10.1016/j.physbeh.2009.09.005.
Lutz, "On-demand activation of the endocannabinoid system in the control of neuronal excitability and epileptiform seizures," Biochem Pharmacol, 68(9):1691-1698 (2004).
Maa et al., "The case for medical marijuana in epilepsy," Epilepsia, 55(6):783-786 (2014); doi: 10.1111/epi.12610.
Mackie, "Cannabinoid receptors as therapeutic targets," Annu Rev Pharmacol Toxicol. 2006;46: 101-22.
Majoosi et al., "Key Attributes of TKDL: Saoot Baraae Sara," Kaamil-al-Sena'ah, Central Council for Research in Unani Medicine, 2005 (with English translation), 2 pages.
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist. Jan. 2011, 1(1):23-31.
Mares et al., Electrical Stimulation-Induced Models of Seizures in Model of Seizures and Epilepsy Asia Pitkanen, Philip A. Schwartzkroin & Solomon L. Moshe (Eds.), pp. 153-159 (2004).
Marinol® Label, Unimed Pharmaceuticals, Inc., Jul. 2006, https://www.accessdata.fda.gov/dmgsatfda docs/label/2006/018651 s025s026lbl.pdf, 11 pages.
Martin et al., "Structure-Anticonvulsant Activity Relationships of Cannabidiol Analogs," National Institute on Drug Abuse, Research Monograph Series, 1987, 79:48-58.

(56) References Cited

OTHER PUBLICATIONS

Mattson et al., "Comparison of carbamazepine, phenobarbital, phenytoin, and primidone in partial and secondarily generalized tonic-clonic seizures," N. Engl. J. Med, 313(3): 145-151, Jul. 18, 1985.
Mattson, et al., "Prognosis for total control of complex partial and secondary generalized tonic clonic seizures," Neurology, 47:68-76 (1996).
McCormick et al., "On the cellular and network bases of epileptic seizures," Annu Rev Physiol, 63:815-846 (2001).
McNamara, "Chapter 19: Pharmacotherapy of the Epilepsies,", Goodman & Gilman's The Pharmacological Basis of Therapeutics 11th ed., McGraw-Hill Companies, pp. 501-525 (2006).
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften, 65(4):174-179 (1978).
Merlis, "Proposal for an international classification of the epilepsies," Epilepsia, 1(1):114-9 (1970).
Miller, et al., "Mapping genetic modifiers of survival in a mouse model of Dravet syndrome," Genes, Brain and Behavior, 13:163-172 (2014).
Monteagudo, E. et al., "Pharmaceutical optimization of lipid-based dosage forms for the improvement of taste-masking, chemical stability and solubilizing capacity of phenobarbital," Drug Development and Industrial Pharmacy, 40(6):783-792 (2014).
Morad et al., "Conversion to Sirolimus-Based Immunosuppression in Maintenance Liver Transplantation Patients," Liver Transplantation, 13:658-664 (2007).
Moral, et al., "Pipeline on the Move," Drugs of the Future, 39(1):49-56 (2014).
Morelli et al., "The effects of cannabidiol and its synergism and bortezomib in multiple myeloma cell lines. A role for transient receptor potential Vanilloid type-2," Int J Cancer, 134(11):2534-2546 (2014).
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabisi et al., "Cannabinoids synergize with carfilzomib, reducing multiple myeloma cells viability and migration," Oncotarget, 7:77553 (2016).
Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).
Ng et al., "Illicit drug use and the risk of new-onset seizures." Am J Epidemiol., 132(1):47-57 (1990).
[No Author Listed] "Convulsive Disorders and their Interference with Driving," Medicos, Retrieved Feb. 10, 2017. Retrieved from the internet URL https://www.medicosporlaseguridadvial.com/en/clinical-subjects/neurologic-diseases/convulsive-disorders-and-their-interference-with-driving, 3 pages.
[No Author Listed] Cannabidiol Therapy for Aicardi Syndrome, Aug. 2014, 4 pages.
[No Author Listed] Cannabinoid. Wikipedia. Retrieved on Mar. 1, 2017. Retrieved from the internet: URL https://en.wikipedia.org/wiki/Cannabinoid, 15 pages.
[No Author Listed] Cover and Table of Contents, J Pharmacology and Exp Therapeutics, Feb. 2010, 332(2), 4 pages.
[No Author Listed] "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.
[No Author Listed] "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL https://www.gwpharm.com/about-us/news/gw-pharmaceuticals-announces-physician-reports-epidiolex%C2%AE-treatment-effect-children, 8 pages.
[No Author Listed] "GW Pharmaceuticals Provides Update on Orphan Program in Childhood Epilepsy for Epidiolex®," GW Pharmaceuticals Press Release, Nov. 15, 2013, retrieved on Jun. 20, 2018, URL https://www.gwpharm.com/about-us/news/gw-pharmaceuticals-provides-update-orphan-program-childhood-epilepsy-epidiolex%C2%AE, 5 pages.
[No Author Listed], "Missouri House passes cannabis extract legislation," Kansas City Star, 2014, https://kansascity.com/news/politics-government/article346747.html, 2 pages.
[No Author Listed] Poloxamer. Published: Nov. 6, 2022; pp. 447-450.
[No Author Listed] "What are the Highest CBD Strains?" Oct. 15, 2014, retrieved on Feb. 16, 2017, URL www.leafscience.com/2014/10/15/highest-cbd-strains/, 2 pages.
Oakley, et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazol-induced seizures in rats," Peptides, 28(6):1214-9 (2007). Epub Apr. 19, 2007.
Pelliccia, A. et al., "Treatment with CBD in oily solution of drug-resistant paediatric epilepsies," 2005 Congress on Cannabis and the Cannabinoids, Leiden, The Netherlands: International Association for Cannabis as Medicine, p. 14., Abstract, 2 pages.
Pereira et al., "Study pharmacologic of the GABAergic and glutamatergic drugs on seizures and status epilepticus induced by pilocarpine in adult Wistar rats," Neurosci Lett. Jun. 4, 2007;419(3):253-7. Epub Apr. 13, 2007.
Pertwee, "Cannabinoid receptor ligands: clinical and neuropharmacological considerations, relevant to future drug discovery and development," Expert Opin Investig Drugs, 9(7):1553-1571 (2000).
Pertwee, R. G., "The Pharmacology and Therapeutic Potential of Cannabidiol," Cannabinoids, Chapter 3, DiMarzo, V. (Ed.), pp. 32-83 (2004).
Pertwee, RG. 2008 "The diverse CB1 and CB2 receptor pharmacology of three plant cannabinoids: 9 tetrahydrocannabinol, cannabidiol and 9 tetrahydrocannabivarin" Br. J Pharmacol. 153(2):199-215.
Petrocellis, et al., "Effects of cannabinoids and cannabinoid-enriched Cannabis extracts on TRP channels and endocannabinoid metabolic enzymes," British Journal of Pharmacology, 163: 1479-1494 (2011).
Physician's Desk Reference, 63rd Ed., 2009, 423-431, 2192-2194, 2639-2242, 3019-3022.
Pohl et al., "Effects of flunarizine on Metrazol-induced seizures in developing rats," Epilepsy, 1(5):302-305 (1987).
Poortman-Van Der Meer, "A contribution to the improvement of accuracy in the quantitation of THC," Forensic Science International, 101(1):1-8 (1999).
Porter et al., "Randomized, multicenter, dose-ranging trial of retigabine for partial-onset seizures," Neurology, 68(15):1197-1204 (2007).
Porter et al., "Report of a parent survey of cannabidiol-enriched cannabis use in pediatric treatment-resistant epilepsy," Epilepsy Behav., 29(3):574-577 (2013).
Potter, D. J., "Cannabis Horticulture," Chapter 4, Handbook of Cannabis, ed. Roger G. Pertwee, pp. 65-88 (2014).
Pouton, "Lipid formulations for oral administration of drugs: non-emulsifying, self-emulsifying and 'self-micro emulsifying' drug delivery systems," Eur J Pharm Sci, 11(Suppl. 2):S93-S98 (2000).
Press, et al., "Parental reporting of response to oral cannabis extracts for treatment of refractory epilepsy," Epilepsy Behav. Apr. 2015; 45:49-52. doi: 10.1016/j.yebeh.2015.02.043. Epub Apr. 3, 2015.
Pruitt et al., "Ethanol in Liquid Preparations Intended for Children," Pediatrics, 73(3):405-407 (1984).
Raab et al., "Multiple myeloma," Lancet, 374(9686):314-339 (2009).
Rabinski [online], "CBD-A: Cannabidiol Acid Cannabinoid Profile," MassRoots, Jul. 2, 2015, retrieved on Jan. 31, 2018, URL https://www.massroots.com/learn/can-the-cbd-a-cannabinoid-help-you/, 4 pages.
Ramantani et al., "Epilepsy in Aicardi—Goutières Syndrome," Official J Eur Paediatric Neurology Society, 18:30-37 (2014).

(56) References Cited

OTHER PUBLICATIONS

Rauca, et al. "The role of superoxide dismutase and alpha-tocopherol in the development of seizures and kindling induced by pentylenetetrazol—influence of the radical scavenger alpha-phenyl-N-tert-butyl nitrone," Brain Res. May 29, 2004;1009(1-2):203-12.
Resstel et al., "5-HTIA receptors are involved in the cannabidiol-induced attenuation of behavioural and cardiovascular responses to acute restraint stress in rats," Br J Pharmacol. Jan. 2009;156(1): 181-8.
Rosenberg et al., "Cannabinoids and Epilepsy," Neurotherapeutics, Oct. 2015, 12(4): 747-768.
Rosenkrantz et al., "Oral and Parenteral Formulations of Marijuana Constituents," J Pharm Sci, 61(7):1106-1112 (1972).
Rubio, et al. "In vivo Experimental Models of Epilepsy," Central Nervous System Agents in Medicinal Chemistry, 10:298-309, 2010.
Russo, "Taming THC: potential cannabis synergy and phytocannabinoid-termoid entourage effects," British J. of Pharm., 163:1333-1364 (2011).
Sadanandasarma et al., "Key Attributes of TKDL: Suddha Bhanga Visista Gunah Aur Matra," Rasatarangini 11th Ed., 720-723 (2000), (with English translation), 8 pages.
SalutarisDrops.com [ online], "Cannabidiol for Aicardi Syndrome," Salutaris, available on or before Oct. 2014, retrieved on Feb. 10, 2017, URL http://web.archive.org/web/20141012220050/ http://salutarisdrops.corn/cannabidiol-aicardi-syndrome/, 3 pages.
Sander, "The epidemiology of epilepsy revisited." Curr Opin Neural. Apr. 2003; 16(2):165-70.
Sandyk et al., "Preliminary trial of cannabidiol in Huntington's Disease," Marihuana: An International Research Report, 157-162 (1988).
Sastri et al., "Key Attributes of TKDL: Vijaya Kalpah (Apasmaranasaka)," Anandakandam 1st ed., 1952:241 (with English translation), 5 pages.
Scuderi et al., "Cannabidiol in medicine: a review of its therapeutic potential in CNS disorders," Phytother Res., 23(5):597-602 (2009).
Shukla. [online], "New Automated Purification Strategies for Scale-Up," PCISyntesis.com, posted Dec. 25, 2017, https://www.pcisynthesis.com/new-automated-purification-strategies-for-scale-up/, 5 pages.
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 140:83-93 (2004).
Strickley, R. G., (Feb. 2004), "Solubilizing Excipients in Oral and Injectable Formulations," Pharmaceutical Research, vol. 21, No. 2, pp. 201-230.
Swann et al., "The effects of seizures on the connectivity and circuitry of the developing brain," Ment Retard Dev Disabil Res Rev., 10(2):96-100 (2004).
Thomas et al., "Cannabidiol displays unexpectedly high potency as an antagonist of CB1 and CB2 receptor agonists in vitro," British J Pharmacology, 150(5):613-623 (1988).
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thumma et al., "Influence of plasticizers on the stability and release of a prodmg of ./19-tetrahydrocannabinol incorporated in poly (ethylene oxide) matrices," Eur J Pharmaceutics and Biopharmaceutics, 70(2):605-614 (2008).
Thurman, D. J. et al., "Standards for epidemiologic studies and surveillance of epilepsy," Epilepsia, 52 (Suppl 7):2-26 (2011).
Thurston, "Avoid Charlotte's Web for Epilepsy," Jun. 26, 2014, URL http://drthurstone.com/charlotted-web-not-safest-option-epilepsy-treatment/, 4 pages.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia., 20:351-363 (1979).
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Usami, Noriyuki, et al. "Synthesis and pharmacological evaluation in mice of halogenated cannabidiol derivatives." Chemical and Pharmaceutical Bulletin (1999); 47.11: 1641-1645.
Utah.gov [online), "2nd Agenda Controlled Substances Advisory Committee Meeting," Nov. 12, 2013, URL httos://www.utah.gov/pmn/files/81459.pdt, 63 pages.
Van Rijckevorsel, "Treatment of Lennox-Gastaut Syndrome: overview and recent findings," Neuropsychiatr Dis Treat, 4(6):1001-1019 (2008).
Velasco et al., "Anticancer mechanisms of cannabinoids," Curr Oncol, 23(2):S23-S32 (2016).
Velisek, "Chapter 11: Models of Chemically-Induced Acute Seizures," Models of Seizures and Epilepsy, pp. 127-152 (2006).
Veliskova, "Chapter 48: Behavioral Characterization of Seizures in Rats," Models of Seizures and Epilepsy, pp. 601-611 (2006).
Vollner et al., "Haschisch XX+ [Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2):1-8 (1990).
Wallace et al., "Assessment of the role of CB 1 receptors in cannabinoid anticonvulsant effects," Eur J Pharmacol. Sep. 28, 2001;428(1):51-7.
Wallace et al., "Pharmacotherapy for Dravet Syndrome," Pediatr. Drugs, 18:197-208 (2016).
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL http://www.pA2online.org/abstrat/abstract.jsp?abid=28533, 1 page, Abstract only.
Wikipedia.org [online], "Cannabinoid," Wikipedia, Apr. 2003, retrieved on Mar. 1, 2017, URL https://en.wikipedia.org/wiki/Cannabinoid, 15 pages.
Wingerchuk, "Cannabis for medical purposes: cultivating science, weeding out the fiction," Lancet. Jul. 24-30, 2004;364(9431):315-6.
Yu et al., "Reduced sodium current in GABAergic intemeurons in a mouse model of severe myoclonic epilepsy in infancy," Nature Neuroscience, Sep. 2006, vol. 9, No. 9, pp. · 1142-·1149.
Yuriev, "Endogenic cannabinoid system is a new perspective object of pharmacotherapeutic effect to disease of nervous system," Ukrainsky Metodichny Chasopis, 6(50):21-29 (2005) (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhao et al., "Chapter 27: Repetitive Seizures in the Immature Brain," Models of Seizures and E[epilepsy, 341-350 (2006).
Zhornitsky, S. and S. Potvin (2012) Cannabidiol in Humans—The Quest for Therapeutic Targets. Pharmaceuticals, 5:529-552; doi: 10.3390/ph5050529.
Zuardi, A.W., et al.; (2006) "Cannabidiol, a Cannabis sativa constituent, as an antipsychotic drug," Braz J Med Biol Res.; 39(4):421-429.
Zuardi et al., "Cannabidiol: from an inactive cannabinoid to a drug with wide spectrum of action," Rev Bras Psiquiatr, 30(3):271-280 (2008).
U.S. Appl. No. 15/640,033, filed Jun. 30, 2017, by Wilkhu et al.
U.S. Appl. No. 16/768,241, filed May 29, 2020, by Guy et al.
U.S. Appl. No. 16/935,005, filed Jul. 21, 2020, by Guy et al.
U.S. Appl. No. 17/296,066, filed May 21, 2021, by Guy et al.
U.S. Appl. No. 17/296,076, filed May 21, 2021, by Guy et al.

(56) References Cited

OTHER PUBLICATIONS

U.S. Appl. No. 17/406,401, filed Aug. 19, 2021, by Wilku et al.
U.S. Appl. No. 17/424,682, filed Jul. 21, 2021, by Guy et al.
U.S. Appl. No. 17/435,892, filed Sep. 2, 2021, by Guy et al.
U.S. Appl. No. 17/585,415, filed Jan. 26, 2022, by Whalley et al.
U.S. Appl. No. 17/627,946, filed Jan. 18, 2022, by Silcock et al.
U.S. Appl. No. 17/689,607, filed Mar. 8, 2022, by Guy et al.
U.S. Appl. No. 17/770,435, filed Apr. 20, 2022, by Guy et al.
U.S. Appl. No. 17/771,184, filed Apr. 22, 2022, by Guy et al.
U.S. Appl. No. 17/771,190, filed Apr. 22, 2022, by Guy et al.
U.S. Appl. No. 17/771,195, filed Apr. 22, 2022, by Guy et al.
U.S. Appl. No. 17/777,677, filed May 18, 2022, by Guy et al.
U.S. Appl. No. 17/777,681, filed May 18, 2022, by Guy et al.
U.S. Appl. No. 17/777,734, filed May 18, 2022, by Guy et al.
U.S. Appl. No. 17/786,949, filed Jun. 17, 2022, by Silcock et al.
U.S. Appl. No. 18/002,437, filed Dec. 19, 2022, by Li et al.
U.S. Appl. No. 18/005,843, filed Jan. 17, 2023, by Checketts et al.
U.S. Appl. No. 18/005,848, filed Jan. 17, 2023, by Checketts et al.
U.S. Appl. No. 18/005,852, filed Jan. 18, 2023, by Checketts et al.
U.S. Appl. No. 18/005,853, filed Jan. 18, 2023, by Checketts et al.
U.S. Appl. No. 18/005,868, filed Jan. 18, 2023, by Checketts et al.
U.S. Appl. No. 18/006,121, filed Jan. 19, 2023, by Checketts et al.
U.S. Appl. No. 18/006,127, filed Jan. 19, 2023, by Checketts et al.
U.S. Appl. No. 18/006,129, filed Jan. 19, 2023, by Checketts et al.
U.S. Appl. No. 18/006,131, filed Jan. 19, 2023, by Checketts et al.
U.S. Appl. No. 18/043,810, filed Mar. 2, 2023, by Loft et al.
U.S. Appl. No. 18/044,941, filed Mar. 10, 2023, by Craig et al.
U.S. Appl. No. 18/161,603, filed Jan. 30, 2023, filed Whalley et al.
U.S. Appl. No. 18/170,235, filed Feb. 16, 2023, by Guy et al.
U.S. Appl. No. 18/186,792, filed Mar. 20, 2023, by Guy et al.
U.S. Appl. No. 18/256,307, filed Jun. 7, 2023, by Checketts et al.
U.S. Appl. No. 18/257,373, filed Jun. 14, 2023, by Silcock et al.
U.S. Appl. No. 18/257,479, filed Jun. 14, 2023, by Tse et al.
U.S. Appl. No. 18/257,537, filed Jun. 14, 2023, by Silcock et al.
U.S. Appl. No. 18/258,485, filed Jun. 20, 2023, by Craig et al.
U.S. Appl. No. 18/292,844, filed Jan. 26, 2024, by Knappertz et al.
U.S. Appl. No. 18/311,221, filed May 2, 2023, by Guy et al.
U.S. Appl. No. 18/446,405, filed Aug. 8, 2023, by Guy et al.
U.S. Appl. No. 18/477,467, filed Sep. 28, 2023, by Wilkhu et al.
U.S. Appl. No. 18/526,795, filed Dec. 1, 2023, by Guy et al.
U.S. Appl. No. 18/546,254, filed Aug. 11, 2023, by Tse et al.
U.S. Appl. No. 18/548,003, filed Aug. 25, 2023, by Knappertz et al.
U.S. Appl. No. 18/560,316, filed Nov. 10, 2023, by Silcock et al.
U.S. Appl. No. 18/560,337, filed Nov. 10, 2023, by Silcock et al.
U.S. Appl. No. 18/560,341, filed Nov. 10, 2023, by Silcock et al.
U.S. Appl. No. 18/560,346, filed Nov. 10, 2023, by Silcock et al.
U.S. Appl. No. 18/597,717, filed Mar. 6, 2024, by Whitehouse et al.
U.S. Appl. No. 18/762,588, filed Jul. 2, 2024, by Guy et al.
U.S. Appl. No. 18/859,454, filed Oct. 23, 2024, by Chen et al.
U.S. Appl. No. 18/862,705, filed Nov. 4, 2024, by Straker et al.
U.S. Appl. No. 18/874,175, filed Dec. 12, 2024, by Straker et al.
U.S. Appl. No. 18/912,442, filed Oct. 10, 2024, by Guy et al.
U.S. Appl. No. 18/921,741, filed Oct. 21, 2024, by Guy et al.
U.S. Appl. No. 19/024,770, filed Jan. 16, 2025, by Guy et al.
U.S. Appl.No. 19,102,763, filed Feb. 10, 2025, by Whalley et al.
U.S. Appl. No. 19/134,833, filed Jun. 2, 2025, by Andrew C. McCreary.
U.S. Appl. No. 19/187,858, filed Apr. 23, 2025, by Geoffrey Guy et al.
U.S. Appl. No. 19/244,951, filed Jun. 20, 2025, by Geoffrey Guy et al.
Chauhan, B. et al., "Preparation and Evaluation of Floating Risedronate SodiumGelucire 43/01 Formulations," Drug Development and Industrial Pharmacy, 31(9):851-860 (Sep. 2008); https://doi.org/10.1080/03639040500271837.
Gattefoss. Capryol 90, lipid specifications. Retrieved Nov. 10, 2025, from https://www.gattefosse.com/pharmaceuticals/product-finder/capryol-90, 6 pages [publication date unknown].
Gattefoss. Gelucire 43/01, lipid specifications. Retrieved Nov. 10, 2025, from https://www.gattefosse.com/pharmaceuticals/product-finder/gelucire-4301, 4 pages [publication date unknown].
Gattefoss. Labrafil M 2125 CS, lipid specifications. Retrieved Nov. 10, 2025, from https://www.gattefosse.com/pharmaceuticals/product-finder/labrafil-m-2125-cs, 5 pages [publication date unknown].
Gattefoss. "The Gelucire Family Semi-Solid Excipients," Pharma Excipients. Retrieved Nov. 10, 2025, from https://www.pharmaexcipients.com/news/the-gelucire-family-semi-solid-excipients-by-gattefosse/, 3 pages [publication date unknown].
Waters et al., "Enhancing the dissolution of phenylbutazone using Syloid® based mesoporous silicas for oral equine applications," Journal of Pharmaceutical Analysis, 8(3):181-186 (Jun. 2018).

* cited by examiner

Lipid-Loaded Formulation Methods

Lipid-Loaded Formulation Methods

Lipid-Loaded Formulation Methods

Solvent Mediated Polymer Formulation Method

ORAL SOLID DOSAGE FORMS COMPRISING CANNABINOIDS

CROSS-REFERENCE TO RELATED APPLICATIONS

This Application is a continuation of U.S. application Ser. No. 18/597,717, filed Mar. 6, 2024, which is a continuation of PCT Application No. PCT/EP2023/072292, filed Aug. 11, 2023; which claims priority to U.S. Provisional Application No. 63/371,292, filed Aug. 12, 2022, the entire contents of which are incorporated herein by reference and relied upon.

BACKGROUND

The contemporary use of cannabinoids in medicine has necessitated finding more effective ways of delivering these poorly soluble compounds. In addition to poor aqueous solubility, cannabinoids are also known to have limited bioavailability and poor stability in various formulations.

Oral delivery remains the preferred route of drug administration due to high patient compliance and ease of administration. However, most cannabinoids are highly lipophilic and poorly water soluble, which can result in oral formulations that display poor pharmacokinetics (e.g., low and highly variable bioavailability) and undesirable side effects. These suboptimal characteristics generally result in unpredictable and inconsistent efficacy after oral administration (e.g., variable onset time and/or peak of observed effects) together with potential safety concerns, e.g., overdosing especially in geriatric use.

While some progress has been made recently using self-emulsifying drug delivery systems, oil-based excipients, and/or ethanol as co-solvent, oral formulations that provide appropriate bioavailability and can reliably deliver sufficient amounts of cannabinoids in a patient-friendly formulation remain challenging.

The present disclosure addresses these and other unmet needs.

BRIEF SUMMARY

In some embodiments, the present disclosure provides a drug-containing particle comprising: (a) one or more cannabinoids; and (b) a porous solid carrier. In embodiments, the one or more cannabinoids are adsorbed onto the porous solid carrier. As used herein "absorbed onto the porous solid carrier" encompasses when the cannabinoids are present on the surface of the solid carrier and/or in the pores of the porous solid carrier. The term "absorbed onto the porous solid carrier" may be used interchangeably with "absorbed onto and/or into the porous solid carrier". In some embodiments, the present disclosure provides a drug-containing particle comprising: (a) one or more cannabinoids; (b) a porous solid carrier; and (c) one or more lipophilic materials. In embodiments, the one or more cannabinoids are adsorbed onto the porous solid carrier and/or into the pores of the porous solid carrier (e.g., onto and/or into the pores solid carrier). In some embodiments, the present disclosure provides a drug-containing particle comprising: (a) one or more cannabinoids; (b) a porous solid carrier; (c) one or more lipophilic materials; and (d) an antioxidant. In embodiments, the one or more cannabinoids are adsorbed onto the porous solid carrier and/or into the pores of the porous solid carrier (e.g., onto and/or into the pores solid carrier). In embodiments, the porous solid carrier has one or more of the following characteristics: (i) average pore volume of 1-2 $cm^3/g$; (ii) average surface area of 250 to 375; or (iii) pore diameters of about 2-50 nm. In embodiments, the porous solid carrier has two or more of the following characteristics: (i) average pore volume of 1-2 $cm^3/g$; (ii) average surface area of 250 to 375; or (iii) pore diameters of about 2-50 nm. In embodiments, the porous solid carrier has an: (i) average pore volume of 1-2 $cm^3/g$; (ii) average surface area of 250 to 375; and (iii) pore diameters of about 2-50 nm. In embodiments, the one or more cannabinoids may be part of a drug substance that contains additional components, such as terpenes, triglycerides and/or sterols. In some embodiments, the porous solid carrier is present as microparticles. In some embodiments, the porous solid carrier has an average particle size ranging from about 1 μm to about 250 μm (e.g., about 50 μm to about 150 μm). In certain embodiments, the porous solid carrier can be highly microporous.

In some embodiments, the porous solid carrier has a porosity ranging from about 75% to about 99%.

In some embodiments, the porous solid carrier has an oil absorbing capacity of about 1 mL/g to about 10 mL/g.

In some embodiments, the porous solid carrier comprises silica ($SiO_2$), microcrystalline cellulose, silicified microcrystalline cellulose, chitosan, isomalt, or a silicate (e.g., magnesium silicate, aluminium magnesium silicate or calcium-magnesium silicate). In certain embodiments, the porous solid carrier comprises an ordered mesoporous silica. In some embodiments, the porous solid carrier comprises silica ($SiO_2$) or a silicate. In some embodiments, the silica is mesoporous silica or amorphous silica. In some embodiments, the silica is mesoporous silica. In some embodiments, the mesoporous silica is Syloid® or Fujisil™ (which can be manufactured to cGMP guidelines). In some embodiments, the mesoporous silica is Syloid® XDP (which can be 3050 and 3150 grades and manufactured to cGMP guidelines).

In some embodiments, the mesoporous silica has an average pore diameter ranging from about 5 nm to about 100 nm (e.g., about 2 nm to about 50 nm).

In some embodiments, the porous solid carrier comprises a silicate. In some embodiments, the silicate comprises a magnesium silicate, aluminium magnesium silicate or calcium-magnesium silicate. In some embodiments, the silicate is an aluminosilicate, such as a magnesium aluminosilicate. In some embodiments, the silicate is Neusilin®.

In some embodiments, the porous solid carrier is present in an amount ranging from about 20% to about 80% by weight based on the total weight of the drug-containing particle.

In some embodiments, the drug-containing particle comprises one or more cannabinoids, wherein the one or more cannabinoids is cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), OH-CBD, CBD-C4, 6-OH-CBD, 7-OH-CBD, 7-COOH-CBD, 11-COOH-THC, or 11-OH-THC or combinations thereof. In some embodiments, the one or more cannabinoids is nabilone. In some embodiments, the drug-containing particle comprises a metabolite of the one or more cannabinoids disclosed herein.

In some embodiments, the one or more cannabinoids is present in an amount ranging from about 5 to about 75% by weight based on the total weight of the drug-containing particle.

In some embodiments, the one or more cannabinoids is present in an amorphous form.

In some embodiments, adsorption of the one or more cannabinoids onto and/or into the porous solid carrier is determined by scanning electron microscopy (SEM), differential scanning calorimetry (DSC), and/or X-ray power diffraction (XRPD).

In some embodiments, substantially all of the one or more cannabinoids is present in the pores and/or surface of the porous solid carrier. In some embodiments, substantially all of the one or more cannabinoids is present within the pores of the porous solid carrier.

In some embodiments, the drug-containing particle further comprises a chelating agent. In some embodiments, the chelating agent is EDTA, citric acid, or a polyphenolic substance (e.g., curcumin).

In some embodiments, the amount of the chelating agent in the drug-containing particle ranges from about 0.05% to about 3% by weight. In some embodiments, the amount of the chelating agent in the drug-containing particle ranges from about 0.05% to about 0.5% by weight.

In some embodiments, the drug-containing particle further comprises one or more antioxidizing agents. In some embodiments, the one or more antioxidizing agents is a tocopherol derivative (e.g., αtocopherol), a carotenoid (e.g., lutein or β-carotene), tocotrienol, ascorbic acid, ascorbyl palmitate, lecithin, butylated hydroxyanisole, butylated hydroxytoluene (BHT), monothiolglycerol, propyl gallate, curcumin, or combinations thereof. In some embodiments, the one or more antioxidizing agents is α-tocopherol, β-carotene, ascorbic acid, ascorbyl palmitate, lecithin, butylated hydroxyanisole, butylataed hydroxytoluene, monothiolglycerol, propyl gallate, or combinations thereof.

In some embodiments, the amount of the one or more antioxidants in the drug-containing particle ranges from about 0.05% to about 3% by weight.

In some embodiments, the drug-containing particle further comprises a chelating agent and one or more antioxidants disclosed herein.

In some embodiments, the drug-containing particle further comprises one or more lipophilic materials. In embodiments, the drug substance is dissolved or suspended in the lipophilic material and then the drug substance is adsorbed onto the porous carrier. In embodiments, the lipophilic material comprises polyethylene oxide-containing fatty acid ester, polyethylene oxide glyceride, polypropylene glycol fatty acid ester, PEG, monoglyceride fatty acid ester, diglyceride fatty acid ester, triglyceride fatty acid ester, propylene glycol diglyceride, polyethylene oxide vegetable oil, or a combination thereof. In embodiments, the lipophilic material comprises polyethylene oxide-containing fatty acid ester. In some embodiments, the one or more lipophilic materials comprises polyethylene oxide-containing fatty acid esters. In some embodiments, the one or more lipophilic materials comprise polyethylene oxide glyceride. In some embodiments, the lipophilic material comprises a vegetable seed oil, a fruit seed oil, kernel oil, mono-, di-, and triglyceride esters of palmitic (C16) and stearic (C18) acids and PEG-32 (MW 1500) mono- and diesters of palmitic (C16) and stearic (C18) acids; mono-, di- and triglyceride esters of fatty acid (C8 to C18); mono-, di-, and triglyceride esters of lauric (C12) and stearic (C18) acids and PEG-6 (MW 300) mono- and diesters of lauric (C12) and stearic (C18) acids; mono-, di-, and triglyceride esters of oleic (C18:1) acid and PEG-6 (MW 300) and mono- and diesters of oleic (C18:1) acid; a mixture of monoesters and diesters of 12-hydroxystearic acid and polyethylene glycol glyceride; PEG-40 hydrogenated castor oil; propylene glycol monocaprylate; propylene glycol monolaurate; medium-chain triglyceride; propylene glycol dicaprolate/dicaprate; PEG-8 (MW 400) mono- and diesters of caprylic (C8) and capric (C10) acids; or combinations thereof. In embodiments, the lipophilic material is mono-, di- and triglyceride esters of fatty acids (C8 to C18); mono-, di-, and triglyceride esters of lauric (C12) and stearic (C18) acids and PEG-6 (MW 300) mono- and diesters of lauric (C12) and stearic (C18) acids; or propylene glycol monocaprylate. In some embodiments, the lipophilic material comprises sesame seed oil, medium-chain triglyceride (MCT) oil, oleic oil, pumpkin seed oil, or any other vegetable or fruit seed oils and combinations thereof.

In some embodiments, the one or more lipophilic materials (e.g., 2 or 3 lipophilic materials) is present in an amount of about 10% to about 75% by weight based on the total weight of the drug-containing particle.

In some embodiments, the drug-containing particle further comprises one or more polymers. In some embodiments, the polymer has a $T_g$ of about 50° C. to about 130° C. In some embodiments, the polymer comprises carboxymethylcellulose, polyvinylpyrrolidone (kollidon VA64), cross linked polyvinyl N-pyrrolidone (crospovidone), hydroxypropyl methylcellulose phthalate (HPMCP 50), polyvinyl alcohol-polyethylene glycol copolymer (kollicoat), polyvinyl caprolactam-polyvinyl acetate-polyethylene glycol graft co-polymer (soluplus), polyvinyl alcohol, or combinations thereof.

In some embodiments, the one or more polymers is present in an amount of about 10% to about 50% by weight based on the total weight of the drug-containing particle. In some embodiments, the polymer is provided as a coating on the drug-containing particle.

In some embodiments, the drug-containing particle disclosed herein releases 50-90% of the one or more cannabinoids in about 1-16 h. In some embodiments, the drug-containing particle disclosed herein releases 50-90% of the one or more cannabinoids in about 3-12 h. In some embodiments, the drug-containing particle disclosed herein releases greater than about 70% of the one or more cannabinoids by about 6 h. In some embodiments, the drug-containing particle disclosed herein releases greater than about 80% of the one or more cannabinoids by about 12 h.

In some embodiments, the drug-containing particle is substantially free of cannabidiorcol (CBD-C1), cannabidivarin (CBDV), and/or cannabidibutol (CBD-C4). In some embodiments, the drug-containing particle comprises no more than about 0.2% by weight of active of CBD-C1. In some embodiments, the drug-containing particle comprises no more than about 0.8% by weight of active of CBDV. In some embodiments, the drug-containing particle comprises about 0.15 to about 0.8% by weight active of CBDV. In some embodiments, the drug-containing particle comprises no more than about 0.5% by weight of active of CBD-C4.

In some embodiments, the present disclosure provides a pharmaceutical composition comprising a drug-containing particle disclosed herein. In some embodiments, the pharmaceutical compositions further comprise one or more pharmaceutically acceptable excipients and/or carriers. In some embodiments, the pharmaceutical composition is in the form of a tablet, capsule, or granule.

In some embodiments, the pharmaceutical compositions are prepared by a process comprising mixing/blending (e.g., high or low shear mixing/blending), spray drying or hot-melt extrusion.

DEFINITIONS

Figure 1:
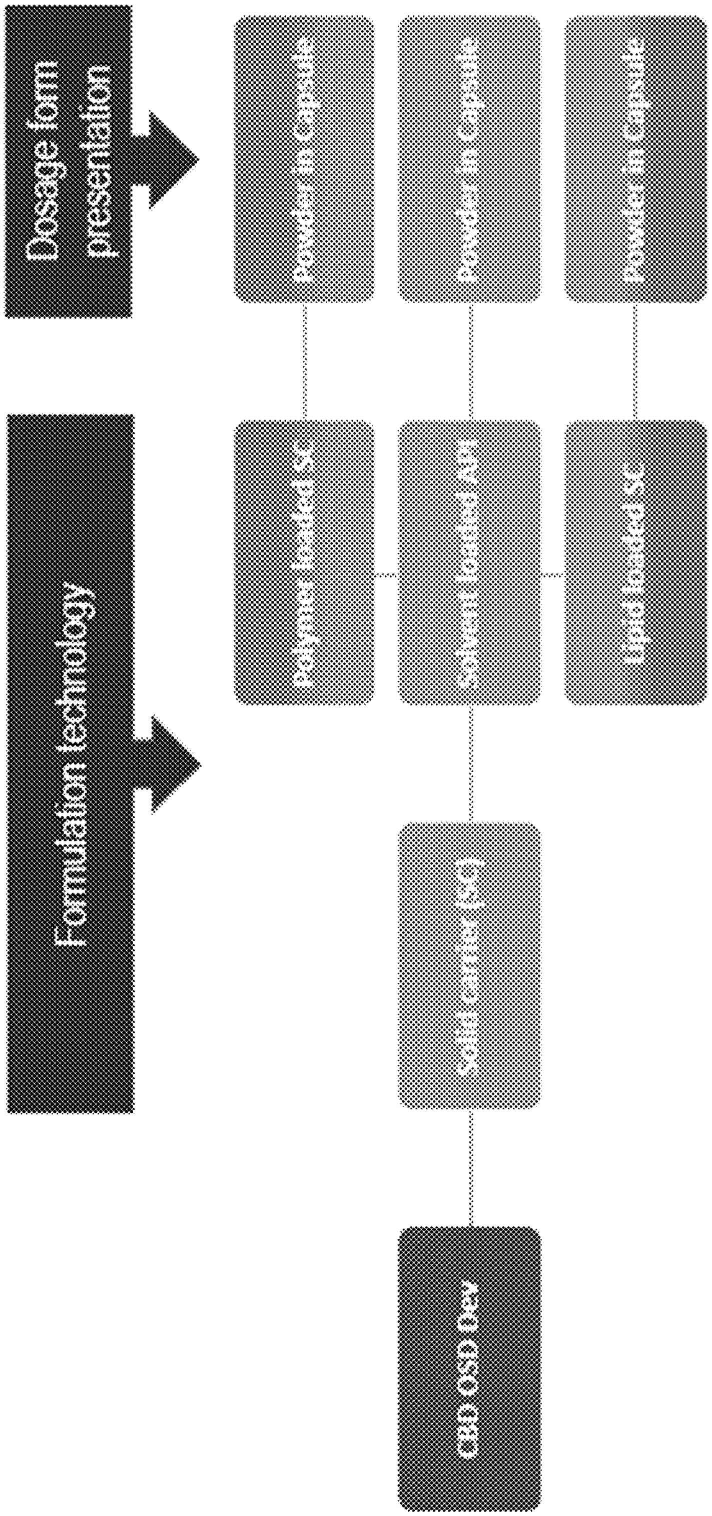
FIG. 1 provides an overview of formulation technologies used to prepare drug-containing particles of the present disclosure.

The term "cannabinoid" as used herein generally refers to one of a class of diverse chemical compounds that act on a cannabinoid receptor in cells that repress neurotransmitter release in the brain. Ligands for these receptor proteins include the endocannabinoids (produced naturally in the body by humans and animals), the phytocannabinoids (found in cannabis and some other plants), and synthetic cannabinoids (manufactured artificially). Thus, the term "cannabinoid" encompasses endocannabinoids and phytocannabinoids.

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

A "synthetic cannabinoid" is one which has been produced by chemical synthesis. This term can include modifying an isolated phytocannabinoid, by, for example, forming a pharmaceutically acceptable salt thereof.

A "substantially pure" cannabinoid is defined as a cannabinoid which is present at greater than 95% (w/w) pure. In some embodiments, "substantially pure" refers to greater than 96% (w/w), greater than 97% (w/w), greater than 98% (w/w), or greater than 99% (w/w) pure.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes."

The term "pharmaceutically acceptable" means biologically or pharmacologically compatible for in-vivo use in animals or humans, and can mean approved by a regulatory agency of the Federal or a state government or listed in the U.S. Pharmacopeia or other generally recognized pharmacopeia (e.g., the European Pharmacopoeia, the British Pharmacopoeia, and the Japanese Pharmacopoeia), for use in animals, and more particularly in humans.

The terms "lipophilic material," "lipophilic materials" and the like can refer to a material that can dissolve in non-polar materials, such as fats, oils, and lipids. General examples of lipophilic materials include fatty acids, fatty alcohols, oils, lipids, butter and fats. As used herein, lipophilic material may be either a class of lipophilic materials, like polyethylene oxide-containing fatty acid ester, or a species of lipophilic material, such as a polyethylene oxide ester of a C8 fatty acid. Additional lipophilic materials are described in U.S. Pat. No. 6,294,192, incorporated by reference in its entirety.

For example, in embodiments, the lipophilic material of the present application comprises MCT oil; oleic oil; mono-, di-, and triglyceride esters of palmitic (C16) and stearic acids and PEG-32 (MW 1500) mono- and diesters of palmitic (C16) and stearic acids (C18); mono-, di- and triglyceride esters of fatty acid (C8 to C18); mono-, di-, and triglyceride esters of lauric (C12) and stearic (C18) acids and PEG-6 (MW 300) mono- and diesters of lauric (C12) and stearic (C18) acids; mono-, di-, and triglycerides and PEG-6 (MW 300) and mono- and diesters of oleic (C18:1) acids; a mixture of monoesters and diesters of 12-hydroxystearic acid and polyethylene glycol glyceride; PEG-40 hydrogenated castor oil; propylene glycol monocaprylate; propylene glycol monolaurate; medium-chain triglyceride; propylene glycol dicaprolate/dicaprate; PEG-8 (MW 400) mono- and diesters of caprylic ($C_8$) and capric ($C_{10}$) acids; or combinations thereof.

The term "lipid-loaded" refers to compositions in which a cannabinoid and lipophilic material are present on a porous solid carrier. In embodiments, the cannabinoid is dissolved or suspended in a lipophilic material and then the resulting solution is combined with a porous solid carrier, such that the cannabinoid is absorbed onto the porous solid carrier. This results in an amorphous form of the cannabinoid.

Throughout the present specification, the terms "about" and/or "approximately" can be used in conjunction with numerical values and/or ranges. The term "about" is understood to mean those values near to a recited value and within art-recognized levels of variation. For example, "about 40 [units]" can mean within ±25% of 40 (e.g., from 30 to 50), within #20%, ±15%, ±10%, ±9%, ±8%, ±7%, ±6%, ±5%, ±4%, ±3%, ±2%, ±1%, less than ±1%, or any other value or range of values therebetween. Furthermore, the phrases "less than about [a value]" or "greater than about [a value]" should be understood in view of the definition of the term "about" provided herein. The terms "about" and "approximately" can be used interchangeably. In embodiments, about can mean within ±10% of a value.

Unless expressly stated to the contrary, all ranges cited herein are inclusive; i.e., the range includes the values for the upper and lower limits of the range as well as all values in between.

DETAILED DESCRIPTION

Solid Dosage Forms

Described herein are oral solid dosage forms comprising cannabinoid-containing drug particles that, when manufactured according to the formulation technologies outlined in FIG. 1, provide improved solubility and oral bioavailability compared to formulations manufactured by other methods known in the art. Among their beneficial properties, the drug-containing particles of the present disclosure were found to be stable, free flowing powders that can exhibit high oil adsorption capacity and rapid drug-release upon contact with gastric fluids.

In some embodiments, the present disclosure provides a drug-containing particle comprising: (a) one or more cannabinoids, terpenes, triglycerides and/or sterols; and (b) a porous solid carrier. In some embodiments, the present disclosure provides a drug-containing particle comprising: (a) one or more cannabinoids and one or more terpenes, triglycerides and/or sterols; and (b) a porous solid carrier. In embodiments, the one or more cannabinoids are present on the surface and/or in the pores of the porous solid carrier. In embodiments, the one or more cannabinoids are present in the pores of the pores porous solid carrier. Association of the cannabinoids on the surface of the porous solid carrier or within the pores of solid carrier may be referred to herein as "adsorption." Thus, in some embodiments, the one or more cannabinoids are adsorbed onto and/or into the porous solid carrier.

In some embodiments, the present disclosure provides a drug-containing particle comprising: (a) one or more cannabinoids and terpenes, and/or sterols; and (b) a porous solid carrier. In embodiments, the one or more cannabinoids are present (adsorbed) on the surface and/or in the pores of the porous solid carrier. In embodiments, the one or more cannabinoids are present in the pores of the pores porous solid carrier. In some embodiments, the present disclosure provides a drug-containing particle comprising: (a) one or more cannabinoids; and (b) a porous solid carrier. In embodiments, the one or more cannabinoids are present (adsorbed) on the surface and/or in the pores of the porous solid carrier. In embodiments, the one or more cannabinoids are present in the pores of the pores porous solid carrier.

In some embodiments, the drug-containing particles have a composition provided in Table 11, Table 12, or Table 15.

Porous Solid Carriers

The porous solid carrier of the present disclosure can be any porous material onto which or into which the one or more cannabinoids can be adsorbed to provide suitable bioavailability and drug release.

In some embodiments, the porous solid carrier comprises silica ($SiO_2$), microcrystalline cellulose (MCC; e.g., Pharmacel 102), silicified microcrystalline cellulose (SMCC; e.g., Pharmacel SMCC90), chitosan, isomalt (e.g., Galen IQ 721), florite, or a silicate. In some embodiments, the porous solid carrier comprises microcrystalline sodium carboxymethylcellulose, microcrystalline cellulose, silicified microcrystalline cellulose, chitosan, or isomalt. In some embodiments, the porous solid carrier comprises silica, microcrystalline cellulose, silicified microcrystalline cellulose, chitosan, isomalt, or a silicate. In some embodiments, the porous solid carrier comprises silica or a silicate. In some embodiments, the porous solid carrier is mesoporous silica or amorphous silica.

In some embodiments, the porous solid carrier disclosed herein is present as microparticles. In some embodiments, the porous solid carrier has an average particle size ranging from about 1 μm to about 1000 μm, e.g., about 1 μm, about 10 μm, about 20 μm, about 30 μm, about 40 μm, about 50 μm, about 60 μm, about 70 μm, about 80 μm, about 90 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, or about 1000 μm, including all ranges and values therebetween. In some embodiments, the porous solid carrier has an average particle size ranging from about 1 μm to about 250 μm. In some embodiments, the porous solid carrier has an average particle size ranging from about 25 μm to about 250 μm. In some embodiments, the porous solid carrier has an average particle size ranging from about 50 μm to about 150 μm. In some embodiments, the porous solid carrier has an average particle size ranging from about 40 μm to about 100 μm. In some embodiments, the porous solid carrier has an average particle size ranging from about 40 μm to about 85 μm. In some embodiments, the porous solid carrier has an average particle size ranging from about 50 μm to about 80 μm. In some embodiments, the porous solid carrier has an average particle size ranging from about 50 μm to about 70 μm. In some embodiments, the porous solid carrier has an average particle size ranging from about 10 μm to about 75 μm. In some embodiments, the porous solid carrier has an average particle size ranging from about 20 μm to about 70 μm. In some embodiments, the porous solid carrier has an average particle size ranging from about 25 μm to about 65 μm.

In some embodiments, the porous solid carrier has a porosity ranging from about 25% to about 99%, e.g., about 25%, about 30%, about 35%, about 40%, about 45%, about 50%, about 55%, about 60%, about 65%, about 70%, about 75%, about 80%, about 85%, about 90%, about 95%, or about 99%, including all ranges and values therebetween. In some embodiments, the porous solid carrier has a porosity ranging from about 50% to about 99%. In some embodiments, the porous solid carrier has a porosity ranging from about 75% to about 99%. In some embodiments, the porous solid carrier has a porosity ranging from about 25% to about 95%. In some embodiments, the porous solid carrier has a porosity ranging from about 50% to about 95%. In some embodiments, the porous solid carrier has a porosity ranging from about 75% to about 95%. In some embodiments, the porous solid carrier has a porosity ranging from about 85% to about 95%. In some embodiments, the porous solid carrier has a porosity greater than about 50%, greater than about 55%, greater than about 60%, greater than about 65%, greater than about 70%, greater than about 75%, greater than about 80%, greater than about 85%, greater than about 90%, or greater than about 95%.

In some embodiments, the porous solid carrier has an average surface area ranging from about 100 $m^2/g$ to about 1000 $m^2/g$, e.g., about 100 $m^2/g$, about 200 $m^2/g$, about 300 $m^2/g$, about 400 $m^2/g$, about 500 $m^2/g$, about 600 $m^2/g$, about 700 $m^2/g$, about 800 $m^2/g$, about 900 $m^2/g$, or about 1000 $m^2/g$, including all ranges and values therebetween. In some embodiments, the porous solid carrier has an average surface area ranging from about 100 $m^2/g$ to about 800 $m^2/g$, about 200 $m^2/g$ to about 800 $m^2/g$, about 200 $m^2/g$ to about 600 $m^2/g$, about 200 $m^2/g$ to about 500 $m^2/g$, about 200 $m^2/g$ to about 400 $m^2/g$, about 300 $m^2/g$ to about 400 $m^2/g$, or about 250 $m^2/g$ to about 350 $m^2/g$, including all ranges and values therebetween.

In some embodiments, the porous solid carrier has an average pore volume ranging from about 0.1 mL/g to about 5 mL/g, e.g., about 0.1 mL/g, about 0.5 mL/g, about 1 mL/g, about 1.25 mL/g, about 1.5 mL/g, about 1.75 mL/g, about 2 mL/g, about 2.25 mL/g, about 2.25 mL/g, about 2.5 mL/g, about 2.75 mL/g, about 3 mL/g, about 3.25 mL/g, about 3.5 mL/g, about 3.75 mL/g, about 4 mL/g, about 4.25 mL/g, about 4.5 mL/g, about 4.75 mL/g, or about 5 mL/g, including all ranges and values therebetween. In some embodiments, the porous solid carrier has an average pore volume ranging from about 1 mL/g to about 5 mL/g. In some embodiments, the porous solid carrier has an average pore volume ranging from about 1.5 mL/g to about 5 mL/g. In some embodiments, the porous solid carrier has an average pore volume ranging from about 1.5 mL/g to about 4 mL/g. In some embodiments, the porous solid carrier has an average pore volume ranging from about 1.5 mL/g to about 3 mL/g. In some embodiments, the porous solid carrier has an average pore volume ranging from about 1.5 mL/g to 2.0 mL/g. In some embodiments, the porous solid carrier has an average pore volume ranging from about 1 mL/g to 2 mL/g. In some embodiments, the porous solid carrier has an average pore volume ranging from about 1 mL/g to 1.9 mL/g.

In some embodiments, the porous solid carrier has an average pore diameter ranging from about 1 nm to about 100 nm, e.g., about 1 nm, about 2 nm, about 3 nm, about 4 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 80 nm, about 85 nm, about 90 nm, about 95 nm, or about 100 nm, including all ranges and values therebetween. In some embodiments, the porous solid carrier has an average pore diameter ranging from about 2 nm to about 60 nm. In some embodiments, the porous solid carrier has an average pore diameter ranging from about 2 nm to about 50 nm. In some embodiments, the porous solid carrier has an average pore diameter ranging from about 10 nm to about 50 nm. In some embodiments, the porous solid carrier has an average pore diameter ranging from about 15 nm to about 30 nm. In some embodiments, the porous solid carrier has an average pore diameter ranging from about 20 nm to about 30 nm. In some embodiments, the porous solid carrier has an average pore diameter ranging from about 15 nm to about 25 nm.

In some embodiments, the porous solid carrier has an oil absorbing capacity of about 1 mL/g to about 10 mL/g, e.g., about 1 mL/g, about 1.5 mL/g, about 2 mL/g, about 2.5 mL/g, about 3 mL/g, about 3.5 mL/g, about 4 mL/g, about 4.5 mL/g, about 5 mL/g, about 5.5 mL/g, about 6 mL/g, about 6.5 mL/g, about 7 mL/g, about 7.5 mL/g, about 8 mL/g, about 8.5 mL/g, about 9 mL/g, about 9.5 mL/g, or about 10 mL/g, including all ranges and values therebetween. In some embodiments, the porous solid carrier has an oil absorbing capacity of about 1 mL/g to about 5 mL/g. In some embodiments, the porous solid carrier has an oil absorbing capacity of about 1 mL/g to about 4 mL/g. In some embodiments, the porous solid carrier has an oil absorbing capacity of about 2 mL/g to about 5 mL/g.

Figure 2:
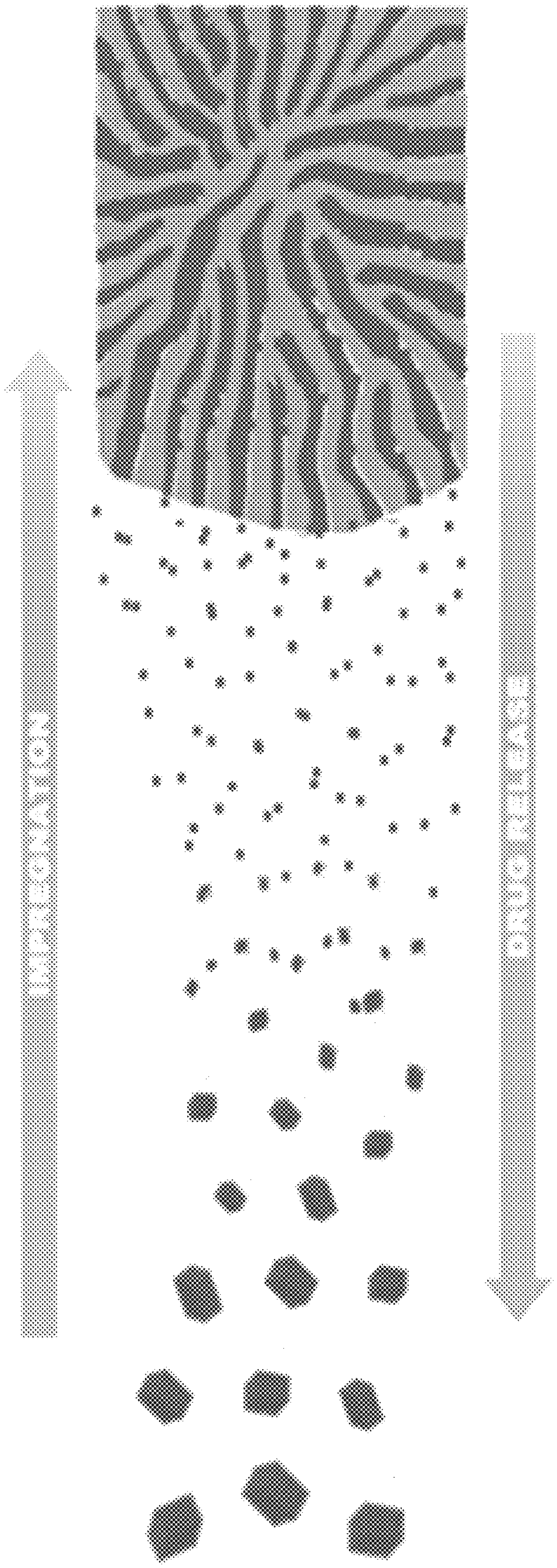
FIG. 2 provides a schematic diagram showing impregnation and release of drug from a porous solid carrier of the present disclosure.
Figure 3:
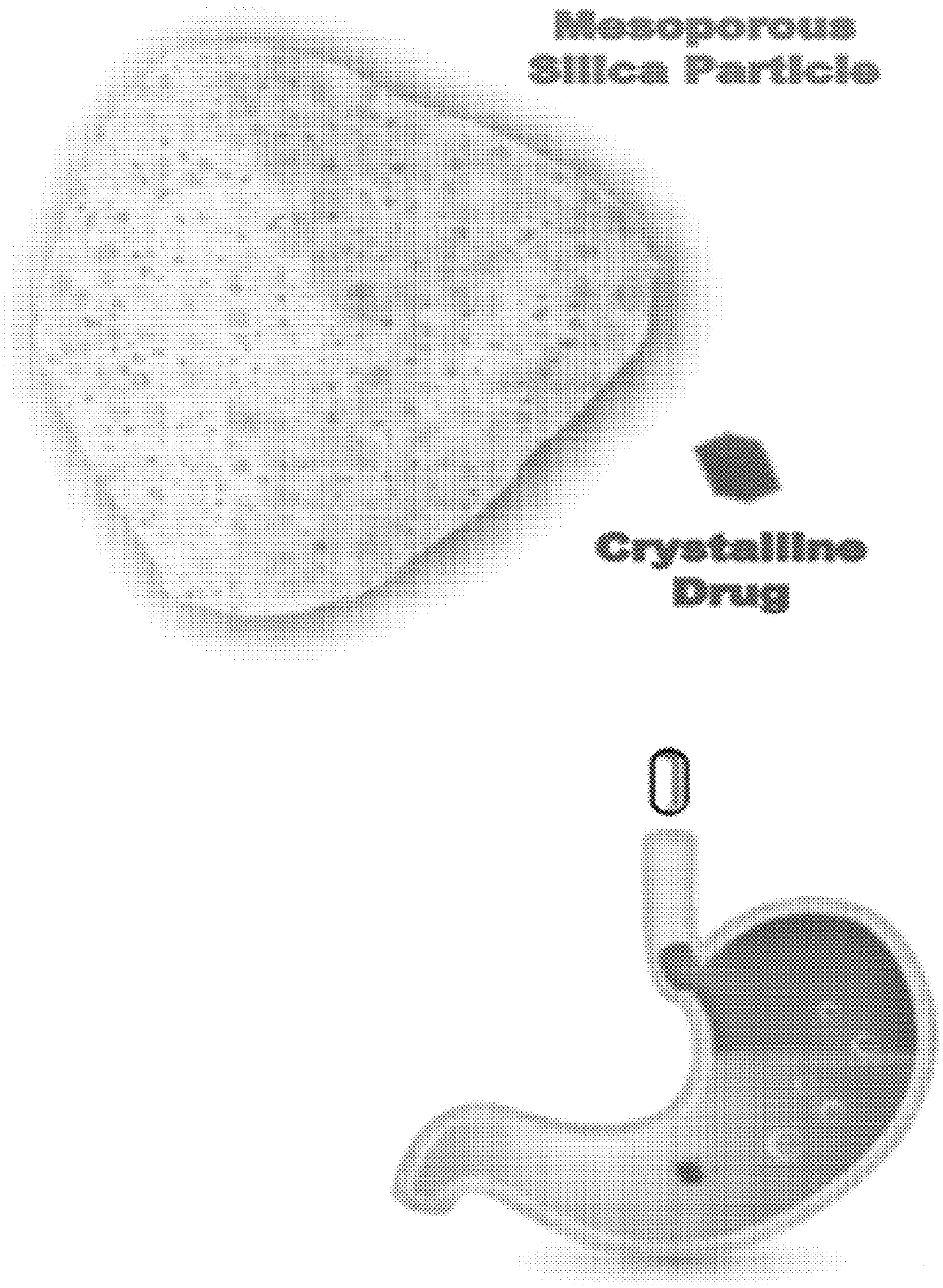
FIG. 3 is a diagram showing that drug can be released from the porous solid carrier of the present disclosure upon contact with gastric fluid.

Without being bound by any particular theory, based on the properties disclosed herein, the internal mesopores of the porous solid carrier (e.g., a silica material described herein) can be impregnated with a concentrated drug solution comprising one or more cannabinoids (FIG. 2). A stable amorphous phase can then result from confinement of the drug in pores of subcritical dimensions and/or from the strength of the absorptive interaction (e.g., H-bonding). On contact with gastric fluids, the confined amorphous drug can be rapidly released (FIG. 3).

In some embodiments, the porous solid carrier is present in an amount ranging from about 10% to about 90% by weight based on the total weight of the drug-containing particle, e.g., about 10%, about 15%, about 20%, about 25%, about 30%, about 35%, about 40%, about 45%, about 50%, about 55%, about 60%, about 65%, about 70%, about 75%, about 80%, about 85%, or about 90%, including all ranges and values therebetween. In some embodiments, the porous solid carrier is present in an amount ranging from about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 20% to about 75%, about 20% to about 70%, about 20% to about 65%, about 20% to about 60%, about 20% to about 55%, about 20% to about 50%, about 20% to about 45%, about 25% to about 55%, about 25% to about 50%, about 30% to about 60%, about 30% to about 55%, about 30% to about 50%, or about 35% to about 50% by weight based on the total weight of the drug-containing particle. In some embodiments, the porous solid carrier is present in an amount ranging from about 30% to about 50% by weight based on the total weight of the drug-containing particle.

In some embodiments, the porous solid carrier is mesoporous silica. In some embodiments, the mesoporous silica is Syloid® or Fujisil™ or Aeroperol®. In some embodiments, the mesoporous silica is Syloid® XDP or Syloid® FP. In some embodiments, the mesoporous silica is Syloid® XDP. In some embodiments, the mesoporous silica is Aeroperol®.

In some embodiments, porous solid carrier has one or more properties of Syloid®, Fujisil™ or Aeroperol® described herein. In some embodiments, porous solid carrier has one or more properties of Syloid® XDP or Syloid® FP. In some embodiments, the porous solid carrier has one or more properties of Syloid® XDP. In some embodiments, the porous solid carrier has one or more properties of Aeroperol®. In embodiments, the porous solid carrier as 1, 2, 3 4 or 5 properties of Syloid® XDP or Aeroperol®. In embodiments, the solid carrier has an average pore volume corresponding to that average pore volume of Syloid® XDP or Aeroperol®. In embodiments, the solid carrier has an average surface area corresponding to the average surface area of Syloid® XDP or Aeroperol®. In embodiments, the solid carrier has pore diameters corresponding to the pore diameters of Syloid® XDP or Aeroperol®.

Syloid® XDP is a commercially available silica-based product (W.R. Grace & Co.—Conn, Columbia, Maryland) that can be used as a porous solid carrier in the drug-containing particles described herein. In some embodiments, the Syloid® XDP of the present disclosure is used to prepare solid dosage forms (e.g., liquisolid formulations) from liquid ingredients. In some embodiments, the porous solid carrier has one or more of the following properties:

| Mesoporosity | High (containing pores with diameters between 2 and 50 nm) |
|---|---|
| Average Particle Size (μm) | 50/150 |
| Pore Volume ($cm^3/g$) | 1.69 |
| Bulk Density (g/mL) | 0.24 |
| Tapped Density (g/mL) | 0.28 |
| Compressibility Index (%) | 16.2 |
| Hausner Ratio | 1.19 |
| Specific Surface Area ($m^2/g$) | 320 |
| pH (USP method) | 5-8 |

*all values presented as averages; values may range by ±20% or ±10%

Fujisil™ is a commercially available silica-based product (Fuji Chemical Industries Co., Ltd.) and can be used as a porous solid carrier in the drug-containing particles described herein. In some embodiments, the Fujisil™ of the present disclosure is used to prepare solid dosage forms (e.g., liquisolid formulations) from liquid ingredients. In some embodiments, the porous solid carrier has one or more of the following properties:

| Form | Amorphous |
|---|---|
| Average Particle Size (μm) | 80 |
| Bulk Density (g/mL) | 0.17 |
| Tapped Density (g/mL) | 0.20 |
| Specific Surface Area ($m^2/g$) | 400 |
| Oil Adsorbing Capacity (mL/g) | 3.3 |

-continued

| Form | Amorphous |
|---|---|
| Pore Volume ($cm^3/g$) | 2.1 |
| Angle of Repose (°) | 30 |
| pH (USP method) | 4.0-8.0 |

*all values presented as averages; values may range by ±20% or ±10%

Aeroperol® is a commercially available silica-based product (W.R. Grace & Co.—Conn, Columbia, Maryland) that can be used as a porous solid carrier in the drug-containing particles described herein. In some embodiments, the Aeroperol® of the present disclosure is used to prepare solid dosage forms (e.g., liquisolid formulations) from liquid ingredients. In some embodiments, the porous solid carrier has one or more of the following properties:

| | |
|---|---|
| Specific surface area (BET) m2/g | 260-320 |
| pH in slurry | 3.5-5.5 |
| Tapped density (g/l) | 280 |
| Average particle size (μm) | 30 |
| Pore volume (ml/g) | 1.5-1.9 |
| Average pore diameter | 22.9 |

*all values presented as averages; values may range by ±20% or ±10%

In some embodiments, the porous solid carrier is a silicate. In some embodiments, the silicate comprises a magnesium silicate, aluminium magnesium silicate or calcium-magnesium silicate. In some embodiments, the silicate is an aluminosilicate, such as a magnesium aluminosilicate. In some embodiments, the silicate is Neusilin®. Neusilin® is a commercially available magnesium aluminosilicate product (Fuji Chemical Industries Co., Ltd.) with the chemical formula $Al_2O_3{\cdot}MgO{\cdot}1.7SiO_2{\cdot}xH_2O$ that can be used as a porous solid carrier in the drug-containing particles described herein. In some embodiments, the Neusilin® of the present disclosure is used to prepare solid dosage forms (e.g., liquisolid formulations) from liquid ingredients. In some embodiments, the Neusilin® of the present disclosure is S1, S2, UFL2, or US2. In some embodiments, the porous solid carrier has one or more of the following properties:

| | Grade | | | |
|---|---|---|---|---|
| | S1 (alkaline) | S2 (alkaline) | UFL2 (neutral) | US2 (neutral) |
| Mesoporosity | The average mesopore diameter ranges from 12.85 to 14.47 nm. Micropores (<1.7 nm in diameter) are also found in both excipients. | | | |
| Average Particle Size (μm) | 112 | 115 | 3.1 | 106 |
| Bulk Density (g/mL) | 0.30-0.37 | 0.29-0.37 | 0.06-0.11 | 0.13-0.18 |
| Tapped Density (g/mL) | 0.36-0.43 | 0.34-0.42 | 0.10-0.17 | 0.16-0.22 |
| Specific Surface Area ($m^2/g$) | 110 | 110 | 300 | 300 |

-continued

| | Grade | | | |
|---|---|---|---|---|
| | S1 (alkaline) | S2 (alkaline) | UFL2 (neutral) | US2 (neutral) |
| Oil Adsorbing Capacity (mL/g) | 1.3 | 1.4 | 2.7-3.4 | 2.7-3.4 |
| Angle of Repose (°) | 30 | 30 | 45 | 30 |
| pH of 4% Slurry | 8.5-10 | 8.5-10 | 6.0-8.0 | 6.0-8.0 |

*values may range by ±20% or ±10%

Cannabinoids and Other Active Agents

The term "drug substance" is used herein to refer to the active agent or mixture of active agents that are absorbed onto the porous solid carrier. In embodiments, the active agent is a cannabinoid. There are many known cannabinoids that are suitable for use in the drug-containing particles disclosed herein. In some embodiments, the cannabinoid is a natural cannabinoid. In some embodiments, the cannabinoid is a natural cannabinoid found in a Cannabis plant. In some embodiments, the cannabinoid is a synthetic cannabinoid. In some embodiments, the cannabinoid is a mixture of natural cannabinoids. In some embodiments, the cannabinoid is a mixture of synthetic cannabinoids. In some embodiments, the cannabinoid is a mixture of natural and synthetic cannabinoids. In some embodiments, the cannabinoid suitable for use in the drug-containing particle is a phytocannabinoid, endocannabinoid, synthetic cannabinoid, or combination thereof. In some embodiments, the drug-containing particles comprise one or more metabolites or synthetically-produced derivatives of the one or more cannabinoids disclosed herein.

In some embodiments, the drug-containing particles comprise one or more cannabinoids, wherein the one or more cannabinoids is cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), OH-CBD, CBD-C4, 6-OH-CBD, 7-OH-CBD, 7-COOH-CBD, 11-COOH-THC, 11-OH-THC, metabolites thereof, combinations thereof, or mixtures thereof.

In some embodiments, the drug-containing particles comprise one or more cannabinoids, wherein the one or more cannabinoids is cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), CBD-C4, combinations thereof, or mixtures thereof. In some embodiments, the one or more cannabinoids is cannabidiol (CBD), cannabidivarin (CBDV), tetrahydrocannabivarin (THCV), cannabigerol (CBG), cannabidiolic acid (CBDA), combinations thereof, or mixtures thereof. In some embodiments, the one of more cannabinoids is CBD.

The drug-containing particle of the present disclosure may also comprise at least one cannabinoid selected from those disclosed in Handbook of Cannabis, Roger Pertwee, Chapter 1, pages 3 to 15.

In some embodiments, the one or more cannabinoids are extracted from a Cannabis plants, and the resulting extract may include additional components extracted from Cannabis plants. Such components may include, but are not limited to, terpenes and sterols.

In some embodiments, the drug-containing particles comprise one or more terpenes. In embodiments, the terpenes comprise one or more sesquiterpenes. Non-limiting examples of terpenes and sesquiterpenes include, but are not limited to, beta-farnesene, selina-3,7 (11)-diene, guaia-3,9-diene, trans-caryophyllene, alpha-caryophyllene, trans-nerolidol, myrcene, trans-phytol, squalene, α-bisabolol, α-tocopherol, or a combination thereof.

In some embodiments, the drug-containing particles comprise one or more sterols, including but not limited to beta-sitosterol, beta-amyrin, campesterol, lupeol, or a combination thereof.

Accordingly, in embodiments, the drug-containing particles described herein comprise CBD, THC, CBDA, CBDV, CBN, CBC, mono-methylated CBG (CBG MME), CBD-C1, CBD-C4, THCV, CBG, OH-CBD, CBL, DHC, and/or various terpenes and sterols described herein (e.g., alpha-bergmatone, alpha-bisbolol, beta-farnesene, selina-3,7(11)-diene, guaia-3,9-diene, trans-caryophyllene, alpha-caryophyllene, trans-nerolidol, myrcene, trans-phytol, squalene, alpha-tocopherol, beta-sitosterol, beta-amyrin, campesterol, lupeol, or combinations thereof.

In some embodiments, the drug-containing particles comprise a drug substance comprising a mixture of CBD, trans-THC, CBC, CBG, CBDV, CBD-C4, cis-THC, terpenes, triglycerides and sterols. In some embodiments, the drug substance comprises 70-100% w/w cannabinoids, 1.0-3.0% w/w terpenes, 0.8-3.0% w/w triglycerides, and/or 0.5-2.0% w/w sterols based on the total weight of the drug substance.

In some embodiments, the mixture comprises the following cannabinoids:

| | |
|---|---|
| CBD | 65-95% w/w |
| trans-THC | 0.4-3.0% w/w |
| CBC | 1.0-4.0% w/w |
| CBG | 0.2-4.0% w/w |
| CBDV | 0.2-1.4% w/w |
| CBD-C4 | 0.1-0.8% w/w |
| Cis-THC | 0.1-1.6% w/w |

In some embodiments, the drug-containing particles comprise a drug substance comprising a mixture of the following cannabinoids based on the total weight of the drub substance:

| | |
|---|---|
| CBD | 99% w/w |
| CBDA | NMT 0.15% w/w |
| CBDV | NMT 1.0% w/w |
| $\Delta^9$ THC | NMT 0.15% w/w |
| CBD-C4 | NMT (0.5% w/w |

In some embodiments, the drug-containing particles comprise nabilone. Nabilone, sold under the brand name Cesamet, consists of a racemic mixture of the following two compounds:

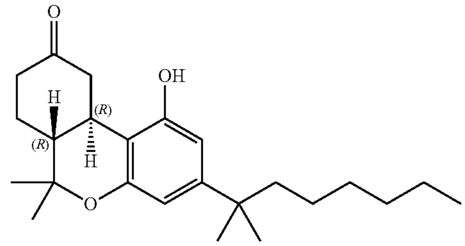

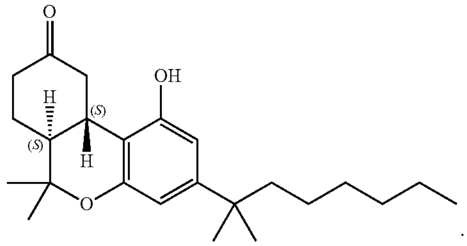

.

In some embodiments, the drug-containing particles comprise:

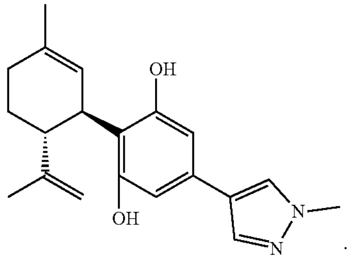 [SMILES: C=C(C)[C@@H]1CCC(C)=C[C@H]1c1c(O)cc(-c2cnn(C)c2)cc1O]

.

or salt thereof. This compound and its therapeutic utility are described in WO 2022/129908, which is incorporated herein by reference in its entirety.

The drug-containing particles of the present disclosure can comprise one or more cannabinoid-containing plant extracts (e.g., nabiximols), described in WO 2007/083098, which is incorporated herein by reference in its entirety. In some embodiments, the drug-containing particles comprise nabiximols. Nabiximols, known also by its trade name Sativex, is available as an oromucosal spray comprising 27 mg of THC, 25 mg of CBD, and lesser amounts of other cannabinoids per milliliter. Nabiximols has been used to treat spasticity, neuropathic pain, and other symptoms of multiple sclerosis.

Table A below provides the structure of certain cannabinoids, terpenes, and sterols along with their standard abbreviations that may be included in the drug-containing particles disclosed herein. The table below is not exhaustive and merely details the cannabinoids and other potential components of the drug-containing particles, which are identified in the present application for reference.

TABLE A
| Non-limiting examples of cannabinoids, sterols, and terpenes, and their abbreviations. |
| --- |
| 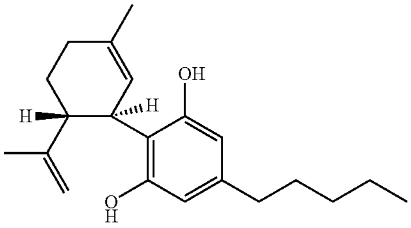 [SMILES: C=C(C)[C@@H]1CCC(C)=C[C@H]1c1c(O)cc(CCCCC)cc1O] |
| Cannabidiol (CBD) |
| 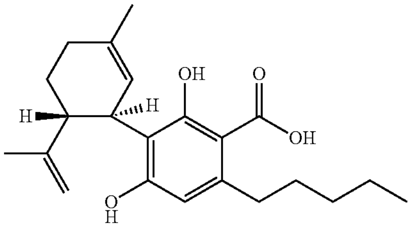 [SMILES: C=C(C)[C@@H]1CCC(C)=C[C@H]1c1c(O)cc(CCCCC)c(C(=O)O)c1O] |
| Cannabidiolic acid (CBDA) |
| 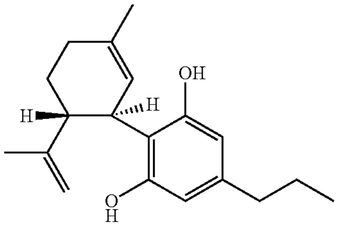 [SMILES: C=C(C)[C@@H]1CCC(C)=C[C@H]1c1c(O)cc(CCC)cc1O] |
| Cannabidivarin (CBDV) |
| 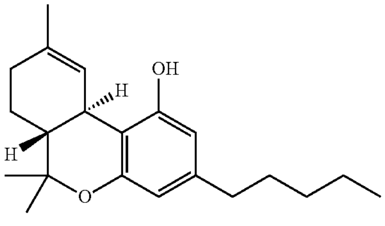 [SMILES: CCCCCc1cc(O)c2c(c1)OC(C)(C)[C@@H]1CCC(C)=C[C@@H]21] |
| trans-Tetrahydrocannabinol (THC) |
| 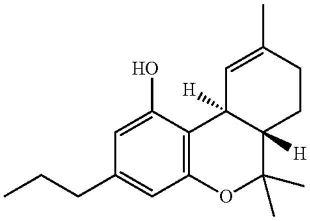 [SMILES: CCCc1cc(O)c2c(c1)OC(C)(C)[C@H]1CCC(C)=C[C@H]21] |
| Tetrahydrocannabivarin (THCV) |

TABLE A-continued
| Non-limiting examples of cannabinoids, sterols, and terpenes, and their abbreviations. |
| --- |
| 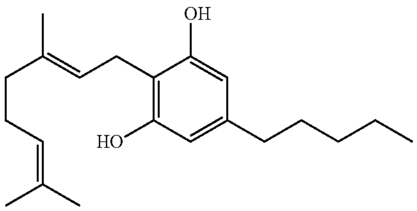 [SMILES: CCCCCc1cc(O)c(C/C=C(\C)CCC=C(C)C)c(O)c1] |
| Cannabigerol (CBG) |
| 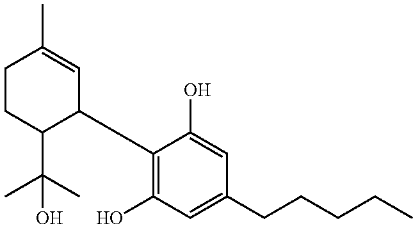 [SMILES: CCCCCc1cc(O)c(C2C=C(C)CCC2C(C)(C)O)c(O)c1] |
| OH-CBD (hydroxy cannabidiol) |
| 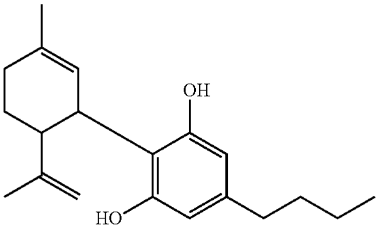 [SMILES: C=C(C)C1CCC(C)=CC1c1c(O)cc(CCCC)cc1O] |
| Butyl-cannabidiol (CBD-C4) |
| 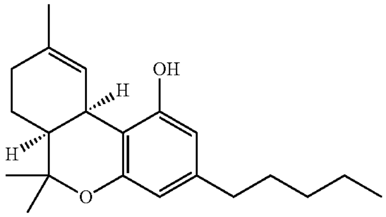 [SMILES: CCCCCc1cc(O)c2c(c1)OC(C)(C)[C@H]1CCC(C)=C[C@@H]21] |
| cis-THC (cis-Tetrahydrocannabinol) |
| 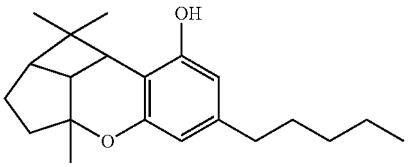 [SMILES: CCCCCc1cc(O)c2c(c1)OC1(C)CCC3C1C2C3(C)C] |
| CBL (Cannabicyclol) |
| 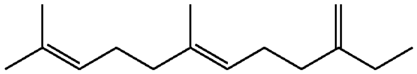 |
| Beta-Farnesene |

TABLE A-continued
Non-limiting examples of cannabinoids, sterols, and terpenes, and their abbreviations.
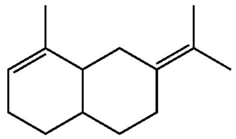
Selina-3,7(11)-diene
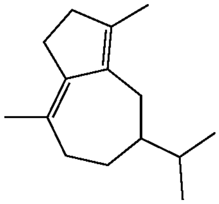
Guaia-3,9-diene
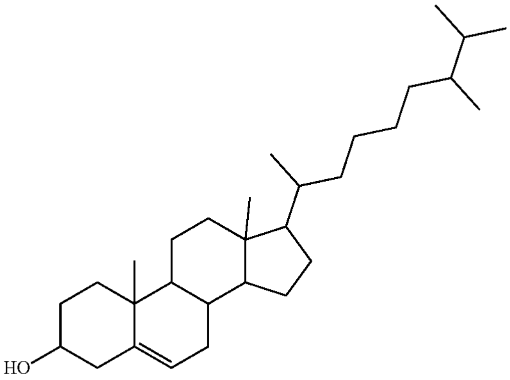 [SMILES: CC(C)C(C)CCCCC(C)C1CCC2C3CC=C4CC(O)CCC4(C)C3CCC12C]
Campesterol
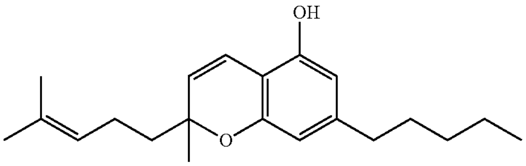 [SMILES: CCCCCc1cc(O)c2c(c1)OC(C)(CCC=C(C)C)C=C2]
Cannabichromene (CBC)
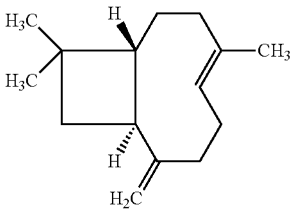
Trans-caryophyllene TABLE A-continued
| Non-limiting examples of cannabinoids, sterols, and terpenes, and their abbreviations. |
| --- |
| 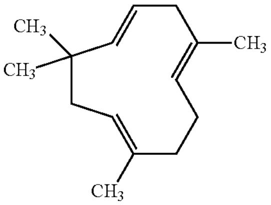 |
| alpha-Caryophyllene |
| 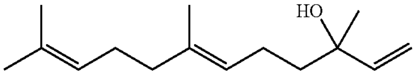 [SMILES: C=CC(C)(O)CC/C=C(\C)CCC=C(C)C] |
| Trans-nerolidol |
| 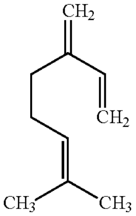 |
| Myrcene |
| 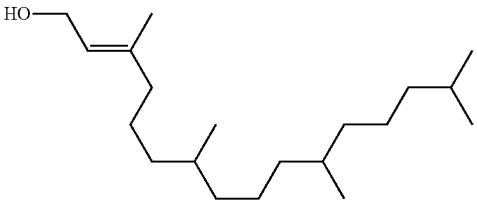 [SMILES: C/C(=C\CO)CCCC(C)CCCC(C)CCCC(C)C] |
| Trans-phytol |
| 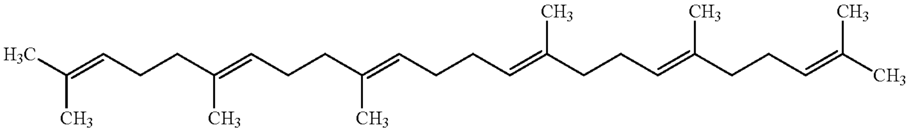 [SMILES: CC(C)=CCC/C(C)=C/CC/C(C)=C/CC/C=C(\C)CC/C=C(\C)CCC=C(C)C] |
| Squalene |
| 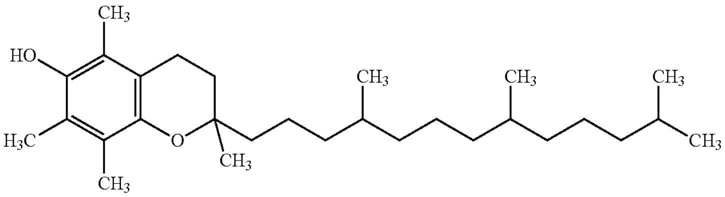 [SMILES: Cc1c(C)c2c(c(C)c1O)CCC(C)(CCCC(C)CCCC(C)CCCC(C)C)O2] |
| alpha-Tocopherol |

TABLE A-continued
| Non-limiting examples of cannabinoids, sterols, and terpenes, and their abbreviations. |
| --- |
| 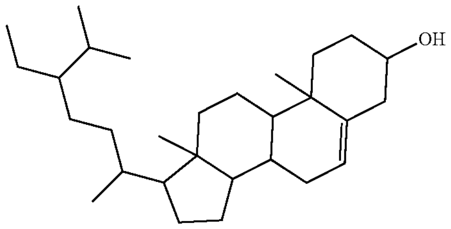 [SMILES: CCC(CCC(C)C1CCC2C3CC=C4CC(O)CCC4(C)C3CCC12C)C(C)C] |
| beta-Sitosterol |
| 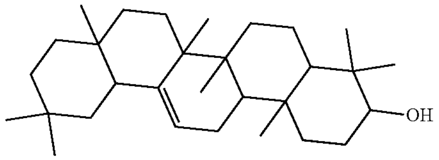 |
| beta-Amyrin |
| 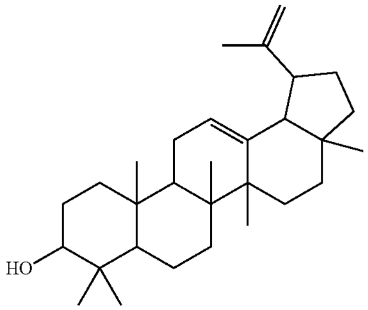 |
| Lupeol |
| 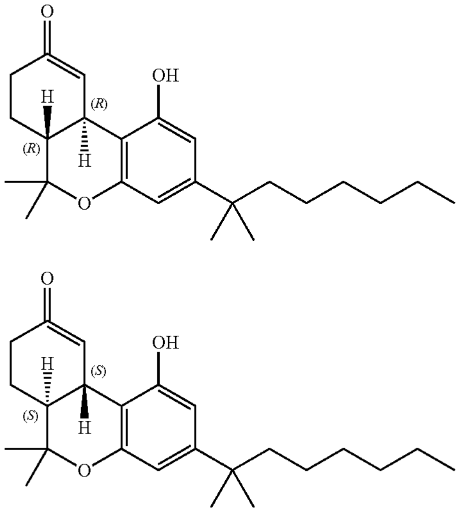 |
| Nabilone (1:1) |
All metabolites and prodrugs of THC, CBD and the remaining cannabinoids are contemplated to be included within this disclosure. Table B shows the structures of certain metabolites of CBD and THC.

TABLE B

Structures of 11-COOH-THC, 11-OH-THC, 7-OH-CBD, 6-OH-CBD, and 7-COOH-CBD.

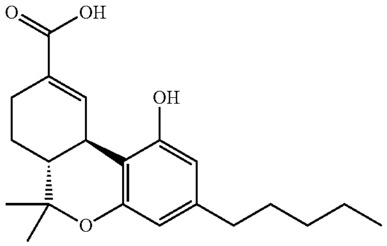 [SMILES: CCCCCc1cc(O)c2c(c1)OC(C)(C)[C@@H]1CCC(C(=O)O)=C[C@@H]21]

11-COOH-THC

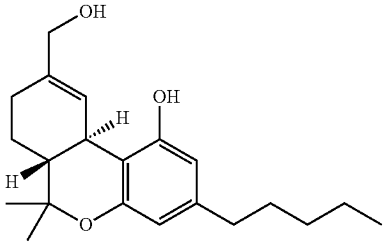 [SMILES: CCCCCc1cc(O)c2c(c1)OC(C)(C)[C@@H]1CCC(CO)=C[C@@H]21]

11-OH-THC

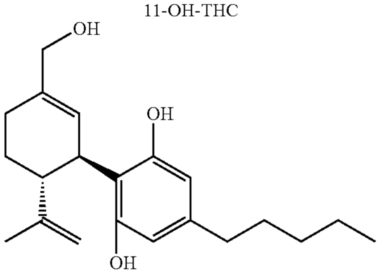

7-OH-CBD

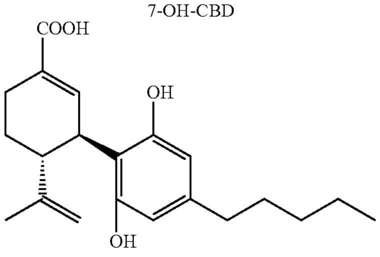

7-COOH-CBD

TABLE B-continued

Structures of 11-COOH-THC, 11-OH-THC, 7-OH-CBD, 6-OH-CBD, and 7-COOH-CBD.

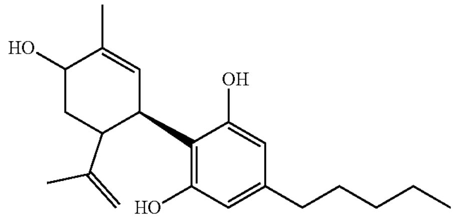 [SMILES: C=C(C)C1CC(O)C(C)=C[C@H]1c1c(O)cc(CCCCC)cc1O]

6-OH-CBD

In embodiments, the drug-containing particles comprise one of the compositions from Table C or Table D:

TABLE C

| Components | Specification Limits | DS-A (% w/w) | DS-B (% w/w) |
|---|---|---|---|
| Total cannabinoids | 76.0-100.0 | 84.6-92.0 | 76.9-82.9 |
| CBD | 68.0-94.0 | 77.4-83.6 | 69.5-75.2 |
| CBD-C4 | 0.2-0.8 | 0.3 | 0.3-0.4 |
| CBDV | 0.2-1.4 | 0.4-0.7 | 0.6-0.7 |
| CBG | 0.2-4.0 | 0.9-1.5 | 0.5-0.6 |
| Cis-THC | 0.2-1.6 | 0.6-0.9 | 0.6-0.7 |
| Trans-THC | 0.4-3.0 | 1.8-1.9 | 1.3-1.5 |
| CBC | 1.0-4.0 | 1.7-2.3 | 1.5-1.8 |
| Total terpenes | 1.0-3.0 | 2.0-2.8 | 4.7-7.3 |
| Total triglycerides | 0.8-3.0 | 1.6-2.6 | N/A |
| Total sterols | 0.5-2.0 | 1.0-1.7 | 0.7-1.5 |

TABLE D

| Component | DS-C | DS-D | DS-E | DS-F |
|---|---|---|---|---|
| CBD | 75.3% w/w | 73.62% w/w | 78.06% w/w | 69.5-83.6% w/w |
| Trans-THC | 1.6% w/w | 1.55% w/w | 0.89% w/w | 1.3-1.9% w/w |
| CBC | 1.9% w/w | 1.72% w/w | 1.86% w/w | 1.5-2.3% w/w |
| CBG | 0.9% w/w | 0.74% w/w | 1.02% w/w | 0.5-1.5% w/w |
| CBDV | 0.4% w/w | 0.36% w/w | 0.63% w/w | 0.4-0.7% w/w |
| CBD-C4 | 0.2% w/w | 0.20% w/w | 0.28% w/w | 0.3-0.4% w/w |
| Total cannabinoids | 82.6% w/w | 80.13% w/w | 85.08% w/w | 76.9-92.0% w/w |

When a combination or mixture of cannabinoids is present in the drug-containing particles of the present disclosure, the combination or mixture may include any suitable ratio of the cannabinoids. By way of example, in some embodiments, the drug-containing particles include about a 100:1, 90:1, 80:1, 70:1, 60:1, 50:1, 45:1, 40:1, 35:1, 30:1, 25:1, 20:1, 15:1, 10:1, 9:1, 8:1, 7:1, 6:1, 5:1, 4:1, 3:1, 2:1, or 1:1 ratio of two cannabinoids disclosed herein.

The one or more cannabinoids may be present in any amount in which the cannabinoids are amorphous when adsorbed onto the porous solid carrier. In some embodiments, the one or more cannabinoids is present in an amount ranging from about 1% to about 75% by weight based on the total weight of the drug-containing particle, e.g., about 1%, about 2.5%, about 5%, about 7.5%, about 10%, about 12.5%, about 15%, about 17.5%, about 20%, about 22.5%, about 25%, about 27.5%, about 30%, about 32.5%, about 35%, about 37.5%, about 40%, about 42.5%, about 45%, about 47.5%, about 50%, about 52.5%, about 55%, about 57.5%, about 60%, about 62.5%, about 65%, about 67.5%, about 70%, about 72.5%, or about 75% by weight based on the total weight of the drug-containing particle, including all ranges and values therebetween. In some embodiments, the one or more cannabinoids is present in an amount ranging from about 5% to about 75%, about 5% to about 60%, about 5% to about 50%, about 10% to about 75%, about 10% to about 60%, about 10% to about 50%, about 15% to about 75%, about 15% to about 60%, about 15% to about 50%, about 20% to about 75%, about 20% to about 60%, about 20% to about 50%; about 25% to about 75%, about 25% to about 60%, about 25% to about 50%; about 30% to about 75%, about 30% to about 60%, about 30% to about 50%, about 35% to about 75%, about 35% to about 60%, about 35% to about 50%, about 40% to about 75%, about 40% to about 60%, or about 40% to about 50% by weight based on the total weight of the drug-containing particle, including all ranges and values therebetween. In some embodiments, the one or more cannabinoids is present in an amount ranging from about 5% to about 75% by weight based on the total weight of the drug-containing particle. In some embodiments, the one or more cannabinoids is present in an amount ranging from about 10% to about 60% by weight based on the total weight of the drug-containing particle. In some embodiments, the one or more cannabinoids is present in an amount ranging from about 25% to about 50% by weight based on the total weight of the drug-containing particle. In some embodiments, the one or more cannabinoids is present in an amount ranging from about 15% to about 40% by weight based on the total weight of the drug-containing particle.

In some embodiments, substantially all of the one or more cannabinoids is present in the pores and/or surface of the porous solid carrier. In some embodiments, substantially all of the one or more cannabinoids is present within the pores of the porous solid carrier. Substantially, in the present context, can refer to about 70%, about 75%, about 80%, about 85%, about 90%, about 95, or about 99% of the one or more cannabinoids being present in the pores and/or surface of the porous solid carrier. In some embodiments, greater than about 70%, greater than about 75%, greater than about 80%, greater than about 85%, greater than about 90%, greater than about 95%, or greater than about 99% of the one or more cannabinoids being present in the pores of the porous solid carrier.

In some embodiments, the one or more cannabinoids is present in an amorphous form. In some embodiments, adsorption of an amorphous form of the one or more cannabinoids onto and/or into the porous solid carrier is determined by scanning electron microscopy (SEM), differential scanning calorimetry (DSC), and/or x-ray powder diffraction (XRPD). Without being bound by any particular theory, the porous solid carriers of the present disclosure can be optimized to stabilize the amorphous form of the one or more cannabinoids with the pores, which is desirable to achieve the targeted drug-release profile.

In some embodiments, the drug-containing particle comprising the one or more cannabinoids is substantially free of cannabidiorcol (CBD-C1), cannabidivarin (CBDV), and/or cannabidibutol (CBD-C4). In some embodiments, the drug-containing particle comprises no more than about 0.5% by weight of active of CBD-C1. In some embodiments, the drug-containing particle comprises no more than about 0.5% by weight of active of CBDV. In some embodiments, the drug-containing particle comprises no more than about 0.2% by weight of active of CBD-C4.

Lipophilic Materials

In some embodiments, the drug-containing particles further comprise one or more lipophilic materials. In embodiments, the drug-containing particles comprise one lipophilic material. In embodiments, the drug-containing particles comprise a combination of two lipophilic materials. In embodiments, the drug-containing particles comprise a combination of three lipophilic materials.

In embodiments in which the drug-containing particles comprise two lipophilic materials, the ratio of the first lipophilic material to the second lipophilic material ranges from about 90:10 to about 10:90, including about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, or about 10:90, inclusive of all values and ranges therebetween.

In embodiments in which the drug-containing particles comprise three lipophilic materials, the ratio of the first lipophilic material to the second lipophilic material to the third lipophilic material ranges from about 98:1:1 to 1:1:98, including 90:1:9, 85:1:14, 80:10:10, 70:15:15; 70:10:20, 60:20:20, 50:25:25; 40:30:30; 30:20:40; 20:10:70; 10:10:80 and 9:1:90, inclusive of all ranges and subranges therebetween.

Hydrophilic-lipophilic balance ("HLB") values refers to the balance of the size and strength of the hydrophilic and lipophilic moieties of a surfactant molecule. HLB values are reported on a scale that ranges from 0-20. Lower HLB values are an indication of high oil affinity (lipophilicity). High HLB values indicate high water-solubility (hydrophilicity). In embodiments, the lipophilic material has a HLB of 1, 2, 3, 4, 5, 6, 7, 8, 9, 10, 11, 12, 13, 14, 15, 16, 17, 18, 19, or 20. In embodiment, the lipophilic material has an HLB value ranging from 1-10 or 10-20. In embodiments, the lipophilic material has an HLB value ranging from 1-3, 4-6, 7-10, 11-14, 15-20. In embodiments, the lipophilic material has an HLB value ranging from 11-15.

Non-limiting examples of lipophilic materials which are useful in the drug-containing particles disclosed herein include pharmaceutically acceptable fats, fatty substances, oils (including vegetable and fruit derived seed/kernel oils), phospholipids, sterols, and waxes. Fats generally refer to esters of glycerol (e.g., mono-, di- or triesters of glycerol and saturated and unsaturated fatty acids). Suitable fats and fatty substances include but not limited to fatty alcohols, including short, medium, and long chain fatty alcohols (such as lauryl, myristyl, stearyl, cetyl or cetostearyl alcohol, etc.), fatty acids and derivatives, including but not limited to fatty acid esters, fatty acid glycerides (mono-, di- and tri-glycerides), and hydrogenated fats. Fats may be either solid or liquid at normal room temperature, depending on their structure and composition.

Suitable oils include pharmaceutically acceptable animal (e.g., fatty acid esters), mineral (e.g., paraffin oils), vegetable (e.g., vegetable and fruit oils), or synthetic hydrocarbons that are liquid at room temperature. Examples of pharmaceutically acceptable oils include but are not limited to: mineral oils such as paraffin oils; vegetable oils such as castor oils, hydrogenated vegetable oil, sesame oil, kernel oil, soybean oil, safflower oil, corn oil, olive oil, cottonseed oil, *arachis* oil, sunflower seed oil, palm oil, pumpkin seed oil, rapeseed oil, and peanut oils; and animal oils and fats such as triglycerides and butters. Partially hydrogenated vegetable oils are derived from natural products and generally comprise a mixture of glycerides of $C_{14-20}$ fatty acids, such as palmitic and stearic acids. Suitable examples of partially hydrogenated vegetable oils include partially hydrogenated cottonseed oil, soybean oil, corn oil, peanut oil, palm oil, sunflower seed oil or mixtures thereof. Chemical equivalents of partially hydrogenated vegetable oils include synthetically produced glycerides of $C_{14-20}$ fatty acids having the same properties as the naturally derived products as hereinbefore described.

Suitable phospholipids include pharmaceutically acceptable plant, animal, and synthetic phospholipids. Examples of pharmaceutically acceptable phospholipids include egg lecithin, soybean lecithin, vegetable lecithin, cholines, phosphatidylethanolamine, and phosphatidylglycerols, such as, but not limited to, phosphatidylcholine, 1,2-dierucoylphosphatidylcholine, 1,2-dimyristoylphosphatidylcholine, 1,2-dioleoylphosphatidylcholine, 1,2-dioleoylphosphatidylserine, 1,2-distearoylphosphatidylglycerol, 1,2-dipalmitoylphosphatidylcholine, 1,2-distearoylphosphatidylcholine, 1,2-distearoylphosphatidylglycerol, egg phosphatidylcholine, egg phosphatidylglycerol, soy phosphatidylcholine, glycerophosphocholine, hydrogenated soybean phosphatidylcholine, lysophosphatidylcholine, lysophosphatidylethanolamine, N-(carbonyl-methoxypolyethylene glycol 2000)-1,2-distearoylphosphatidylethanolamine sodium salt, muramyltripeptide-phosphatidylethanolamine, 1-palmitoyl-2-linoleoylphosphatidylcholine, 1-palmitoyl-2-linoleoylphosphatidylglycerol, 1-palmitoyl-2-oleoylphosphatidylcholine, 1-palmitoyl-2-oleoylphosphatidylglycerol, polyenylphosphatidylcholine, 1-palmitoyl-2-stearoylphosphatidylcholine, 1-palmitoyl-2-stearoylphosphatidylglycerol, 1-stearoyl-2-linoleoylphosphatidylcholine, 1-stearoyl-2-linoleoylphosphatidylglycerol, sphingomyelin, 1-stearoyl-2-oleoyl phosphatidylcholine, 1-stearoyl-2-oleoyl phosphatidylglycerol, sodium taurocholic acid, 1,2-diacyl-sn-glycero-3-phosphocholine, 2-dipalmitoyl-sn-glycero-3-phosphocholine, 1,2-distearoyl-sn-glycero-3-phosphocholine, 1-plamitoyl-2-stearoyl-sn-glycero-3-phosphocholine, and the like.

Suitable waxes include animal waxes, plant waxes, mineral waxes, and petroleum waxes. Examples of waxes include, but are not limited to, glyceryl behenate, glyceryl monostearate, stearic acid, palmitic acid, lauric acid, carnauba wax, cetyl alcohol, glyceryl stearate beeswax, paraffin wax, ozokerite, candelilla wax, cetyl alcohol, stearyl alcohol, spermaceti, carnauba wax, bayberry wax, montan, ceresin, and microcrystalline waxes.

In some embodiments, lipohilic materials suitable for use in the drug-containing particles disclosed herein include fatty acid glycerol esters, polyethylene oxide-containing fatty acid esters, and combinations thereof.

In some embodiments, the drug-containing particles of the present disclosure include one or more fatty acid glycerol esters. As used herein the term "fatty acid glycerol esters" refers to esters formed between glycerol and one or more fatty acids including mono-, di-, and triesters (i.e., glycerides). Suitable fatty acids include saturated and unsaturated fatty acids having from eight (8) to twenty-two (22) carbons atoms (i.e., C8-C22 fatty acids). In certain embodiments, suitable fatty acids include C12-C18 fatty acids. The fatty acid glycerol esters useful in the formulations can be provided by commercially available sources. A representative source for the fatty acid glycerol esters is a mixture of mono-, di-, and triesters commercially available as PECEOL® (Gattefosse, Saint Priest Cedex, France), commonly referred to as "glyceryl oleate" or "glyceryl monooleate." In some embodiments, when PECEOL® is used as the source of fatty acid glycerol esters in the formulations, the fatty acid glycerol esters comprise from about 32% to about 52% by weight fatty acid monoglycerides, from about 30% to about 50% by weight fatty acid diglycerides, and from about 5 to about 20% by weight fatty acid triglycerides. The fatty acid glycerol esters comprise greater than about 60% by weight oleic acid (C18:1) mono-, di-, and triglycerides. Other fatty acid glycerol esters include esters of palmitic acid (C16) (less than about 12%), stearic acid (C18) (less than about 6%), linoleic acid (C18:2) (less than about 35%), linolenic acid (C18:3) (less than about 2%), arachidic acid (C20) (less than about 2%), and eicosanoic acid (C20:1) (less than about 2%). PECEOL® can also include free glycerol (typically about 1%). In one embodiment, the fatty acid glycerol esters comprise about 44% by weight fatty acid monoglycerides, about 45% by weight fatty acid diglycerides, and about 9% by weight fatty acid triglycerides, and the fatty acid glycerol esters comprise about 75% by weight oleic acid (C18:1) mono-, di-, and triglycerides. Other fatty acid glycerol esters include esters of palmitic acid (C16) (about 4%), stearic acid (C18:0) (about 2%), linoleic acid (C18:2) (about 12%), linolenic acid (C18:3) (less than 1%), arachidic acid (C20) (less than 1%), and eicosanoic acid (C20:1) (less than 1%).

In other embodiments, the formulation may include a mixture fatty acid glycerol ester, for example any of those disclosed herein. In still other embodiments, one or more fatty acid glycerol ester may be used in combination with other lipophilic materials as described herein, such one or more polyethylene oxide-containing fatty acid esters as described herein.

In some embodiments, the drug-containing particles described herein comprise at least one polyethylene oxide-containing lipophilic material, such as polyethylene oxide-containing fatty acid esters. As used herein, the term "polyethylene oxide-containing fatty acid ester" refers to a fatty acid ester that includes a polyethylene oxide group (i.e., also known as a polyethylene glycol group) covalently coupled to the fatty acid through an ester bond. Polyethylene oxide-containing fatty acid esters include mono- and di-fatty acid esters of polyethylene glycol (PEG). Suitable polyethylene oxide-containing fatty acid esters are derived from fatty acids including saturated and unsaturated fatty acids having from eight (8) to twenty-two (22) carbons atoms (i.e., a polyethylene oxide ester of a C8-C22 fatty acid). In certain embodiments, suitable polyethylene oxide-containing fatty acid esters are derived from fatty acids including saturated and unsaturated fatty acids having from twelve (12) to eighteen (18) carbons atoms (i.e., a polyethylene oxide ester of a C12-C18 fatty acid). Representative polyethylene oxide-containing fatty acid esters include saturated C8-C22 fatty acid esters. In certain embodiments, suitable polyethylene oxide-containing fatty acid esters include saturated C12-C18 fatty acids.

The molecular weight of the polyethylene oxide group of the polyethylene oxide-containing fatty acid ester can be varied to optimize the solubility of the therapeutic agent in the drug-containing particles. Representative average molecular weights for the polyethylene oxide groups can be from about 350 to about 6000. In one embodiment, the average molecular weight for the polyethylene oxide group is about 1500, about 2000, about 4000, about 6000, including any values or ranges therebetween. In one embodiment, the average molecular weight for the polyethylene oxide group is about 1500.

In some embodiments, when the drug-containing particles include a polyethylene oxide-containing fatty acid in the lipophilic material, the lipophilic material may include only one type of polyethylene oxide-containing fatty acid. In other embodiments, the polyethylene oxide-containing fatty acid in the lipophilic material may include a mixture of polyethylene oxide-containing fatty acid esters (mono- and di-fatty acid esters of PEG). In embodiments, the polyethylene oxide-containing fatty acid ester is an ester of caproic acid (C6), caprylic acid (C8), capric acid (C10), lauric acid (C12), palmitic acid (C16), stearic acid (C18), oleic acid (C18:1), linoleic acid (C18:2), linolenic acid (C18:3), arachidic acid (C20), eicosenoic acid (C20:1), or behenic acid (C22). In embodiments, the polyethylene oxide-containing fatty acid ester is a lauric acid ester, a palmitic acid ester, or a stearic acid ester (i.e., mono- and di-lauric acid esters of polyethylene glycol, mono- and di-palmitic acid esters of PEG, mono- and di-stearic acid esters of PEG). Mixtures of these esters can also be used.

The polyethylene oxide-containing fatty acid esters useful in the formulations of the present disclosure can be provided by commercially available sources. Representative polyethylene oxide-containing fatty acid esters (mixtures of mono- and diesters) are commercially available under the designation GELUCIRE® (Gattefosse, Saint Priest Cedex, France).

In embodiments, the lipophilic material of the present disclosure comprises polyethylene oxide-containing fatty acid ester, polyethylene oxide glyceride, polypropylene glycol fatty acid ester, PEG, monoglyceride fatty acid ester, diglyceride fatty acid ester, triglyceride fatty acid ester, propylene glycol diglyceride, polyethylene oxide vegetable oil, or a combination thereof.

In some embodiments, the lipophilic material comprises: 1) saturated or unsaturated C8-C22 fatty acid monoglyceride; 2) saturated or unsaturated C8-C22 fatty acid diglyceride; 3) saturated or unsaturated C8-C22 fatty acid triglyceride; 4) polyethylene glycol (PEG); 5) PEG-fatty acid (C8-C22) monoester; 6) PEG-fatty acid (C8-C22) diester, or any combinations thereof. In some embodiments, the lipophilic material comprises monoglyceride, diglyceride, and/or triglyceride ester of C6-C18 fatty acid. In some embodiments, the lipophilic material comprises polyethylene glycol (e.g., PEG-4, PEG-6, PEG-7, PEG-8, PEG-32, PEG-75, PEG-100, PEG-150, PEG-14M, or PEG-20M). In some embodiments, the lipophilic material comprises polyethylene glycol-containing C8-C22 fatty acid. In some embodiments, the lipophilic material comprises polyethylene glycol-containing C8-C22 fatty acid monoester. In some embodiments, the lipophilic material comprises polyethylene glycol-containing C8-C22 fatty acid diester. In some embodiments, the lipophilic material comprises mono-, di-, or triglyceride and a polyethylene glycol described herein. In some embodiments, the lipophilic material comprises mono-, di-, and triglycerides and polyethylene glycol-containing fatty acid monoesters described herein. In some embodiments, the lipophilic material comprises mono-, di-, and triglycerides and polyethylene glycol-containing fatty acid diesters described herein. In embodiments, the lipophilic material comprises any combination of components described in this paragraph.

In some embodiments, the one or more lipophilic material in the drug-containing particle comprises one or more polyethylene oxide-containing fatty acid ester. In some embodiments, the one or more lipophilic material in the drug-containing particle one or more comprises glyceride fatty acid ester. In some embodiments, the polyethylene oxide-containing fatty acid ester or glyceride fatty acid ester comprises one more fatty acid resides. In embodiments, the fatty acid residue comprises a residue of C6-C22 fatty acid, for example, C6-C20 fatty acid, C8-C20 fatty acid, C8-C18 fatty acid, C8-C16 fatty acid, C8-C14 fatty acid, C8-12 fatty acid, C8-C10 fatty acid, including any values or ranges therebetween. In embodiments, the fatty acid residue comprises a residue of C8-C20 fatty acid. In some embodiments, the C6-C20 fatty acid comprises a residue of caproic acid (C6), caprylic acid (C8), capric acid (C10), lauric acid (C12), palmitic acid (C16), stearic acid (C18), oleic acid (C18:1), linoleic acid (C18:2), linolenic acid (C18:3), arachidic acid (C20), eicosenoic acid (C20:1), or behenic acid (C22). In some embodiments, the C8-C20 fatty acid comprises a residue of caprylic acid (C8), capric acid (C10), lauric acid (C12), palmitic acid (C16), stearic acid (C18), or arachidic acid (C20). In some embodiments, the one or more lipophilic material in the drug-containing particle comprises polyethylene glycol derivatives of vegetable oil. In some embodiments, the one or more lipophilic material in the drug-containing particle comprises C8-C20 monoglyceride. In some embodiments, the one or more lipophilic material in the drug-containing particle comprises C8-C20 diglyceride. In some embodiments, the one or more lipophilic material in the drug-containing particle comprises C8-C20 triglyceride.

In some embodiments, the lipophilic material comprises stearoyl polyoxyl glyceride, stearoyl polyethylene oxide, lauroyl polyoxyl glyceride, oleoyl polyoxyl glyceride, monoesters/diesters of hydroxystearic acid and polyethylene glycol, PEG-hydrogenated castor oil, propylene glycol monocaprylate, propylene glycol monolaurate, medium-chain triglyceride, propylene glycol dicaprolate/dicaprate, caprylocaproyl polyoxyl glyceride, or combinations thereof.

In some embodiments, the lipophilic material comprises mono-, di-, and triglyceride of fatty acid and PEG-32 (MW 1500) mono- and diester of palmitic (C16) and stearic acids (C18); mono-, di- and triglyceride ester of fatty acid (C8 to C18); mono-, di-, and triglyceride and PEG-6 (MW 300) mono- and diester of lauric (C12) and stearic (C18) acids; mono-, di-, and triglycerides and PEG-6 (MW 300) and mono- and diesters of oleic (C18:1) acids; a mixture of monoesters and diesters of 12-hydroxystearic acid and polyethylene glycol glyceride; PEG-40 hydrogenated castor oil; propylene glycol monocaprylate; propylene glycol monolaurate; medium-chain triglyceride; propylene glycol dicaprolate/dicaprate; PEG-8 (MW 400) mono- and diesters of caprylic (C8) and capric (C10) acids; or combinations thereof.

In some embodiments, the lipophilic material comprises a mixture of mono-, di-, and triglyceride esters of palmitic (C16) and stearic (C18) acids and PEG-32 (MW 1500) mono- and diester of palmitic (C16) and stearic (C18) acid (e.g., stearoyl polyoxyl-32 glyceride: GELUCIRE® 50/13); mono-, di- and triglyceride esters of fatty acid (C8 to C18)

(e.g., hard fat: GELUCIRE® 43/01); mono-, di-, and triglyceride esters of lauric (C12) and stearic (C18) acids and PEG-6 (MW 300) mono- and diesters of lauric (C12) and stearic (C18) acids (e.g., lauroyl polyoxyl-6-glyceride: LABRAFIL® M 2130); mono-, di-, and triglyceride esters of oleic (C18:1) acid and PEG-6 (MW 300) mono- and diesters of oleic (C18:1) acid (e.g., oleoyl polyoxyl-6-glyceride: LABRAFIL®1944); polyethylene glycol mono- and diesters of 12-hydroxystearic acid (e.g., CRODASOL™ HS); PEG-40 hydrogenated castor oil (e.g., CRODURET™ 40), propylene glycol monocaprylate (e.g., CAPRYOL® 90); propylene glycol monolaurate (e.g., LAUROGLYCOL® 90); medium-chain triglyceride (e.g., LABRAFAC™ lipophile WL1349, MIGLYOL® 810N); propylene glycol dicaprolate/dicaprate (e.g., LABRAFAC™ PG); PEG-8 (MW 400) mono- and diesters of caprylic ($C_8$) and capric ($C_{10}$) acids (e.g., caprylocaproyl polyoxyl-8-glyceride: LABRASOL® ALF), or combinations thereof.

In some embodiments, the one or more lipophilic materials of the present disclosure comprise polyethylene oxide-containing fatty acid esters (e.g., GELUCIRE® 44/14, GELUCIRE® 50/13, GELUCIRE® 53/10, and GELUCIRE® 48/16). The numerals in these designations refer to the melting point and hydrophilic/lipophilic balance (HLB) of these materials, respectively. GELUCIRE® 44/14, GELUCIRE® 50/13, and GELUCIRE® 53/10 are mixtures of (a) mono-, di-, and triesters of glycerol (glycerides) and (b) mono- and diesters of polyethylene glycol (macrogols). In some embodiments, the lipophilic material comprising polyethylene oxide-containing fatty acid esters further include free polyethylene glycol (e.g., PEG 1500). In embodiments, the one or more lipophilic materials of the present disclosure comprise polyglycolized glycerides that are prepared by the alcoholysis reaction of natural oils with polyethylene glycols (PEG).

GELUCIRE® 44/14 is a lauroyl polyoxyl/macrogol 32 glycerides NF/EP and comprises of a fraction of mono, di-, and triglycerides and mainly PEG-32 (MW 1500) mono- and diesters of lauric acid (C12). GELUCIRE® 50/13 is a stearoyl polyoxyl/macrogol 32 glyceride as per National formulary (NF)/European pharmacopoeia (EP) and comprises mono-, di-, and triglycerides and PEG-32 (MW 1500) mono- and diesters of palmitic (C16) and stearic acids (C18).

GELUCIRE® 43/01 is a hard fat as per European Pharmacopoeia (EP and National formulary (NF), composed of mono-, di- and triglyceride esters of fatty acids (C8 to C18).

GELUCIRE® 48/16 is a pure PEG ester. In some embodiments, the lipophilic material of the present disclosure comprises mono-, di-, and triglycerides and PEG-32 (MW 1500) mono- and diesters of palmitic (C16) and stearic acids (C18) (GELUCIRE® 50/13). In some embodiments, the lipophilic material comprises mono-, di- and triglyceride esters of fatty acids (C8 to C18) (GELUCIRE® 43/01).

Lauric acid (C12) is the predominant fatty acid component of the glycerides and polyethylene glycol esters in GELUCIRE® 44/14. GELUCIRE® 44/14 is referred to as a mixture of glyceryl dilaurate (lauric acid diester with glycerol) and PEG dilaurate (lauric acid diester with polyethylene glycol), and is commonly known as PEG-32 glyceryl laurate (Gattefosse) lauroyl macrogol-32 glycerides EP, or lauroyl polyoxylglycerides USP/NF. GELUCIRE® 44/14 includes lauric acid (C12) esters (30% to 50%), myristic acid (C14) esters (5 to 25%), palmitic acid (C16) esters (4 to 25%), stearic acid (C18) esters (5 to 35%), caprylic acid (C8) esters (less than 15%), and capric acid (C10) esters (less than 12%). GELUCIRE® 44/14 may also include free glycerol (typically less than about 1%). In a representative formulation, GELUCIRE® 44/14 includes lauric acid (C12) esters (about 47%), myristic acid (C14) esters (about 18%), palmitic acid (C16) esters (about 10%), stearic acid (C18) esters (about 11%), caprylic acid (C8) esters (about 8%), and capric acid (C10) esters (about 12%). GELUCIRE® 44/14 is produced by the reaction of hydrogenated palm kernel oil with polyethylene glycol (average molecular weight 1500). GELUCIRE® 44/14 comprises about 20% mono-, di- and, triglycerides, about 72% mono- and di-fatty acid esters of polyethylene glycol 1500, and about 8% polyethylene glycol 1500.

Palmitic acid (C16) (40-50%) and stearic acid (C18) (48-58%) are the predominant fatty acid components of the glycerides and polyethylene glycol esters in GELUCIRE® 50/13. GELUCIRE® 50/13 is known as PEG-32 glyceryl palmitostearate (Gattefosse), stearoyl macrogolglycerides EP, or stearoyl polyoxylglycerides USP/NF). GELUCIRE® 50/13 includes palmitic acid (C16) esters (40% to 50%), stearic acid (C18) esters (48 to 58%) (stearic and palmitic acid esters greater than about 90%), lauric acid (C12) esters (less than 5%), myristic acid (C14) esters (less than 5%), caprylic acid (C8) esters (less than 3%), and capric acid (C10) esters (less than 3%). GELUCIRE® 50/13 may also include free glycerol (typically less than about 1%). In a representative formulation, GELUCIRE® 50/13 includes palmitic acid (C16) esters (about 43%), stearic acid (CIS) esters (about 54%) (stearic and palmitic acid esters about 97%), lauric acid (C12) esters (less than 1%), myristic acid (C14) esters (about 1%), caprylic acid (C8) esters (less than 1%), and capric acid (C10) esters (less than 1%). GELUCIRE® 50/13 is known as PEG-32 glyceryl stearate (Gattefosse).

In some embodiments, the one or more lipophilic materials of the present disclosure comprise fatty acid diester glyceride (e.g., lauroyl macrogol-6 glyceride, also known as lauroyl polyoxyl-6 glyceride, or LABRAFIL® M2130). Exemplary fatty acid diesters glycerides include oleoyl macrogol-6 glyceride or oleoyl polyoxyl-6 glyceride (e.g., LABRAFIL® M2130, LABRAFIL® M1944), and linoleoyl macrogol-6 glyceride (also known as LABRAFIL® M2125, corn oil PEG-6 ester, or linoleoyl polyoxyl-6 glyceride). LABRAFIL® M2130 comprises mono-, di-, and triglycerides PEG-6 (MW 300) and mono- and diesters of lauric (C12) and stearic (C18) acid LABRAFIL® M1944 comprises mono-, di-, and triglycerides and PEG-6 (MW 300) and mono- and diesters of oleic (C18:1) acid. LABRAFIL® M2125 comprises of mono-, di-, and triglycerides and PEG-6 (MW 300) and mono- and diesters of linoleic (C18:2) acid. In some embodiments, the lipophilic material of the present disclosure comprises lauroyl polyoxyl-6 glyceride (LABRAFIL® M2130). In some embodiments, the lipophilic material comprises oleoyl polyethylene glycol-6 glyceride (LABRAFIL® M1944).

In some embodiments, the one or more lipophilic materials of the present disclosure comprise a mixture of monoesters and diesters of 12-hydroxystearic acid and polyethylene glycol (CRODASOL™ HS HP), multi-compendial mixture of caprylocaproyl polyethylene glycol glyceride (CRODASOL™ CCMG 400), polysorbate 20 (and) PEG-25 hydrogenated castor oil and propylene glycol (CRODASOL™ PHC), PEG-6 caprylic/capric glyceride and PEG-60 almond glyceride (CRODASOL™ AC), or a combination thereof. In some embodiments, the one or more lipophilic materials is a mixture of monoesters/diesters of 12-hydroxystearic acid and polyethylene glycol (CRODASOL™ HS HP).

In some embodiments, the one or more lipophilic materials of the present disclosure comprise a vegetable-derived, ethoxylated nonionic surfactant (e.g., PEG-40 hydrogenated castor oil, also known as CRODURET™). In embodiments, the one or more lipophilic materials comprise PEG-40 hydrogenated castor oil (CRODURET™ 40), PEG-50 hydrogenated castor oil (CRODURET™ 50), PEG-60 hydrogenated castor oil (CRODURET™ 60), PEG-7 hydrogenated castor oil (CRODURET™ 7), or a mixture thereof. In embodiments, the one or more lipophilic materials comprise PEG-40 hydrogenated castor oil (CRODURET™ 40).

In some embodiments, the one or more lipophilic materials of the present disclosure comprise propylene glycol monocaprylate (e.g., CAPRYOL® 90, propylene glycol esters of caprylic acid (C8)).

In some embodiments, the one or more lipophilic materials of the present disclosure comprise propylene glycol laurate (e.g., LAUROGLYCOL® 90 or LAUROGLYCOL FCC also known as propylene glycol monolaurate). In embodiments, the propylene glycol laurate is a mixture of mono and diesters of lauric acid. In embodiments, the propylene glycol laurate comprises a ratio of monoesters to esters of about 90:10. In embodiments, the lipophilic material comprising propylene glycol laurate may also contain esters of caprylic acid, capric acid myristic acid, and/or palmitic acid.

In some embodiments, the one or more lipophilic materials of the present disclosure comprise caprylocaproyl polyoxyl-8 glyceride (e.g., LABRASOL® ALF). In embodiments, such glycerides comprise PEG-8 (MW 400) mono- and diesters of caprylic ($C_8$) and capric ($C_{10}$) acids. In embodiments, the glycerides comprise mono-, di- and triglycerides of caprylic ($C_8$) and capric ($C_{10}$) acids.

In embodiments, the drug-containing particle comprises one or more triglycerides. The triglyceride may be short-chain, medium-chain, long-chain triglyceride, or very long-chain triglyceride, or any combination thereof, or any combination of short-chain triglycerides, or any combination of medium-chain triglycerides, any combination of long-chain triglycerides, or any combination of very long-chain triglycerides. In embodiments, short-chain triglycerides comprise a fatty acid having a trial comprising 1-5 carbon atoms. In embodiments, medium-chain triglycerides comprise a fatty acid having a trial comprising 6-12 carbon atoms. In embodiments, medium-chain triglycerides comprise a fatty acid having a trial comprising 13-21 carbon atoms. In embodiments, medium-chain triglycerides comprise a fatty acid having a trial comprising 22 or more carbon atoms. The hydrocarbon chain in the triglyceride may be saturated or unsaturated. When the hydrocarbon chain is unsaturated, it may have any number of double or triple bonds, e.g., 1, 2, 3, 4, 5, 6, 7, 8, 9, or 10.

In some embodiments, the one or more lipophilic materials of the present disclosure comprise a medium-chain triglyceride (e.g., LABRAFAC™ lipophile WT 1349). In some embodiments, the one or more lipophilic materials comprise medium chain triglycerides of caprylic (C8) and capric acid (C10) (LABRAFAC™ lipophile WT 1349) or glycerol triester of caprylic and capric acid (MIGLYOL® 810, MIGLYOL® 812, MIGLYOL® 829, or MIGLYOL® 840). In embodiments, the one or more lipophilic materials comprise propylene glycol ester of caprylic (C8) and capric acid (C10) (LABRAFAC™ PG). In embodiments, the one or more lipophilic materials comprise glycerol monocaprylocaprate (type I) comprising caprylic (C8) and capric acid (C10) (LABRAFAC™ MC60).

In some embodiments, the lipophilic material comprises one or more vegetable seed oils, including but not limited to kernel oil, borage oil, coconut oil, cottonseed oil, soybean oil, safflower oil, sunflower oil, castor oil, hydrogenated castor oil, corn oil, olive oil, palm oil, peanut oil, peppermint oil, poppy seed oil, canola oil, soybean oil, hydrogenated soybean oil, pumpkin oil, pumpkin seed oil, medium-chain triglyceride (MCT) oil (e.g., MCT oil derived from coconut oil and/or palm oil), oleic oil (e.g., derived from olive and/or canola oil), fruit seed oil, and sesame oil. In some embodiments, the lipophilic material comprises sesame oil, pumpkin oil, or combinations thereof. In some embodiments, the lipophilic material comprises kernel oil, sesame seed oil, MCT oil, oleic oil, pumpkin seed oil, or a mixture thereof. In embodiments, the lipophilic material comprises one or more vegetable oil. In embodiments, the vegetable oil comprises one or more vegetable seed oil, fruit seed oil, kernel oil, sesame seed oil, medium-chain triglyceride (MCT) oil, oleic oil, pumpkin seed oil, transesterified vegetable oil, polyoxyethylene hydrogenated vegetable oil, PEG-hydrogenated castor oil or a combination thereof.

In some embodiments, the one or more lipophilic materials is present in an amount sufficient to provide the one or more cannabinoids in amorphous form. In some embodiments, the one or more lipophilic materials is present in an amount ranging from about 1% to about 75% by weight based on the total weight of the drug-containing particle (e.g., about 1%, 5%, 10%, 15%, 20%, 25%, 30%, 35%, 40%, 45%, 50%, 55%, 60%, 65%, 70%, or 75%, including all values and ranges therein). In some embodiments, the one or more lipophilic materials is present in an amount ranging from about 5% to about 75% by weight based on the total weight of the drug-containing particle. In some embodiments, the one or more lipophilic materials is present in an amount ranging from about 10% to about 75% by weight based on the total weight of the drug-containing particle. In some embodiments, the one or more lipophilic materials is present in an amount ranging from about 15% to about 75% by weight based on the total weight of the drug-containing particle. In some embodiments, the one or more lipophilic materials is present in an amount ranging from about 20% to about 75% by weight based on the total weight of the drug-containing particle). In some embodiments, the one or more lipophilic materials is present in an amount ranging from about 5% to about 50% by weight based on the total weight of the drug-containing particle. In some embodiments, the one or more lipophilic materials is present in an amount ranging from about 10% to about 50% by weight based on the total weight of the drug-containing particle. In some embodiments, the one or more lipophilic materials is present in an amount ranging from about 15% to about 50% by weight based on the total weight of the drug-containing particle. In some embodiments, the one or more lipophilic materials is present in an amount ranging from about 20% to about 50% by weight based on the total weight of the drug-containing particle.). In some embodiments, the one or more lipophilic materials is present in an amount ranging from about 5% to about 75% by weight based on the total weight of the drug-containing particle. In some embodiments, the one or more lipophilic materials is present in an amount ranging from about 10% to about 75% by weight based on the total weight of the drug-containing particle. In some embodiments, the one or more lipophilic materials is present in an amount ranging from about 15% to about 75% by weight based on the total weight of the drug-containing particle. In some embodiments, the one or more lipophilic materials is present in the drug-containing particles in about 5%, about 10%, about 15%, about 20%, about 25%, about 30%, about 35%, about 40%, about 45%, about 50%, about 55%, about 60%, about 65%, about 70%, or about 75% by weight based on the total weight of the drug-containing particle.

Polymers

In some embodiments, the drug-containing particle further comprises one or more polymers. In some embodiments, the polymer has a glass transition temperature ($T_g$) ranging from about 50° C. to about 130° C. In some embodiments, the polymer comprises polyvinylpyrrolidone (kollidon VA64), cross linked polyvinyl N-pyrrolidone (crospovidone), hydroxypropyl methylcellulose phthalate (HPMCP 50), polyvinyl alcohol-polyethylene glycol copolymer (kollicoat), polyvinyl caprolactam-polyvinyl acetate-polyethylene glycol graft co-polymer (soluplus), polyvinyl alcohol, or combinations thereof.

In some embodiments, the one or more polymers is present in an amount ranging from about 10% to about 50% by weight based on the total weight of the drug-containing particle (e.g., about 10%, 15%, 20%, 25%, 30%, 35%, 40%, 45%, or 50%, including all values and ranges therein). In some embodiments, the polymer is provided as a coating on the drug-containing particle.

Chelating Agents (CA) and Antioxidizing Agents (AO)

The drug-containing particles disclosed herein optionally include a chelating agent. In some embodiments, the chelating agent is EDTA, citric acid or curcumin.

In some embodiments, the amount of the chelating agent in the drug-containing particle ranges from about 0.05% to about 3% by weight, e.g., about 0.05%, about 0.10%, about 0.20%, about 0.30%, about 0.40%, about 0.50%, about 0.60%, about 0.70%, about 0.80%, about 0.90%, about 1%, about 1.10%, about 1.20%, about 1.30%, about 1.40%, about 1.50%, about 1.60%, about 1.70%, about 1.80%, about 1.90%, about 2%, about 2.10%, about 2.20%, about 2.30%, about 2.40%, about 2.50%, about 2.60%, about 2.70%, about 2.80%, about 2.90%, or about 3%, including all ranges and values therebetween. In some embodiments, the amount of the chelating agent in the drug-containing particle ranges from about 0.05% to about 0.5% by weight. In some embodiments, the amount of the chelating agent in the drug-containing particle ranges from about 0.05% to about 0.4% by weight, from about 0.05% to about 0.35% by weight, from about 0.05% to about 0.3% by weight, from about 0.05% to about 0.25% by weight, or from about 0.05% to about 0.2% by weight.

The drug-containing particles disclosed herein optionally include one or more antioxidizing agents. In some embodiments, the one or more antioxidizing agents is a tocopherol derivative (e.g., α-tocopherol), a carotenoid (e.g., lutein or β-carotene), tocotrienol, ascorbic acid, ascorbyl palmitate, lecithin, butylated hydroxyanisole, butylated hydroxytoluene (BHT), monothiolglycerol, propyl gallate, curcumin, or combinations thereof. In some embodiments, the one or more antioxidizing agents is α-tocopherol, β-carotene, ascorbic acid, ascorbyl palmitate, lecithin, butylated hydroxyanisole, butylated hydroxytoluene, monothiolglycerol, propyl gallate, or combinations thereof. In some embodiments, the one or more antioxidizing agents is α-tocopherol.

In some embodiments, the amount of the one or more antioxidants in the drug-containing particle ranges from about 0.05% to about 3% by weight, e.g., about 0.05%, about 0.10%, about 0.20%, about 0.30%, about 0.40%, about 0.50%, about 0.60%, about 0.70%, about 0.80%, about 0.90%, about 1%, about 1.10%, about 1.20%, about 1.30%, about 1.40%, about 1.50%, about 1.60%, about 1.70%, about 1.80%, about 1.90%, about 2%, about 2.10%, about 2.20%, about 2.30%, about 2.40%, about 2.50%, about 2.60%, about 2.70%, about 2.80%, about 2.90%, or about 3%, including all ranges and values therebetween. In some embodiments, the amount of the one or more antioxidants in the drug-containing particle ranges from about 0.05% to about 2.5% by weight, from about 0.05% to about 2.0% by weight, from about 0.05% to about 1.5% by weight, from about 0.05% to about 1.0% by weight, or from about 0.05% to about 0.5% by weight. In some embodiments, the amount of the one or more antioxidants in the drug-containing particle is about 0.05% to about 2.0% by weight. In some embodiments, the one or more antioxidants in the drug-containing particle is about 0.1% to about 1.5% by weight. In some embodiments, the one or more antioxidants are present in the drug-containing particle at about 0.2%, about 0.6%, or about 1.0%.

In some embodiments, the drug-containing particles comprise any combination of a chelating agent and one or more antioxidants disclosed herein. In some embodiments, the chelating agent is EDTA, citric acid, or a polyphenolic substance (e.g., curcumin) and the one or more antioxidizing agents is a tocopherol derivative (e.g., α-tocopherol), a carotenoid (e.g., lutein or β-carotene), tocotrienol, ascorbic acid, ascorbyl palmitate, lecithin, butylated hydroxyanisole, butylated hydroxytoluene (BHT), monothiolglycerol, propyl gallate, curcumin, or combinations thereof. In some embodiments, the drug-containing particles comprise one of the following combinations of antioxidant(s) and chelating agent (CA):

| Chelating Agent | Antioxidant(s) |
|---|---|
| citric acid | ascorbic acid |
| citric acid | α-tocopherol |
| citric acid | β-carotene |
| citric acid | lecithin |
| curcumin | ascorbic acid |
| curcumin | α-tocopherol |
| curcumin | β-carotene |
| curcumin | lecithin |
| citric acid | ascorbic acid, α-tocopherol |
| citric acid | β-carotene, α-tocopherol |
| citric acid | lecithin, α-tocopherol |
| curcumin | ascorbic acid, α-tocopherol |
| curcumin | β-carotene, α-tocopherol |
| curcumin | lecithin, α-tocopherol |
| citric acid | ascorbyl palmitate |
| curcumin | ascorbyl palmitate |
| citric acid | ascorbyl palmitate, α-tocopherol |
| curcumin | ascorbyl palmitate, α-tocopherol |

Drug-Release Profiles

The release of the one or more cannabinoids from the drug-containing particle can be immediate release or modified release, depending on the application. In some embodiments, drug-containing particles are formulated for immediate release. In some embodiments, the drug-containing particles are formulated for modified release, e.g., delayed or extended release. In some embodiments, the drug-containing particles disclosed herein release 50-90% of the one or more cannabinoids in about 1-16 h. In some embodiments, the drug-containing particles disclosed herein release 50-90% of the one or more cannabinoids in about 2-12 h. In some embodiments, the drug-containing particles disclosed herein release 50-90% of the one or more cannabinoids in about 3-12 h. In some embodiments, the drug-containing particles disclosed herein release at least about 50% of the one or more cannabinoids by about 30 min, about 1 h, about 2 h, about 3 h, about 4 h, about 5, about 6, about 7, about 8, about 9, about 10, about 11, or about 12 h. In some embodiments, the drug-containing particles disclosed herein release at least about 60% of the one or more cannabinoids by about 30 min, about 1 h, about 2 h, about 3 h, about 4 h, about 5, about 6, about 7, about 8, about 9, about 10, about 11, or about 12 h. In some embodiments, the drug-containing particles disclosed herein release at least about 70% of the one or more cannabinoids by about 30 min, about 1 h, about 2 h, about 3 h, about 4 h, about 5, about 6, about 7, about 8, about 9, about 10, about 11, or about 12 h. In some embodiments, the drug-containing particles disclosed herein release at least about 80% of the one or more cannabinoids by about 30 min, about 1 h, about 2 h, about 3 h, about 4 h, about 5, about 6, about 7, about 8, about 9, about 10, about 11, or about 12 h. In some embodiments, the drug-containing particles disclosed herein release at least about 90% of the one or more cannabinoids by about 30 min, about 1 h, about 2 h, about 3 h, about 4 h, about 5, about 6, about 7, about 8, about 9, about 10, about 11, or about 12 h.

In embodiments, the drug-containing particles disclosed herein release at least 20% in 10 minutes. In embodiments, the drug-containing particles disclosed herein release 20-50% in 10 minutes. In embodiments, the drug-containing particles disclosed herein release at least 30% in 15 minutes. In embodiments, the drug-containing particles disclosed herein release 30-70% in 15 minutes. In embodiments, the drug-containing particles disclosed herein release at least 40% in 20 minutes. In embodiments, the drug-containing particles disclosed herein release 40-80% in 20 minutes. In embodiments, the drug-containing particles disclosed herein release at least 45% in 30 minutes. In embodiments, the drug-containing particles disclosed herein release 45-85% in 30 minutes. In embodiments, the drug-containing particles disclosed herein release at least 50% in 45 minutes. In embodiments, the drug-containing particles disclosed herein release 50-85% in 50 minutes.

In embodiments, drug release (dissolution) is measured under U.S. Pharmacopeia (USP) dissolution test (711). In embodiments, drug release (dissolution) is measured using Apparatus I or Apparatus II. In embodiments, dissolution (release) rate is tested using USP Apparatus II (paddle at 75 rpm) in 900 mL in an appropriate buffer at 37±0.5° C. In some embodiments, the buffer has a pH in the range of from about 1 to about 7, e.g., about 1, about 1.5, about 2, about 2.5, about 3, about 3.5, about 4, about 4.5, about 5, about 5.5, about 6, about 6.5, about 6.8, and about 7, inclusive of all values and subranges therebetween. The pH of the buffer can be selected based on the approximate pH in the digestive tract where release is measured. For example, a pH of 1 may be used to measure dissolution in the stomach, whereas a higher pH up to pH 7.4 (e.g., 4.5, 5, 5.5, etc.) can be used to measure dissolution in the intestines. The test conditions (e.g., run time, media, run time, speed, volume, etc.) can be varied.

In embodiments, drug release (dissolution) is measured under dissolution test conditions described in Table A1.

TABLE A1

| Dissolution test parameters | |
|---|---|
| Dissolution apparatus | Type II, Paddles |
| Dissolution media | 3.9% LABRASOL ®: 0.1% Tween (v/v) in deionized Water |
| Media volume | 900 mL |
| Paddle speed | 75 RPM |
| Sampling times (mins) | 0, 10, 20, 30, 40, 50, 60, 90, 120, 150 and 180 min |
| Sampling volume | 4 mL without replacement. |

In embodiments, drug release (dissolution) is measured under dissolution test conditions described in Table AB.

TABLE AB

| Dissolution test parameters | |
|---|---|
| Dissolution apparatus | Type II, Paddles |
| Dissolution media | 4.0% LABRASOL ® (v/v) in deionized Water |
| Media volume | 900 mL |
| Paddle speed | 75 RPM |
| Sampling times (mins) | 0, 10, 20, 30, 40, 50, 60, 90, 120, 150 and 180 min |
| Sampling volume | 4 mL without replacement |

In embodiments, the dissolution test is performed for 30 minutes for immediate release. In embodiments, the dissolution test is performed for at least 3 hours for the delayed release (e.g., 3, 4, 5, 6, 7, 8, 9, 10, 11, 12 or more hours). In some embodiments, the buffer is 0.1 M HCl at pH 1, 0.01 M HCl at pH 2, or acetate buffer at pH 4.5.

For the enteric coated components, dissolution testing may be conducted using USP Apparatus II (paddle at 75 rpm) in 900 mL in a first buffer at pH 4.5 at 37±0.5° C. for 3 hours, followed by testing in 900 mL of a second buffer at pH 6.8.

In some embodiments, the drug-containing particles disclosed herein are formulated to be bioequivalent compared to conventional formulations that, for example, do not include a porous solid carrier. In some embodiments, the convention formulation comprises the one or more cannabinoids (e.g., CBD) dissolved in sesame oil. That is, in some embodiments, the drug-containing particles have an average maximum blood plasma concentration ($C_{max}$), an average AUC, and/or an average $T_{max}$ which is within the about 80% to about 125% of each of the average $C_{max}$, average AUC, and average $T_{max}$ of conventional oil-based cannabinoid drug products when administered to a human or animal, such as in a mouse model, a rat model, a beagle dog model, or a minipig model. $C_{max}$, AUC, and $T_{max}$, as used herein, refer to the average or median values measured for a population of subjects.

In some embodiments, the drug-containing particles disclosed herein are formulated to have improved pharmacokinetic properties compared to conventional formulations that, for example, do not include a porous solid carrier. That is, in some embodiments, the drug-containing particles have an average maximum blood plasma concentration ($C_{max}$) or an average AUC that is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% greater than the average $C_{max}$ or average AUC of conventional oil-based cannabinoid drug products when administered to a human or animal, such as in a mouse model, a rat model, a beagle dog model, or a minipig model. $C_{max}$ or AUC as used herein, refer to the average or median values measured for a population of subjects.

In some embodiments, administration of the drug-containing particles when administered at a dose equivalent to 10 mg/kg provide an AUC ranging from about 80% to about 125% of about 722 ng*hr/mL. In such embodiments, the AUC is about 550 ng*hr/mL to about 950 ng*hr/mL, for example, about 550 ng*hr/mL, about 570 ng*hr/mL, about 590 ng*hr/mL, about 610 ng*hr/mL, about 630 ng*hr/mL, about 650 ng*hr/mL, about 670 ng*hr/mL, about 690 ng*hr/mL, about 710 ng*hr/mL, about 730 ng*hr/mL, about 750 ng*hr/mL, about 770 ng*hr/mL, about 790 ng*hr/mL, about 810 ng*hr/mL, about 830 ng*hr/mL, about 850 ng*hr/mL, about 870 ng*hr/mL, about 890 ng*hr/mL, about 910 ng*hr/mL, about 930 ng*hr/mL, or about 950 ng*hr/mL, including all values and ranges in between.

In some embodiments, administration of the drug-containing particles at a dose equivalent to 10 mg/kg provides an $C_{max}$ of about 80% to about 125% of about 150 ng/ml. In such embodiments, the subject has an $C_{max}$ of about 50 ng/ml to about 190 ng/ml, for example, about 50 ng/mL, about 60 ng/mL, about 70 ng/ml, about 80 ng/ml, about 90 ng/ml, about 100 ng/ml, about 120 ng/mL, about 140 ng/ml, about 160 ng/mL, about 180 ng/mL, to about 190 ng/ml including all values and ranges in between.

In some embodiments, administration of the drug-containing particles provides a relative bioavailability (Frel %) in a subject of about 30% to about 600% (e.g., about 30%, about 40%, about 50%, about 60%, about 70%, about 80%, about 90%, about 100%, about 110%, about 120%, about 140%, about 160%, about 180%, about 200%, about 220%, about 240%, about 260%, about 280%, about 300%, about 320%, about 340%, about 360%, about 380%, about 400%, about 420%, about 440%, about 460%, about 480%, about 500%, about 520%, about 540%, about 560%, about 580%, about 600%, including any values or ranges therebetween) compared to CBD dissolved in sesame oil comprising the same dose of CBD. In embodiments, administration of the drug-containing particles in a formulation of the present disclosure provides a relative bioavailability (Frel %) of about 100% to about 600% compared to CBD dissolved in sesame oil comprising the same dose of CBD. In embodiments, administration of the drug-containing particles in a formulation of the present disclosure provides a relative bioavailability (Frel %) of about 30% to about 100% compared to CBD dissolved in sesame oil comprising the same dose of CBD.

Drug-Containing Particles

In some embodiments, the pharmaceutical composition comprises about 10-60% of a drug substance described herein and about 20%-80% of the porous solid carrier. In some embodiments, the pharmaceutical composition comprises about 15-40% of a drug substance described herein and about 40%-60% of the porous solid carrier.

In some embodiments, the pharmaceutical composition comprises about 10-60% of a drug substance described herein, about 20%-80% of the porous solid carrier, and about 10-50% of one or more lipophilic materials. In some embodiments, the pharmaceutical composition comprises about 15-40% of a drug substance described herein, about 40%-60% of the porous solid carrier, and about 15-35% of one or more lipophilic materials.

In some embodiments, the pharmaceutical composition comprises about 10-60% drug substance described herein, about 20%-80% of the porous solid carrier, and about 10-50% of one or more lipophilic materials, and about 0.1-2% of an antioxidant. In some embodiments, the pharmaceutical composition comprises about 15-40% of a drug substance described herein, about 40%-60% of the porous solid carrier, about 15-35% of one or more lipophilic materials, and about 0.2-1% of an antioxidant.

Methods of Manufacturing Drug-Containing Particles

Figure 4:
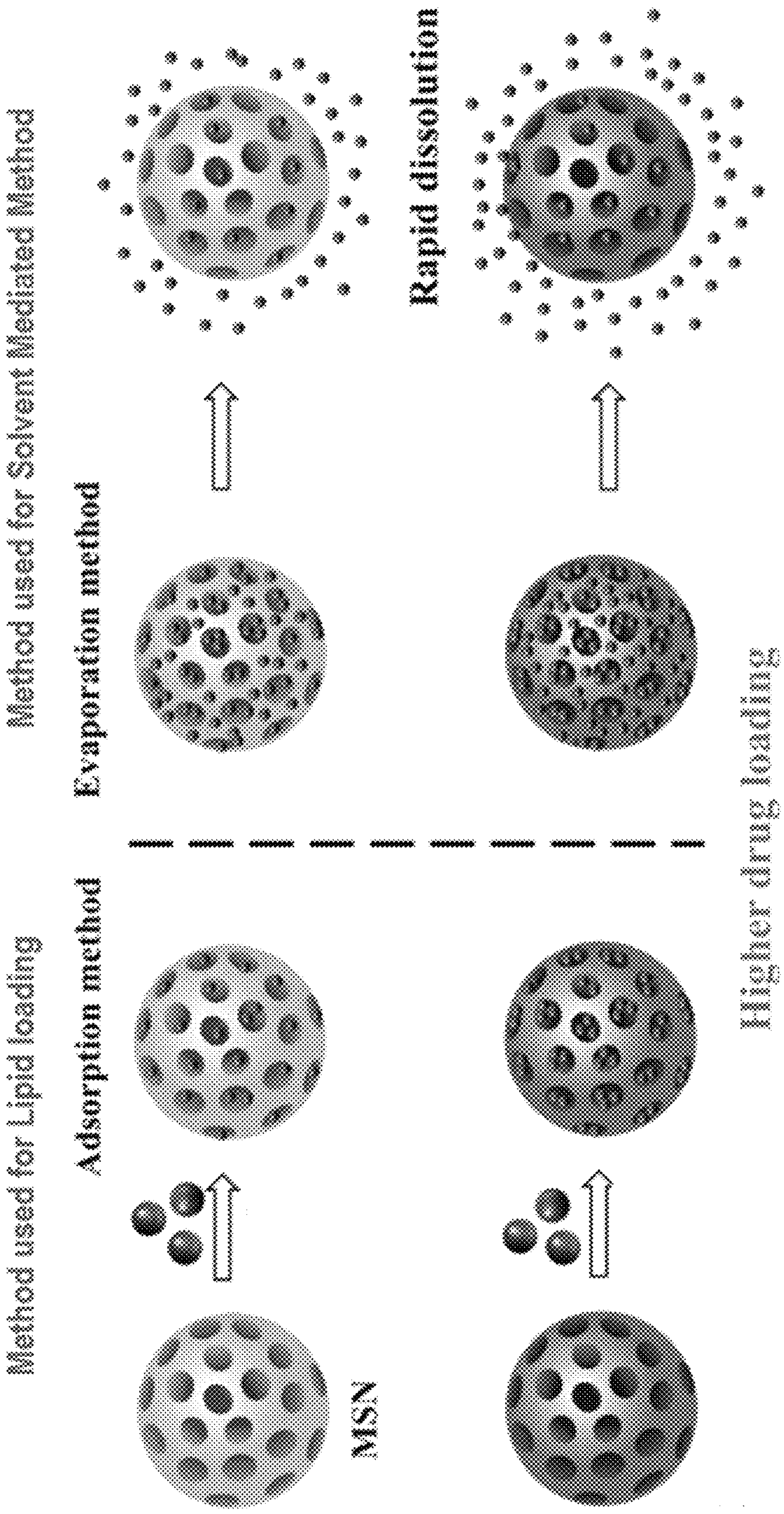
FIG. 4 shows a schematic diagram comparing aspects of lipid-loading and solvent-mediated methods for adsorbing drug into mesoporous silica.

In some embodiments, the drug-containing particles of the present disclosure are manufactured according to a solvent-mediated method, wherein the one or more cannabinoids are loaded onto a porous solid carrier (e.g., mesoporous silica) from a solution (see FIG. 4). In some embodiments, the solvent-mediated method is carried out according to the steps provided in FIG. 5. In some embodiments, the drug-containing particles manufactured according to a solvent-mediated method disclosed herein are free-flowing powders. In some embodiments, the free-flowing powders are stable at elevated temperature (e.g., 25° C. or 40° C.) for a period greater than 1 week, greater than 2 weeks, greater than 3 weeks, greater than 4 weeks, greater than 5 weeks, greater than 6 weeks, greater than 7 weeks, greater than 8 weeks, greater than 9 weeks, greater than 10 weeks, greater than 11 weeks, or greater than 12 weeks.

Figure 8:
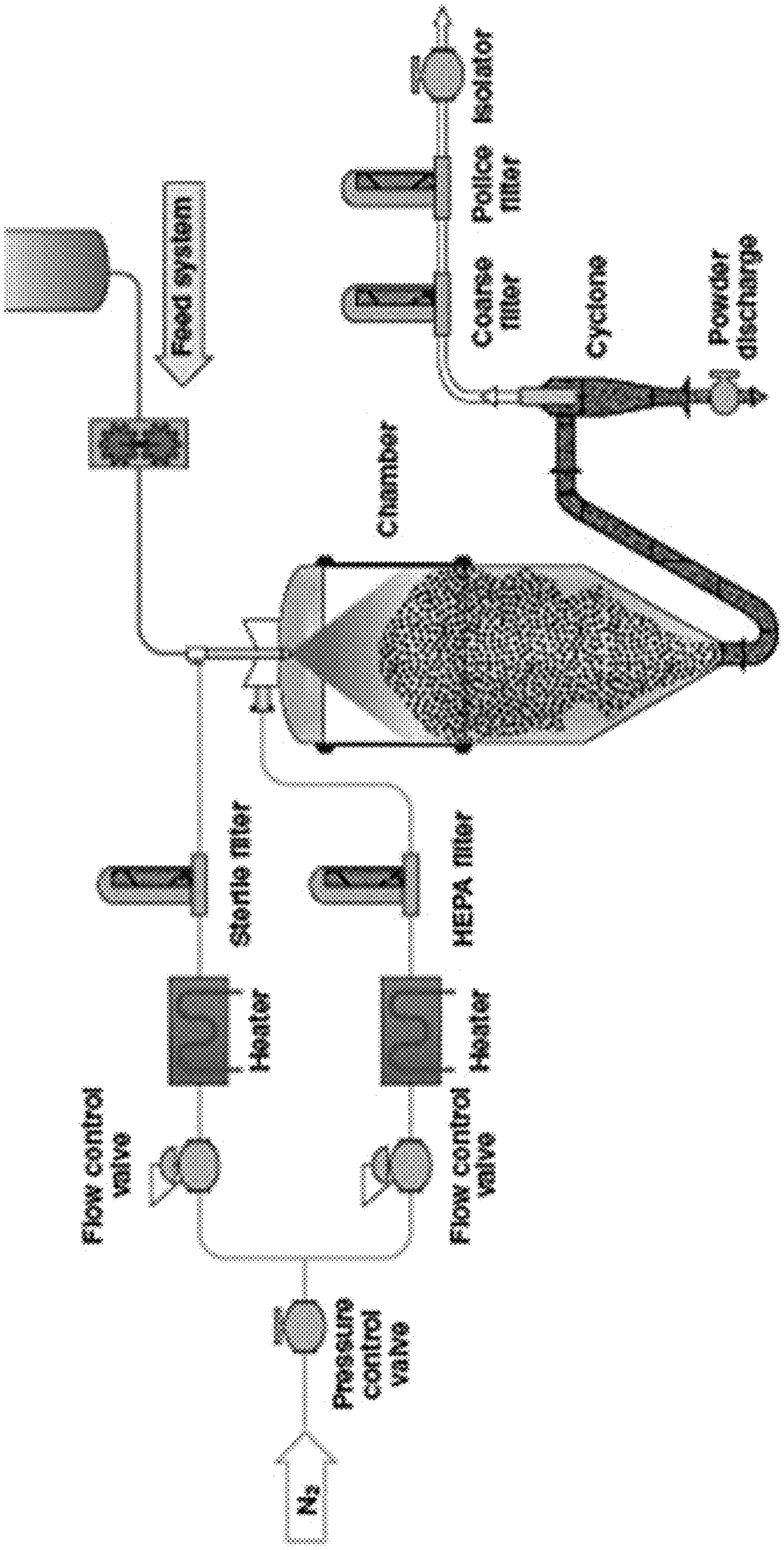
FIG. 8 shows an exemplary spray drying apparatus that can be used to prepare the drug-containing particles of the present disclosure.

In some embodiments, the drug-containing particles of the present disclosure are manufactured according to a solvent-mediated method, wherein the one or more cannabinoids, one or more polymers disclosed herein, and one or more optional antioxidants disclosed herein are loaded onto a porous solid carrier (e.g., mesoporous silica) from a solution. In some embodiments, the solvent-mediated method is carried out according to the steps provided in FIG. 8.

In some embodiments, the solvent-mediated process disclosed herein comprises spray drying or lyophilisation of a solution of the one or more cannabinoids or derivatives, one or more polymers disclosed herein, and one or more optional antioxidants disclosed herein onto a porous solid carrier. In some embodiments, the solvent-mediated process comprising spray drying is carried out according to the steps provided in FIG. 9A-C or FIG. 10.

In some embodiments, the method of preparing the drug-containing particles of the present disclosure comprises:

(a) combining a porous solid carrier, one or more cannabinoids, optional polymer, one or more optional antioxidants, and an optional chelating agent to form a mixture;

(b) adding solvent, under optional heating, to the mixture to form a slurry;

(c) sonicating and/or agitating the slurry for a period of time; and (d) evaporating the solvent to obtain a dry powder.

In some embodiments, the agitation of step (c) comprises low-shear or high-shear powder mixing techniques, e.g., hand-mixing or use of mechanically-driven paddles, blade mixers or twin-screw mixers.

The evaporation of step (d) can be carried out according to any suitable method known in the art. In some embodiments, the evaporation of step (d) is carried out at reduced pressure. In some embodiments, the evaporation of step (d) is carried out a reduced pressure and/or elevated temperature. In certain embodiments, the evaporating can be carried out by removing solvent at an appropriate temperature, by spray drying, by lyophilization, or a combination thereof. In some embodiments, the evaporation comprises secondary drying, which for example, can be carried out in a vacuum oven until residual solvents are within ICH limits.

In some embodiments, the drug-containing particles of the present disclosure are manufactured according to a lipid-loaded method, wherein the one or more cannabinoids is combined with a lipophilic material disclosed herein, and mixed with a porous solid carrier to facilitate loading (see FIG. 4). In some embodiments, the lipid-loaded method is carried out according to one or more of the processes provided in FIG. 12. In some embodiments, the drug-containing particles manufactured according to a lipid-loaded method disclosed herein are free-flowing powders. In some embodiments, the free-flowing powders are stable at elevated temperature (e.g., 25° C. or 40° C.) for a period greater than 1 week, greater than 2 weeks, greater than 3 weeks, greater than 4 weeks, greater than 5 weeks, greater than 6 weeks, greater than 7 weeks, greater than 8 weeks, greater than 9 weeks, greater than 10 weeks, greater than 11 weeks, or greater than 12 weeks.

In some embodiments, the method of preparing the drug-containing particles of the present disclosure comprises:

(a) combining one or more cannabinoids, one or more lipophilic materials, one or more optional antioxidants, and an optional chelating agent to form a mixture;

(b) stirring the mixture of step (a) for a period of time until homogeneous;

(c) adding the homogenous mixture of step (b) to the porous solid carrier; and (d) stirring the mixture of step (c) for a period of time until homogenous.

Pharmaceutical Compositions

In some embodiments, the present disclosure provides a pharmaceutical composition comprising a plurality of drug-containing particles disclosed herein. In some embodiments, the pharmaceutical composition comprises one or more pharmaceutically acceptable excipients and/or carriers. In some embodiments, the pharmaceutical composition is in the form of a tablet, capsule, or granule. In embodiments, the drug-coated particles can be filled into a capsule or compressed, optionally in combination with various excipients as described herein into a tablet. The pharmaceutical compositions disclosed herein can be prepared by any suitable method known in the art. In some embodiments, the method comprises blending the drug-containing particles with the one or more pharmaceutically acceptable excipients and/or carriers. In some embodiments, the method comprises a dry granulation (roller compaction) process.

Pharmaceutically acceptable excipients include fillers, diluents, glidants, disintegrants, binders and lubricants. Other pharmaceutically acceptable excipients include acidifying agents, alkalizing agents, preservatives, antioxidants, buffering agents, chelating agents, coloring agents, complexing agents, emulsifying and/or solubilizing agents, flavors, perfumes, humectants, sweetening agents and wetting agents.

Flavoring agents and flavor enhancers make the dosage form more palatable to the patient. Common flavoring agents and flavor enhancers for pharmaceutical products that may be included in the composition and/or combination of the present invention include fruit flavoring agents, sucrose, maltol, vanillin, ethyl vanillin, menthol, citric acid, fumaric acid, ethyl maltol, and tartaric acid.

In some embodiments, the drug-containing particles disclosed herein are prepared in a formulation that has one of the following non-limiting compositions:

| | % w/v | | | | | | |
|---|---|---|---|---|---|---|---|
| | 1 | 2 | 3 | 4 | 5 | 6 | 7 |
| ethanol solution | 7.90 | 7.90 | 7.90 | 7.90 | 7.90 | 7.90 | 7.90 |
| Sucralose | 0.05 | 0.05 | 0.05 | 0.05 | 0.05 | 0.05 | 0.05 |
| Strawberry Flavor | 0.02 | 0.02 | 0.02 | 0.02 | 0.02 | 0.02 | 0.02 |
| CBD | 10.00 | 10.00 | 10.00 | 10.00 | 10.00 | 10.00 | 10.00 |
| Antioxidant | 0.05 | 0.12 | 0.15 | 0.18 | 0.05 | 0.12 | 0.15 |
| Chelating Agent | 0.06 | 0.06 | 0.06 | 0.06 | 0.06 | 0.06 | 0.06 |
| Sesame seed oil | 73.53 | 73.46 | 73.43 | 73.40 | 73.53 | 73.46 | 73.43 |

| | % w/v | | | | | | |
|---|---|---|---|---|---|---|---|
| | 8 | 9 | 10 | 11 | 12 | 13 | 14 |
| ethanol solution | 7.90 | 7.90 | 7.90 | 7.90 | 7.90 | 7.90 | 7.90 |
| Sucralose | 0.05 | 0.05 | 0.05 | 0.05 | 0.05 | 0.05 | 0.05 |
| Strawberry Flavor | 0.02 | 0.02 | 0.02 | 0.02 | 0.02 | 0.02 | 0.02 |
| CBD | 10.00 | 10.00 | 10.00 | 10.00 | 10.00 | 10.00 | 10.00 |
| Antioxidant 1 | 0.18 | 0.05 | 0.15 | 0.18 | 0.05 | 0.15 | 0.18 |
| Antioxidant 2 | 0.00 | 0.12 | 0.12 | 0.12 | 0.12 | 0.12 | 0.12 |
| Chelating Agent | 0.06 | 0.06 | 0.06 | 0.06 | 0.06 | 0.06 | 0.06 |
| Sesame seed oil | 73.40 | 73.41 | 73.31 | 73.28 | 73.41 | 73.31 | 73.28 |

EMBODIMENTS

1. A drug-containing particle comprising:

(a) one or more cannabinoids; and (b) a porous solid carrier, wherein the one or more cannabinoids are adsorbed onto and/or into the porous solid carrier.

2. The drug-containing particle of embodiment 1, wherein the porous solid carrier is a microparticle.

3. The drug-containing particle of embodiment 1 or 2, wherein the porous solid carrier has an average particle size ranging from about 1 μm to about 250 μm.

4. The drug-containing particle of any one of embodiments 1-3, wherein the porous solid carrier has an average particle size ranging from about 50 μm to about 150 μm, or about 40 μm to 100 μm.

5. The drug-containing particle of any one of embodiments 1-4, wherein the porous solid carrier has a porosity ranging from about 75% to about 99%.

6. The drug-containing particle of any one of embodiments 1-5, wherein the porous solid carrier has an average surface area ranging from about 100 $m^2/g$ to about 1000 $m^2/g$.

7. The drug-containing particle of any one of embodiments 1-6, wherein the porous solid carrier has an average pore volume ranging from about 0.1 mL/g to about 5 mL/g.

8. The drug-containing particle of any one of embodiments 1-7, wherein the porous solid carrier has an average pore volume ranging from about 1 mL/g to about 2 mL/g.

9. The drug-containing particle of any one of embodiments 1-7, wherein the porous solid carrier has an average pore diameter ranging from about 1 nm to about 100 nm.

10. The drug-containing particle of any one of embodiments 1-9, wherein the porous solid carrier has an average pore diameter ranging from about 2 nm to about 60 nm.

11. The drug-containing particle of any one of embodiments 1-9, wherein the porous solid carrier has an average pore diameter ranging from about 10 nm to about 50 nm.

12. The drug-containing particle of any one of embodiments 1-11, wherein the porous solid carrier has an average pore diameter ranging from about 15 nm to about 30 nm.

13. The drug-containing particle of any one of embodiments 1-12, wherein the porous solid carrier has one or more of the following characteristics:

(i) average pore volume ranging from 1-2 $cm^3/g$;
(ii) average surface area ranging from 250 to 375; or
(iii) pore diameters ranging from about 2-50 nm.

14. The drug-containing particle of any one of embodiments 1-13, wherein the porous solid carrier has two or more of the following characteristics:
(i) average pore volume ranging from 1-2 $cm^3/g$;
(ii) average surface area ranging from 250 to 375; or
(iii) pore diameters ranging from about 2-50 nm.

15. The drug-containing particle of any one of embodiments 1-14, wherein the porous solid carrier has an:
(i) average pore volume ranging from 1-2 $cm^3/g$;
(ii) average surface area ranging from 250 to 375; and
(iii) pore diameters ranging from about 2-50 nm.

16. The drug-containing particle of any one of embodiments 1-14, wherein the porous solid carrier comprises silica ($SiO_2$), microcrystalline cellulose, silicified microcrystalline cellulose, chitosan, isomalt, or a silicate.

17. The drug-containing particle of any one of embodiments 1-16 wherein the porous solid carrier comprises silica or a silicate.

18. The drug-containing particle of any one of embodiments 1-17, wherein the porous solid carrier comprises silica.

19. The drug-containing particle of any one of embodiments 16-18, wherein the silica comprises mesoporous silica or amorphous silica.

20. The drug-containing particle of any one of embodiments 16-19, wherein the silica comprises mesoporous silica.

21. The drug-containing particle of any one of embodiments 1-11, wherein the porous solid carrier comprises a silicate.

22. The drug-containing particle of embodiment 21, wherein the silicate comprises an aluminosilicate.

23. The drug-containing particle of embodiment 22, wherein the silicate comprises a magnesium aluminosilicate.

24. The drug-containing particle of any one of embodiments 1-23, wherein the porous solid carrier is present in an amount ranging from about 20% to about 80% by weight based on the total weight of the drug-containing particle.

25. The drug-containing particle of any one of embodiments 1-24, wherein the solid carrier is present in an amount ranging from about 30% to about 50% by weight based on the total weight of the drug-containing particle.

26. The drug-containing particle of any one of embodiments 1-25, wherein the one or more cannabinoids comprise cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), CBD-C4, OH-CBD, CBD-C4, 6-OH-CBD, 7-OH-CBD, 7-COOH-CBD, 11-COOH-THC, or 11-OH-THC.

27. The drug-containing particle of any one of embodiments 1-26, wherein the one or more cannabinoids comprise CBD.

28. The drug-containing particle of any one of embodiments 1-27, wherein the one or more cannabinoids is present in an amount ranging from about 5% to about 75% by weight based on the total weight of the drug-containing particle.

29. The drug-containing particle of any one of embodiments 1-28, wherein the one or more cannabinoids is present in an amount ranging from about 10% to about 60% by weight based on the total weight of the drug-containing particle.

30. The drug-containing particle of any one of embodiments 1-29, wherein the one or more cannabinoids is present in an amount ranging from about 15% to about 40% by weight based on the total weight of the drug-containing particle.

31. The drug-containing particles of any one of embodiments 1-30, wherein the ratio of the porous solid carrier to the drug substance is 10:1 to 1:5.

32. The drug-containing particles of any one of embodiments 1-30, wherein the ratio of the porous solid carrier to the drug substance is 2:1 to 1:2.

33. The drug-containing particle of any one of embodiments 1-32, wherein the one or more cannabinoids is present in an amorphous form.

34. The drug-containing particle of any one of embodiments 1-33, wherein adsorption is determined by SEM, DSC, and/or XRPD.

35. The drug-containing particle of any one of embodiments 1-34, wherein substantially all of the one or more cannabinoids is adsorbed into the pores of the porous solid carrier.

36. The drug-containing particle of any one of embodiments 1-35, wherein the one or more cannabinoids is adsorbed into the pores of the porous solid carrier.

37. The drug-containing particle of any one of embodiments 1-36, comprising a lipophilic material.

38. The drug-containing particle of embodiment 39, wherein the lipophilic material comprises a stabilization agent, a viscosity-modifying agent, and/or a processability enhancer.

39. The drug-containing particle of embodiment 37 or 38, wherein the lipophilic material comprises one or more non-ionic surfactants.

40. The drug-containing particle of embodiment 39, wherein the one or more non-ionic surfactants comprise polyoxyethylene sorbitan fatty acid ester (polysorbate, Tween®), polyoxyethylene 15 hydroxy stearate (macrogol 15 hydroxy stearate, solutol HS15®), polyoxyethylene castor oil derivative (Cremophor® EL, ELP, RH 40), polyoxyethylene stearate (Myrj®), sorbitan fatty acid ester (Span®), polyoxyethylene alkyl ether (Brij®), polyoxyethylene nonylphenol ether (Nonoxynol®), or a combination thereof.

41. The drug-containing particle of embodiment 39 or 40, wherein the lipophilic material comprises one or more polyoxylglycerides.

42. The drug-containing particle of any one of embodiments 39-41, wherein the lipophilic material comprises one or more polyethylene oxide-containing fatty acid ester, one or more fatty acid glycerol esters, one or more.

43. The drug-containing particle of embodiment 33 or 34, wherein the lipophilic material comprises one or more stearoyl polyoxyl-32 glyceride (gelucire 50/13), lauroyl polyoxyl-6-glyceride (labrafil M 2130), oleoyl polyoxyl-6-glyceride (labrafil 1944), monoesters/diesters of 12-hydroxystearic acid and macrogol (crodasol HS), PEG-40 hydrogenated castor oil (croduret 40), propylene glycol monocaprylate (capryol 90), medium-chain triglyceride (labrafac 1349), propylene glycol dicaprolate/dicaprate (labrafac PG), caprylocaproyl polyoxyl-8-glyceride (labrasol ALF), or a combination thereof.

44. The drug-containing particle of any one of embodiments 37-43, wherein the lipophilic material is present in an amount of about 1% to about 75% by weight based on the total weight of the drug-containing particle.

45. The drug-containing particle of any one of embodiments 37-43, wherein the lipophilic material is present in an amount of about 25% to about 35% by weight based on the total weight of the drug-containing particle.

46. The drug-containing particle of any one of embodiments 1-45, wherein the weight ratio of the solid carrier to the combined weight of the drug substance and lipophilic material ranges from 3:1 to 1:1.

47. The drug-containing particle of embodiment 37 or 38, wherein the lipophilic material is sesame seed oil or pumpkin seed oil.

48. The drug-containing particle of embodiment 47, wherein the lipophilic material is present in an amount of about 25% to about 75% by weight based on the total weight of the drug-containing particle.

49. The drug-containing particle of embodiment 47, wherein the sesame oil is present in an amount of about 45% to about 60% by weight based on the total weight of the drug-containing particle.

50. The drug-containing particle of any one of embodiments 1-49, comprising a polymer.

51. The drug-containing particle of embodiment 50, wherein the polymer has a $T_g$ of about 50° C. to about 130° C.

52. The drug-containing particle of embodiment 50 or 51, wherein the polymer comprises polyvinylpyrrolidone (kollidon VA64), cross linked polyvinyl N-pyrrolidone (crospovidone), hydroxypropyl methylcellulose phthalate (HPMCP 50), polyvinyl alcohol-polyethylene glycol copolymer (kollicoat), polyvinyl caprolactam-polyvinyl acetate-polyethylene glycol graft co-polymer (soluplus), polyvinyl alcohol, or a combination thereof.

53. The drug-containing particle of any one of embodiments 50-52, wherein the polymer is present in an amount of about 1% to about 75% by weight based on the total weight of the drug-containing particle.

54. The drug-containing particle of any one of embodiments 50-53, wherein the polymer is present in an amount of about 10% to about 50% by weight based on the total weight of the drug-containing particle.

55. The drug-containing particle of any one of embodiments 50-54, wherein the polymer is provided as a coating on the drug-containing particle.

56. The drug-containing particle of any one of embodiments 1-55, further comprising a chelating agent.

57. The drug-containing particle of embodiment 56, wherein the chelating agent comprises EDTA, citric acid, or curcumin.

58. The drug-containing particle of embodiment 56, wherein the chelating agent comprises citric acid or curcumin.

59. The drug-containing particle of any one of embodiments 56-58, wherein the amount of the chelating agent ranges from about 0.05% to about 3% by weight based on the total weight of the drug-containing particle.

60. The drug-containing particle of any one of embodiments 56-58, wherein the amount of the chelating agent ranges from about 0.05% to about 0.1% by weight based on the total weight of the drug-containing particle.

61. The drug-containing particle of any one of embodiments 1-60, comprising one or more antioxidants.

62. The drug-containing particle of embodiment 61, wherein the one or more antioxidants comprises α-tocopherol, β-carotene, ascorbic acid, ascorbyl palmitate, lecithin, butylated hydroxyanisole, butylated hydroxytoluene, monothiolglycerol, propyl gallate, or combinations thereof.

63. The drug-containing particle of embodiment 61 or 62 wherein the antioxidant comprises α-tocopherol.

64. The drug-containing particle of any one of embodiments 61-63, wherein the amount of the one or more antioxidants ranges from about 0.05% to about 3% by weight based on the total weight of the drug-containing particle.

65. The drug-containing particle of embodiment 64, wherein the amount of the one or more antioxidants ranges from about 0.2-1% by weight based on the total weight of the drug-containing particle.

66. The drug-containing particle of any one of embodiments 1-65, wherein about 30-90% of the one or more cannabinoids is released in about 3-12 h.

67. The drug-containing particle of any one of embodiments 1-65, wherein about 50-90% of the one or more cannabinoids released in about 3-12 h.

68. The drug-containing particle of any one of embodiments 1-65, wherein greater than about 80% of the one or more cannabinoids released by about 12 h.

69. The drug-containing particle of any one of embodiments 1-66, comprising no more than about 0.2% by weight of cannabidiorcol (CBD-C1).

70. The drug-containing particle of any one of embodiments 1-69, comprising no more than about 0.8% by weight of cannabidivarin (CBDV).

71. The drug-containing particle of any one of embodiments 1-70, comprising less than about 0.5% by weight of cannabidibutol (CBD-C4).

72. A pharmaceutical composition comprising a plurality of drug-containing particles of any one of embodiments 1-71 or combination thereof, and at least one pharmaceutically acceptable excipient.

73. The pharmaceutical composition of embodiment 72, wherein the pharmaceutical composition is a tablet, capsule, or granule.

74. The pharmaceutical composition of any one of embodiments 1-73, wherein the drug-containing particle is prepared by a process comprising spray drying or hot-melt extrusion.

75. A method of preparing the drug-containing particle of any one of embodiments 1-32 and 51-73, comprising:

(a) combining the porous solid carrier, the one or more cannabinoids, and optionally the polymer to form a mixture;

(b) adding a solvent to the mixture to form a slurry;

(c) sonicating and/or agitating the slurry; and (d) evaporating the solvent to obtain a dry powder.

76. A method of preparing the drug-containing particle of any one of embodiments 1-50 and 51-73, comprising:

(a) combining the one or more cannabinoids and the one or more lipophilic materials to form a mixture;

(b) stirring the mixture of step (a) until homogeneous;

(c) adding the homogenous mixture of step (b) to the porous solid carrier; and (d) stirring the mixture of step (c) until homogenous.

NUMBERED EMBODIMENTS—II

1. A drug-containing particle comprising:

(a) a drug substance comprising one or more cannabinoids; and (b) a porous solid carrier, wherein the one or more cannabinoids are adsorbed onto the porous solid carrier, and wherein the porous solid carrier has one or more of the following characteristics:

(i) average pore volume of about 1 mL/g to about 2 mL/g;

(ii) average surface area of about 250 $m^2/g$ to about 375 $m^2/g$; or (iii) pore diameters of about 2 nm to about 50 nm.

2. The drug-containing particle of embodiment 1, wherein the porous solid carrier is a microparticle.

3. The drug-containing particle of embodiment 1 or 2, wherein the porous solid carrier has an average particle size of about 1 μm to about 250 μm.

4. The drug-containing particle of any one of embodiments 1-3, wherein the porous solid carrier has an average particle size of about 50 μm to about 150 μm, or about 40 μm to 100 μm.

5. The drug-containing particle of any one of embodiments 1-4, wherein the porous solid carrier has a porosity of about 75% to about 99%.

6. The drug-containing particle of any one of embodiments 1-5, wherein the porous solid carrier has an average pore diameter of about 10 nm to about 50 nm.

7. The drug-containing particle of any one of embodiments 1-6, wherein the porous solid carrier has an average pore diameter of about 15 nm to about 30 nm.

8. The drug-containing particle of any one of embodiments 1-7, wherein the porous solid carrier has two or more of the following characteristics:

(a) average pore volume of about 1 mL/g to about 2 mL/g;

(d) average surface area of about 250 $m^2/g$ to about 375 $m^2/g$; or (c) pore diameter of about 2 nm to about 50 nm.

9. The drug-containing particle of any one of embodiments 1-8, wherein the porous solid carrier has an:

(a) average pore volume of about 1 mL/g to about 2 mL/g;

(d) average surface area of about 250 $m^2/g$ to about 375 $m^2/g$; and (c) pore diameter of about 2 nm to about 50 nm.

10. The drug-containing particle of any one of embodiments 1-9, wherein the porous solid carrier comprises silica ($SiO_2$), microcrystalline cellulose, silicified microcrystalline cellulose, chitosan, isomalt, or a silicate.

11. The drug-containing particle of any one of embodiments 1-10 wherein the porous solid carrier comprises silica or a silicate.

12. The drug-containing particle of any one of embodiments 1-11, wherein the porous solid carrier comprises silica.

13. The drug-containing particle of any one of embodiments 10-12, wherein the silica comprises mesoporous silica or amorphous silica.

14. The drug-containing particle of any one of embodiments 10-12, wherein the silica comprises mesoporous silica.

15. The drug-containing particle of any one of embodiments 1-14, wherein the porous solid carrier comprises a silicate.

16. The drug-containing particle of embodiment 15, wherein the silicate comprises an aluminosilicate.

17. The drug-containing particle of embodiment 15, wherein the silicate comprises a magnesium aluminosilicate.

18. The drug-containing particle of any one of embodiments 1-17, wherein the porous solid carrier is present in an amount of about 20% to about 80% by weight based on the total weight of the drug-containing particle.

19. The drug-containing particle of any one of embodiments 1-18, wherein the solid carrier is present in an amount of about 30% to about 50% by weight based on the total weight of the drug-containing particle.

20. The drug-containing particle of any one of embodiments 1-19, wherein the one or more cannabinoids comprise cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), CBD-C4, OH-CBD, CBD-C4, 6-OH-CBD, 7-OH-CBD, 7-COOH-CBD, 11-COOH-THC, or 11-OH-THC.

21. The drug-containing particle of any one of embodiments 1-20, wherein the one or more cannabinoids comprise CBD.

22. The drug-containing particle of any one of embodiments 1-21, wherein the one or more cannabinoids is present in an amount of about 5% to about 75% by weight based on the total weight of the drug-containing particle.

23. The drug-containing particle of any one of embodiments 1-22, wherein the one or more cannabinoids is present in an amount of about 10% to about 60% by weight based on the total weight of the drug-containing particle.

24. The drug-containing particle of any one of embodiments 1-23, wherein the one or more cannabinoids is present in an amount of about 15% to about 40% by weight based on the total weight of the drug-containing particle.

25. The drug-containing particles of any one of embodiments 1-24, wherein the ratio of the porous solid carrier to the drug substance is 10:1 to 1:5.

26. The drug-containing particles of any one of embodiments 1-24, wherein the ratio of the porous solid carrier to the drug substance is 2:1 to 1:2.

27. The drug-containing particle of any one of embodiments 1-26, wherein the one or more cannabinoids is present in an amorphous form.

28. The drug-containing particle of any one of embodiments 1-27, wherein adsorption is determined by scanning electron microscopy (SEM), differential scanning calorimetry (DSC), and/or X-ray power diffraction (XRPD).

29. The drug-containing particle of any one of embodiments 1-28, wherein substantially all of the one or more cannabinoids is adsorbed into the pores of the porous solid carrier.

30. The drug-containing particle of any one of embodiments 1-29, wherein the one or more cannabinoids is adsorbed into the pores of the porous solid carrier.

31. The drug-containing particle of any one of embodiments 1-30, comprising a lipophilic material.

32. The drug-containing particle of embodiment 31, wherein the lipophilic material comprises a stabilization agent, a viscosity-modifying agent, and/or a processability enhancer.

33. The drug-containing particle of embodiment 31 or 32, wherein the lipophilic material comprises one or more non-ionic surfactants.

34. The drug-containing particle of embodiment 33, wherein the one or more non-ionic surfactants comprise polyoxyethylene sorbitan fatty acid ester (polysorbate, Tween®), polyoxyethylene 15 hydroxy stearate (macrogol 15 hydroxy stearate, solutol HS15®), polyoxyethylene castor oil derivative (Cremophor® EL, ELP, RH 40), polyoxyethylene stearate (Myrj®), sorbitan fatty acid ester (Span®), polyoxyethylene alkyl ether (Brij®), polyoxyethylene nonylphenol ether (Nonoxynol®), or a combination thereof.

35. The drug-containing particle of any one of embodiments 31-34, wherein the lipophilic material comprises polyethylene oxide-containing fatty acid ester, polyethylene oxide glyceride, polypropylene glycol fatty acid ester, PEG, monoglyceride fatty acid ester, diglyceride fatty acid ester, triglyceride fatty acid ester, propylene glycol diglyceride, polyethylene oxide vegetable oil, or a combination thereof.

36. The drug-containing particle of embodiment 35, wherein the lipophilic material comprises polyethylene oxide glyceride.

37. The drug-containing particle of embodiment 35 or 36, wherein the lipophilic material comprises mono-, di-, and triglyceride esters of palmitic (C16) and stearic (C18) acids and PEG-32 (MW 1500) mono- and diesters of palmitic (C16) and stearic (C18) acids; mono-, di- and triglyceride esters of fatty acid (C8 to C18); mono-, di-, and triglyceride esters of lauric (C12) and stearic (C18) acids and PEG-6 (MW 300) mono- and diesters of lauric (C12) and stearic (C18) acid; mono-, di-, and triglyceride esters of oleic (C18:1) acid and PEG-6 (MW 300) and mono- and diesters of oleic (C18:1) acid; a mixture of monoesters and diesters of 12-hydroxystearic acid and polyethylene glycol glyceride; PEG-40 hydrogenated castor oil; propylene glycol monocaprylate; propylene glycol monolaurate; medium-chain triglyceride; propylene glycol dicaprolate/dicaprate; PEG-8 (MW 400) mono- and diesters of caprylic ($C_8$) and capric (C10) acids; or combinations thereof.

38. The drug-containing particle of embodiments 35 or 36, wherein the lipophilic material is mono-, di- and triglyceride esters of fatty acid (C8 to C18); mono-, di-, and triglyceride esters of lauric (C12) and stearic (C18) acids and PEG-6 (MW 300) mono- and diesters of lauric (C12) and stearic (C18) acids; or propylene glycol monocaprylate.

39. The drug-containing particle of embodiment 35, wherein the vegetable oil comprises one or more vegetable seed oil, fruit seed oil, kernel oil, sesame seed oil, medium-chain triglyceride (MCT) oil, oleic oil, pumpkin seed oil, transesterified vegetable oil, polyoxyethylene hydrogenated vegetable oil, PEG40-hydrogenated castor oil or a combination thereof.

40. The drug-containing particle of embodiment 39, wherein the lipophilic material is sesame seed oil or pumpkin seed oil.

41. The drug-containing particle of any one of embodiments 31-38, wherein the lipophilic material is present in an amount of about 1% to about 75% by weight based on the total weight of the drug-containing particle.

42. The drug-containing particle of any one of embodiments 31-39, wherein the lipophilic material is present in an amount of about 25% to about 35% by weight based on the total weight of the drug-containing particle.

43. The drug-containing particle of any one of embodiments 1-42, wherein the weight ratio of the solid carrier to the combined weight of the drug substance and lipophilic material ranges from 3:1 to 1:1.

44. The drug-containing particle of embodiment 43, wherein the lipophilic material is present in an amount of about 25% to about 75% by weight based on the total weight of the drug-containing particle.

45. The drug-containing particle of embodiment 40, wherein the sesame oil is present in an amount of about 45% to about 60% by weight based on the total weight of the drug-containing particle.

46. The drug-containing particle of any one of embodiments 1-45, comprising a polymer.

47. The drug-containing particle of embodiment 44, wherein the polymer has a $T_g$ of about 50° C. to about 130° C.

48. The drug-containing particle of embodiment 46 or 47, wherein the polymer comprises polyvinylpyrrolidone (kollidon VA64), cross linked polyvinyl N-pyrrolidone (crospovidone), hydroxypropyl methylcellulose phthalate (HPMCP 50), polyvinyl alcohol-polyethylene glycol copolymer (kollicoat), polyvinyl caprolactam-polyvinyl acetate-polyethylene glycol graft co-polymer (soluplus), polyvinyl alcohol, or a combination thereof.

49. The drug-containing particle of any one of embodiments 46-48, wherein the polymer is present in an amount of about 1% to about 75% by weight based on the total weight of the drug-containing particle.

50. The drug-containing particle of any one of embodiments 46-49, wherein the polymer is present in an amount of about 10% to about 50% by weight based on the total weight of the drug-containing particle.

51. The drug-containing particle of any one of embodiments 46-50, wherein the polymer is provided as a coating on the drug-containing particle.

52. The drug-containing particle of any one of embodiments 1-51, further comprising a chelating agent.

53. The drug-containing particle of embodiment 52, wherein the chelating agent comprises EDTA, citric acid, or curcumin.

54. The drug-containing particle of embodiment 52, wherein the chelating agent comprises citric acid or curcumin.

55. The drug-containing particle of any one of embodiments 52-54, wherein the amount of the chelating agent ranges from about 0.05% to about 3% by weight based on the total weight of the drug-containing particle.

56. The drug-containing particle of any one of embodiments 52-54, wherein the amount of the chelating agent ranges from about 0.05% to about 0.1% by weight based on the total weight of the drug-containing particle.

57. The drug-containing particle of any one of embodiments 1-56, comprising one or more antioxidants.

58. The drug-containing particle of embodiment 57, wherein the one or more antioxidants comprises α-tocopherol, β-carotene, ascorbic acid, ascorbyl palmitate, lecithin, butylated hydroxyanisole, butylated hydroxytoluene, monothiolglycerol, propyl gallate, or combinations thereof.

59. The drug-containing particle of embodiment 57 or 58, wherein the antioxidant comprises α-tocopherol.

60. The drug-containing particle of any one of embodiments 57-59, wherein the amount of the one or more antioxidants ranges from about 0.05% to about 3% by weight based on the total weight of the drug-containing particle.

61. The drug-containing particle of embodiment 60, wherein the amount of the one or more antioxidants ranges from about 0.2% to about 1% by weight based on the total weight of the drug-containing particle.

62. The drug-containing particle of any one of embodiments 1-61, wherein about 30% to about 90% of the one or more cannabinoids is released in about 3 h to about 12 h.

63. The drug-containing particle of any one of embodiments 1-61, wherein about 50% to about 90% of the one or more cannabinoids released in about 3 h to about 12 h.

64. The drug-containing particle of any one of embodiments 1-61, wherein greater than about 80% of the one or more cannabinoids released by about 12 h.

65. The drug-containing particle of any one of embodiments 1-64, comprising no more than about 0.2% by weight of cannabidiorcol (CBD-C1).

66. The drug-containing particle of any one of embodiments 1-65, comprising no more than about 0.8% by weight of cannabidivarin (CBDV).

67. The drug-containing particle of any one of embodiments 1-66, comprising less than about 0.5% by weight of cannabidibutol (CBD-C4).

68. A pharmaceutical composition comprising a plurality of drug-containing particles of any one of embodiments 1-67 or combination thereof, and at least one pharmaceutically acceptable excipient.

69. The pharmaceutical composition of embodiment 68, wherein the pharmaceutical composition is a tablet, capsule, or granule.

70. The pharmaceutical composition of any one of embodiments 1-69, wherein the drug-containing particle is prepared by a process comprising spray drying or hot-melt extrusion.

71. A method of preparing the drug-containing particle of any one of the preceding embodiments, comprising:

(a) combining the porous solid carrier, the one or more cannabinoids, and optionally the polymer to form a mixture;
(b) adding a solvent to the mixture to form a slurry;
(c) sonicating and/or agitating the slurry; and
(d) evaporating the solvent to obtain a dry powder, thereby absorbing the one or more cannabinoids onto the porous solid carrier.

72. A method of preparing the drug-containing particle of any one of embodiments 1-45 and 52-69, comprising:

(a) combining the one or more cannabinoids and the one or more lipophilic materials to form a mixture;
(b) stirring the mixture of step (a) until homogeneous;
(c) adding the homogenous mixture of step (b) to the porous solid carrier; and
(d) stirring the mixture of step (c) until homogenous, thereby absorbing the one or more cannabinoids onto the porous solid carrier.

73. The drug-containing particle of any one of embodiments 1-61, wherein at least 20% of the one or more cannabinoids is released in 10 minutes from the drug-containing particle.

74. The drug-containing particle of any one of embodiments 1-61 and 73, wherein 20-50% of the one or more cannabinoids is released in 10 minutes from the drug-containing particle.

75. The drug-containing particle of any one of embodiments 1-61 and 74, wherein at least 30% of the one or more cannabinoids is released in 15 minutes from the drug-containing particle.

76. The drug-containing particle of any one of embodiments 1-61 and 73-75, wherein at least 30-70% of the one or more cannabinoids is released in 15 minutes from the drug-containing particle.

77. The drug-containing particle of any one of embodiments 1-61 and 73-76, wherein at least 40% of the one or more cannabinoids is released in 20 minutes from the drug-containing particle.

78. The drug-containing particle of any one of embodiments 1-61 and 73-77, wherein 40-80% of the one or more cannabinoids is released in 20 minutes from the drug-containing particle.

79. The drug-containing particle of any one of embodiments 1-61 and 73-78, wherein at least 45% of the one or more cannabinoids is released in 30 minutes from the drug-containing particle.

80. The drug-containing particle of any one of embodiments 1-61 and 73-79, wherein 45-85% of the one or more cannabinoids is released in 30 minutes from the drug-containing particle.

81. The drug-containing particle of any one of embodiments 1-61 and 73-80, wherein at least 50% of the one or more cannabinoids is released in 45 minutes from the drug-containing particle.

82. The drug-containing particle of any one of embodiments 1-61 and 73-81, the drug-containing particles disclosed wherein 50-85% of the one or more cannabinoids is released in 50 minutes from the drug-containing particle.

83. The drug-containing particle of any one of the preceding embodiments, wherein drug release is measured using U.S. Pharmacopeia (USP) dissolution test (711).

84. The drug-containing particle of embodiment 83, wherein drug release is measured using Apparatus II.

85. The drug-containing particle of embodiment 83 or 84, wherein drug release is measured using 0.1 M HCl buffer at pH 1.

EXAMPLES

Example 1: Evaluation of Solvent-Mediated Drug Loading on Mesoporous Silica

Figure 5:
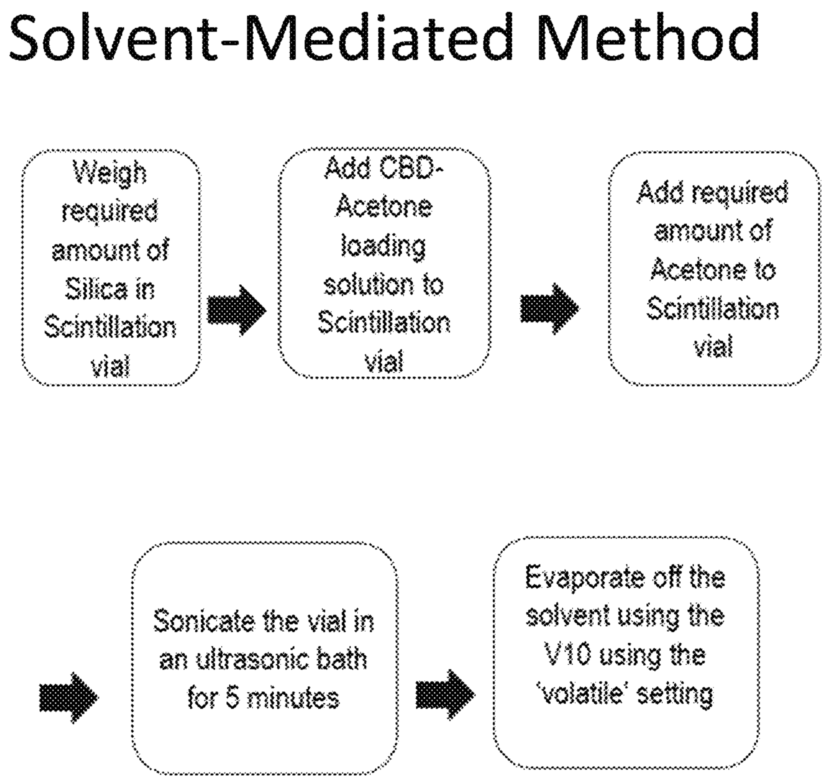
FIG. 5 provides a flowchart describing the lab-scale preparation of drug-containing particles of the present disclosure by a solvent-mediated method.

Drug-containing particles having the compositions provided in Table 1 were prepared according to the solvent-mediated manufacturing method described in FIG. 5.

TABLE 1

Compositions of CBD-containing particles prepared by solvent-mediated manufacturing.

| Porous Solid Carrier (% w/w) | Cannabinoid (% w/w) |
|---|---|
| Fujisil 71.4 | CBD 28.6 |
| Fujisil 50.0 | CBD 50.0 |
| Fujisil 25.1 | CBD 74.9 |
| Syloid 71.3 | CBD 28.7 |
| Syloid 50.2 | CBD 49.8 |
| Syloid 25.1 | CBD 74.9 |

Stability Testing: Stability of the CBD-containing drug particles in Table 1 was evaluated after 7 days at the accelerated temperature condition of 60° C. Stability success criteria are shown in Table 2A The amounts of CBD degradants CBE I, CBE II, and OH-CBD, and THC are provided as percent of the active ingredient are shown in Table 2B.

TABLE 2A

Stability Criteria

| Text | Initial | |
|---|---|---|
| XRPD | No sharp peaks representative of crystalline API. | |
| DSC | Single $T_g/T_m$ with no evidence of crystalline CBD melt. | |
| SEM | No evidence of particles with morphology of crystalline API. | |
| Assay/ Degradants | No evidence of significant degradation, no evidence of significant THC formation. | |
| Powder density | Powder density allows for filing size 0 capsule with at least 100 mg active | |
| 60° C. storage | THC | NMT 2.0% active |
| | CBE I | NMT 0.5% active |
| | CBE II | NMT 0.5% active |
| | OH-CBD | NMT 0.2% active |

TABLE 2A-continued

| Stability Criteria | |
|---|---|
| Text | Initial |
| Individual unknown degradants | NMT 0.2% active |
| Total unspecified degradants | NMT 1.0% active |

TABLE 2B

Stability of drug-particles after 7 days at at 60° C.

| Sample | CBD (% of Initial) | CBE I | CBE II | OH-CBD | THC | Total Unknowns |
|---|---|---|---|---|---|---|
| Syloid CBD 25% w/w | 103.57 | 1.20 | 0.41 | ND | 0.05 | 0.53 |
| Syloid CBD 50% w/w | 102.06 | 0.35 | 0.10 | ND | 0.19 | 0.29 |
| Fujisil CBD 25% w/w | 109.83 | 0.95 | 0.82 | 0.06 | ND | 1.04 |
| Fujisil CBD 50% w/w | 106.51 | 0.92 | 0.34 | ND | 0.04 | 0.25 |
| Fujisil CBD 75% w/w | 101.69 | 0.37 | 0.12 | ND | 0.04 | 0.15 |

ND = Not detected; CBE 1, CBE II, OH-CBD, THC and total unknowns provided in wt. % of CBD.

Figure 23A:
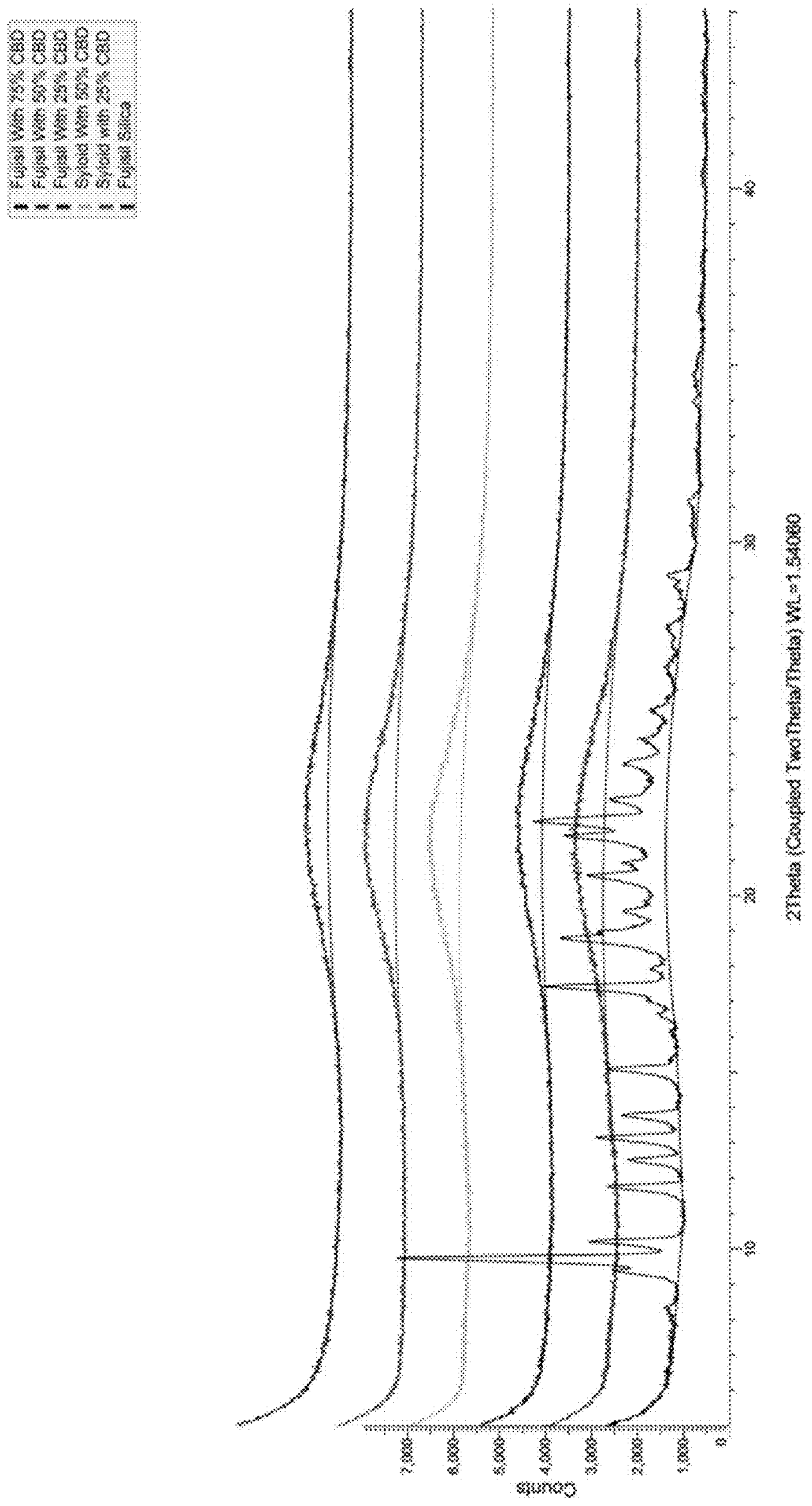
FIG. 23A shows x-ray pattern diffractogram (XRPD) for solvent-loaded drug-containing particles at timepoint 0.
Figure 23B:
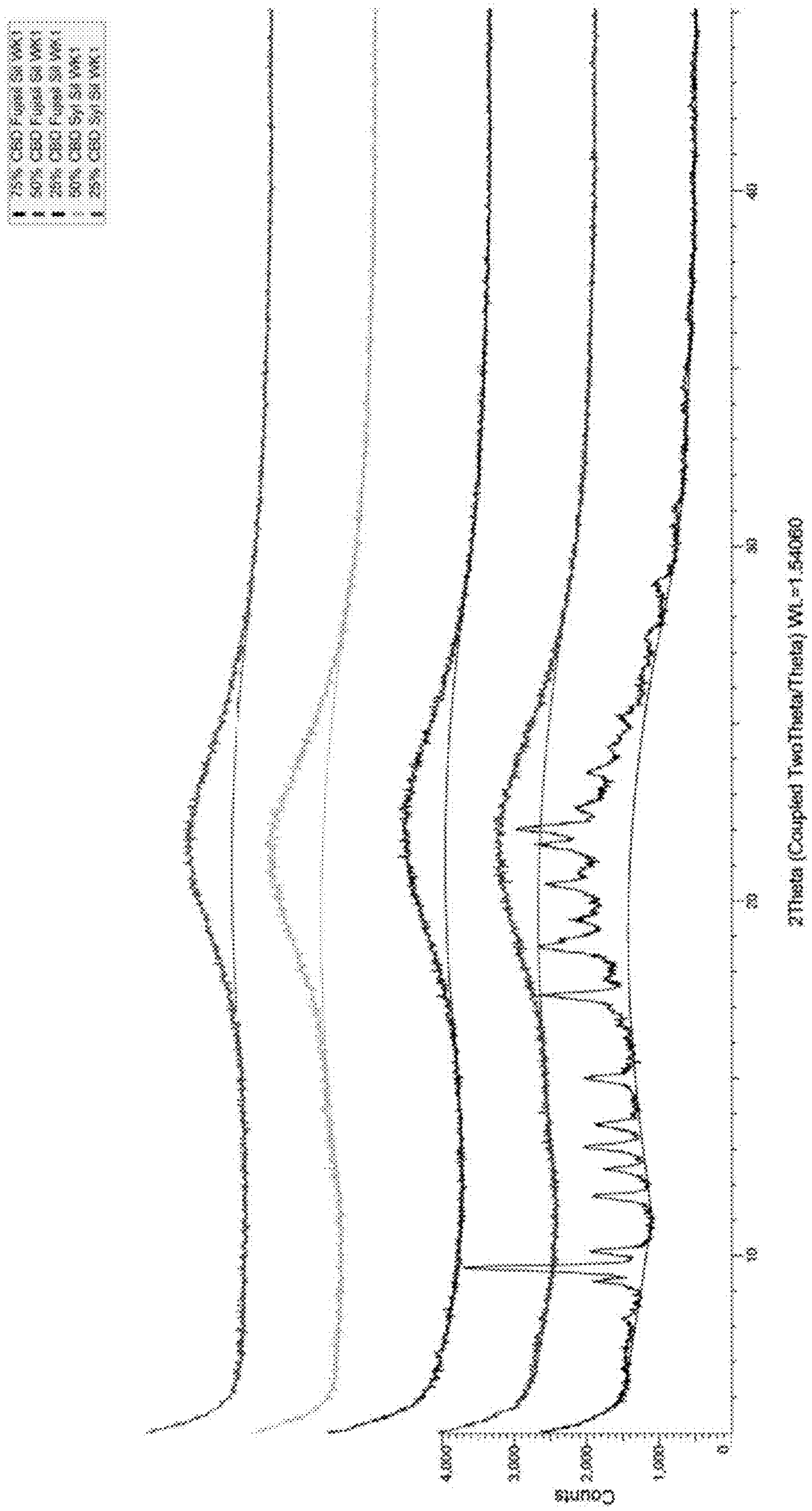
FIG. 23B shows x-ray pattern diffractogram (XRPD) for solvent-loaded drug-containing particles after 1 week.

The formulations were stored at 60° C. and amorphicity was assessed by XRPD at 0 and 7 days. XRPD diffractograms at the initial timepoint and 1 week time point are shown in FIG. 23A and FIG. 23B, respectively. The diffractograms indicate that all 25% w/w and 50% w/w batches were amorphous by XRPD. The 75% w/w Fujisil batch was not amorphous and showed peaks indicative of crystalline CBD. There was no change in amorphous state of any of the batches after storage at 60° C. for 7 days.

Figure 6:
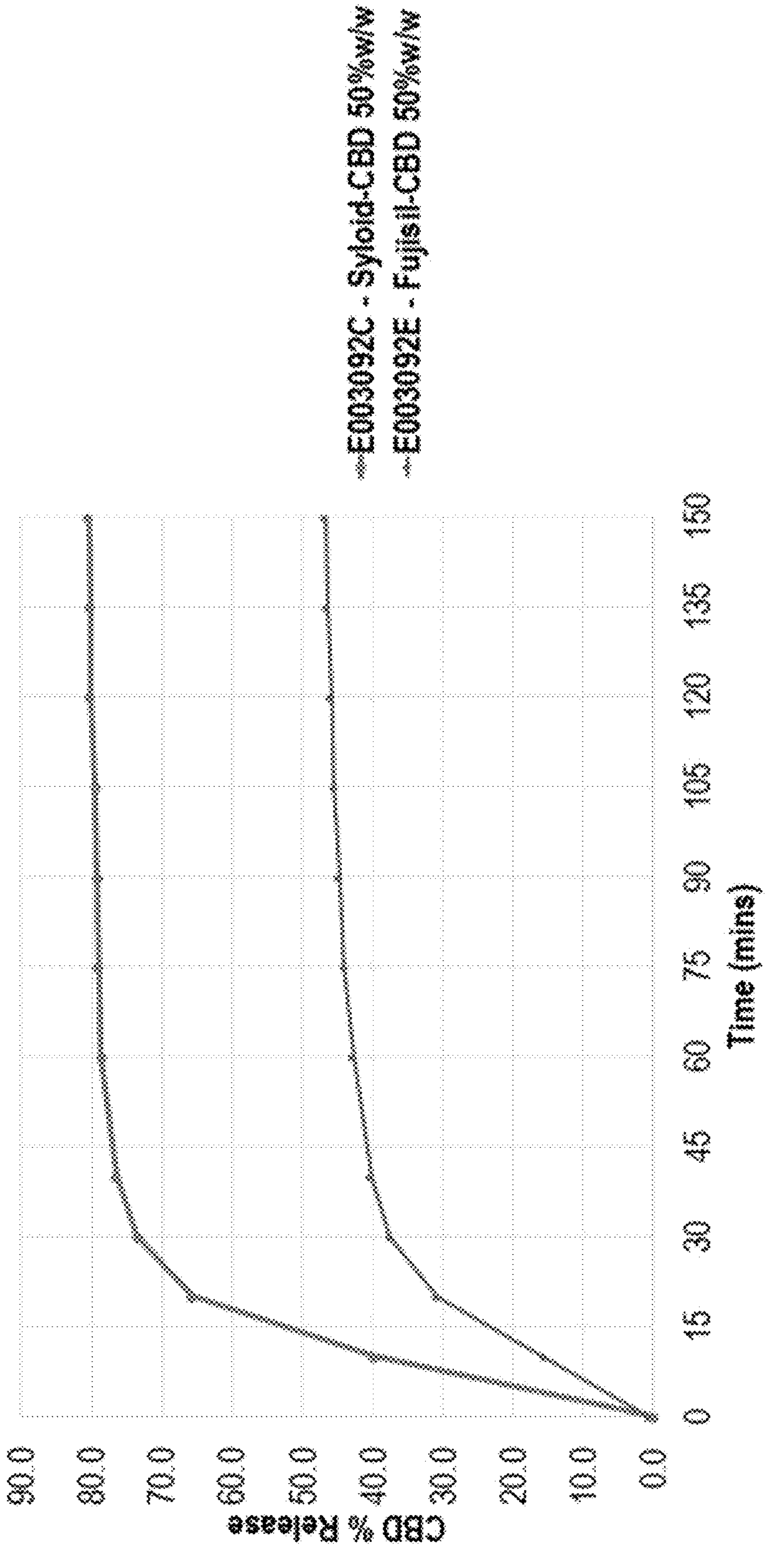
FIG. 6 provides a graph of CBD release from Syloid® and Fujisil™ loaded with 50% w/w of drug.

Drug-release Profiles of Table 2: Drug release from Syloid particles containing CBD at 50% w/w and Fujisil particles containing CBD at 50% w/w were evaluated. As shown in FIG. 6, CBD was effectively released from Syloid silica, reaching 80% at the 60-minute timepoint. In addition, Syloid exhibited superior flow properties after loaded drug substance loading compared to Fukisil. Thus, Syloid was selected for further development.

Figure 7:
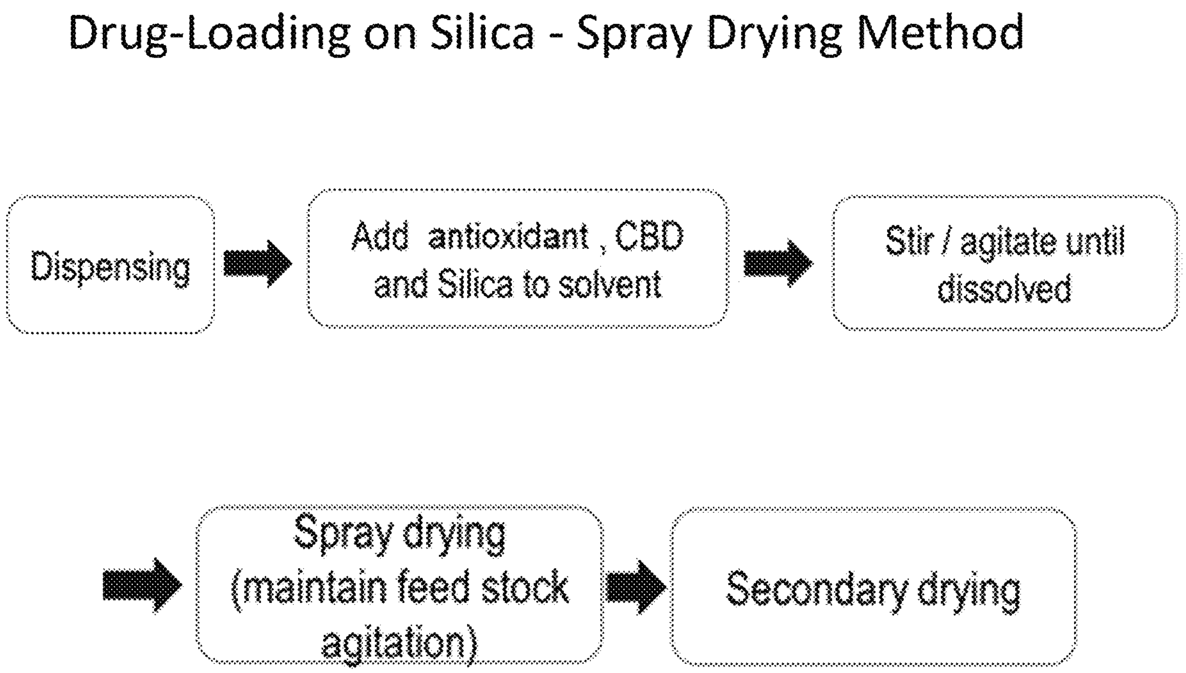
FIG. 7 provides a flowchart describing the lab-scale preparation of drug-containing particles of the present disclosure by a formulation method comprising spray drying.

Example 2: Evaluation of CBD-Loaded Mesoporous Silica Drug Particles Prepared by Spray Drying The properties of the spray dried drug-containing particles provided in Tables 3 and 4 were evaluated. These particles were prepared according to the method described in FIG. 7. An exemplary spray drying apparatus is described in FIG. 8.

TABLE 3

Compositions of CBD-containing Syloid ® particles subjected to spray drying

| Material | Feedstock Composition (% w/w) | Final Syloid ® XDP Composition (% w/w) (after drying/removal of acetone) | Material | Feedstock Composition (% w/w) | Final Syloid ® XDP Composition (% w/w) (after drying/removal of acetone) |
|---|---|---|---|---|---|
| CBD | 16.6 | 50.0 | CBD | 20.0 | 60.1 |
| Syloid XDP | 16.6 | 50.0 | Syloid XDP | 13.3 | 39.9 |
| Acetone | 66.8 | 0 | Acetone | 66.7 | 0 |

TABLE 4

Compositions of CBD-containing Neusilin ® particles subjected to spray drying.

| Material | Feedstock Composition (% w/w) | Final Syloid ® XDP Composition (% w/w) (after drying) |
|---|---|---|
| CBD | 17.5 | 50.0 |
| Neusilin | 17.5 | 50.0 |
| Acetone | 65.0 | — |

The spray drying method was carried out on a Buchi B-290 apparatus using the following parameters:

Inlet temp: 60° C. (Syloid)/80° C. (Neusilin)

Chiller temp: −20° C.

Aspirator: 100%

Feed rate: 20 g/min

Q-flow: 65 mm (Syloid)/60 mm (Neusilin)

Nozzle size: 2.1 mm

Post-collection drying: 2 d at 30° C. under dynamic vacuum (Syloid)/24 h at 40° C. under vacuum (Neusilin)

In each case, the materials tested were easily processed and no handling issues were observed.

Example 3: Evaluation of CBD/Lipid-Loaded Mesoporous Silica Drug Particles

Figure 9A:
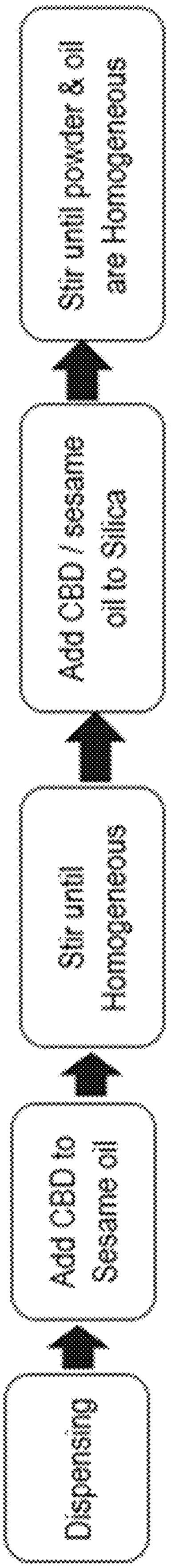
FIG. 9A provides a flowchart describing a CBD/sesame oil-loaded mesoporous silica drug particle formulations 1-6 of Table 5 manufacturing method used to prepare drug-containing particles of the present disclosure.
Figure 9B:
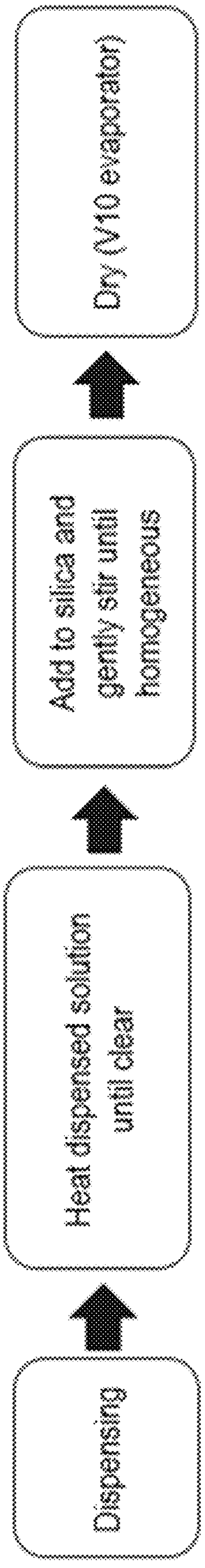
FIG. 9B provides a flowchart describing a CBD/lipid-loaded mesoporous silica drug particle formulations 7-10 manufacturing method used to prepare drug-containing particles of the present disclosure.
Figure 9C:
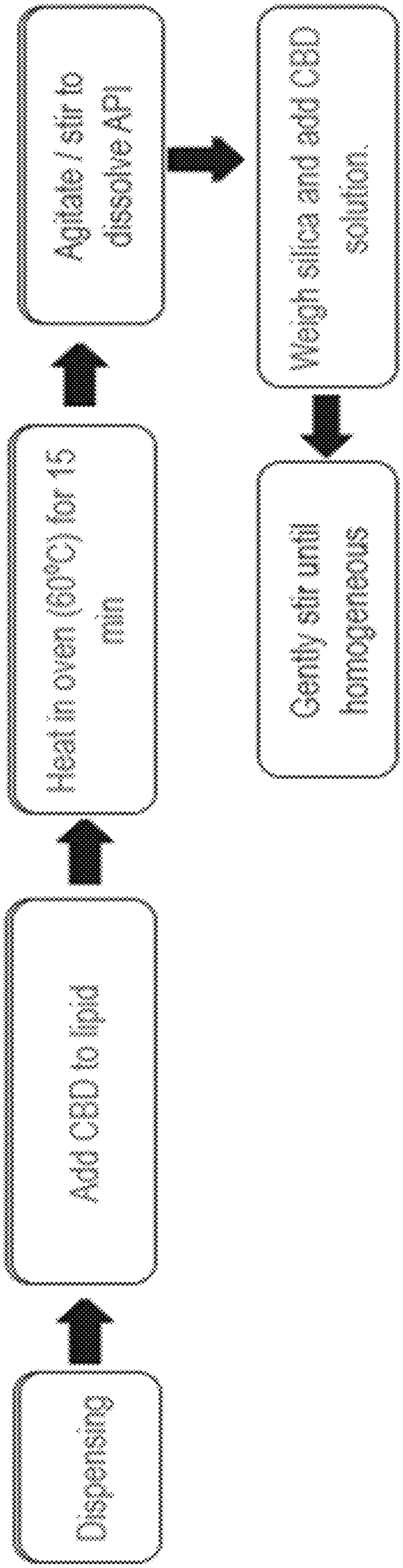
FIG. 9C provides a flowchart describing a CBD/lipid-loaded mesoporous silica drug particle formulations 1-10 of Table 8 manufacturing method used to prepare drug-containing particles of the present disclosure.

The compositions of various CBD/lipid-loaded mesoporous silica drug particles prepared according to the methods provided in FIGS. 9A-C are provided in Table 5.

In particular, CBD/sesame oil-loaded mesoporous silica drug particle formulations 1-6 of Table 5 were prepared according to the process described in FIG. 9A. CBD/lipid-loaded mesoporous silica drug particle formulations 7-10 were prepared according to the process described in FIG. 9B.

For the formulations provided in Table 5, all compositions showed amorphicity, confirming adsorption of the cannabinoid. Crystallinity was observed when drug-loading was greater than 60%.

TABLE 5

Compositions of CBD/Sesame Seed oil-loaded drug particles.

| Formulation | Material | % w/w |
|---|---|---|
| 1 | Syloid XDP | 50.0 |
| | 10% CBD in Sesame Seed Oil | 50.0 |
| | Overall CBD | 5.0 |
| 2 | Syloid XDP | 33.33 |
| | 10% CBD in Sesame Seed Oil | 66.67 |
| | Overall CBD | 6.7 |

TABLE 5-continued

| Compositions of CBD/Sesame Seed oil-loaded drug particles. | | |
|---|---|---|
| Formulation | Material | % w/w |
| 3 | Syloid XDP | 40.0 |
| | 10% CBD in Sesame Seed Oil | 60.0 |
| | Overall CBD | 6.0 |
| 4 | Syloid XDP | 30.0 |
| | 30% CBD in Sesame Seed Oil | 70.0 |
| | Overall CBD | 21.0 |
| 5 | Syloid XDP | 50.0 |
| | 30% CBD in Sesame Seed Oil | 50.0 |
| | Overall CBD | 15.0 |
| 6 | Syloid XDP | 40.0 |
| | 30% CBD in Sesame Seed Oil | 60.0 |
| | Overall CBD | 18.0 |
| 7 | Syloid XDP | 40.0 |
| | 30% CBD in Sesame Seed Oil with α-tocopherol | 60.0 |
| | Overall CBD | 15.0 |
| 8 | Syloid XDP | 50.0 |
| | 30% CBD in Sesame Seed Oil with α-tocopherol | 50.0 |
| | Overall CBD | 18.0 |
| 9 | Syloid XDP | 60.0 |
| | 30% CBD in Sesame Seed Oil | 40.0 |
| | Overall CBD | 15.1 |
| 10 | Syloid XDP | 50.0 |
| | 30% CBD in Sesame Seed Oil | 50.0 |
| | Overall CBD | 18.0 |

Sesame seed oil was replaced with pumpkin seed oil and a primary solution of 12.48% CBD (w/w), 37.40% pumpkin seed oil (w/w), and 0.1% α-tocopherol was prepared. This solution was added to Neusilin® in a 1:1, 1.5:1, and 2.3:1 ratio to provide drug particles with 17.5%, 15.0%, and 12.5% (w/w) CBD loading. This composition was found to be amorphous.

Other solid and liquid lipophilic materials were evaluated for the ability solubilize CBD. The solid lipophilic materials evaluated are provided below in Table 6A and the solubility observations are provided in Table 6B. The liquid lipophilic materials evaluated are provided in Table 7A and solubility observations are provided in Table 7B.

TABLE 6A

| Solid Lipophilic Materials | |
|---|---|
| Lipid | HLB Value |
| Gelucire 50/13 | 11 |
| Gelucire 48/16 | 14 |
| Gelucire 44/14 | 11 |
| Gelucire 43/01 | 1 |
| Labrafil M 2130 CS | 9 |
| Crodasol HS | 15 |
| Croduret 40 | 13 |
| Croduret 50 | 14 |
| Peceol | 1 |

TABLE 7A

| Liquid Lipophilic Materials | |
|---|---|
| Lipid | HLB Value |
| Transcutol | 14 |
| Labrasol ALF | 12 |
| Kolliphor EL | 12 |
| Polysorbate 80 | 15 |
| Polysorbate 60 | 15 |
| Capryol 90 | 3 |
| Polysorbate 20 | 15 |
| Capryol PGMC | 3 |
| Labrafac PG | 1 |
| Lab Lipo 1349 | 1 |
| Labrafil 1944 | 9 |
| Labrafil 2125 | 9 |
| Oleic Acid | 1 |
| Corn oil | 1 |
| Cottonseed oil | 1 |

The solid lipophilic materials were loaded with CBD at three concentrations: 300, 400, and 500 mg/g. Each mix was then heated to 60° C. for half an hour and then agitated to dissolve. 10 grams of each combination was made in a clear glass scintillation vial and allowed to cool before it was assessed using DSC to determine if there was any undissolved CBD present. Any excipients which showed CBD to be fully soluble at 500 mg/g were further assessed at 540, 560 and 600 mg/g. The results are shown in Table 6B.

TABLE 6B

| CBD Solubility Observations | |
|---|---|
| Lipid | Observations |
| Gelucire 50/13 | Soft solid at all CBD concentrations |
| Gelucire 48/16 | Solid at 300 and 400 mg/g Liquid above 500 mg/g. |
| Gelucire 44/14 | Solid at 300 Liquid above 400 mg/g |
| Gelucire 43/01 | Soft solid at all CBD concentrations |
| Labrafil M 2130 CS | Soft solid at all CBD concentrations |
| Crodasol HS | Liquid at all CBD concentrations |
| Croduret 40 | Liquid at all CBD concentrations |
| Croduret 50 | Liquid at all CBD concentrations |
| Peceol | Became liquid at 300 mg/g and became progressive more solid at higher CBD loadings. |

Each liquid lipophilic material was heated at 40° C. for 30 minutes in an oven before being combined with the CBD. 10 g of CBD was combined with 5 g of lipophilic material to create a saturated mixture. These were agitated for at least 8 hours at 300 rpm using a shaker plate. After agitation the solutions were centrifuged at 14800 rpm for 90 minutes to separate out any remaining undissolved CBD crystals. The resulting supernatant was sampled and assayed for CBD content to confirm the saturation solubility of the lipid. The solubility results are presented below in Table 7B.

TABLE 7B

| Solubility Observations | |
|---|---|
| Lipid | CBD (mg/g) |
| Transcutol | 653.2 |
| Labrasol ALF | 630.8 |
| Kolliphor EL | 603.9 |
| Polysorbate 80 | 598.4 |
| Polysorbate 60 | 588.5 |
| Capryol 90 | 582.2 |
| Polysorbate 20 | 565.9 |
| Capryol PGMC | 565.3 |
| Labrafac PG | 501.8 |
| Labrafac 1349 | 427.6 |
| Labrafil 1944 | 424.2 |
| Labrafil 2125 | 412.6 |
| Oleic Acid | 347.2 |

TABLE 7B-continued

| Solubility Observations | |
|---|---|
| Lipid | CBD (mg/g) |
| Corn oil | 276.1 |
| Cottonseed oil | 255.2 |

The lipophilic materials advanced for further development are shown in Table 8A.

Table 8A. Advanced Lipophilic Materials

TABLE 8

| Advanced Lipophilic Materials | |
|---|---|
| Excipient | Justification |
| Gelucire 50/13 | Remained solid at high CBD concentrations and possesses a high HLB value compared to other solid excipients selected |
| Gelucire 43/01 | Remained solid at high CBD concentrations and possesses a low HLB value compared to other solid excipients selected |
| Labrafil M 2130 CS | Remained solid at high CBD concentrations and possesses a medium HLB value compared to other solid excipients selected |
| Crodasol HS | CBD showed high solubility. Similar properties to Cruduret 40 and 50 but selected due to its different chemical structure. |
| Croduret 40 | CBD showed high solubility. Similar properties to Cruduret 50 but selected in order to reduce number of options as results from both would be likely be similar. |
| Capryol 90 | Selected due to high solubility of CBD and the potential for this excipient to increase intestinal permeability. |
| Labrafac 1349 | Selected as it can potentially increase intestinal permeability but has a lower HLB than Capryol 90, allowing for investigation into the effect of HLB. |
| Labrafac PG | Selected as it can potentially increase intestinal permeability but has a lower HLB than Capryol 90, allowing for investigation into the effect of HLB. |
| Labrasol ALF | CBD showed high solubility. And ALF has the potential to increase intestinal permeability. |
| Labrafil 1944 | Selected as it can potentially reduce the effect of the first pass |

Additional CBD/lipid-loaded mesoporous silica drug particles, such as formulations 1-10 in Table 8B, were prepared without antioxidant according to the process described in FIG. 9C.

Figure 10:
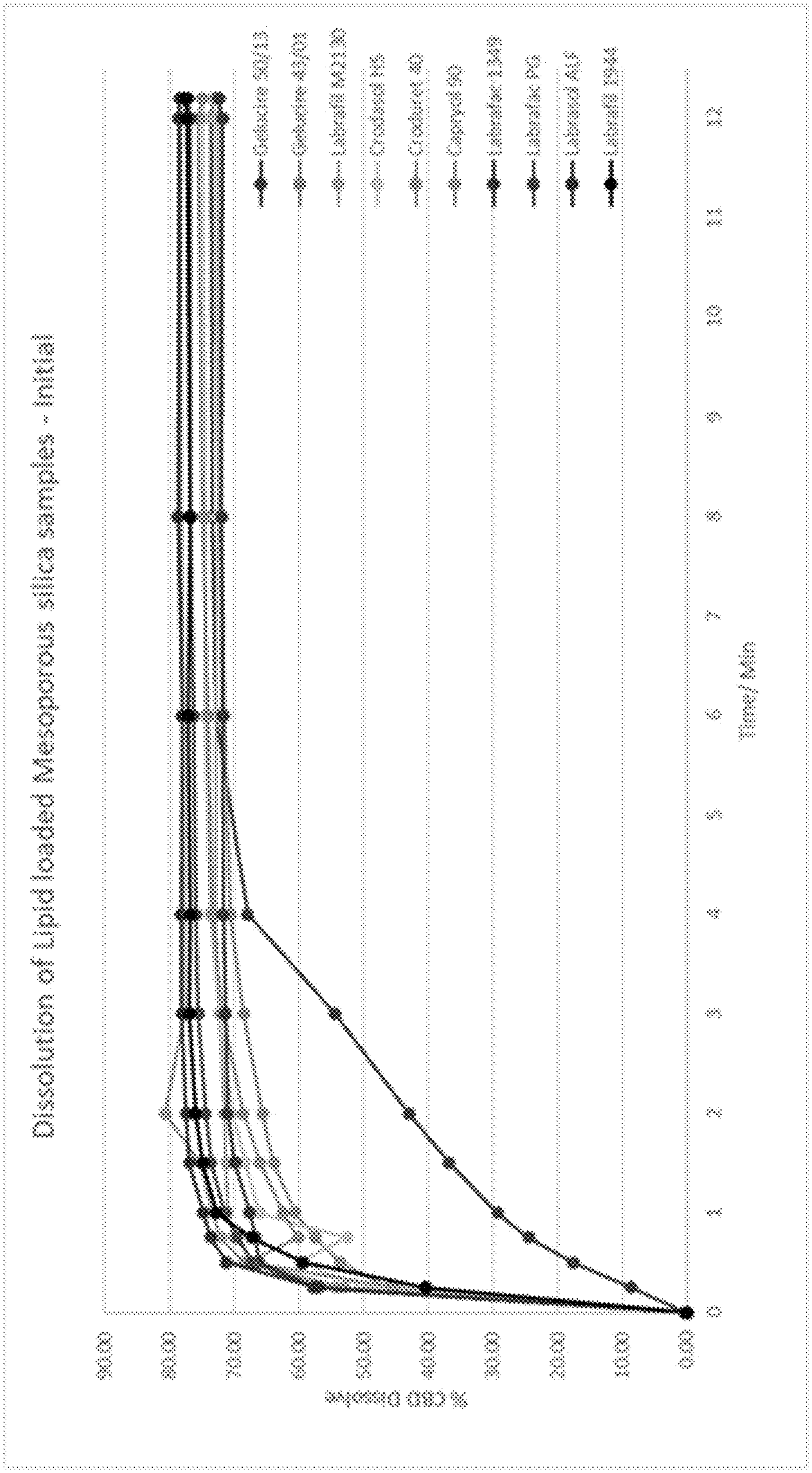
FIG. 10 provides a graph of CBD release from lipid-loaded mesoporous silica samples of the present disclosure.

Drug release from each of the CBD/lipid-loaded particles was measured using dissolution test conditions described in Tables A1 (Gelucire and Capryol samples) and A2 (Labrafil sample) and the results are summarized in the dissolution graph of FIG. 10. In all cases, between about 70% and 80% of the CBD in the drug particle was released within about 6 h.

TABLE 8B

| Compositions of CBD/lipid-loaded drug particles. | | |
|---|---|---|
| Formulation | Material | % w/w |
| 1 | Syloid XDP | 50.0 |
| | CBD | 24.0 |
| | Gelucire 50/13 | 26.0 |
| 2 | Syloid XDP | 50.0 |
| | CBD | 24.0 |
| | Gelucire 43/01 | 26.0 |
| 3 | Syloid XDP | 50.0 |
| | CBD | 24.0 |
| | Labrafil M2130 | 26.0 |

TABLE 8B-continued

| Compositions of CBD/lipid-loaded drug particles. | | |
|---|---|---|
| Formulation | Material | % w/w |
| 4 | Syloid XDP | 50.0 |
| | CBD | 20.0 |
| | Crodasol HS | 30.0 |
| 5 | Syloid XDP | 50.0 |
| | CBD | 20.0 |
| | Croduret 40 | 30.0 |
| 6 | Syloid XDP | 50.0 |
| | CBD | 23.2 |
| | Capryol 90 | 26.8 |
| 7 | Syloid XDP | 50.0 |
| | CBD | 17.0 |
| | Labrafac 1349 | 33.0 |
| 8 | Syloid XDP | 50.0 |
| | CBD | 20.0 |
| | Labrafac PG | 30.0 |
| 9 | Syloid XDP | 50.0 |
| | CBD | 25.2 |
| | Labrasol ALF | 24.8 |
| 10 | Syloid XDP | 50.0 |
| | CBD | 17.0 |
| | Labrafil 1944 | 33.0 |

The stability of the formulations in Table 8 was evaluated after 4 weeks at 25° C. and 60% RH and 6 weeks at 40° C. and 75% RH. The results are summarized in Tables 9 and 10, respectively. Each formulation was found to be amorphous and highly stable.

TABLE 9

| Stability evaluated after 4 weeks at 25° C. and 60% RH. | | | | | | |
|---|---|---|---|---|---|---|
| Sample | CBD % of initial | CBE I | CBE II | THC | Total RRTs | Amorphous |
| Gelucire 50/13 | 99.75 | <LOQ | <LOQ | <LOQ | ND | Yes |
| Gelucire 43/01 | 94.43 | <LOQ | 0.08 | 0.05 | 0.05 | Yes |
| Labrafil M2130 | 93.61 | <LOQ | <LOQ | <LOQ | 0.06 | Yes |
| Crodasol HS | 93.60 | <LOQ | <LOQ | <LOQ | 0.23 | Yes |
| Croduret 40 | 92.58 | <LOQ | ND | <LOQ | 0.12 | Yes |
| Capryol 90 | 92.10 | <LOQ | <LOQ | <LOQ | 0.08 | Yes |
| Labrafac 1349 | 95.11 | <LOQ | <LOQ | <LOQ | 0.09 | Yes |
| Labrafac PG | 94.15 | <LOQ | <LOQ | <LOQ | 0.09 | Yes |
| Labrasol ALF | 91.78 | 0.07 | <LOQ | <LOQ | 0.15 | Yes |
| Labrafil 1944 | 94.10 | 0.09 | <LOQ | <LOQ | 0.34 | Yes |

TABLE 10

| Stability evaluated after 6 weeks at 40° C. and 75% RH. | | | | | | |
|---|---|---|---|---|---|---|
| Sample | CBD % of initial | CBE I | CBE II | THC | Total RRTs | Amorphous |
| Gelucire 50/13 | 93.27 | 0.50 | 0.28 | <LOQ | 0.22 | Yes |
| Gelucire 43/01 | 90.66 | 0.29 | 0.11 | 0.12 | 0.14 | Yes |
| Labrafil M2130 | 92.41 | 0.34 | 0.14 | <LOQ | 0.16 | Yes |
| Crodasol HS | 89.01 | 0.77 | 0.45 | <LOQ | 0.68 | Yes |
| Croduret 40 | 89.60 | 0.85 | 0.57 | <LOQ | 0.98 | Yes |
| Capryol 90 | 93.27 | 0.51 | 0.21 | <LOQ | 0.08 | Yes |
| Labrafac 1349 | 91.86 | 0.51 | 0.21 | 0.07 | 0.14 | Yes |
| Labrafac PG | 92.73 | 0.64 | 0.26 | <LOQ | 0.21 | Yes |
| Labrasol ALF | 89.43 | 0.84 | 0.44 | <LOQ | 0.41 | Yes |
| Labrafil 1944 | 93.11 | 0.41 | 0.14 | <LOQ | 0.29 | Yes |

CBD/lipid-loaded mesoporous silica drug particles with antioxidant were also prepared according to the process described in FIG. 9C, and the stability of these materials was evaluated. The compositions of these drug particles are summarized in Table 11.

TABLE 11

| Compositions of CBD/lipid-loaded drug particles with antioxidant. | | |
|---|---|---|
| Formulation | Material | % w/w |
| 1 | Syloid XDP | 50.0 |
| | CBD | 24.0 |
| | Gelucire 50/13 | 25.8 |
| | α-tocopherol | 0.2 |
| 2 | Syloid XDP | 50.0 |
| | CBD | 24.0 |
| | Gelucire 43/01 | 25.80 |
| | α-tocopherol | 0.2 |
| 3 | Syloid XDP | 50.0 |
| | CBD | 24.0 |
| | Labrafil M2130 | 25.8 |
| | α-tocopherol | 0.2 |
| 4 | Syloid XDP | 50.0 |
| | CBD | 20.0 |
| | Crodasol HS | 29.8 |
| | α-tocopherol | 0.2 |
| 5 | Syloid XDP | 50.0 |
| | CBD | 20.0 |
| | Croduret 40 | 25.8 |
| | α-tocopherol | 0.2 |
| 6 | Syloid XDP | 50.0 |
| | CBD | 23.2 |
| | Capryol 90 | 26.6 |
| | α-tocopherol | 0.2 |
| 7 | Syloid XDP | 50.0 |
| | CBD | 17.0 |
| | Labrafac 1349 | 32.8 |
| | α-tocopherol | 0.2 |
| 8 | Syloid XDP | 50.0 |
| | CBD | 20.0 |
| | Labrafac PG | 29.8 |
| | α-tocopherol | 0.2 |
| 9 | Syloid XDP | 50.0 |
| | CBD | 25.3 |
| | Labrasol ALF | 24.5 |
| | α-tocopherol | 0.2 |
| 10 | Syloid XDP | 50.0 |
| | CBD | 17.0 |
| | Labrafil 1944 | 32.8 |
| | α-tocopherol | 0.2 |

The stability of the formulations in Table 11 was evaluated after 6 weeks at 25° C. and 60% RH and 6 weeks at 40° C. and 75% RH. The results are summarized in Tables 12 and 13, respectively. Each formulation was found to be amorphous and highly stable.

TABLE 12

| Stability with antioxidant evaluated after 6 weeks at 25° C. and 60% RH. | | | | | | |
|---|---|---|---|---|---|---|
| Sample | CBD % of initial | CBE I | CBE II | THC | Total RRTs | Amorphous |
| Gelucire 50/13 | 96.9 | <LOQ | ND | <LOQ | ND | Yes |
| Gelucire 43/01 | 90.5 | <LOQ | <LOQ | <LOQ | ND | Yes |
| Labrafil M2130 | 97.8 | <LOQ | <LOQ | <LOQ | ND | Yes |
| Crodasol HS | 93.6 | <LOQ | ND | <LOQ | ND | Yes |
| Croduret 40 | 94.7 | <LOQ | ND | <LOQ | ND | Yes |
| Capryol 90 | 95.7 | <LOQ | <LOQ | <LOQ | ND | Yes |
| Labrafac 1349 | 95.7 | <LOQ | <LOQ | <LOQ | ND | Yes |
| Labrafac PG | 96.2 | <LOQ | <LOQ | <LOQ | ND | Yes |
| Labrasol ALF | 94.3 | <LOQ | <LOQ | <LOQ | ND | Yes |
| Labrafil 1944 | 94.3 | 0.19 | ND | <LOQ | 0.36 | Yes |

TABLE 13

| Stability with antioxidant evaluated after 6 weeks at 40° C. and 75% RH. | | | | | | |
|---|---|---|---|---|---|---|
| Sample | CBD % of initial | CBE I | CBE II | THC | Total RRTs | Amorphous |
| Gelucire 50/13 | 93.0 | 0.22 | 0.10 | <LOQ | N/A | Yes |
| Gelucire 43/01 | 93.1 | 0.31 | 0.12 | 0.12 | 0.08 | Yes |
| Labrafil M2130 | 93.3 | 0.34 | 0.15 | <LOQ | ND | Yes |
| Crodasol HS | 90.7 | 0.20 | ND | <LOQ | ND | Yes |
| Croduret 40 | 93.4 | 0.11 | ND | <LOQ | ND | Yes |
| Capryol 90 | 93.3 | 0.33 | 0.15 | <LOQ | ND | Yes |
| Labrafac 1349 | 92.8 | 0.30 | <LOQ | <LOQ | ND | Yes |
| Labrafac PG | 92.3 | 0.35 | 0.15 | <LOQ | ND | Yes |
| Labrasol ALF | 93.8 | 0.29 | 0.13 | <LOQ | ND | Yes |
| Labrafil 1944 | 90.8 | 0.56 | ND | <LOQ | 0.34 | Yes |

CBE I was observed in Labrafil 1944 compositions after 6 weeks at 25 C/60% RH. Croduret 40, Crodasol HS, and Labrafac PG displayed lower CBD solubility compared to counterpart lipids with similar HLB values. Based on these observations, these four lipophilic materials were not selected for commercial development.

Compositions containing propylene glycol monocaprylate (Capryol 90) were evaluated for CBD solubility and stability. CBD was dissolved in propylene glycol monocaprylate (Capryol 90) and loaded on to Aeroperl®. The formulation is shown in Table 14. Other lipids were also tested, and crystallization was observed. Additional lipid candidates are to be screened.

TABLE 14

| Composition of CBD dissolved in Propylene Glycol Monocaprylate (Capryol 90) and loaded on Aeroperl Mesoporous Silica particles with anti-oxidant. | |
|---|---|
| Material | % w/w |
| Aeroperl 300 | 50% |
| CBD | 30% |
| Capryol 90 | 19% |
| Alpha-Tocopherol | 1% |

The stability of the formulations in Table 14 was evaluated after 6 weeks at weeks at 40° C. and 75% RH. The results are summarized in Tables 15. Formulation was found to be amorphous and highly stable.

TABLE 15

| Stability after 6 week at 40° C./75% RH | | | | | | |
|---|---|---|---|---|---|---|
| Sample | % CBD of label claim | CBE I | CBE II | THC | Total RRTs | Amorphous |
| 1 | 101.04 | 0.05 | ND | 0.04 | <LOQ | Yes |

Next, formulations were prepared using a mixture of two or three lipophilic materials. The formulations are provided in Table 16.

TABLE 16

| Composition of CBD dissolved in single lipid or a combination of lipids and loaded on Syloid XDP Mesoporous Silica particles with antioxidant | | |
|---|---|---|
| Formulation | Material | % w/w |
| 1 | Syloid XDP | 50% |
| | CBD | 30% |
| | Miglyol 810N (MCT)* | 19% |
| | Alpha-Tocopherol | 1% |
| 2 | Syloid XDP | 50% |
| | CBD | 30% |
| | Lauroglycol 90 | 19% |
| | Alpha-Tocopherol | 1% |
| 3 | Syloid XDP | 50% |
| | CBD | 30% |
| | Lauroglycol 90 | 9.5% |
| | Capryol 90 | 9.5% |
| | Alpha-Tocopherol | 1% |
| 4 | Syloid XDP | 45% |
| | CBD | 29% |
| | Miglyol 810N | 6.25% |
| | Labrafac Lipophile WL1349 | 6.25% |
| | Gelucire 43/01 | 12.5% |
| | Alpha-Tocopherol | 1% |
| 5 | Syloid XDP | 50% |
| | CBD | 30% |
| | Miglyol 810N | 4.75% |
| | Labrafac Lipophile WL1349 | 4.75% |
| | Labrafil M2130CS | 9.5% |
| | Alpha-Tocopherol | 1% |
| 6 | Syloid XDP | 50% |
| | CBD | 30% |
| | Miglyol 810N | 4.75% |
| | Labrafac Lipophile WL1349 | 4.75% |
| | Capryol 90 | 9.5% |
| | Alpha-Tocopherol | 1% |

*MTC; medium chain triglyceride

The binary and ternary lipid mixtures were completely miscible, and provided a medium in which CBD could be dissolved and loaded onto the mesoporous silica. The stability of the compositions described in Table 16 was evaluated after 6 weeks at weeks at 40° C. and 75% RH. The results are summarized in Table 17. CBD retained its amorphous state and was chemically stable in these compositions.

TABLE 17

| Stability of formulations in Table 16 after a 3 week at 40 C./75% RH | | | | | | |
|---|---|---|---|---|---|---|
| Sample | % CBD of label claim | CBE i | CBE II | THC | Total RRTs | Amorphous |
| 1 | 101.75 | 0.09 | ND | 0.06 | <LOQ | Yes |
| 2 | 101.30 | 0.09 | 0.03 | 0.04 | 0.05 | Yes |
| 3 | 101.50 | 0.08 | 0.03 | 0.03 | <LOQ | Yes |
| 4 | 100.78 | 0.08 | 0.03 | 0.05 | 0.05 | Yes |
| 5 | 101.55 | 0.09 | 0.04 | 0.04 | <LOQ | Yes |
| 6 | 101.38 | 0.08 | ND | 0.04 | <LOQ | Yes |

Figure 11:
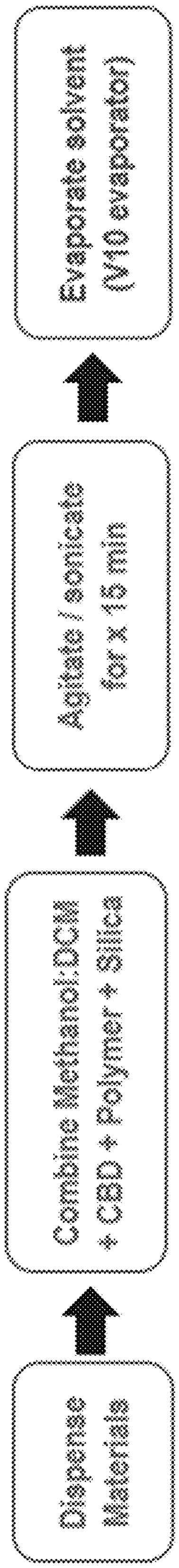
FIG. 11 provides a flowchart describing the lab-scale preparation of drug-containing particles of the present disclosure by a solvent-mediated polymer formulation method.

Example 4: Preparation of CBD/Polymer Formulations by Solvent-Mediated Manufacturing CBD/polymer-loaded drug particles having the composition provided in Table 18 were prepared according to the process described in FIG. 11.

TABLE 18

| Composition of CBD-containing particles including a polymer component. | |
|---|---|
| Material | % w/w |
| CBD | 40.0 |
| Polymer | 10.0 |
| Syloid XDP | 49.8 |
| α-tocopherol (antioxidant) | 0.2 |

The following polymers were each in the above composition:

HPMCP 50 (hydroxypropyl methylcellulose phthalate)

Kollidon K30 (polyvinylpyrrolidone)

Kollidon VA64 (polyvinylpyrrolidone/vinyl acetate)

Soluplus (polyvinyl caprolactam-polyvinyl acetate-polyethylene glycol graft co-polymer)

Kollicoat MAE (polyvinyl alcohol-polyethylene glycol copolymer)

Figure 12:
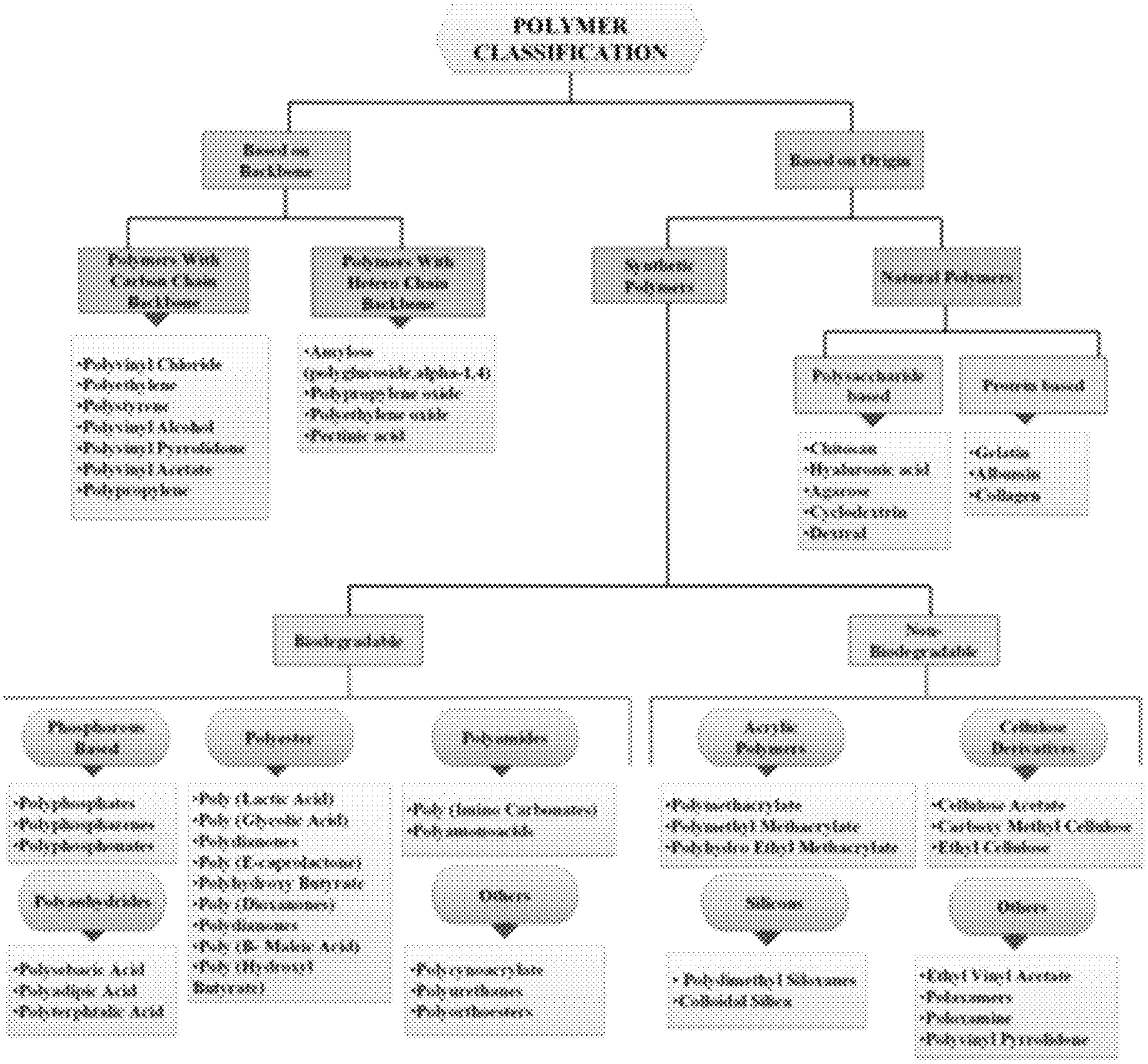
FIG. 12 is a chart showing classes of polymers suitable for use in the drug-containing particles of the present disclosure.

Additional polymers suitable for inclusion in these formulations are listed in FIG. 12.

To determine if drug-containing particles comprising amorphous CBD and polymer could be produced via a continuous manufacturing process, a spray drying process was evaluated.

Table 19 provides the CBD-containing drug particle compositions comprising Syloid® XDP silica that were prepared according to the spray drying method disclosed herein.

TABLE 19

| Compositions of CBD and polymer-containing particles subjected to spray drying. | | |
|---|---|---|
| Material | Feedstock Composition (% w/w) (where solids content of the feedstock solution = 50% w/w) | Final Composition (% w/w) (after drying/ removal of DCM/MeOH) |
| CBD | 20 | 40 |
| Polymer | 4.9 | 9.8 |
| α-tocopherol | 0.1 | 0.2 |
| Syloid XDP | 25 | 50 |
| DCM:MeOH (1:1) | 50 | 0 |

The spray drying method was carried out on a Buchi B-290 apparatus using the following parameters:

Inlet temp: 80° C.

Chiller temp: −20° C.

Aspirator: 100%

Feed rate: 20 g/min

Q-flow: 60 mm

Nozzle size: 2.1 mm

Post-collection drying: 24 h at 40° C. under vacuum

Kollidon K30 was evaluated in the formulation, however drug-containing particles incorporating this polymer did not process well and further optimization is required.

Example 5: Stability Studies for Lipid-Loaded Mesoporous Silica Drug Particles Containing Antioxidants The presence of antioxidant was evaluated in two stages to investigate its impact on stability.

Stage 1: Formulations containing 100 mg of CBD per capsule were evaluated at two levels (0% and 0.2%) of alpha-tocopherol and stability was measured over 6 weeks at ambient conditions and accelerated conditions, 40° C./75%

RH and 25° C./60% RH. The formulations tested are described in Example 3, Table 6. To evaluate the effect of alpha-tocopherol, 0.2% of alpha-tocopherol were added to the formulations described in Table 6. Changes in API (CBD) content and impurities were measured over 6 weeks and shown in FIGS. 13-17. A summary of the formulations tested are shown in Table 20. Table 21 shows the specifications set for viable product candidates.

Figure 13A:
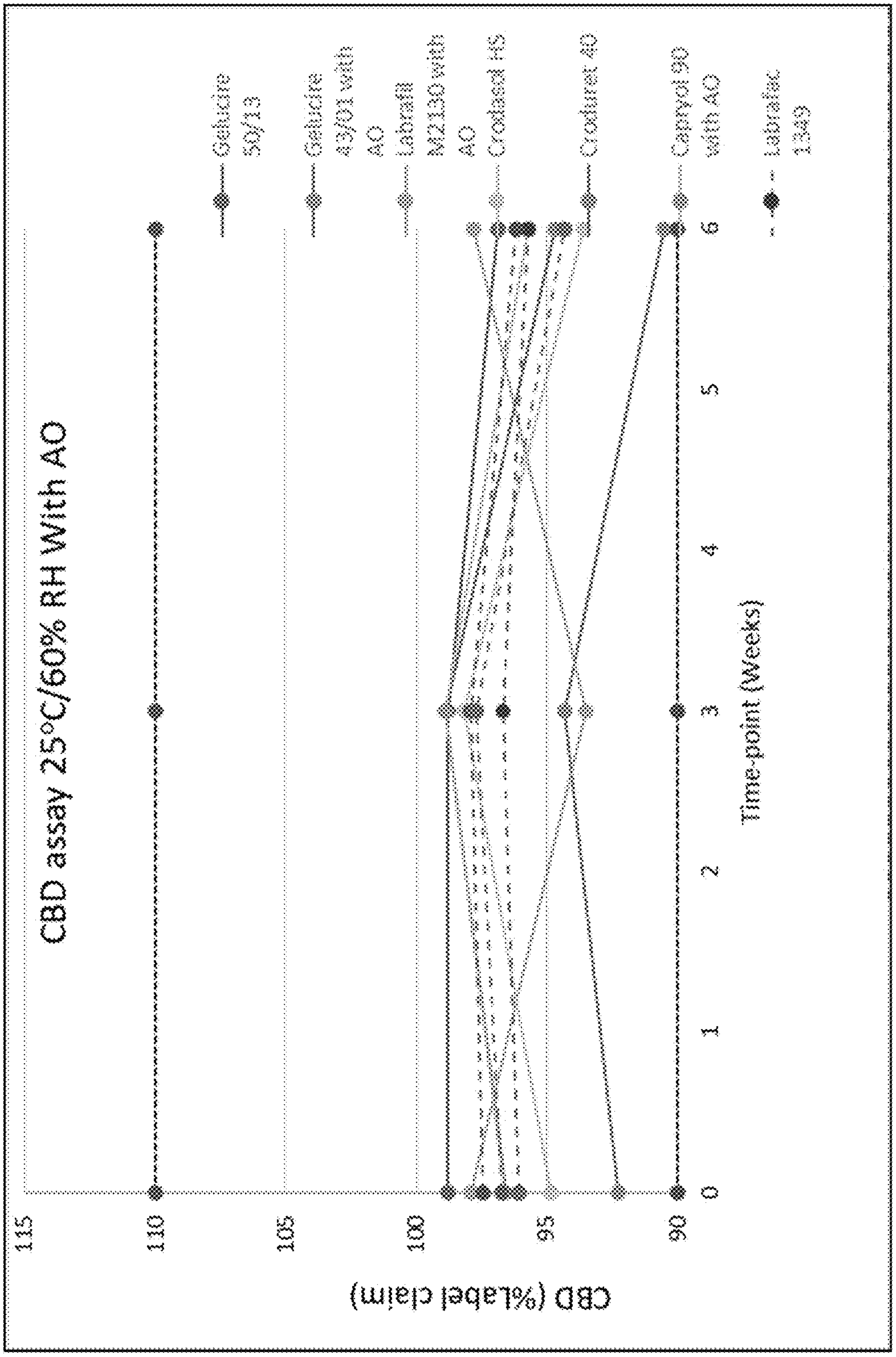
FIG. 13A shows changes in CBD content in the lipid-loaded formulations described in Example 3, Table 6 prepared with mesoporous silica described herein and further containing 0.2% alpha-tocopherol.
Figure 13B:
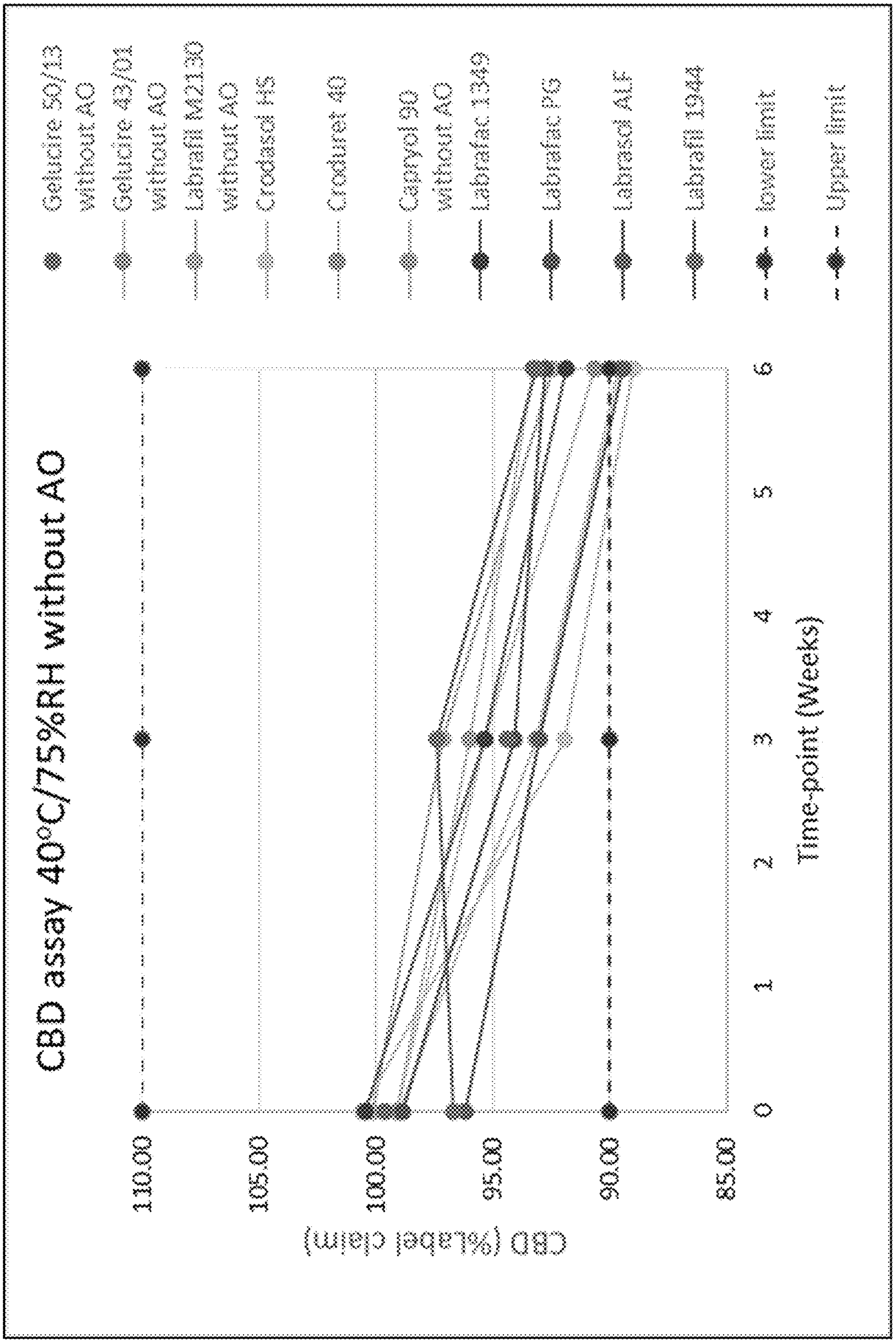
FIG. 13B shows changes in CBD content in the same lipid-loaded formulations prepared without alpha-tocopherol.
Figure 14A:
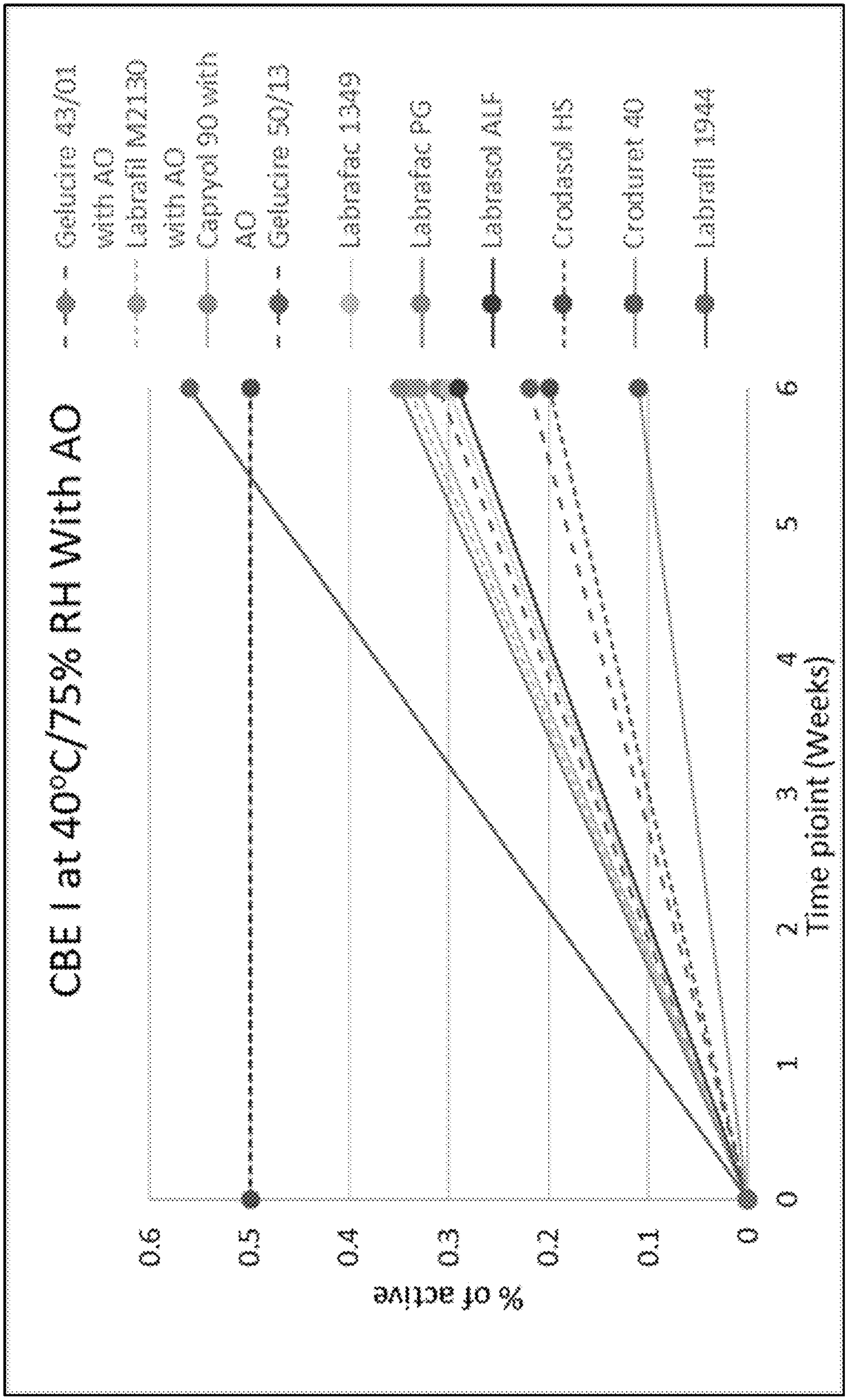
FIG. 14A shows changes in CBE I content in the lipid-loaded formulations described herein containing 0.2% alpha-tocopherol.
Figure 14B:
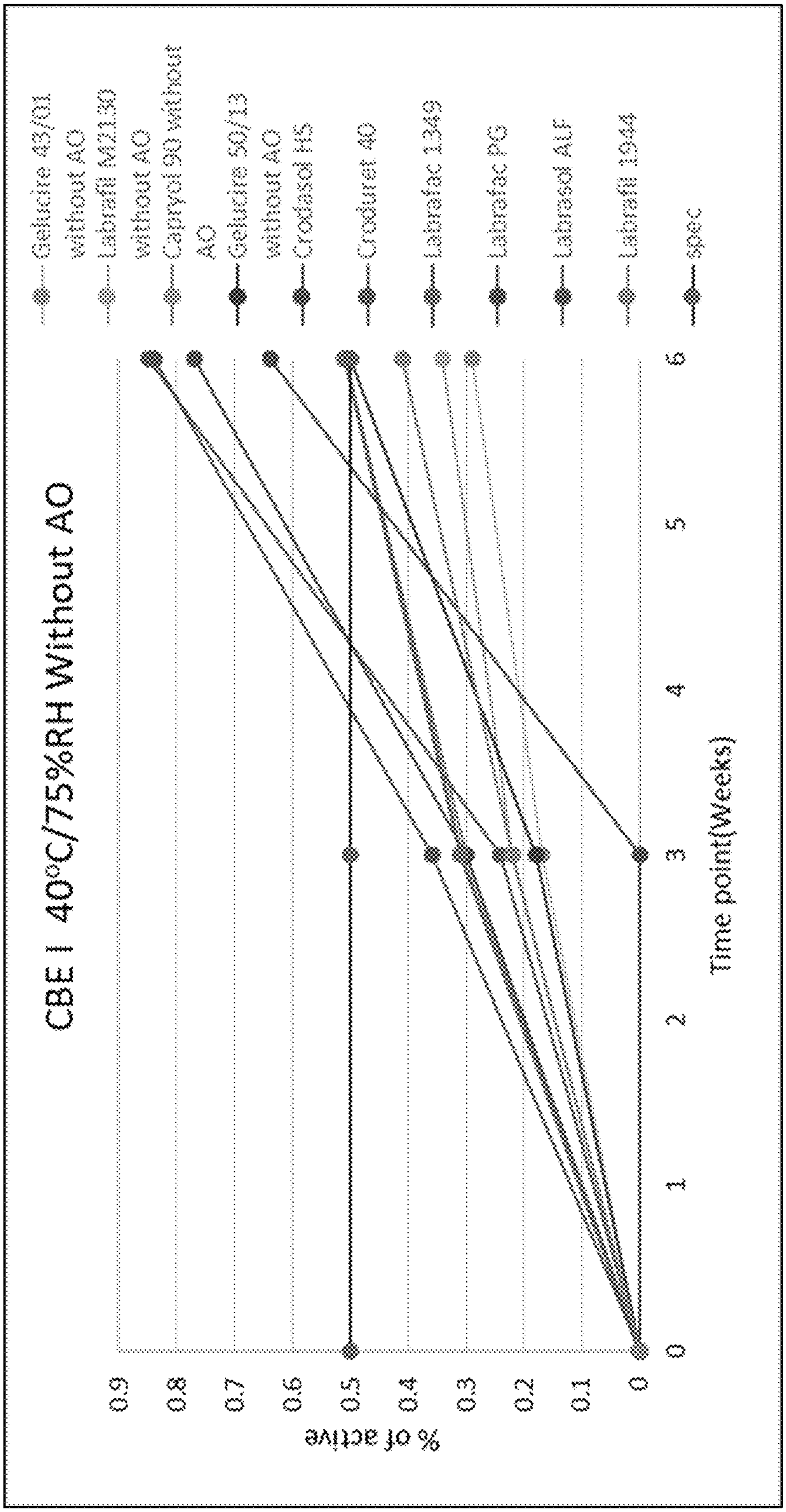
FIG. 14B shows changes in CBE I content in the same lipid-loaded formulations prepared without 0.2% alpha-tocopherol.
Figure 15A:
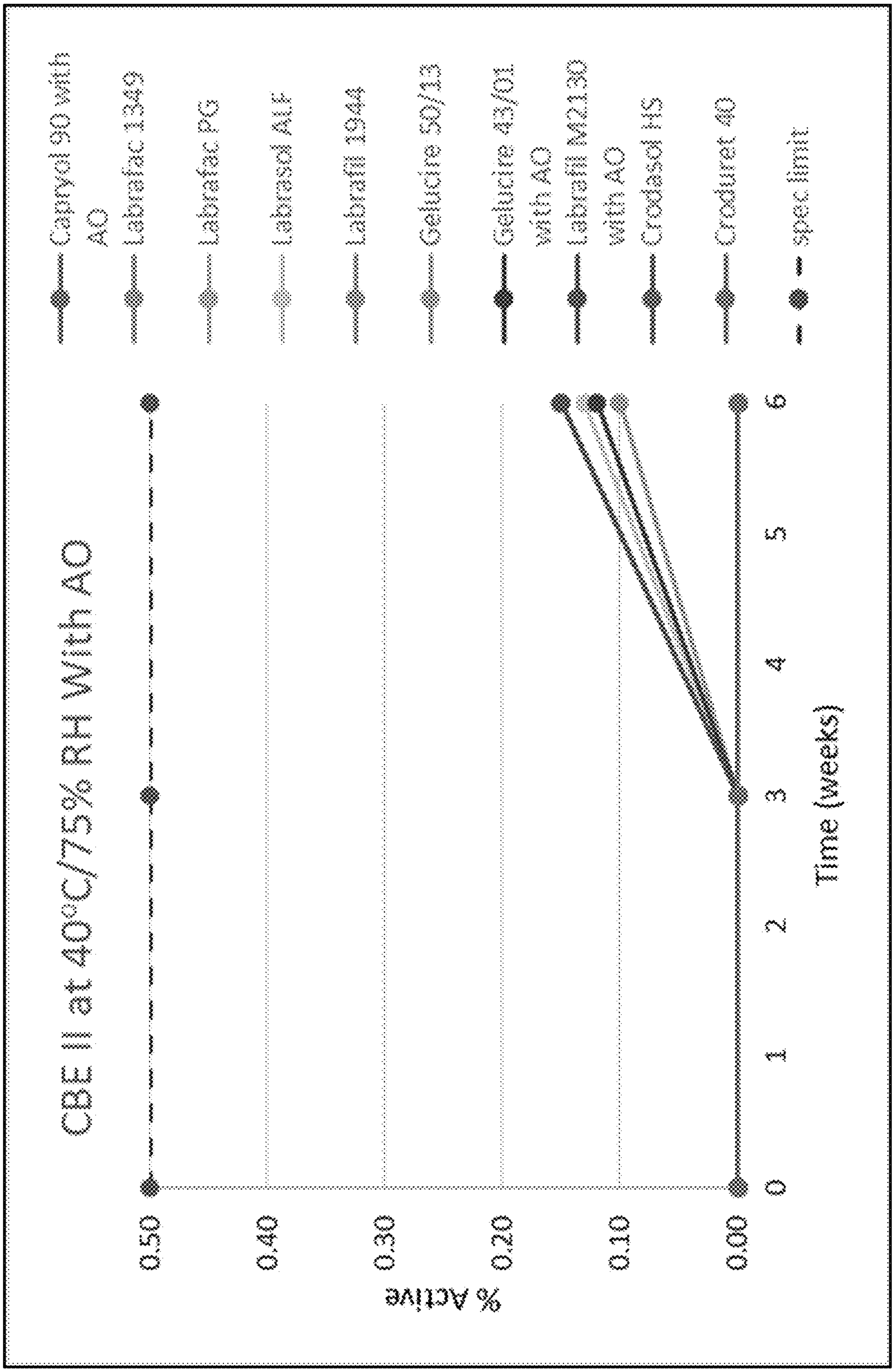
FIG. 15A shows changes in CBE II content in the lipid-loaded formulations described herein containing 0.2% alpha-tocopherol.
Figure 15B:
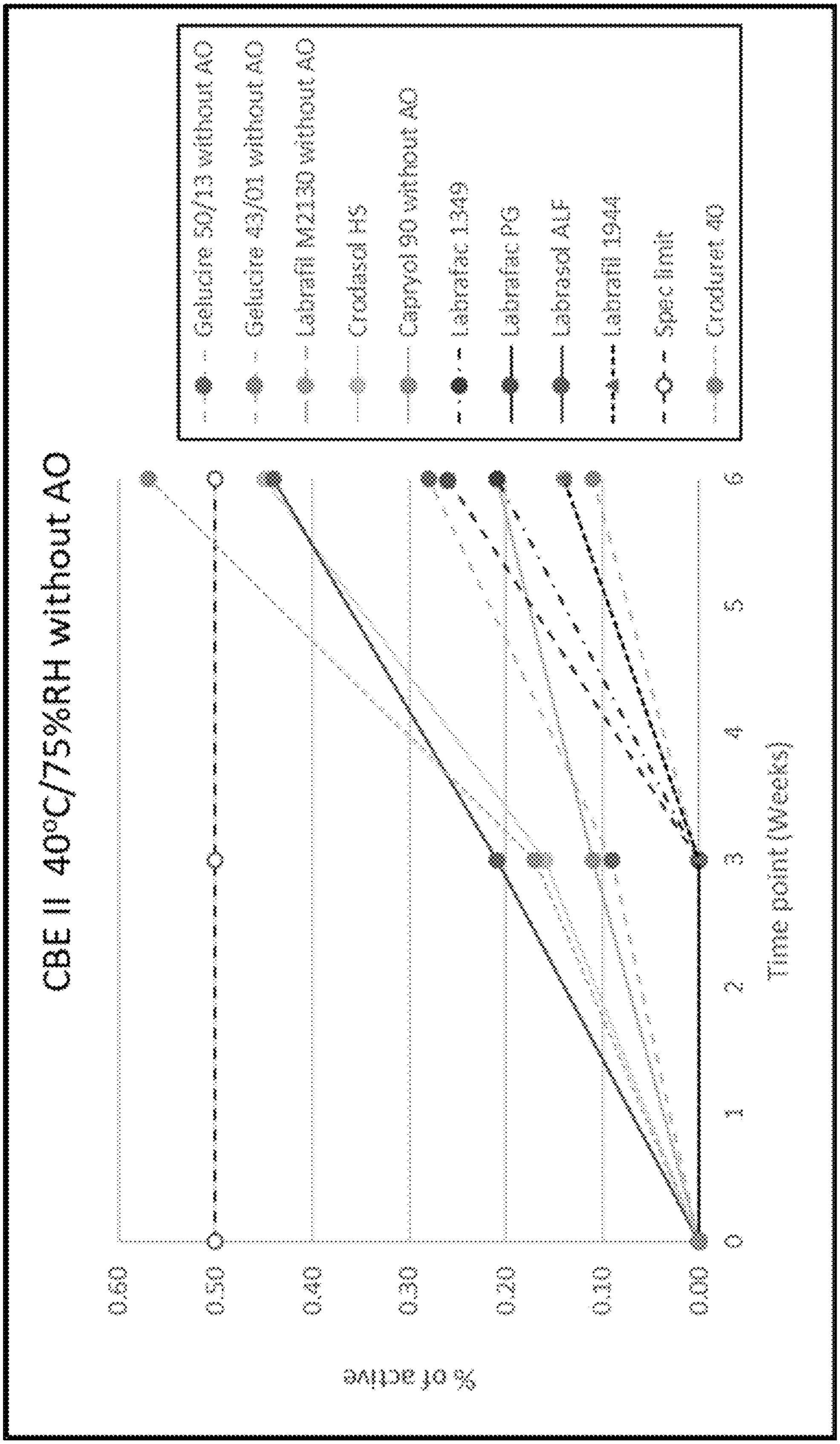
FIG. 15B shows changes in CBE II content in the same lipid-loaded formulations prepared without 0.2% alpha-tocopherol.
Figure 16A:
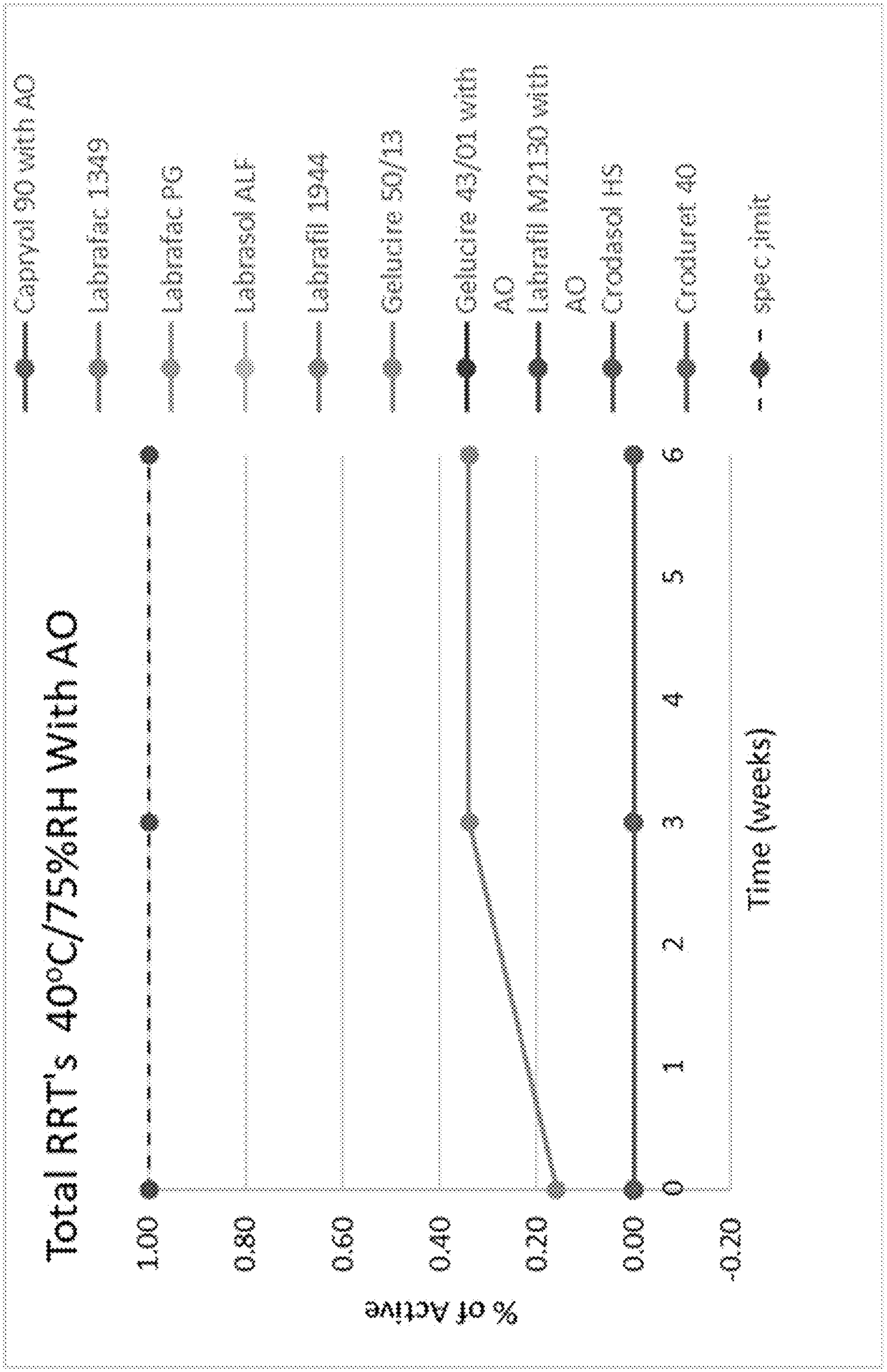
FIG. 16A shows changes in OH-CBD content in the lipid-loaded formulations described herein containing 0.2% alpha-tocopherol.
Figure 16B:
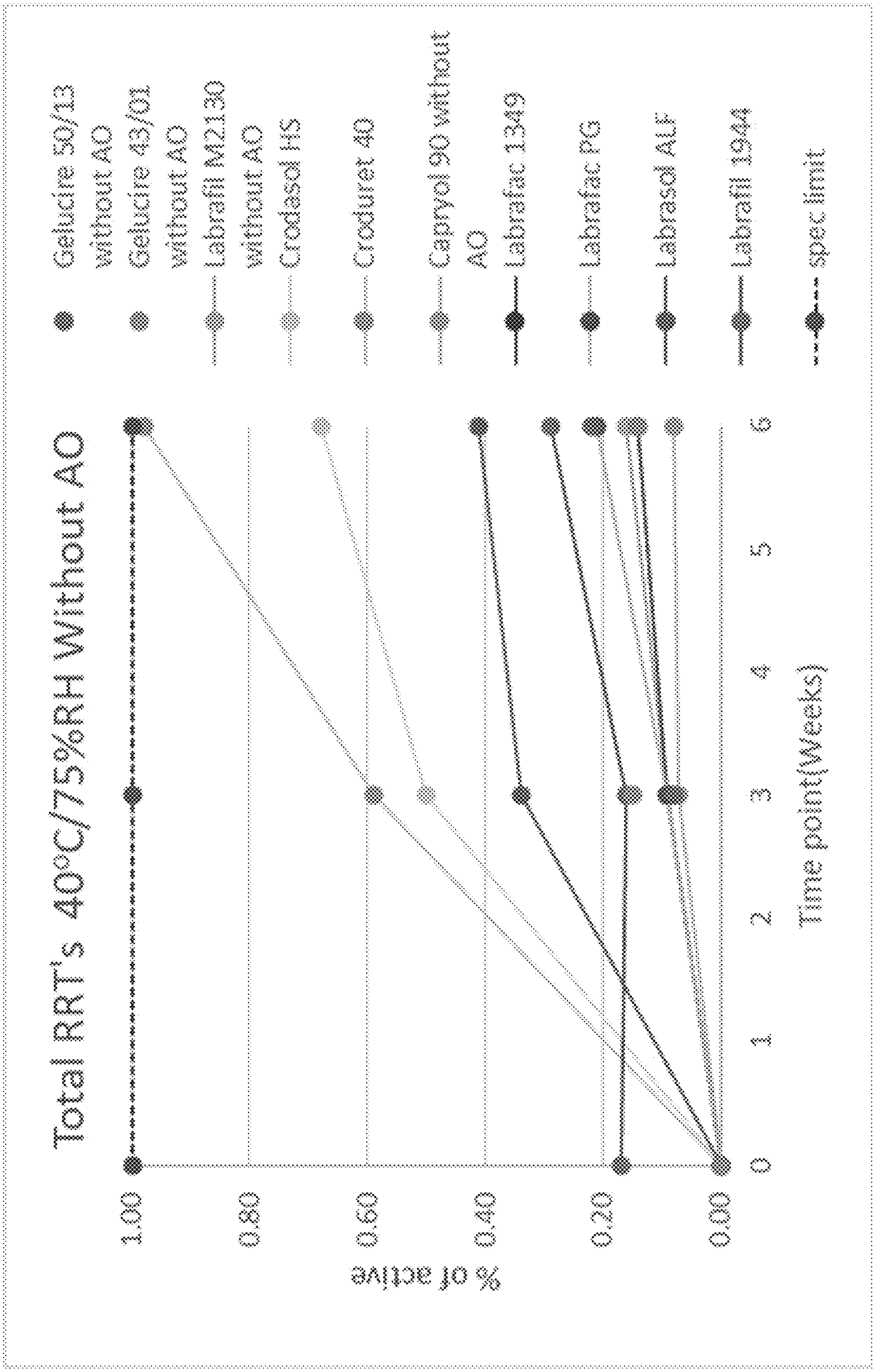
FIG. 16B shows changes in OH-CBD content in the same lipid-loaded formulations prepared without 0.2% alpha-tocopherol.
Figure 17A:
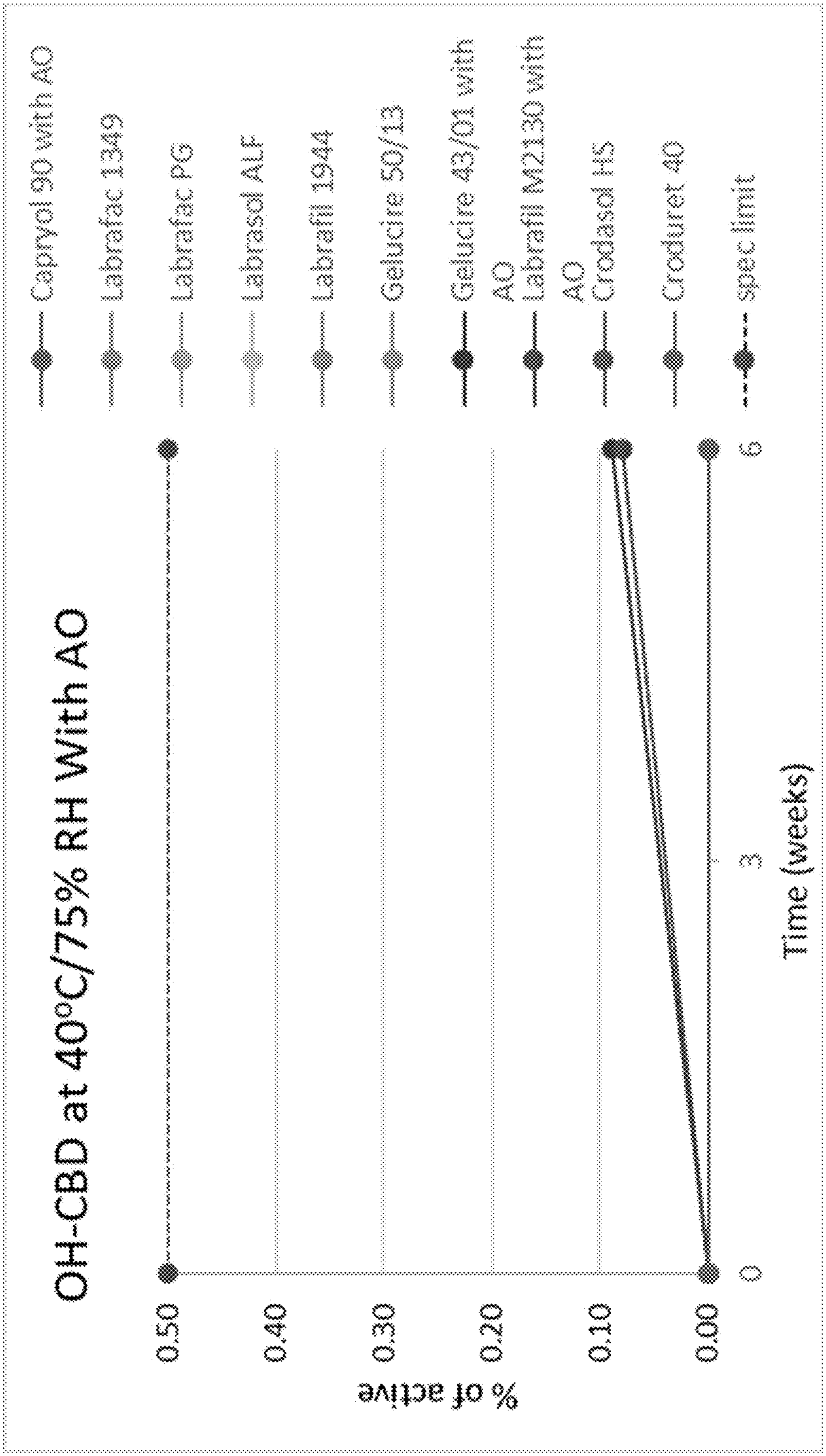
FIG. 17A shows changes in OH-CBD content in the lipid-loaded formulations described herein containing 0.2% alpha-tocopherol.
Figure 17B:
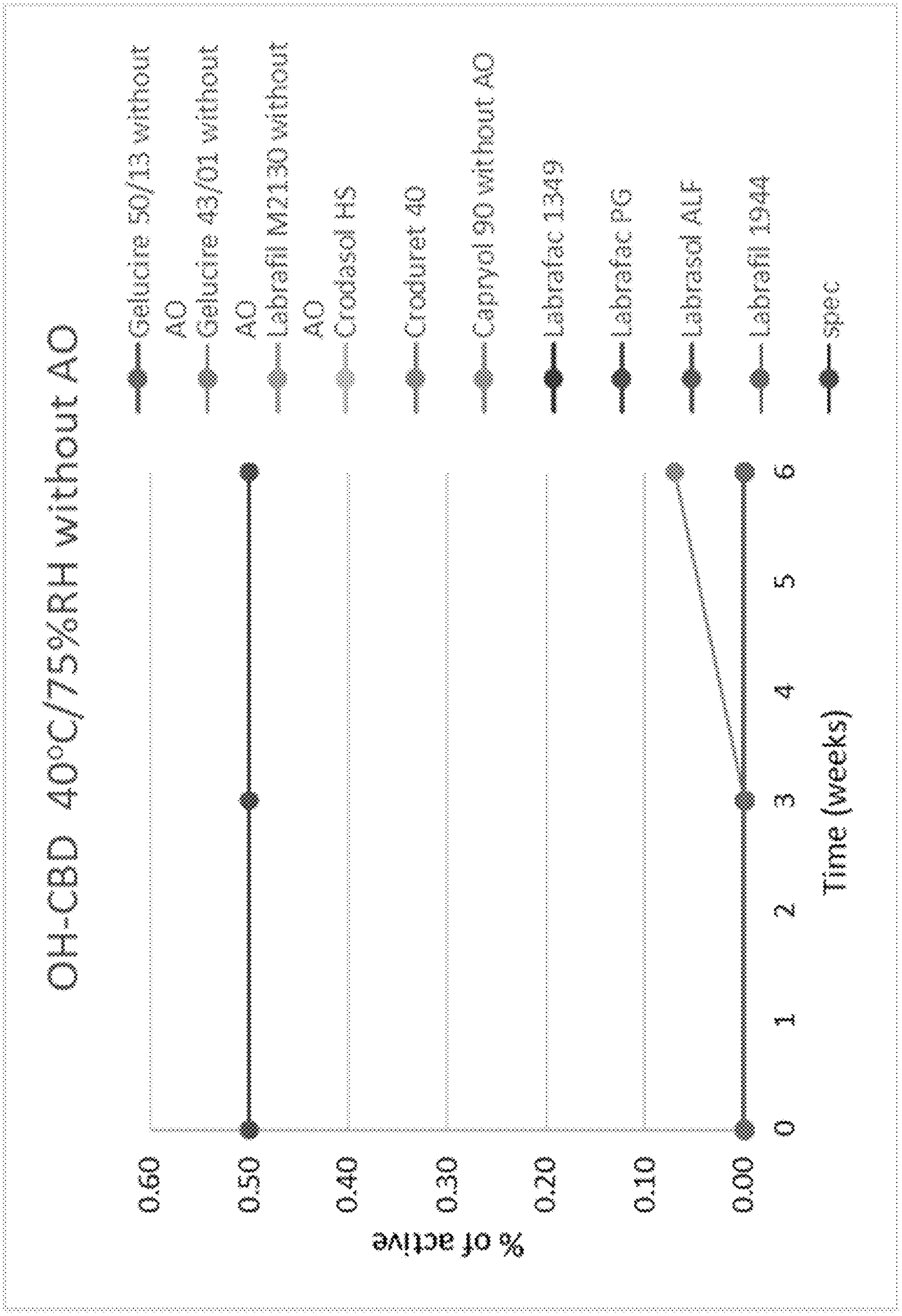
FIG. 17B shows changes in OH-CBD content in the same lipid-loaded formulations prepared without 0.2% alpha-tocopherol.
Figure 18A:
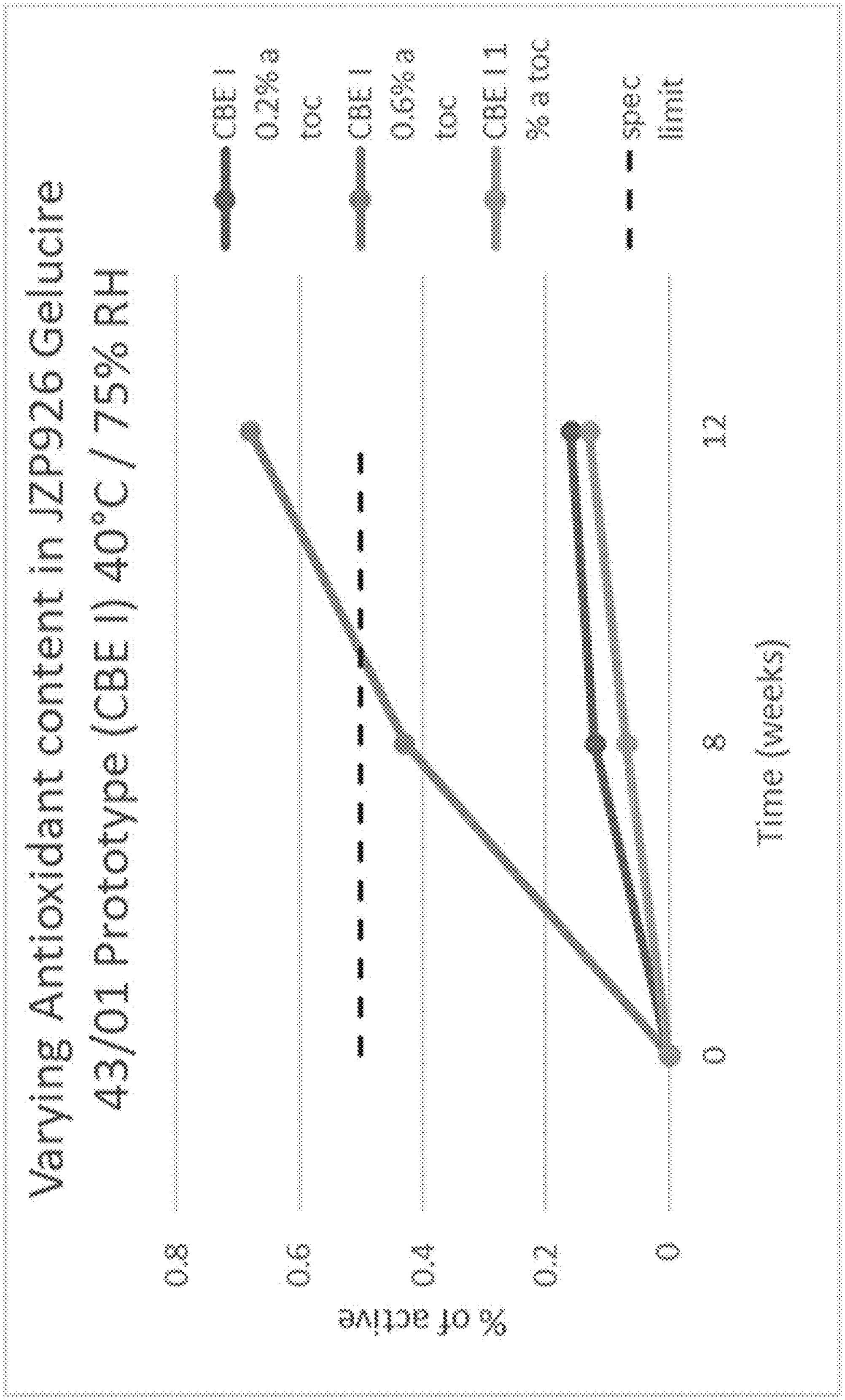
FIG. 18A shows CBE I content in hard fat-loaded formulations described herein containing 0.2%, 0.6% and 1% alpha-tocopherol at 40° C./75% RH.
Figure 18B:
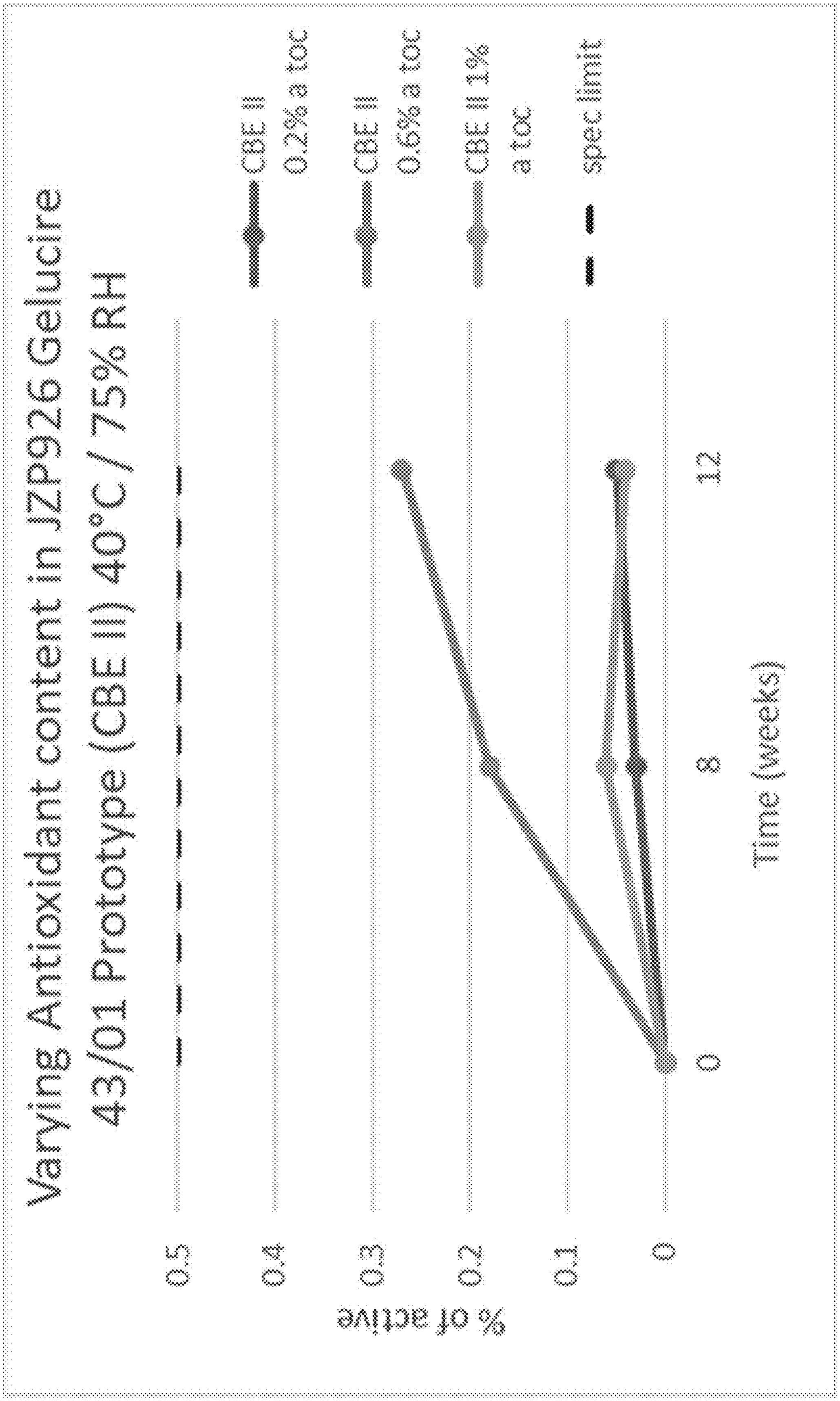
FIG. 18B shows CBE II content in hard fat-loaded formulations described herein containing 0.2%, 0.6% and 1% alpha-tocopherol at 40° C./75% RH.
Figure 18C:
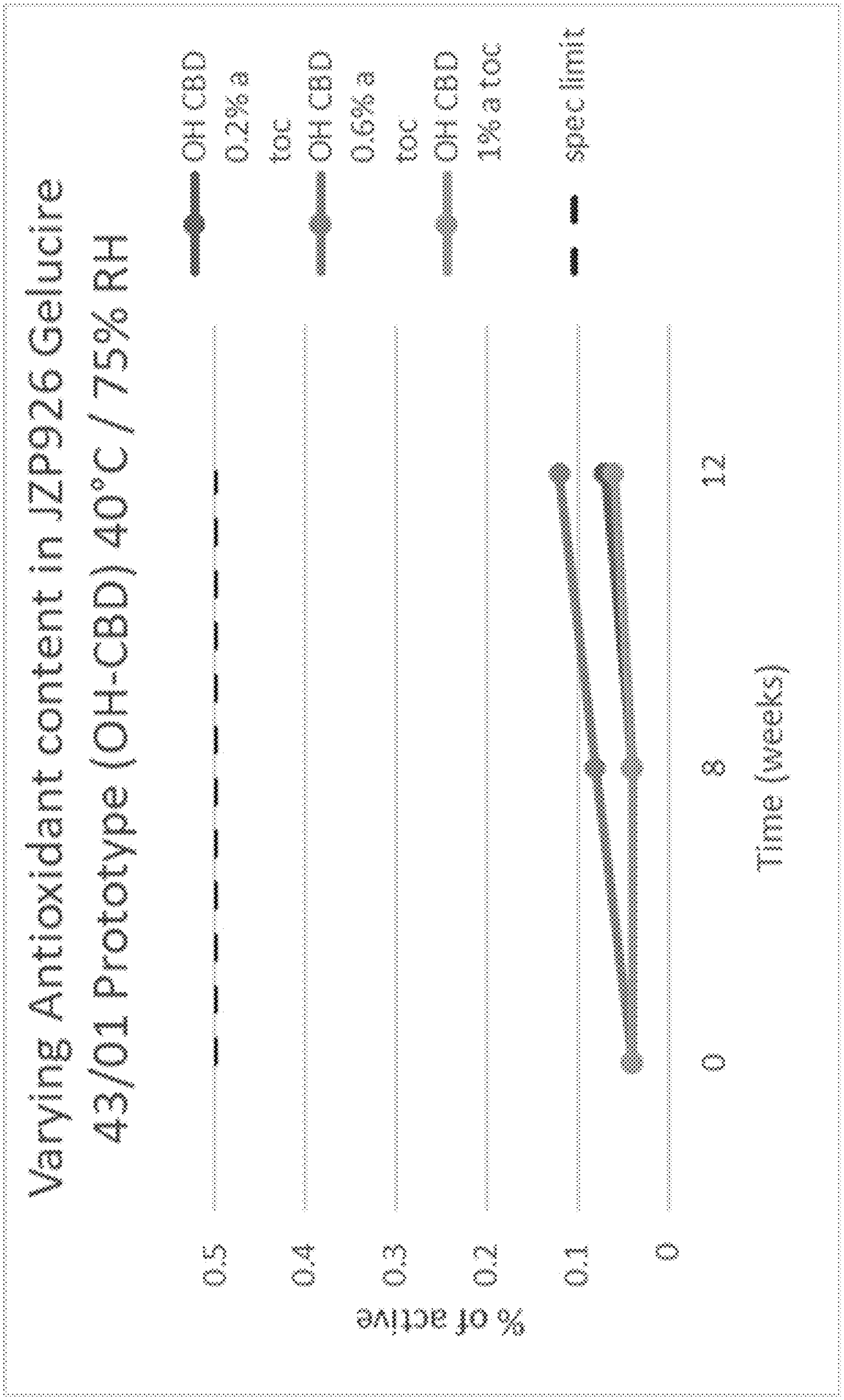
FIG. 18C shows OH-CBD content in hard fat-loaded formulations described herein containing 0.2%, 0.6% and 1% alpha-tocopherol at 40° C./75% RH.
Figure 18D:
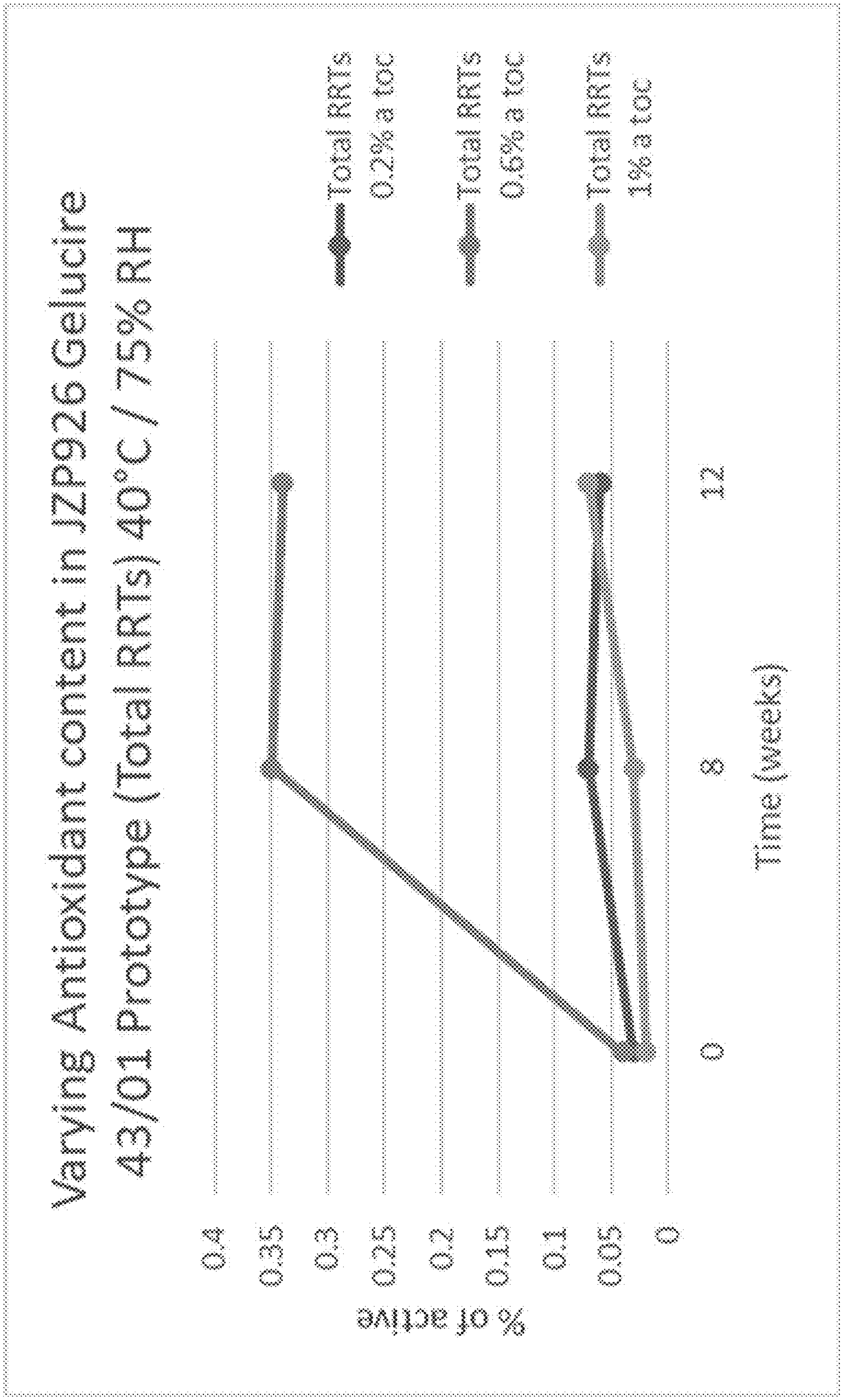
FIG. 18D shows additional unknown degradant content in hard fat-loaded formulations described herein containing 0.2%, 0.6% and 1% alpha-tocopherol at 40° C./75% RH.
Figure 19A:
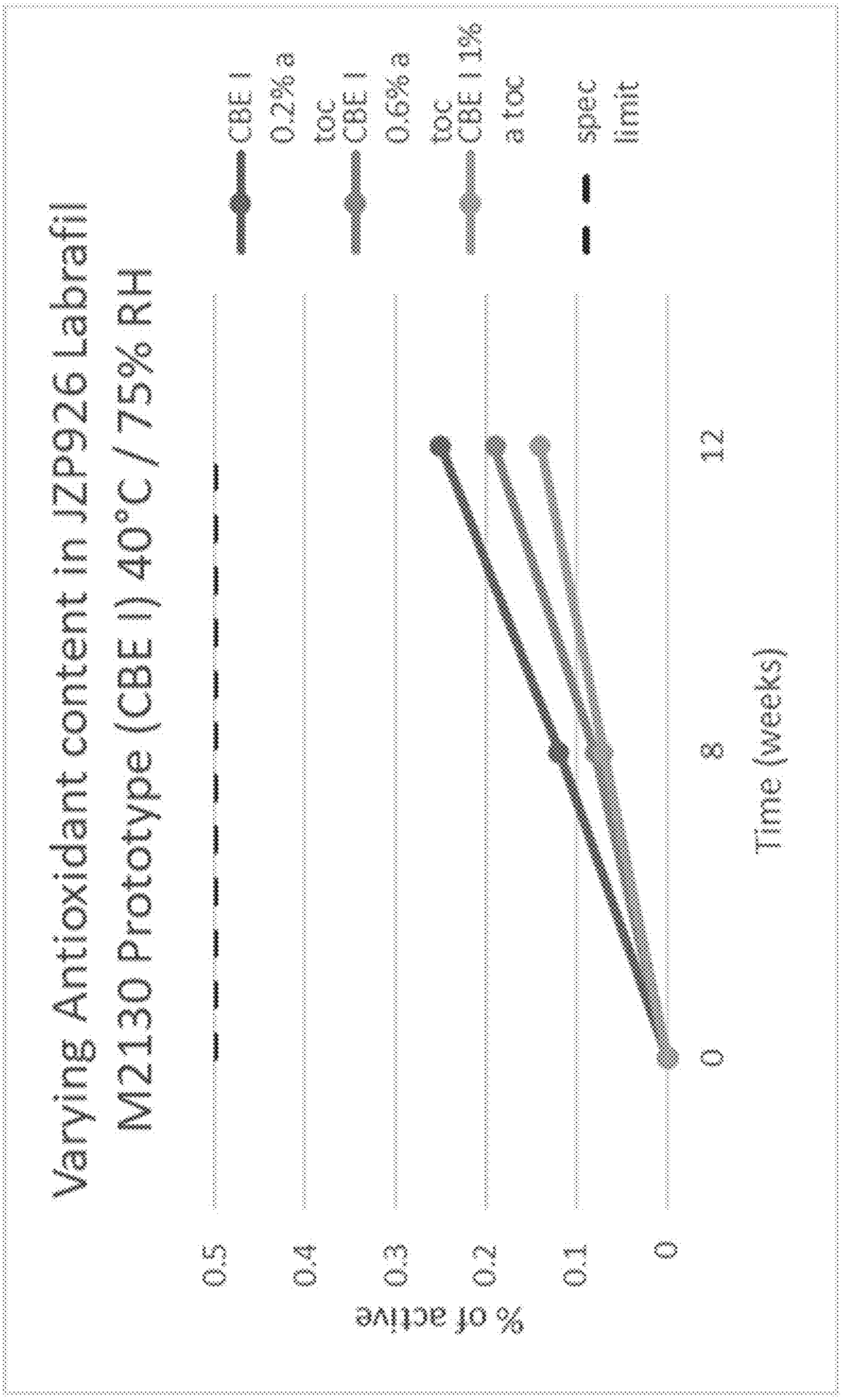
FIG. 19A shows CBE I content in lauroyl polyoxyl-6 glyceride-loaded formulations described herein containing 0.2%, 0.6% and 1% alpha-tocopherol at 40° C./75% RH.
Figure 19B:
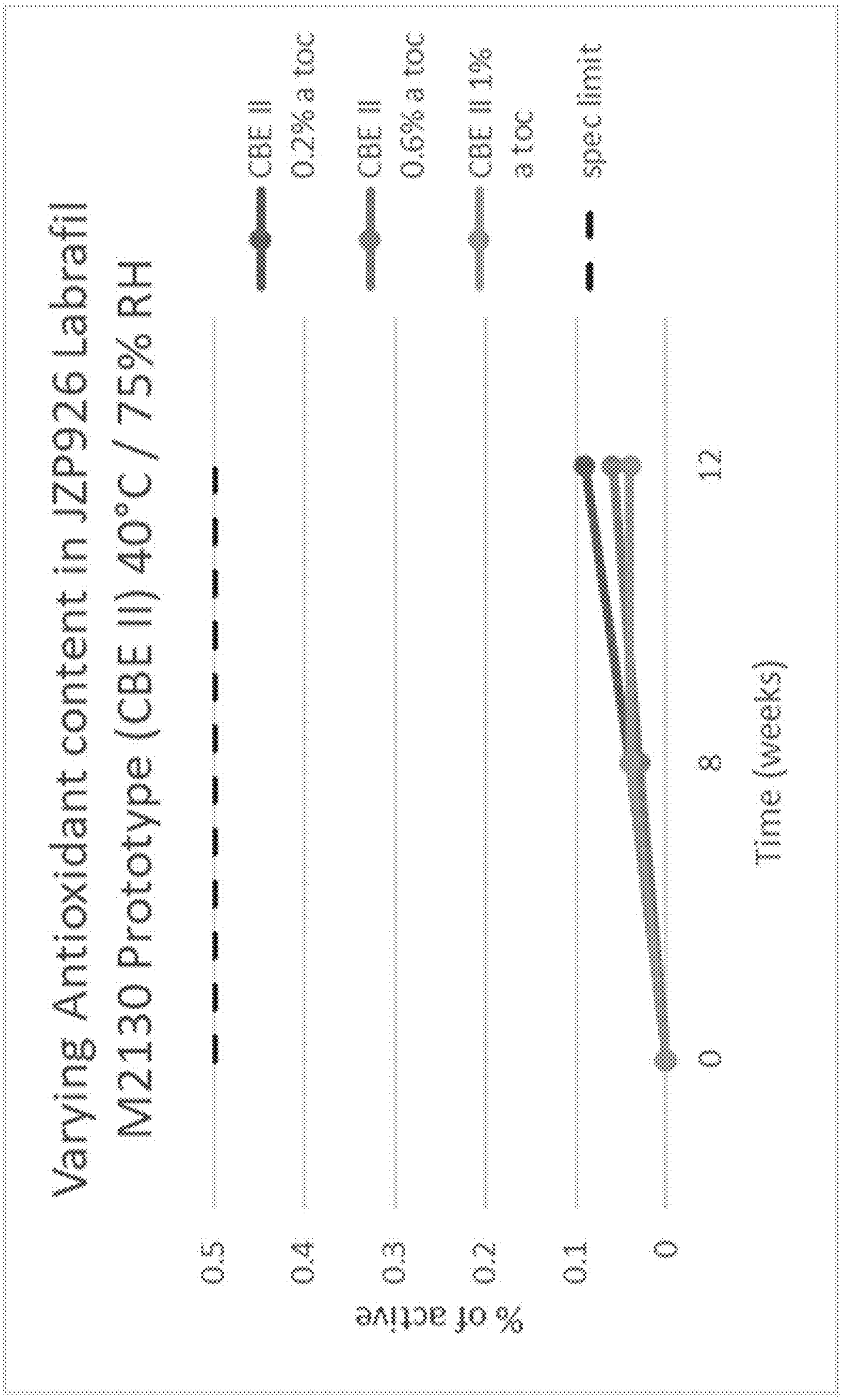
FIG. 19B shows CBE II content in lauroyl polyoxyl-6 glyceride-loaded formulations described herein containing 0.2%, 0.6% and 1% alpha-tocopherol at 40° C./75% RH.
Figure 19C:
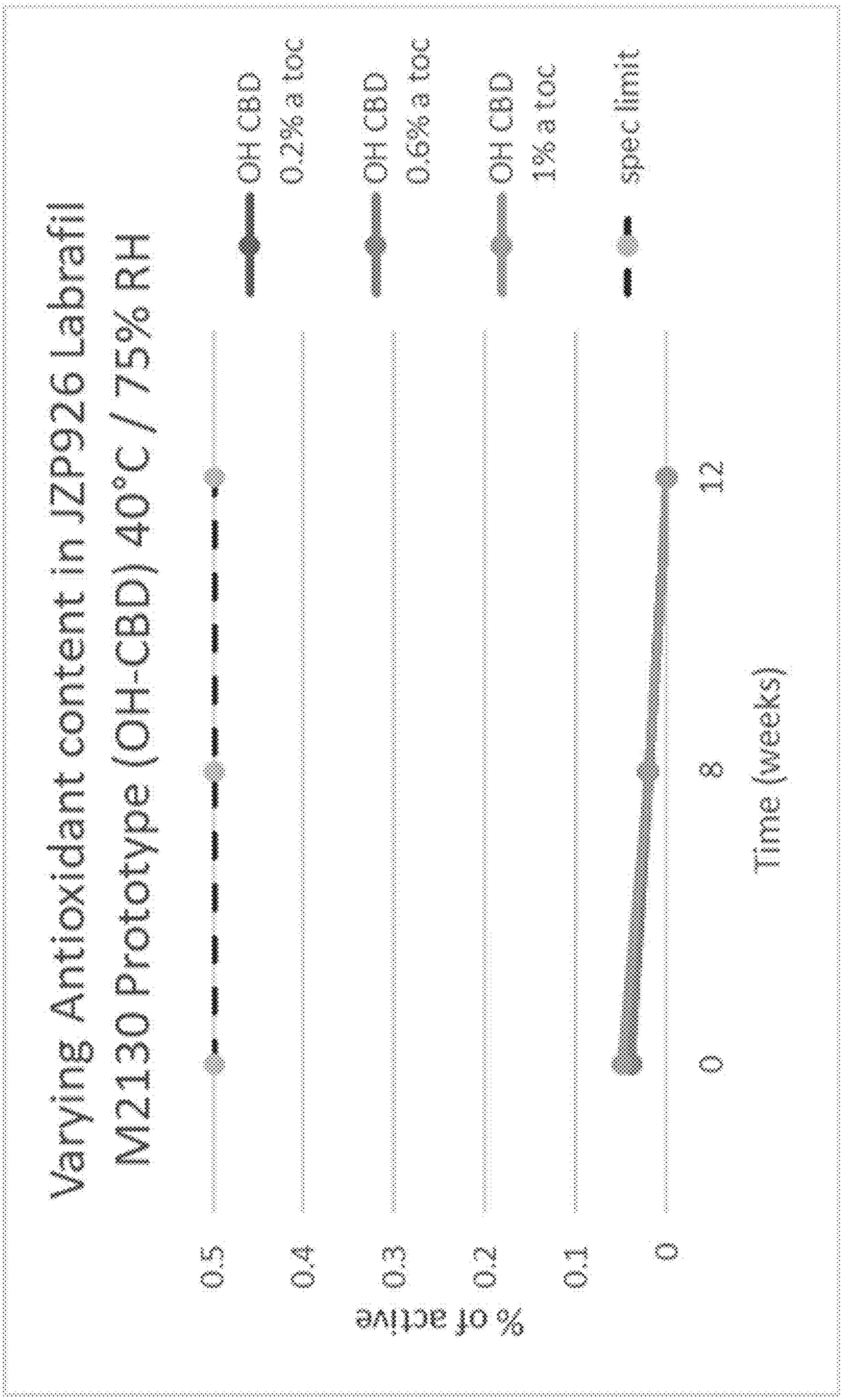
FIG. 19C shows OH-CBD content in lauroyl polyoxyl-6 glyceride-loaded formulations described herein containing 0.2%, 0.6% and 1% alpha-tocopherol at 40° C./75% RH.
Figure 19D:
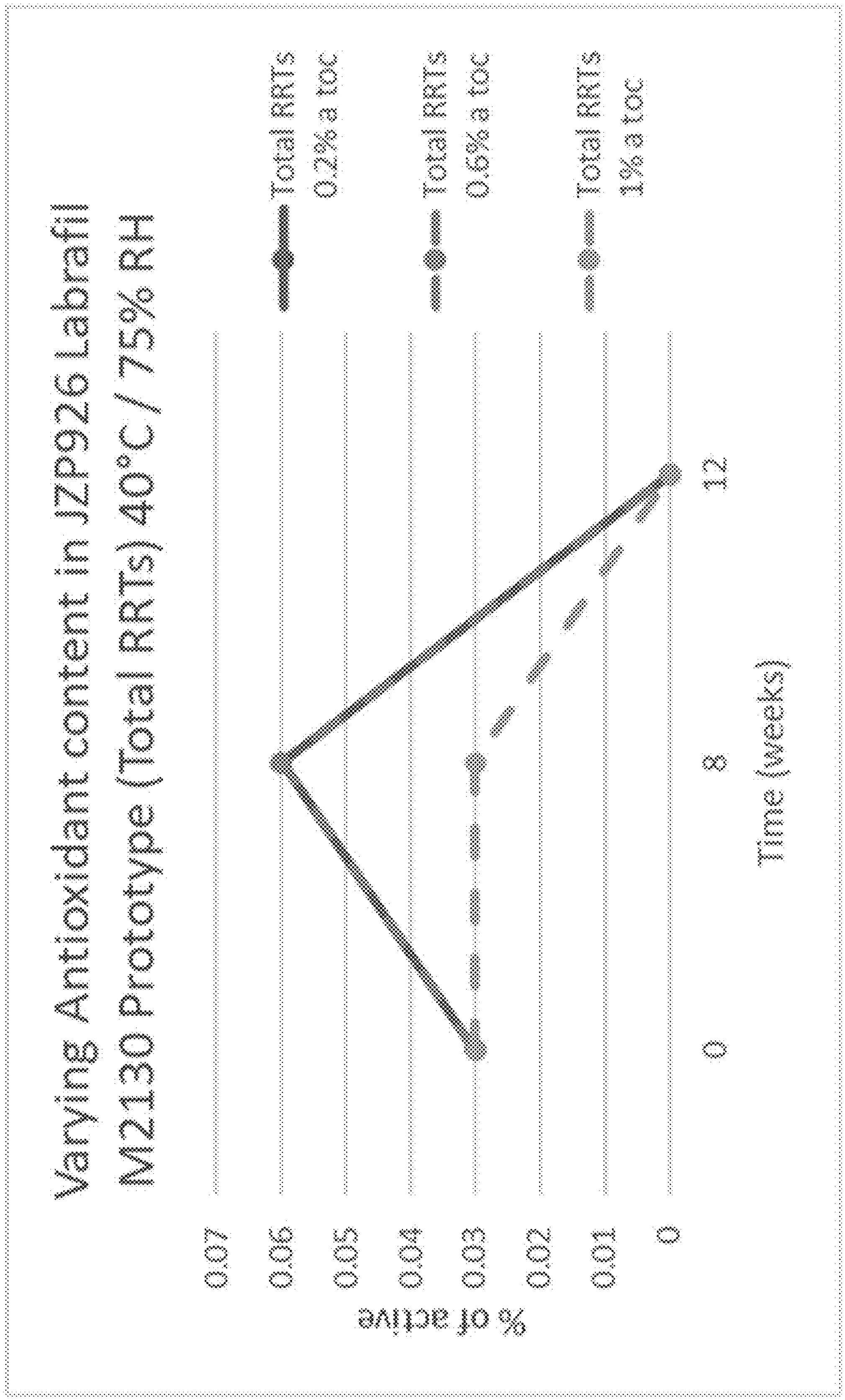
FIG. 19D shows additional unknown degradant content in lauroyl polyoxyl-6 glyceride-loaded formulations described herein containing 0.2%, 0.6% and 1% alpha-tocopherol at 40° C./75% RH.
Figure 20A:
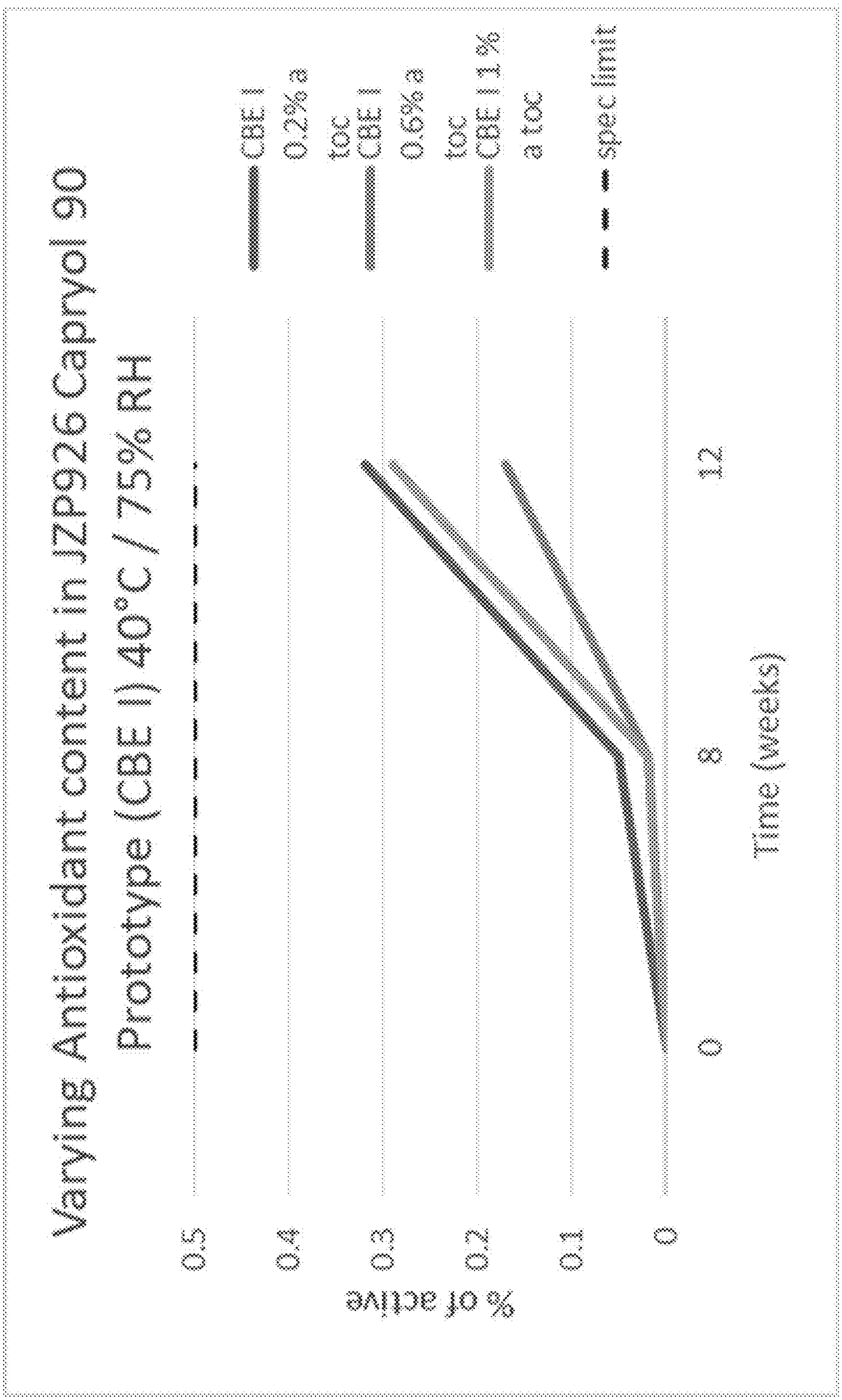
FIG. 20A shows CBE I content in propylene glycol monocaprylate-loaded formulations described herein containing 0.2%, 0.6% and 1% alpha-tocopherol at 40° C./75% RH.
Figure 20B:
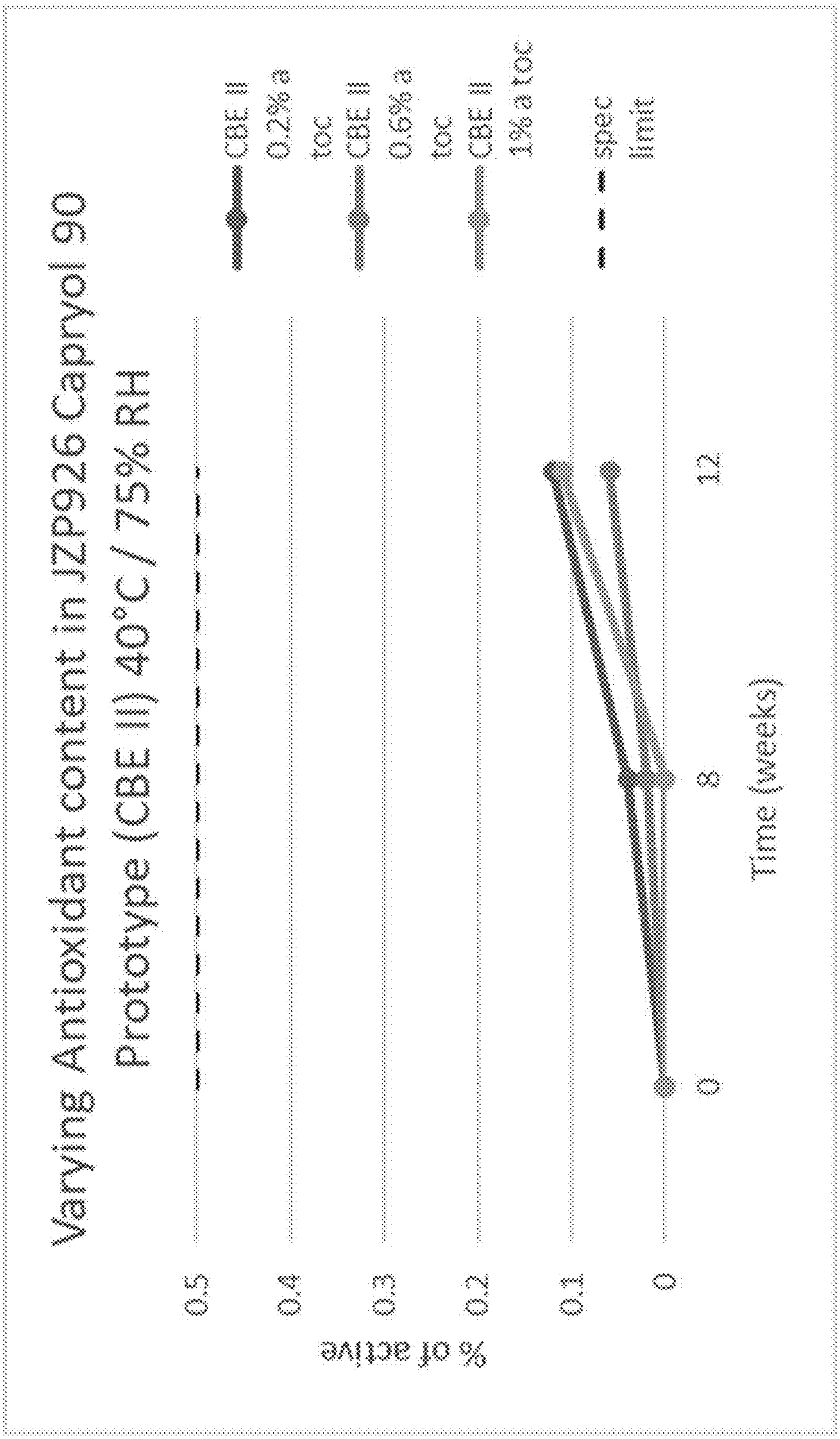
FIG. 20B shows CBE II content in propylene glycol monocaprylate-loaded formulations described herein containing 0.2%, 0.6% and 1% alpha-tocopherol at 40° C./75% RH.
Figure 20C:
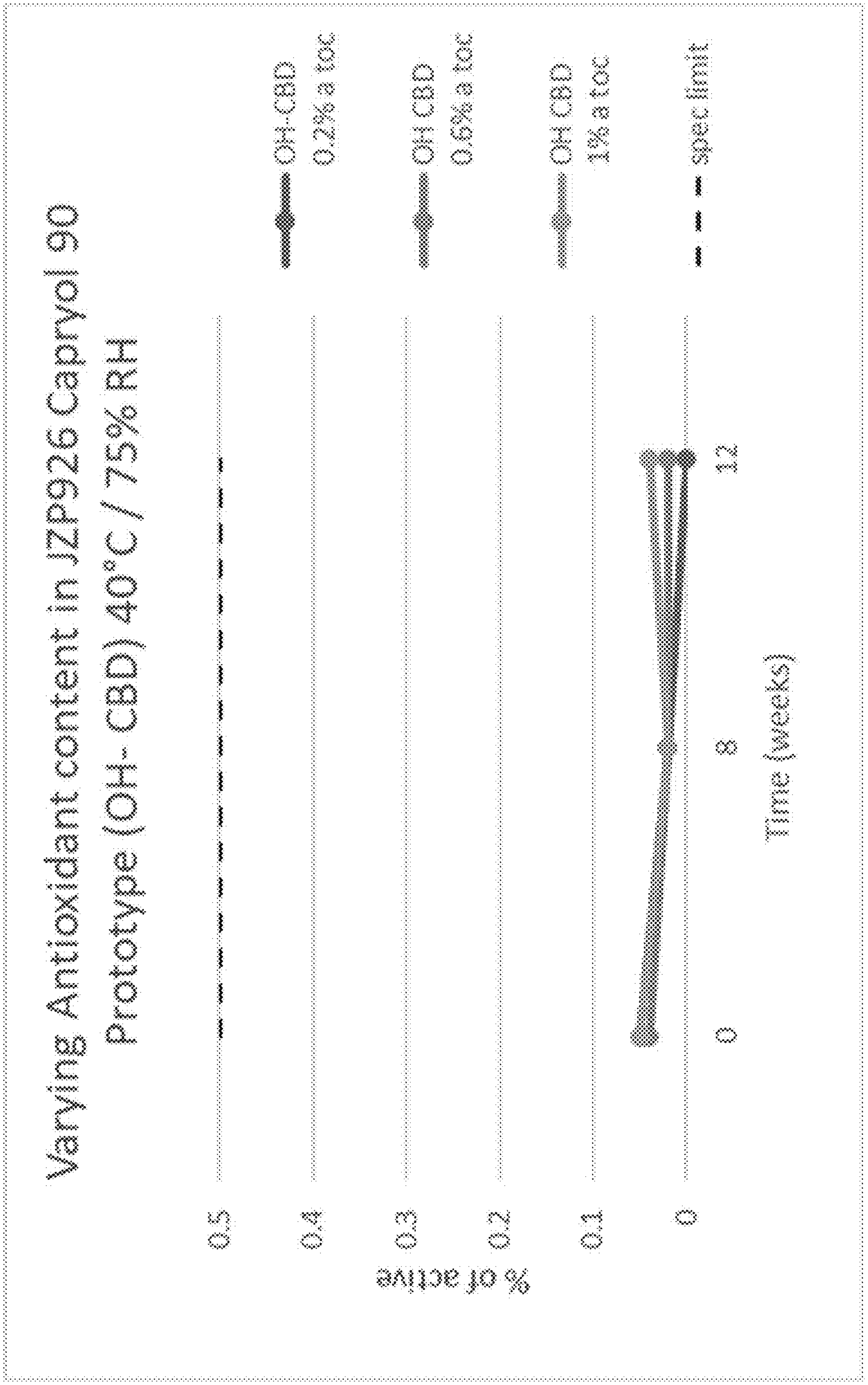
FIG. 20C shows OH-CBD content in propylene glycol monocaprylate-loaded formulations described herein containing 0.2%, 0.6% and 1% alpha-tocopherol at 40° C./75% RH.
Figure 20D:
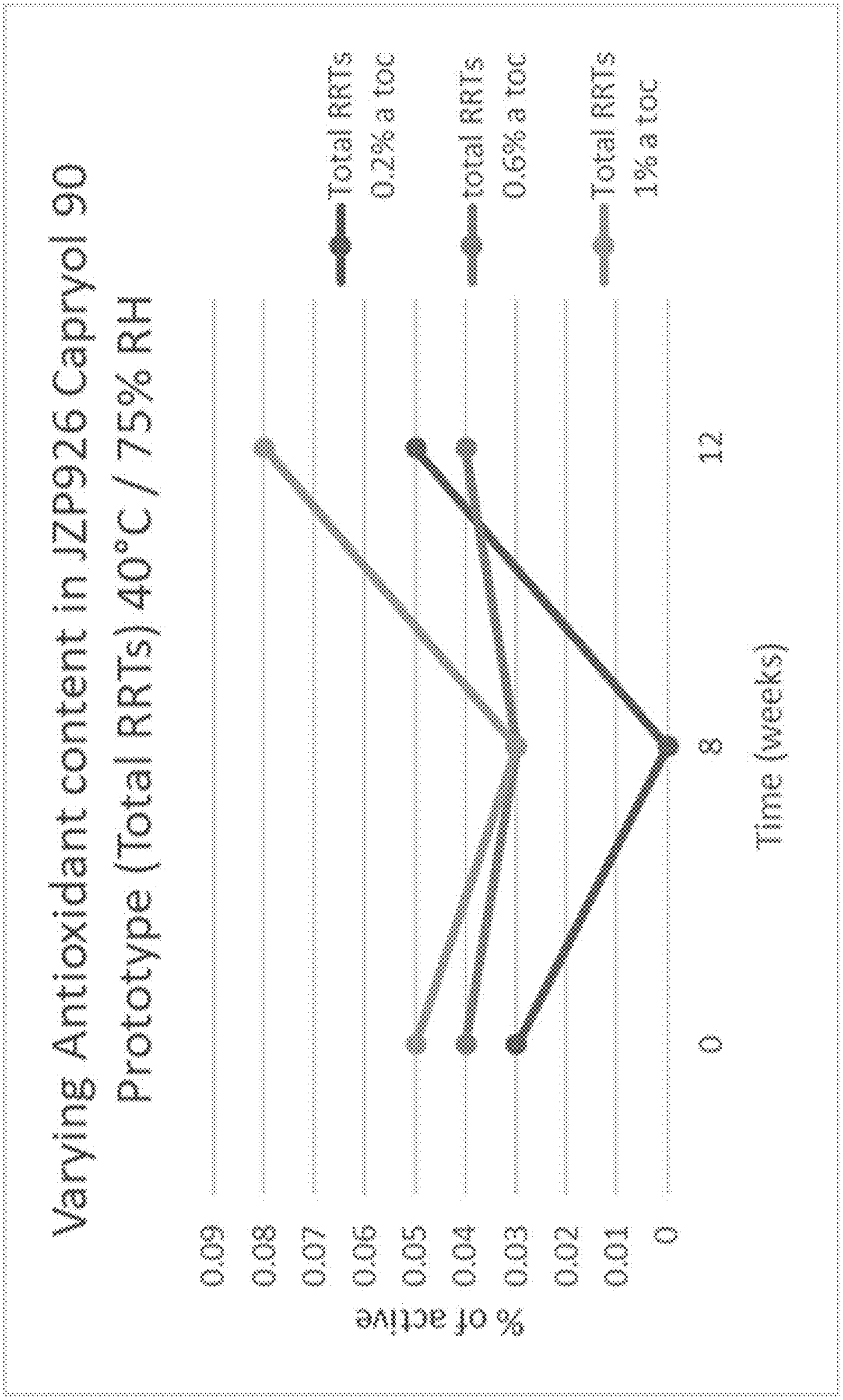
FIG. 20D shows additional unknown degradant content in propylene glycol monocaprylate-loaded formulations described herein containing 0.2%, 0.6% and 1% alpha-tocopherol at 40° C./75% RH.

FIG. 13A shows that 0.2% alpha-tocopherol protects CBD from decomposition at 25° C./60% RH over 6 weeks, whereas FIG. 13B shows a decline in CBD content measured for similar formulations prepared without alpha-tocopherol. Similar trends were observed when measuring degradants under accelerated conditions. Specifically, the presence of alpha-tocopherol reduced the amount of CBE I (FIG. 14A v. FIG. 14B), CBE II (FIG. 15A v. FIG. 15B), and other unknown degradants (FIG. 16A v. FIG. 16B). Formulations containing alpha-tocopherol demonstrate better stability performance when compared to formulations without alpha-tocopherol under the same accelerated storage conditions, except for OH-CBD (FIG. 17A v. FIG. 17B)

TABLE 20

| Compositions with Antioxidant | | | |
|---|---|---|---|
| Lipid % w/w | | API % w/w | Syloid 3050 % w/w |
| Gelucire 50/13 | 26 | 24 | 50 |
| Gelucire 43/01 | | | |
| Labrafil M2130 | | | |
| crodasol HS | 30 | 20 | |
| Croduret 40 | | | |
| Labrafac PG | | | |
| Capryol 90 | 26.75 | 23.25 | |
| Labrafac 1349 | 33 | 17 | |
| Labrafil 1944 | | | |
| Labrasol ALF | 24.75 | 25.25 | |

TABLE 21

| Stability Criteria | | |
|---|---|---|
| Chemical Test<br>Assay | Applied Specification Limits<br>CBD within +/−10% of label claim | |
| Degradants | CBE I | NMT 0.5% active |
| (storage at | CBE II | NMT 0.5% active |
| 25° C./60% RH | OH-CBD | NMT 0.5% active |
| and 40° C./75% RH) | Individual Unknown Degs | NMT 0.2% active |
| | Total unspecified Degs | NMT 1.0% active |

*NMT = not more than

Stage 2: Formulations containing 100 mg CBD per capsule and 0.2%, 0.6% or 1.0% of alpha-tocopherol were assessed for stability over 12 weeks at 25° C./60% RH, 30° C./65% RH and 40° C./75% RH conditions.

The compositions of the tested formulations are summarized in Table 22.

TABLE 22

| Compositions | | | | |
|---|---|---|---|---|
| Lipid % w/w | | API % w/w | Syloid 3050% w/w | Antioxidant % w/w |
| Gelucire ® 43/01<br>Labrafil ® M2130<br>Capryol ® 90 | Q.S.<br>to 100% | 24 | 50 | 0.2/0.6/1.0%<br>variants |

Figure 24:
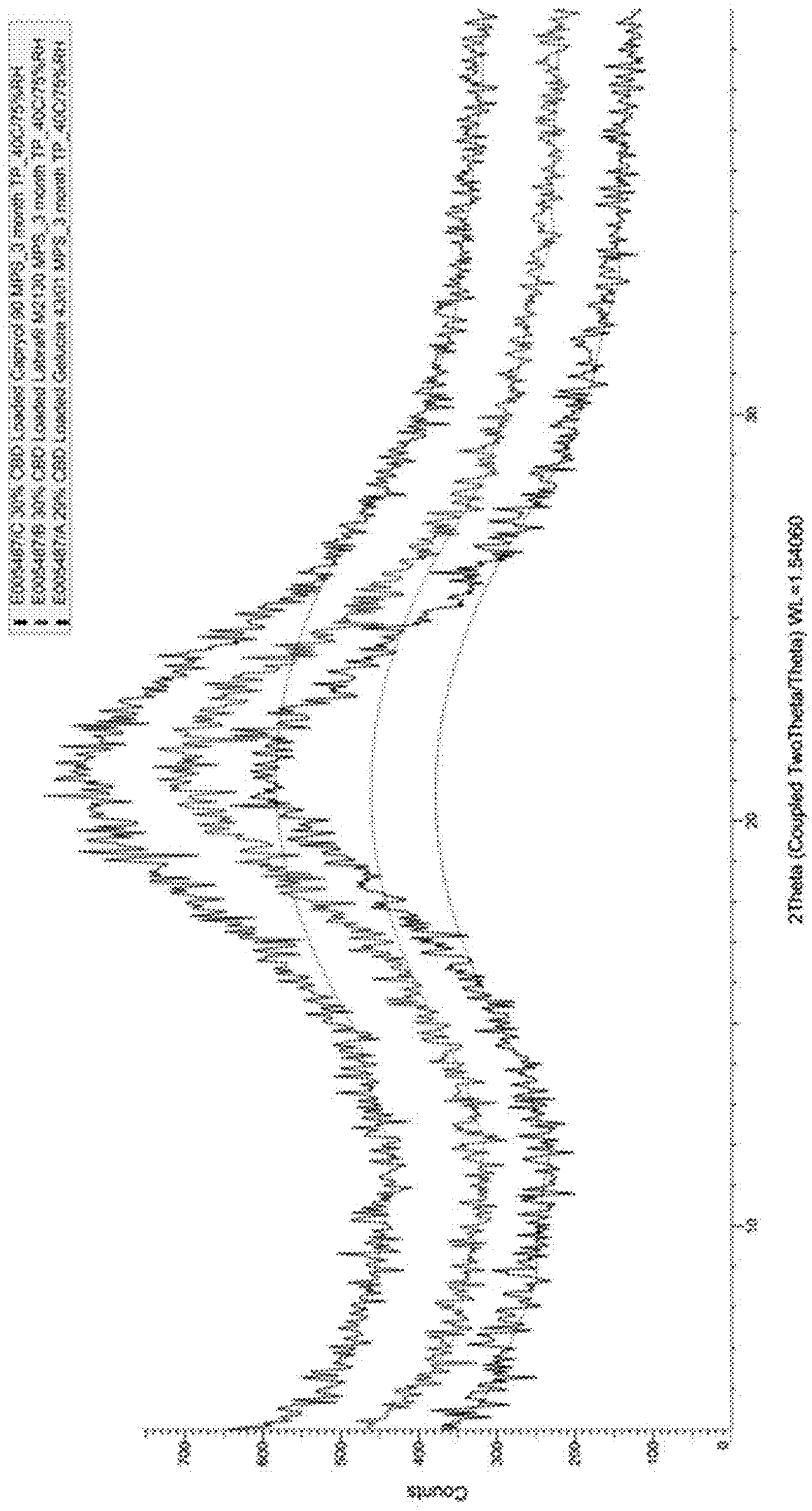
FIG. 24 shows x-ray pattern diffractogram (XRPD) showing amorphicity of CBD when absorbed onto and/or into the porous carrier using the lipid-loading process described herein.

The XRPD diffractograms of the tested formulations at the 12 week time point are shown in FIG. 24. No changes in amorphous state of the formulations were observed with storage at 40° C./75% RH for 12 weeks.

FIGS. 18A-D show that 0.2%, 0.6% and 1% alpha-tocopherol generally protects CBD from decomposition in Gelucire® 43/10-loaded formulations at 40° C./75% RH over 12 weeks, as measured by the amount of the amount of degradants CBE I, CBE II, OH-CBD, and total degradants. However, Gelucire® 43/01 shows anomalous data with 0.6% alpha-tocopherol content yielding poorest results with 0.2% and 1% performing better.

FIGS. 19A-D show that 0.2%, 0.6% and 1% alpha-tocopherol generally protects CBD from decomposition in Labrafil® M2130-loaded formulations at 40° C./75% RH over 12 weeks, as measured by the amount of the amount of degradants CBE I, CBE II, OH-CBD, and total degradants. Best performance is demonstrated by 1% (w/w), alpha tocopherol content.

FIGS. 20A-D show that 0.2%, 0.6% and 1% alpha-tocopherol generally protects CBD from decomposition in Capryol® 90-loaded formulations at 40° C./75% RH over 12 weeks, as measured by the amount of the amount of degradants CBE I, CBE II, OH-CBD, and total degradants. Best performance is demonstrated by 0.6% (w/w), alpha tocopherol content.

Example 6: Capsule Preparations

The drug-containing particles were prepared as described in Example 3 and added to capsules. Capsules containing 100 mg of a cannabinoid drug substance and 150 mg a cannabinoid drug substance were prepared as described in Tables 23 and 24.

TABLE 23

| 100 mg Capsules. | | | | |
|---|---|---|---|---|
| item | function | % w/w | mg/g | mg/dose |
| Formulation 1A | | | | |
| CBD | API | 24.00 | 240.00 | 100.00 |
| Gelucire 43/01 | lipid | 25.80 | 258.00 | 107.50 |
| Alpha tocopherol | Antioxidant | 0.20 | 2.00 | 0.83 |
| Syloid XDP 3050 | Solid Carrier | 50.00 | 500.00 | 208.34 |
| Corrected capsule fill weight 416.67 | Total | 100.00 | 1000.00 | 416.67 |
| Formulation 2 | | | | |
| CBD | API | 24.00 | 240.00 | 100.00 |
| Labrafil M2130 | lipid | 25.80 | 258.00 | 107.50 |
| Alpha tocopherol | Antioxidant | 0.20 | 2.00 | 0.83 |
| Syloid XDP 3050 | Solid Carrier | 50.00 | 500.00 | 208.34 |
| Corrected capsule fill weight 416.67 | Total | 100.00 | 1000.00 | 416.67 |
| Formulation 3 | | | | |
| CBD | API | 23.25 | 232.50 | 100.00 |
| Capryol 90 | lipid | 26.55 | 265.50 | 114.19 |
| Alpha tocopherol | Antioxidant | 0.20 | 2.00 | 0.86 |
| Syloid XDP 3050 | Solid Carrier | 50.00 | 500.00 | 215.05 |
| Corrected capsule fill weight 430.11 | Total | 100.00 | 1000.00 | 430.10 |

TABLE 24

| 150 mg Capsules. | | | | |
|---|---|---|---|---|
| item | function | % w/w | mg/g | mg/dose |
| Formulation 1B | | | | |
| CBD | API | 29.00 | 290.00 | 150.00 |
| Gelucire 43/01 | lipid | 25.00 | 250.00 | 129.31 |
| Alpha tocopherol | Antioxidant | 1.00 | 10.00 | 5.17 |
| Syloid XDP 3050 | Solid Carrier | 45.00 | 450.00 | 232.76 |
| | Total | 100.00 | 1000.00 | 517.24 |
| Formulation 2B | | | | |
| CBD | API | 30.00 | 300.00 | 150.00 |
| Labrafil M2130 | lipid | 19.00 | 190.00 | 95.00 |
| Alpha tocopherol | Antioxidant | 1.00 | 10.00 | 5.00 |
| Syloid XDP 3050 | Solid Carrier | 50.00 | 500.00 | 250.00 |
| | Total | 100.00 | 1000.0 | 500.00 |
| Formulation 3C | | | | |
| CBD | API | 30.00 | 300.00 | 150.00 |
| Capryol 90 | lipid | 19.00 | 190.00 | 95.00 |

TABLE 24-continued

| 150 mg Capsules. | | | | |
|---|---|---|---|---|
| item | function | % w/w | mg/g | mg/dose |
| Alpha tocopherol | Antioxidant | 1.00 | 10.00 | 5.00 |
| Syloid XDP 3050 | Solid Carrier | 50.00 | 500.00 | 250.00 |
| | Total | 100.00 | 1000.00 | 500.00 |

Example 7. Dog Studies

The compositions described in Table 25 were administered to beagle dogs. Blood plasma levels and gastrointestinal tolerability were evaluated compared to an oral solution of CBD in sesame oil prepared in capsules ("CBD Oral Solution in capsules). The results are also presented in Table 25.

TABLE 25

| | | Frel % Mean [Range] | | Clinical Observations* | | | |
|---|---|---|---|---|---|---|---|
| | | | | | Liquid/ | | Loss of |
| Test Item | Platform type | Day 1 | Steady State (Day 3 or 7) | Vomit | Soft Faeces | Total Obs | appetite# (Y/N) |
| CBD Oral Solution in capsules | Solution | — | — | 0.00 | 1.75 | 3.25 | Y (1/4) |
| IR capsules | Capsule (gel fill) | | | 1.25 | 2.00 | 3.25 | Y (1/4) |
| 24% CBD Gelucire 50/13 MPS | Capsule (lipid-loaded carrier) | 513 [217-886] | 88 [63-107] | 0.33 | 1.33 | 3.33 | N |
| 24% CBD Gelucire 43/01 MPS | | 146 [126-180] | 271 [105-598] | 0.33 | 0.67 | 1.33 | N |
| 23.25% CBD Capryol 90 MPS | | 148 [92-258] | 126 [80-198] | 0.00 | 0.66 | 1.67 | N |
| 17% CBD Labrafac 1349 Size | | 202 [103-274] | 117 [86-143] | 1.00 | 2.67 | 4.00 | N |
| 25.25% CBD Labrasol ALF MPS | | 91 [61-145] | 63 [27-85] | 0.33 | 2.00 | 2.33 | N |
| 24% CBD Labrafil M2130 MPS | | 359 [60-658] | 123 [116-130] | 0.00 | 1.00 | 1.00 | N |
| 20% CBD Kollidon 30 SDP Capsules | Capsule (spray dried powder fill) | 9 [5-15] | 65 [28-102] | 0.00 | 0.50 | 2.00 | Y (2/2) |
| 20% CBD Kollidon VA64 SDP Capsules | | 20 [2-38] | 24 [5-43] | 0.00 | 0.50 | 0.50 | Y (1/2) |
| 20% CBD Soluplus SDP Capsules | | 22 [15-30] | 65 [39-79] | 0.00 | 0.00 | 0.33 | Y (2/3) |
| 300 mg CBD Capryol 90 Capsules | Capsule (lipid fill) | 54 [40-100] | 59 [15-89] | 0.00 | 1.33 | 1.33 | N |
| 300 mg CBD Gelucire 43/01 Capsules | | 63 [0-189] | 24 [1-51] | 0.00 | 0.33 | 1.00 | N |
| 300 mg CBD Labrafil M2130 Capsules | | 91 [9-159] | 55 [23-101] | 0.00 | 1.00 | 1.00 | N |
| 300 mg Labrasol ALF size 00 Capsules | | 183 [49-480] | 79 [61-101] | 0.00 | 0.33 | 0.33 | N |
| 300 mg CBD Gelucire 50/13 Capsules | | 235 [30-573] | 180 [52-288] | 0.00 | 1.33 | 1.33 | N |
| 107 mg CBD Capryol 90 MPS 3050 | Capsule (lipid loaded carrier fill) | 305 [201-507] | 123 [103-154] | 0.00 | 1.33 | 1.67 | N |
| 106 mg CBD Labrafil M2130 MPS 3050 | | 335 [53-528] | 96 [61-155] | 0.33 | 1.00 | 2.33 | N |
| 107 mg CBD Gelucire 43/01 MPS 3050 | | 164 [89-215] | 127 [84-195] | 0.33 | 2.00 | 2.67 | Y (1/3) |
| 52 mg CBD Capryol 90 MPS 3050 | | 198 [143-263] | 215 [149-323] | 0.00 | 0.33 | 0.33 | Y (1/3) |
| 53 mg CBD Labrafil M2130 MPS 3050 | | 249 [122-445] | 225 [133-384] | 0.00 | 0.33 | 0.33 | N |
| 53 mg CBD Gelucire 43/01 MPS 3050 | | 252 [65-533] | 240 [86-485] | 0.00 | 1.33 | 1.33 | Y (1/3) |
| 152 mg CBD-Capryol 90 MPS 3050 | Capsule (lipid loaded carrier fill | 300 [176-533] | 114 [90.7-142] | 0.00 | 2.00 | 2.00 | N |
| 147 mg CBD-Labrafil M2130 MPS 3050 | | 464 [221-880] | 132 [73-242] | 0.33 | 1.33 | 2.00 | N |
| 155 mg CBD-Gelucire 43/01 MPS 3050 | | 154 [134-176] | 82 [68-100] | 10.00 | 2.00 | 2.33 | N |

Target Profile

Similar or better bioavailability compared to CBD Oral Solution in capsules

No vomiting

Liquid/soft feces<2

Total obs<3.25

No loss of appetite

Figure 21A:
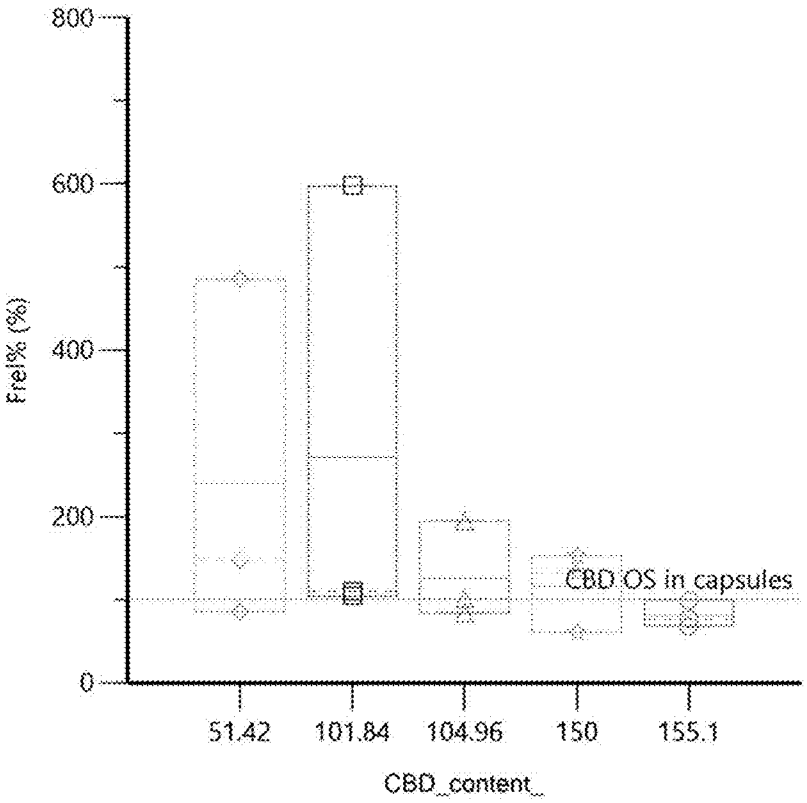
FIG. 21A shows relative bioavailability (in Frel %) of formulations containing different ratios of CBD to lipophilic material, as measured in beagle dogs.
Figure 21B:
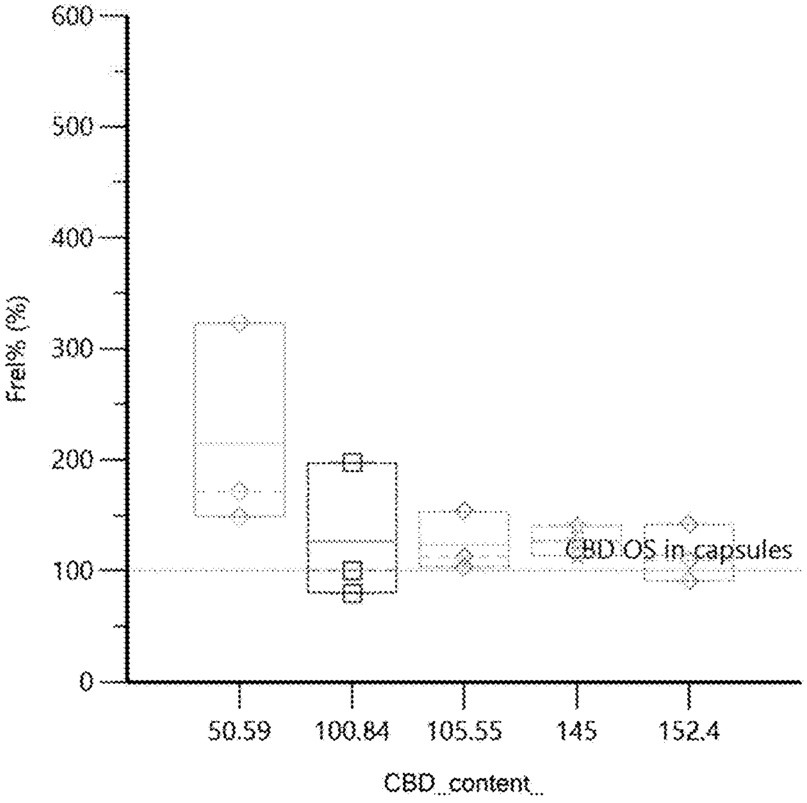
FIG. 21B shows relative bioavailability (in Frel %) of formulations containing different ratios of CBD to lipophilic material, as measured in beagle dogs.
Figure 21C:
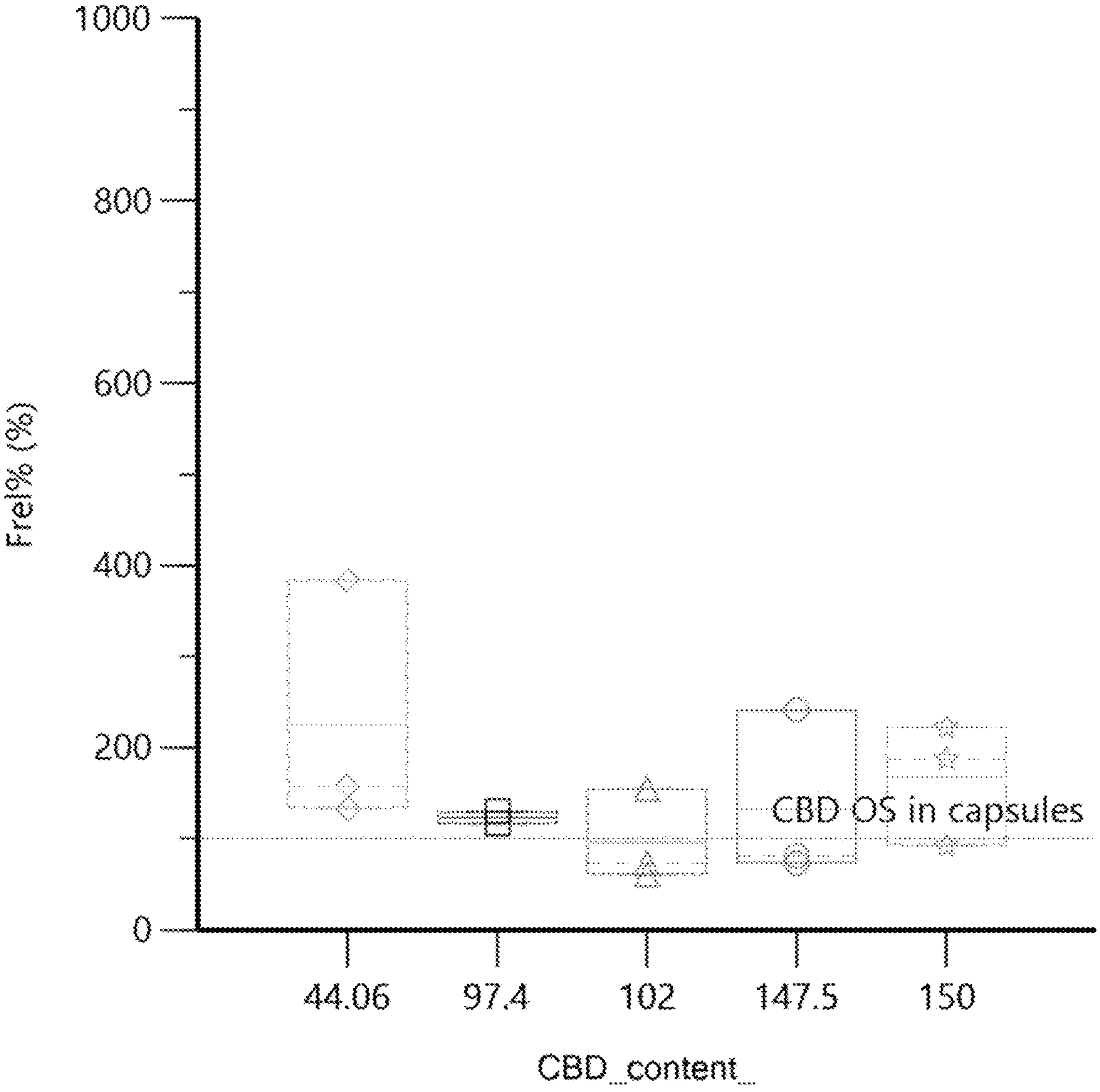
FIG. 21C shows relative bioavailability (in Frel %) of formulations containing different ratios of CBD to lipophilic material, as measured in beagle dogs. The Y-axis is reported as % Frel, which measures the % of the average plasma concentration (AUC) relative to the average plasma concentration CBD dissolved in sesame oil and prepared in capsules ("CBD OS in capsules").

CBD Oral Solution in capsules set the baseline for the target profile. Product candidates had equivalent or superior properties to CBD Oral Solution. Compositions not satisfying the target profile were not advanced. As shown in Table 25, the compositions containing CBD dissolved in lipid and loaded onto a porous solid carrier ("lipid-loaded carrier") displayed superior pharmacokinetics compared to compositions containing CBD dissolved in the same lipid (see also Table 26) and spray dried compositions prepared with the same lipid. In addition, lipid-loaded carrier composition displayed superior gastrointestinal tolerability than all compositions, including CBD Oral Solution. FIGS. 21A-C show that the wt ratio of CBD to lipophilic material does not significantly affect bioavailability.

CBD is retained in amorphous form even without use of an antioxidant

Syloid retained free-flowing powder properties with drug loading of 24%

Neuselin retained free-flowing powder properties with drug loading of 21%

Like sesame seed oil, pumpkin seed oil was assessed with MPS and Neusilin and exhibited desirable properties.

Introduction of chelating agent and/or AO combination was found to provide improved stability for the formulations.

Example 8. Rat Studies

Figure 22A:
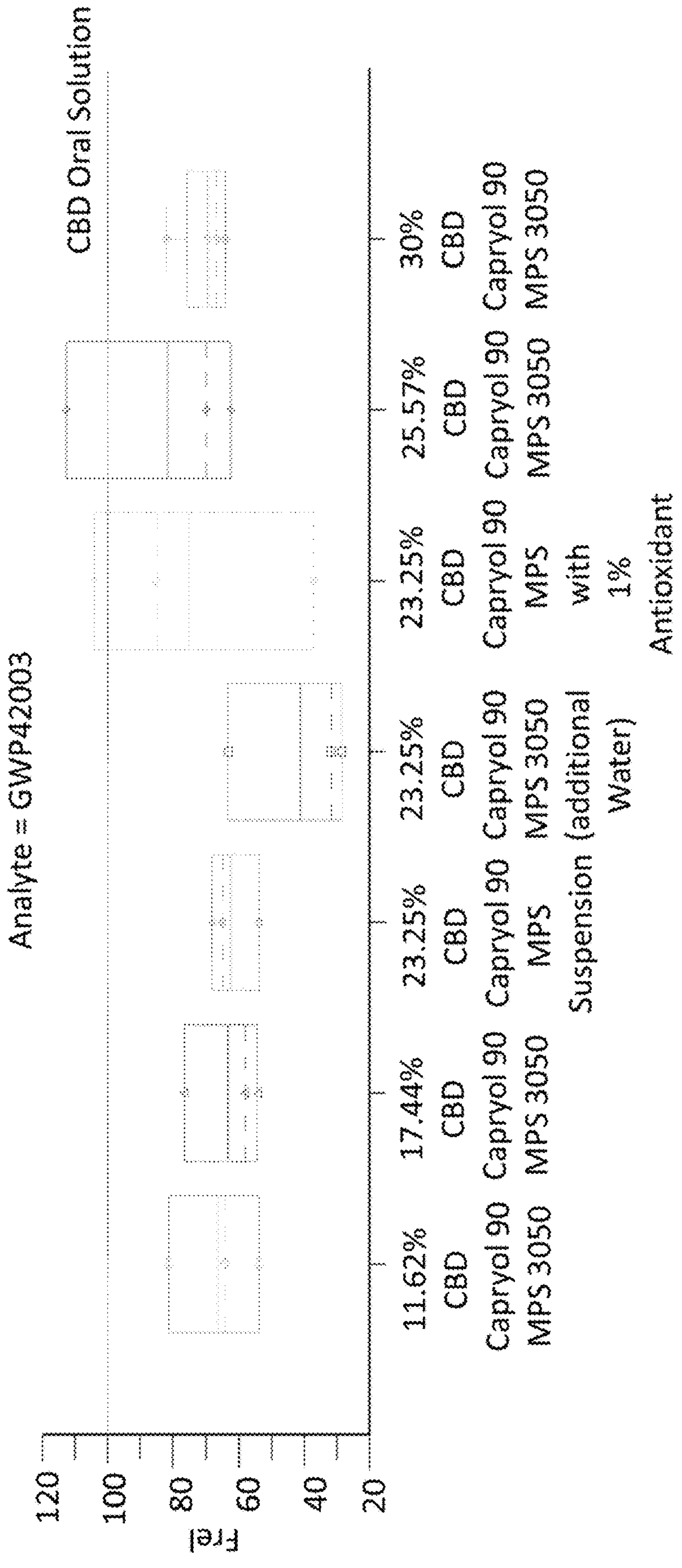
FIG. 22A shows relative bioavailability (in Frel %) of formulations containing different ratios of CBD to lipophilic material in rats, as described in Example 8.
Figure 22B:
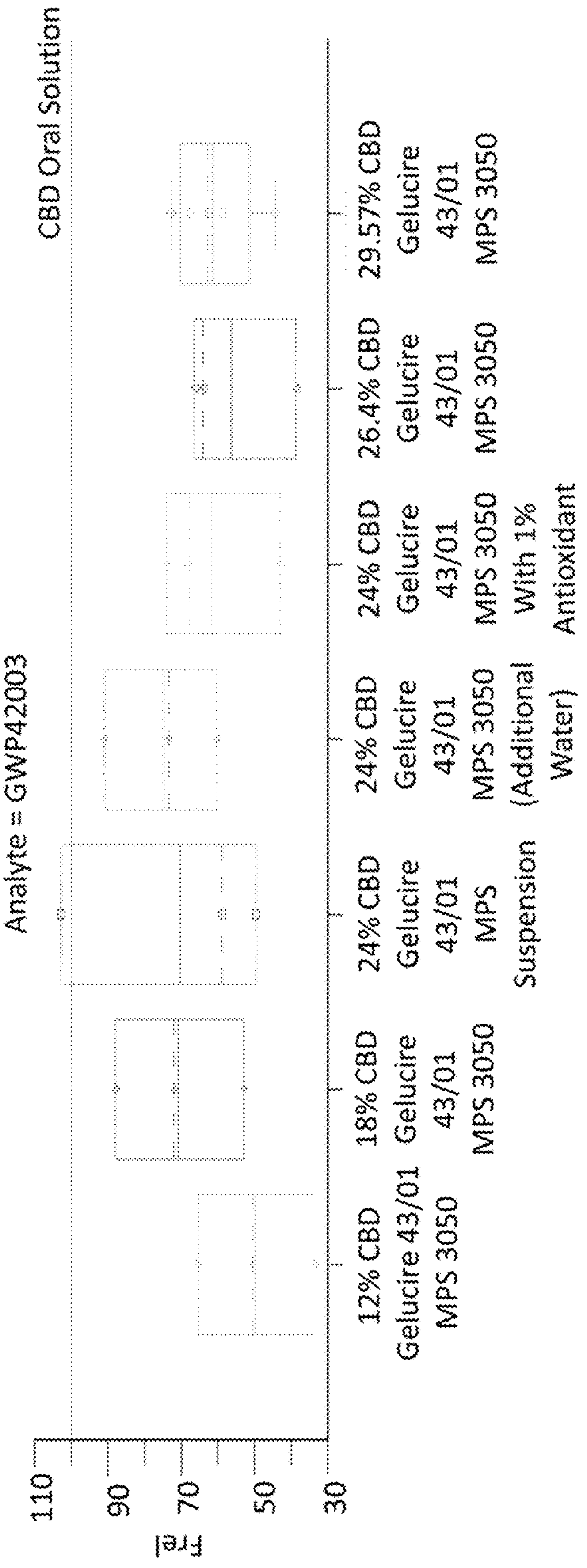
FIG. 22B shows relative bioavailability (in Frel %) of formulations containing different ratios of CBD to lipophilic material in rats, as described in Example 8.
Figure 22C:
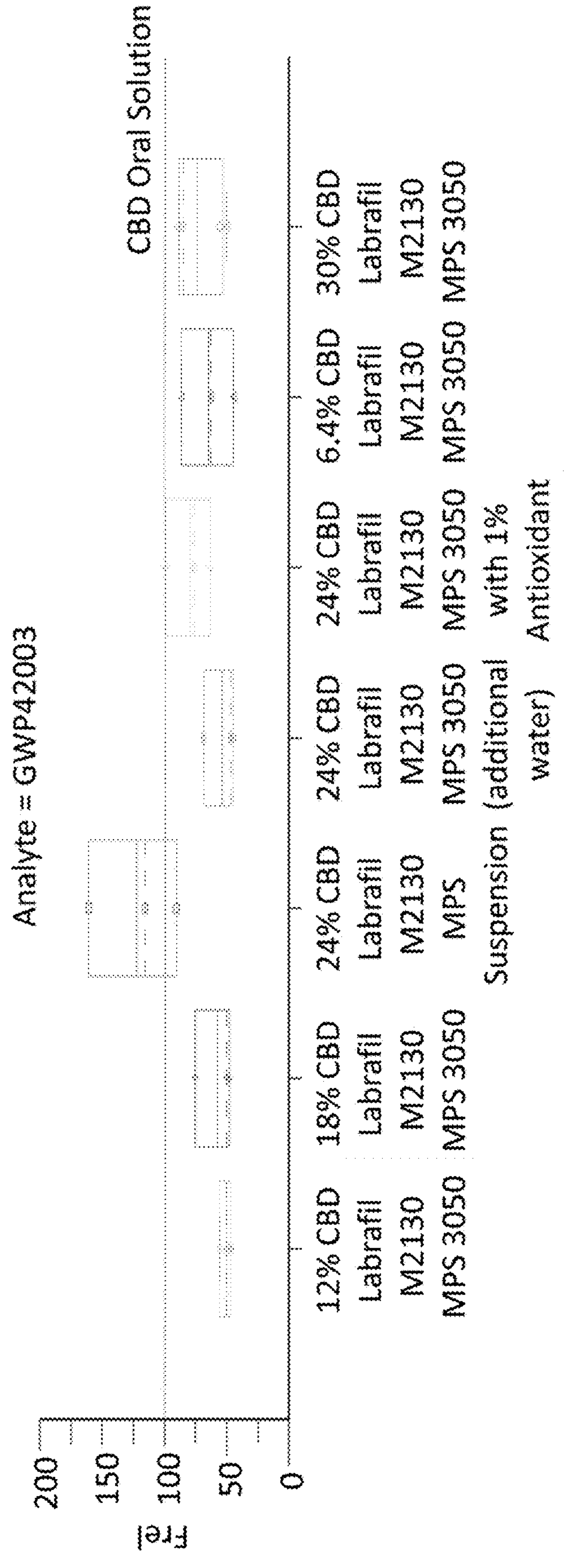
FIG. 22C shows relative bioavailability (in Frel %) of formulations containing different ratios of CBD to lipophilic material in rats, as described in Example 8.

The compositions described in Table 25 were administered to rats. Bioavailability of the compositions was evaluated compared to an oral solution of CBD in sesame oil or suspension in water-methylcellulose (FIGS. 22A-C). No adverse events were observed in rat model study.

TABLE 26

| | Frel % Mean [Range] | | Clinical Observations* | | |
|---|---|---|---|---|---|
| Test Item | Day 1 | Steady State (Day 3 or 7) | Vomit | Liquid/ Soft Faeces | Total Obs |
| 24% CBD Gelucire 43/01 MPS | 146 [126-180] | 271 [105-598] | 0.33 | 0.67 | 1.33 |
| 300 mg CBD Gelucire 43/01 | 63 [0-189] | 24 [1-51] | 0.00 | 0.33 | 1.00 |
| 23.25% CBD Capryol 90 MPS | 148 [92-258] | 126 [80-198] | 0.00 | 0.66 | 1.67 |
| 300 mg CBD Capryol 90 | 54 [40-100] | 59 [15-89] | 10.00 | 1.33 | 1.33 |
| 24% CBD Labrafil M2130 MPS | 359 [60-658] | 123 [116-130] | 0.00 | 1.00 | 1.00 |
| 300 mg CBD Labrafil M2130 | 91 [9-159] | 55 [23-101] | 0.00 | 1.00 | 1.00 |
| 25.25% CBD Labrasol ALF MPS | 91 [61-145] | 63 [27-85] | 10.33 | 2.00 | 2.33 |
| 300 mg Labrasol ALF | 183 [49-480] | 79 [61-101] | 0.00 | 0.33 | 0.33 |
| 24% CBD Gelucire 50/13 MPS | 513 [217-886] | 88 [63-107] | 0.33 | 1.33 | 3.33 |
| 300 mg CBD Gelucire 50/13 | 235 [30-573] | 180 [52-288] | 0.00 | 1.33 | 1.33 |

Compositions prepared with porous carrier and GELUCIRE® 40/01, CAPRYOL® 90, and LABRAFIL® M2130 were had a favorable profile and were selected for advancement.

TABLE 27

| Selected lead prototype formulations | Justification for selection | Non-selected formulations | Justification for non-selection |
|---|---|---|---|
| 24% CBD-Gelucire 43/01 MPS 3050 | Highest bioavailability and GI tolerability compared to the other live lipid as well as reference formulations (i.e. Epidiolex, CBR IR capsules and Granules) | 24% CBD-Gelucire 50/13 MPS 3050 | Increased adverse event lower tolerability. Bioavailability lowest of the six lipids. |
| 24% CBD-Labrafil M2130 MPS 3050 | Higher bioavailability and GI tolerability as observed by low adverse events compared to reference formulations | 17% CBD-labrafac 1349 MPS 3050 | Lowest tolerability high adverse effect. Lower drug load thus Increased pill burden |
| 23.25% CBD-Capryol 90 MPS | Lower adverse effect compared to Labrasol ALF and Labrafac 13449 although bioavailability lesser than the two lipids | 25.25% CBD-Labrasol ALF MPS 3050 | Lower bioavailability and Gastric tolerability |

SUMMARY

Lipid-loaded formulations provide a favorable profile with encouraging physical and chemical data being generated.

The invention claimed is:

1. A drug-containing particle comprising:

a. a drug substance comprising cannabidiol, wherein the cannabidiol is present at an amount ranging from about 15% to about 40% by weight based on the total weight of the drug-containing particle;

b. a porous solid carrier at an amount ranging from about 10% to about 60% by weight based on the total weight of the drug-containing particle;

c. a lipophilic material at an amount ranging from about 20% to about 35% by weight based on the total weight of the drug-containing particle; and d. one or more antioxidants, wherein the drug substance is adsorbed onto the porous solid carrier, wherein the porous solid carrier comprises a mesoporous silica or an amorphous silica, wherein the porous solid carrier has an average pore volume of about 1 mL/g to 2 mL/g; and wherein the lipophilic material comprises:

mono-, di- and triglyceride esters of C8-C18 fatty acids;

mono-, di-, and triglyceride esters of lauric and stearic acids and PEG-6 mono- and diesters of lauric and stearic acids; or propylene glycol monocaprylate; or combinations thereof.

2. The drug-containing particle of claim 1, wherein the drug substance further comprises no more than about 0.5% by weight of active of cannabidiorcol (CBD-C1), no more than about 0.5% by weight of active of cannabidivarin (CBDV), or no more than about 0.2% by weight of active of cannabidibutol (CBD-C4).

3. The drug-containing particle of claim 1, wherein the cannabidiol is present in an amount ranging from about 20% to about 35% by weight based on the total weight of the drug-containing particle.

4. The drug-containing particle of claim 1, wherein the cannabidiol is present in non-crystalline form as measured by X-ray powder diffraction.

5. The drug-containing particle of claim 1, wherein the porous solid carrier comprises a mesoporous silica.

6. The drug-containing particle of claim 1, wherein the porous solid carrier is present in an amount ranging from about 30% to about 50% by weight based on the total weight of the drug-containing particle.

7. The drug-containing particle of claim 1, wherein the porous solid carrier has an average pore volume of about 1 mL/g to 1.9 mL/g.

8. The drug-containing particle of claim 1, wherein the porous solid carrier has an average surface area of about 250 $m^2/g$ to about 375 $m^2/g$.

9. The drug-containing particle of claim 1, wherein the porous solid carrier has an average pore diameter of about 2 nm to about 50 nm.

10. The drug-containing particle of claim 1, wherein the porous solid carrier is a microparticle.

11. The drug-containing particle of claim 1, wherein the porous solid carrier has an average particle size of about 50 μm to about 150 μm.

12. The drug-containing particle of claim 1, wherein the porous solid carrier has a porosity of about 75% to about 99%.

13. The drug-containing particle of claim 1, wherein the lipophilic material comprises mono-, di- and triglyceride esters of C8-C18 fatty acids.

14. The drug-containing particle of claim 1, wherein the lipophilic material comprises mono-, di-, and triglyceride esters of lauric and stearic acids and PEG-6 mono- and diesters of lauric and stearic acids.

15. The drug-containing particle of claim 1, wherein the lipophilic material comprises propylene glycol monocaprylate.

16. The drug-containing particle of claim 1, wherein the lipophilic material comprises mono-, di-, and triglyceride esters of lauric and stearic acids and PEG-6 mono- and diesters of lauric and stearic acids, or propylene glycol monocaprylate.

17. The drug-containing particle of claim 1, wherein the one or more antioxidants comprises alpha-tocopherol, β-carotene, ascorbic acid, ascorbyl palmitate, lecithin, butylated hydroxyanisole, butylated hydroxytoluene, monothioglycerol, propyl gallate, or a combination thereof.

18. The drug-containing particle of claim 1, wherein the one or more antioxidants comprises alpha-tocopherol.

19. The drug-containing particle of claim 1, wherein the amount of the one or more antioxidants ranges from about 0.05% to about 1.5% by weight based on the total weight of the drug-containing particle.

20. The drug-containing particle of claim 1, wherein the amount of the one or more antioxidants ranges from about 0.2% to about 1% by weight based on the total weight of the drug-containing particle.

21. The drug containing particle of claim 1, further comprising a chelating agent.

22. The drug-containing particle of claim 21, wherein the chelating agent comprises EDTA, citric acid, curcumin, or a combination thereof.

23. The drug containing particle of claim 1, wherein at least 50% of the cannabidiol is released from the drug-containing particle in 1 hour, as measured under USP 711 with a Type II apparatus at pH 6.8.

24. A pharmaceutical composition comprising a plurality of the drug containing particles of claim 1.

25. The drug-containing particle of claim 1, wherein the porous solid carrier has an average surface area of about 320 $m^2/g$ to about 375 $m^2/g$.

26. The drug-containing particle of claim 1, wherein the porous solid carrier has an average pore diameter of about 15 nm to about 30 nm.

27. The drug-containing particle of claim 1, wherein the porous solid carrier comprises mesoporous silica and has an average surface area of about 320 $m^2/g$ to about 375 $m^2/g$ and an average pore volume of about 1 mL/g to about 1.9 mL/g.

* * * * *